(12) United States Patent
Gong et al.

(10) Patent No.: US 11,331,332 B2
(45) Date of Patent: May 17, 2022

(54) TREATMENT OF INCREASED LIPID LEVELS WITH STEROL REGULATORY ELEMENT BINDING PROTEIN CLEAVAGE-ACTIVATING PROTEIN (SCAP) INHIBITORS

(71) Applicants: Regeneron Pharmaceuticals, Inc., Tarrytown, NY (US); University of Maryland, Baltimore, Baltimore, MD (US)

(72) Inventors: Da-Wei Gong, Baltimore, MD (US); James A. Perry, Baltimore, MD (US); Alan Shuldiner, Tarrytown, NY (US); Nehal Gosalia, Tarrytown, NY (US); Cristopher Van Hout, Tarrytown, NY (US)

(73) Assignees: Regeneron Pharmaceuticals, Inc., Tarrytown, NY (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/823,832

(22) Filed: Mar. 19, 2020

(65) Prior Publication Data
US 2020/0297753 A1 Sep. 24, 2020

Related U.S. Application Data

(60) Provisional application No. 62/820,895, filed on Mar. 20, 2019.

(51) Int. Cl.
| | | |
|---|---|---|
| C07H 21/04 | (2006.01) |
| A61K 31/7105 | (2006.01) |
| C12N 9/22 | (2006.01) |
| C12Q 1/6827 | (2018.01) |
| C12Q 1/6853 | (2018.01) |

(52) U.S. Cl.
CPC ............ *A61K 31/7105* (2013.01); *C12N 9/22* (2013.01); *C12Q 1/6827* (2013.01); *C12Q 1/6853* (2013.01); *C12N 2310/11* (2013.01); *C12N 2310/14* (2013.01); *C12N 2310/20* (2017.05); *C12N 2310/531* (2013.01)

(58) Field of Classification Search
None
See application file for complete search history.

(56) References Cited

U.S. PATENT DOCUMENTS

2005/0014177 A1  1/2005  Ranade et al.
2021/0095277 A1  4/2021  Lindholm et al.

FOREIGN PATENT DOCUMENTS

| WO | 2008011467 | 1/2008 |
| WO | 2008036638 | 3/2008 |
| WO | 2017100542 | 6/2017 |

OTHER PUBLICATIONS

Eberle et al., "SREBF-1 Gene Polymorphisms Are Associated With Obesity and Type 2 Diabetes in French Obese and Diabetic Cohorts", Diabetes, 2004, 53(8), pp. 2153-2157.
Jensen et al., "Dose-dependent effects of siRNA-mediated inhibition of SCAP on PCSK9, LDLR, and plasma lipids in mouse and rhesus monkey", Journal of Lipid Research, 2016, 57(12), pp. 2150-2162.
Laaksonen et al., "Genetic variant of the SREBF-1 gene is significantly related to cholesterol synthesis in man", Atherosclerosis, 2006, 185(1), pp. 206-209.
Li et al., "SCAP knockdown in vascular smooth muscle cells alleviates atherosclerosis plaque formation via up-regulating autophagy in ApoE −/− mice", The FASEB Journal, 2019, 33(3), pp. 3437-3450.
Moon et al., "The Scap/SREBP Pathway Is Essential for Developing Diabetic Fatty Liver and Carbohydrate-Induced Hypertriglyceridemia in Animals", Cell Metabolism, 2011, 15(2), pp. 240-246.
Murphy et al., "siRNA-mediated inhibition of SREBP cleavage-activating protein reduces dyslipidemia in spontaneously dysmetabolic rhesus monkeys", Metabolism Clinical and Experimental, 2017, 71, pp. 202-212.
Salek et al., "Effects of SREBF-1a and SCAP polymorphisms of plasma levels of lipids, severity, progression and regression of coronary atherosclerosis and response to therapy with fluvastatin", Journal of Molecular Medicine, 2002, 80(11) pp. 737-744.
Snpdev, "Referecne SNP (refSNP) Cluster Report: rs746678809", 2018, http://www.ncbi.nlm.nih.gov/projects/SNP/snp_ref.cgi?do_not_redirect&rs=rs746678809.
Sun et al., "SCAP gene polymorphisms decrease the risk of non-alcoholic fatty liver disease in females with metabolic syndrome", Journal of Genetics, 2013, 92, pp. 565-570.
Yahagi et al., "Absence of sterol regulatory element-binding protein-1 (SREBP-1) ameliorates fatty livers but not obesity of insulin resistance in Lep(ob)/Lep(ob) mice", The Journal of Biological Chemistry, 2002, 277(22), pp. 19353-19357.

(Continued)

*Primary Examiner* — Kimberly Chong
(74) *Attorney, Agent, or Firm* — Stradley Ronon Stevens & Young, LLP

(57) ABSTRACT

The present disclosure provides methods of treating subjects having increased lipid levels and/or increased triglyceride levels, methods of identifying subjects having an increased risk of developing an increased lipid level and/or increased triglyceride level, methods of detecting human Sterol Regulatory Element Binding Protein Cleavage-Activating Protein (SCAP) variant nucleic acid molecules and variant polypeptides, and SCAP variant nucleic acid molecules and variant polypeptides.

16 Claims, 3 Drawing Sheets
Specification includes a Sequence Listing.

(56) References Cited

OTHER PUBLICATIONS

International Search Report and Written Opinion for PCT Application PCT/US2020/023532 (10536WO01)).
International Search Report and Written Opinion for PCT Application PCT/US2020/023564 (10537WO01)).
Enjoji et al., "Nutrition and Nonalcoholic Fatty Liver Disease: The Significance of Cholesterol", International Journal of Hepatology, 2012, pp. 1-6.
Horie et al., "MicroRNA-33b knock-in mice for an intron of sterol regulatory element-binding factor 1 (Srebf1) exhibit reduced HDL-C in vivo", Scientific Reports, 2014 4(5312), pp. 1-7.
Lee et al., "The cellular function of SCAP in metabolic signaling", Experimental & Molecular Medicine, 2020, 52, pp. 724-729.
Non-Final Office Action dated Aug. 25, 2021 in related U.S. Appl. No. 16/823,634.
Non-Final Office Action dated Feb. 17, 2022 in related U.S. Appl. No. 16/823,634.
Liu et al., "Delivery strategies of the CRISPR-Cas9 gene-editing system for therapeutic applications", Journal of Controlled Release, 2017, 266, pp. 17-26.
Talebi et al., "Sustained SREBP-1-dependent lipogenesis as a key mediator of resistance to BRAF-targeted therapy", Mature Communications, 2018, 9(2500), pp. 1-11.

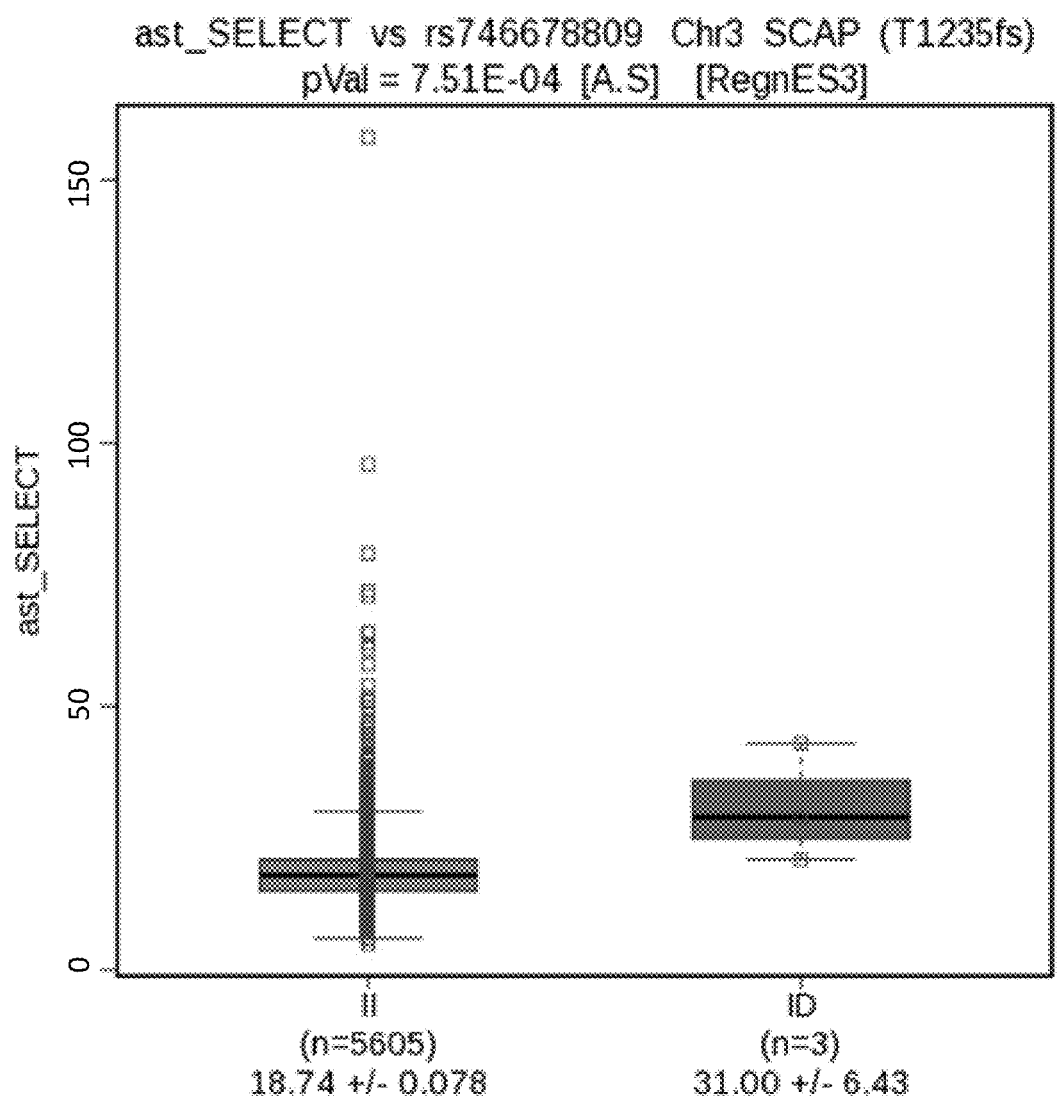

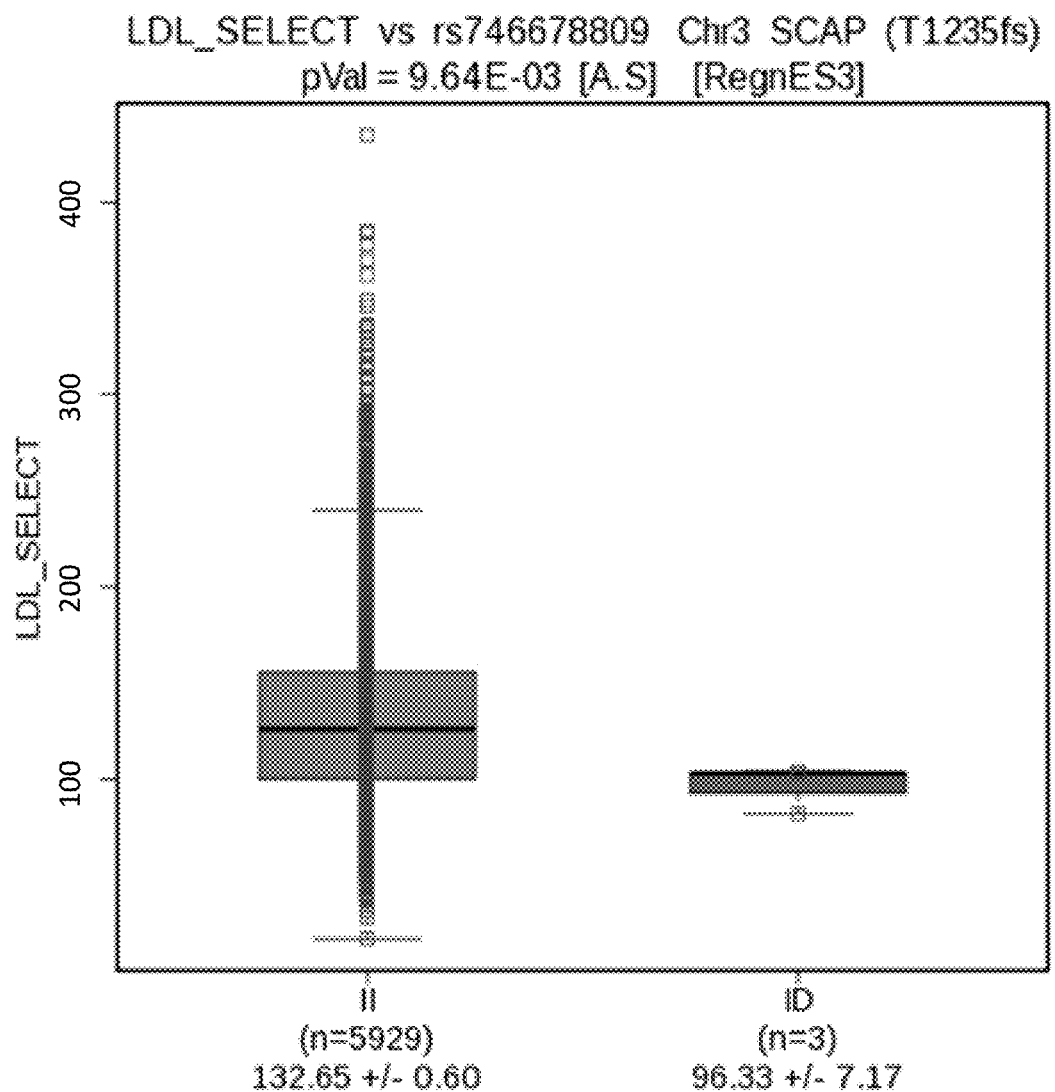

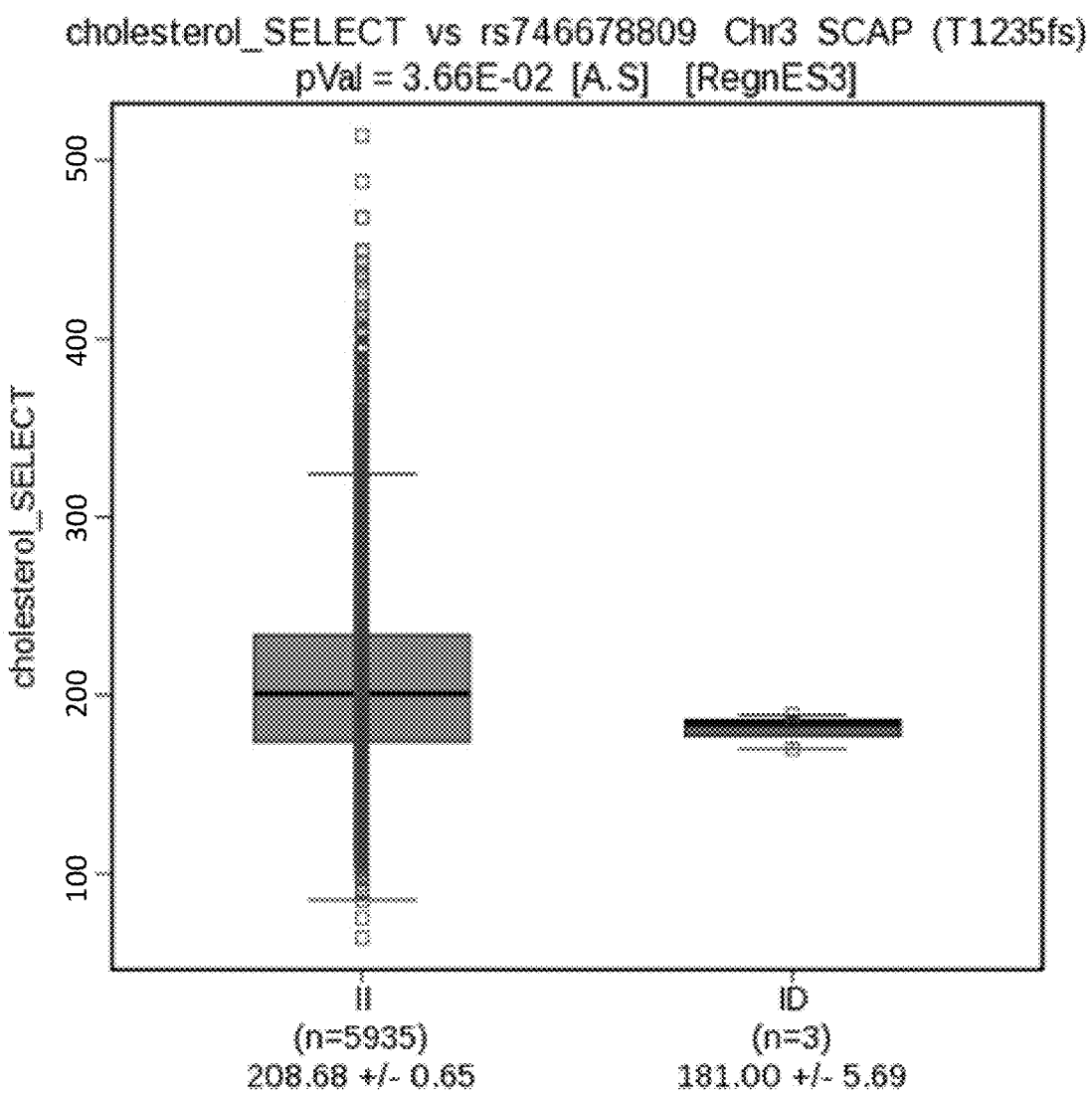

SEQUENCE LISTING

<160> NUMBER OF SEQ ID NOS: 53

<210> SEQ ID NO 1
<211> LENGTH: 62271
<212> TYPE: DNA
<213> ORGANISM: homo sapien

<400> SEQUENCE: 1
agaggtgaag gggcgggcac ccggcggcca ggagagagag ggagggcgcc acgcaccgga    60

```
ctgcgggccg agagcgcgca cgccgcgctc cgcccctgct gccgcccccg tcgccgccgc    120
cgccgccgcc gcagcttggg aggtgctgcc accacaggta ccgtcacgcg ggtgctcagg    180
gcgcctgccc gcgggcccca gctcgacccc agccgcgtgg agctgggagt tccggaatgg    240
gggccgctag gttcggggagt gcgtgggcat ggcgctgtcc agcagccgtg cgggccggcc    300
ctggagaccg caggccggca aggaggcagg gccgcgcgtc cccaccccca acccggccgt    360
gtccctgcac cggccggccc ctggagctcc gcgtccccac cagacctccg cggggcccctg   420 gtgtgacggg gggagatgcg cggcgtcgca tcccctggcc tagttgctcc gggaagctgt    480
tgtagaacct gctttggtgc tgtttgggtt ttccggagtg cggggggagag caggttctcc    540 actttgcctc ttttggaaga tcttattgag agacaacgct agttgctttg ctggttttgc    600
ttggtttcta gttttccgta ttgcttaaac ctcaactttg ctcactaatg ttgcttctgt    660
ttacttctga gtgggtttat gacctcagta tttaaccggc ttataatgtc acgatagcgt    720
tagttgcagg gagccctggc tccggactgt ttgaatcaca gaaagttgtg cagatgggaa    780
tgcggagggg ggggcagtga gtcgctgtgg gggctctggc aggggtcagc ccctggttcg    840
ggtcactcac tgctccacct tgtatggcga cagtcggagc taggtgaata aactcttctt   900 ggggatttg taatacttat cgtgaagcgg ccatagaaaa ggtttaatgt tagcgttgcg    960
tgtgtttctt ttatttggcc aaaaatttgt ggagtttggt tatgccgtgt ctttattggt    1020
ttgctgtcag gtcaggatat tgagcaaaag actgacgctt ttattaggga gtcagggtcg   1080
agggtgtcta gttagtgctg tatccatttt aggtgttcct cagtgatgcc taaagacttg    1140
ttttttgttt gtttgtttgg agacagggtc tcactctgtc tcccaggctg gagtgcagtg    1200
gcgcgatctc ggctcactgc agccttgatt tcctgggctc aggtgatcct cccacctcag    1260
cctccccagt agctgggaca gcaggtgtgt gccaccacgc ccggctaatt tttgtatttt    1320
tttgtagaga tgggggtctt gctgtgttgc ccaggctggc ttttaactcc tgggctcaag    1380
cattatacaa gccttggcct cccaaagtgt tggtattaca ggcgtgaacc accgtgcccg    1440
gccaagacct gtatctttta aaatgtgtgt taatatagtt tacattttag gtgttttaca    1500
catttgcagt attcccactg agcacatgat gtaaaaaaca ctatataaat atatttaaca    1560
ctgtataaat atatttccat atttattctt ttggtcataa attgaaatgg aaagaattag    1620 gcttttttaaa tttattatga actgatctga tgtttgaatg ctctctcttt tctttctttc    1680
tttttttttt tgagatggag tctcgctctg tcgcccaggc tggagtgcag tggcgccatc    1740
tcggctcact gcaccctccg cctgccgggt tcaagcgatt ctcctgcctc agcctcccaa    1800
gtagctggga ctacaggcgc ccgccaccat gcccggctac tttttttgtat ttttagtaga    1860 gacgggtttt caccgtgtta gccaggatcg tctctatctc ctgacctcat gatccgtccg    1920
cttcggcctc ccaaagtgct gggattacag gcgtgagcca ccgcgcctgg cttgaatgct    1980
ctctcttttc ttttgctgtt gcggcaaaaa cgccccctct ctagagatct ccgtggactt    2040
tataatcact ggtttgggggc ccttcccccg ttccctcagt cactgtcatt aggtgggtaa    2100
aaagtttact acaagtttat tactagaaaa atggaggcat atgcgattca ggaattaaat    2160
aaactaaaaa aggaaagaaa aagtgtgcct gtgggcttca ctgcaggtat gtatattaac    2220
atttggtggt agactttagg gatgttttct ctctcagaat ctagccatgc atgtgaatgt    2280
gcctcaggga tcctggaatg acaggttcat gtgctgtttg cttactctca ccattggtgg    2340
ttgccagtgt tttaccggct ctgacaggta cttcatatac agtttgtgtc atcacccccg    2400
```

```
ttgaacagat gagaggactc ctcatagaga agctgggttc ttacaaggtc acccagcttg    2460
tcaagggtgg atcatccttc aaaccaggtc tgccacacct ctgccacctg agctccttcc    2520
gttagaactt gctaccttac tgagttggct aaagaaacaa ggttcaggtg tcgtcttttg    2580
ccactcagag taataattct gggtgatatc gagcacttgt gctgtttagg cagtgtccta    2640
ggtactgtaa tattagctta tctcacttag ttttcataat aaccaggtga gataacactg    2700
ttatcacccc ctttacggag agttttagaa aagttatttg actggccctg ggtcacctag    2760
cgaatttgag acggagtgtg ttgtgtgcaa actgagattt ggctgacaaa agagtccatc    2820
cttttatgct gttcttgtac ctgcttccac agtctgtttt ttttttttt ttttttgagat    2880
ggagtttcgc tcttcttgcc caggctggag tgcaatggcg tgatctcagc tcactgcaac    2940
ctccgcctcc caggttcaag cgattctcct gcctcagcct cctgagtagc tgggattaca    3000
ggcatgcact accacgcctg gctaattttg tatttttagt agaggcgagg tttctcccta    3060
ttggtcaggc tggtctcaga ctcccgatct caggtgatcc gcccgcctcg gcctcccaaa    3120
gtgctgggat tacaggcgtg agccactgca cgcagcccac agtctttcct gttgctcatt    3180
ggcaggtaag ggtagtggaa gaaggtggta ggggtggtgg gaggaagcca gcgtcactga    3240
ctctagtgtg gggatggtgg aactcagcaa gaaggtgaca gcaatttgac cactgccatt    3300
tgacagtttc tgcttaagca gtcaagggca ctaacctaga atggttgcag ggatgctaaa    3360
tcataaggaa gctttgcagt ggggtccaaa gttggtatgt aagcataaag atgcacgtgg    3420
atctcaggaa aaaaataaaa ctaattttcc tgtttatttc agcttcattt aattattatt    3480
attattatta ttattttatt ttattttttt ttttgagac ggagtctcgc tctgtcgccc    3540
aggccggact gcggactgca gtggcgcaat ctcggctcac tgcaagctcc gcttcccggg    3600
tttacgccat tctcctgcct cagcctcccg agtagctggg actacaggcg cccgccaccg    3660
cgcccggcta atttttttgt atttttagta gagacggggt ttcaccttgt tagccaggat    3720
ggtctcgatc tcctgacctc atgatccact cgcctcggcc tcccaaagtg ctgggattac    3780
aggcgtgagc caccgcgccc ggccccattt aattattatt attatttttt tgagatggag    3840
tctcactcaa tctgttgccc aggctggagt gcattgatgc tatctcggtt tactgcaatc    3900
ttggtctcct gcctcagcct cccgagtagc tgggattaca gctgtgcacc accacacctg    3960
gctaattttg tattttagt agagatgggg tttcaccata ttggttaggc tggtctcaaa    4020
ctcctggcct caagtgatcc acccaccttg acctcccaaa gtgctgggat tacaggcatg    4080
aaccaccata ataattttta ttatgtactt tataatgtac actgtattat cactgtagta    4140
catatataat ttatatgtaa gtgtacatgt attgggagca tatacttgaa ttttgttgt    4200
tgggcattca tgatcaaaac atttgggaac cagtggctta tttgatattt agcattttca    4260
gaaagcataa aatatacaag gtgttggcca ggcacagtgg ctcatgcctg taatctcagc    4320
actttgggag gctgaggagg gtggatcacc tgaggtcagg agttcgagac cagcctgacc    4380
aacatgtgtg aaacccgtc tccactataa atacaaaagt tagccaggtg tggtggcatg    4440
cgcctgtagt atacctctaa gtatactaga actatgttga tgttttcctc tctctgcctt    4500
ggccactagg aagctcagag tcaagtttgt atccagggtc ttccagcttg tgcttaagtg    4560
ttttaatcgt ctagattgtt tttaatggtt tctgctcttt gtctcaggtt ttactataaa    4620
atacataaca catttccttc ccgttctaaa tattactgtg attgtattct tatagccaaa    4680
tctttgttct tattcttatt ttattttatt ttttatactg ttgaatccct ctgagccttg    4740
cctttccctg cctcctcttc tgtactcatt tttgctaaaa tttgtaaggg gataaattct    4800
```

```
tgaaaagctt tgcacatttt gaagacttgt ttgtttttta atatttatta tagtaaaact    4860
caaatataca tccaaataga gagcaataag cccttgtgta cctatcactc agttatgtct    4920
gtcacttagt cattaacttg gggacactct tgtttcatct atatccttta atcctcatta    4980 tactttttt tgggggggaga agtttattaa ttgataggtg ttactttggg gtaaatgagg    5040
agggagccca ctagtatgct ggggaactgg taaggttttt ttgtttttttt cttgaaacag    5100 agtcttgctc ttgtcgccca ggctggagtg cagtggtgcg atctcggctc actgcaacct    5160 tcgccccct gggttcaagc gactctcctg cctcagcctc ccaagtagct gggattacag    5220
gcacctgcca ccacacctgg ctagttttg tactttagt agatgggatt tcaccatgtt     5280
ggccaggcta gtcttgaact cctgacctcc ggtgatctgc ctgcctcggc ctcccaaagt    5340
gttgggatta taggcgtgag ccactgcgcc ccgcaaaggt tcttttcttt gggatccttt    5400
cctgtcctta gagaagaccc tttagctttc tgcctgagga gctgatgcct agttgtcagg    5460
ctttcttctt gcccagataa gggtgttaac tcctgtgtac agatgttcac ttaatccttt    5520
ttaccagtcc cacatctcac tatagcccta tgctacacct gggtttctcc atcccaagcc    5580
cctttagggt ctctagtgcc agtcttcttc ctcattggct atgtcccta ggttcttttt    5640 tattttcccc aacggtgatg cacttactga gcagatgcag taatcttctt acctgagcct    5700
acatataacc attggcctaa atgtatgatg gtttgccagc atcagcaata agactggtaa    5760
tggggtaaaa aacaagttct cttaaggcta gctcttgatc ccctgttgta agctgaccaa    5820
cttaatctga aaataatttg cagcatgtaa atattttagg attagagcca tctgtataca    5880
cacttaaaag tagttttgct accattacat tagtctaaaa gagttaccta agaatgccaa    5940
acgatatttt gttcgaatgc cttggttatt taatttaaa agcatttctt tcaaaaccgc     6000
ttctctcttc acaatagtag agctgtggca gtgaactaag aggtcaagga ttcagtgaat    6060
ctgtggctaa tttcttgttc caatctgaga gctctctttg cactatgatc aaaatggagt    6120
cttgccaact gcccagggta atagccttgc aagtctcttc cttgttgagc aatgaatata    6180
agttccacat ggctggggag gcctcacaat catggcagaa ggtgaaagag gagcaaaggc    6240
atgtcttaca tggtggcagg caagcctctt ctcattatac ttttaaaatt atttggtggc    6300
tgggtgcagt ggctcatgcc tgtaatccca gcactttggg aggccaaggt gggtggatca    6360
cttgaggtca gaagttcaag accagcttgg ccaacatggt gaaaccttgc ctgtactaaa    6420
aatacaaaaa ttagcagggt catggtggca cgcacctgta attctagcta cttgggaagc    6480
tgaggaagaa ttgtttggac ccagaggtaa aggttgcagt gagccaggat cgtgtcacag    6540
cactccagcc tgggtgaccg aacaagactc tcaaaacaaa caaacaaaaa ttatttggtg    6600
attttttttt tgagacggag tctccttgtc actcaagctg gaatgcaacg gcgtggtctc    6660
tgctcaccgc aacctttgcc tcccggttca agcgattctt ctgtctcagc ttaccaagta    6720
gctgggacta caggcatgtg ccaccacacc cggctaattt ttgtattttt tgtagagata    6780
gggtttcacc atgttggcca ggctggtctt gaactcctga cctcaagtga tctgcccacc    6840
ttggcatccc caagtgctgg gattgcaggt gtgagccaac gtgcctggcc cattttaacc    6900 attttaagt gtactattta gtgacattaa atgtattcac attgttatgc aaccatcatc     6960
actatccatt tccagaatgt tttcattatt ctacatagaa actatcgatc caggagccat    7020
atgtagaaag ctgaaactgg atcccttcct tacaccttat acaaaaatca attcaagatg    7080
gattaaagac ttaaatgtta gacctaaaac cataaaaacc ctagaagaaa acctaggcaa    7140
```

-continued

```
taccattcag gccataggca tgggcaagga cttcatgact aaaacaccaa aagcaatggc    7200
aacaaaagcc aaaattgaca aatgggatct aattaaacta aagagcttct acacagcaaa    7260
agaaactacc atcagactga acaggcaacc tacagagtgg gagaaaattt ttacaatcta    7320
cccatctgac aaagggctaa tatccagaat ctacaaagaa cttaaacaga tttacaagaa    7380
aaaaatcaaa caaccctatc aaaagtgggt gaagcatat gaacagacac ttctcaaaag    7440
aagacattta tgcagccaac agacacatga aaaaatgctt gtcgtcactg gccatcagag    7500
aaatgcaaat caaaccaca atgagatacc ctcacaccag ttagaatggg gatcattaaa    7560
aagtcaggaa acaacaggtg ctggagagga tgtggagaaa taggaaccct tttacactgt    7620
tggtgggact gtaaactagt tcaaccattg tggaagacag tgtggcgatt cctcaaggat    7680
ctagaactag aaataccatt tgacccagcc atcccattac tgggcatata cccaaaggat    7740
tataaatcat gctgctataa aggcacatgc acacgtatgt ttattacggc actattcaca    7800
atagcaaaga cttggaacca acccaaatgt ccatcaatga tagactggat taagaaaatg    7860
tggcacatat acaccatgga atactatgca gccataaaaa aggtgagtt catgtccttt    7920 ataggtacat ggatgaagct ggaaaccatc attctgagca aactatcgca aggacagaaa    7980
accaaacacc gcatgttctc actcataggt gggaattgaa caatgagaac acctggacat    8040
gggaacatca ctcaccaggg cctgccgggg gatgggggga gggggagggg atagcattag    8100
gagataaacc taatgtaaat gacgagttaa cgggtgcagc acaccaacat ggcacatgta    8160
tgcatatgta acaaacctgt atgttgtgca catgtaccca agggccagtg ggtgggaatt    8220
ggtatctcat tgtgatttca atttgtattt tctaaggaat attgatgttg agcaattttt    8280
catatgttga ttggccattt gtatatcttc tttttttgttg ttgtttgggt tttttttttct    8340 ttttctttt cttgagacgg ggtcttcttg ctctgttgcc cagactgcag tggcgcaatc    8400
acagttgact gcagcctcaa gcctctggtc ccaagtgatc ctcccacctc agtcttccaa    8460
gtagctggga ctgcaggcat gtgcccccat gcctggctta tattcatatt ttttgtggag    8520
atggggtttc accatgttgc ctaggctggc cttgaactcc tgagctcaag tgacccatcc    8580
acctcagcct tccaaagtgg tgggattaca ggcatgagcc accccaccga gcctgtatat    8640
cttctttaga gaaatgttca ttcaagtcct tttctcactt tgagttatta attgttattt    8700
tgttgttatt gttgagttgt aggaattctt tacaaattct ggatattaaa cccttgttag    8760
atatatgatt tgtgaatagt ttctcccatt ctgttggtta gcatttcact ctctttattg    8820
tgtgatttgc acaattttta actttttttt tttttttctttt tttaagacag agtctccctc    8880
agtcacccag ggtggagtgc agtgctacag tgttggctca ttgcagcctc cacttcctgg    8940
actcaagcag tcctcccacc tcagcctctc aagtagctga aactacaggt gcacaccacc    9000
atgcctggct aatttttttt gtatttattt ttttttaaga tatgggtct tgccatgttg    9060 tccaggctgg tctcaaactt ctgagctcaa gcagtccgct tgccttggct tcccaaagtg    9120
ctaggattaa ggcgtgagcc accacgcccg gccaaaagtt tttaatttt atgaattcca    9180 gtttatcaat tttttctttt tgttgcctat acttttcaat ccttgctaaa ctcagcatca    9240
tgaagatctt tttcttatat tttccttctaa gggcttaca gttttagctc ttctttttt    9300 atttatttga tctatttttga gttaattttt gtgtataaga gtccaacttc acttttgcgt    9360
gtaactatcc agttttccca gtagcatttg ttgaagagac tgtcctttcc ccagtgactg    9420
gtcatggcat ctttgtcaaa aatcagttga ttatatttgt gagagtttat ttttgggttc    9480
ttttttcttc ttcttttcttt ttttttcaggt tagatgggta gtgctgacat cataacaagg    9540
```

```
ttcaagaatg actcatctca catgtgtgtg aaacacccag gtatcatact gatgaactac    9600
agaagatctg ggctctctat tgttttatat gtctgacctt atgccagtac cacattgttc    9660
tgcttactgt agctttatag taagttttga aatcaggaag tgtgagtcct caacttagtt    9720
cttgttttc aagtttgttt tggctattca gggttccac ttttttcttt ggacaaagta     9780
atggggagaa tttctttctt ttttttttt tttttttttg gttttaaga cagtctcact      9840
ctgttgtcag gctggagtgc agtgacgcaa tcttggctca ctgcaaactc cacctcctgg    9900
gttcaagcga ttctcctgcc tcagcctcct gagtagttga tattacaggc acctgccacc    9960
acgcccagct aattttttgta ttttttagtag agacgggggtt tcaccatgtt ggccaagatg  10020
gtctcgatct cttgacctca tgacccacct gccttggcct cccaaagtgg tgggattaca   10080
ggcgtgggcc actgcaccca gcttttttttt ttttgttttt ttaaacaagt aaatggaaag   10140
aaatcccacg ttcatggatt ggaagacaat attctttttt tttttttgag acggagtctt   10200
gctctgtcac ctaggctgga atgcattggc gcagtcactg ctcactacag ccttgagctc   10260
ccaggctcaa gtgatcctcc cacctcagcc tgctaagtag gtgggactac aggaatgtac   10320
tactgtgcct ggctaattaa aaaattttt gtagagatgg agtctcactg tgttgcccag    10380
gctggtcttg aggactccag ggctcaagca gtcctcccca cttgacctcc caaagtgctg   10440
ggtttacagg catgggccac cgtgcctggc cagctgttag aattttgata gggattgcat   10500
tgcattttga tatggattgc gttttgtagat agctttggat aacgttgtca tttaaagaat   10560
attgtcttcc cagcctggcc aacatggtga accctgtctc tactaacaa tacaaaaatt    10620
atccaggtgt ggtggcatac acctgtaatc ccagttactc aggaggctga tacaggagaa   10680
tcgcttgaac ctgggaggcg gagattgcag tgaaccgaga ttgtgccact gcactccagc   10740
ctgggtgaca gagcaagact ctgtctaaaa aaagaaaaa aaaaaagaa tatcatcttc      10800
caatccatga aagtgggaaa gtgggatttc tttccccttta ttttacgtct ttaatttgtt   10860
tcagcaatgt ttcagtttat gtcttttgtc tcccttgctt aaatttattc ctaagtatt    10920
tattcttttt gatgctatta taaatggaat gttttcctaa ttttgttttt agattgttca   10980
ctgtcagtga acaatagaaa tgcaactgat ttttgcatgt tcattttgca tcctacaact   11040
ttgttgaatt catttattag ctgtgtgtgt gtgtaatctt tagggttttc tacatgtaag   11100
atcatgtcat ctaggaacgg aaataatttt actacttcct gtccagttga gatgcctgga   11160
gagaaagggt aaatgaggca gtgagaaggt tcttgcttaa tttctctggc taaaactttt   11220
cagtactgga ttaaatagaa gtggcatcct tgtcttgttc ctgattttag gggaaaagct   11280
tttagtctttt caccatcaag tgtgatgtaa gctgtgagat tttcatatat acccctttat   11340
tatgttgagg atattgcctt ctattcctat ttcattgagt atttttttaat caaaagtta   11400
tcttgaattt tgttaaatgc ttttttctgca tcagttggga tgatcattgt ttttctcctt   11460
cattctagta atgtggcata ttaccttaat tgattttttgt taaaccatcc ttgcactttg   11520
ggataaaatt ccacttgtca tctgagatgt atgtttaata tctactttaa aaaaaaaac    11580
acaaatcagt cccagcctgg gcaacatagt gagaccctca tctctacaaa aataaaaaaa   11640
agcctggtgc agtggctcac gcctgtaatc ccagcacttt gagaggccga ggcaggcgga   11700
tcacctgaga tcaggagttc aagaccagcc tgactaacat ggtgaaaccc cgtctctact   11760
aaaaatagaa aaattagcca ggcttagtgg gaagcgcctg taatcccagc tactcaggag   11820
gctaaggcag gagaattgct tgaacctggg aggcggaggt tgcagtgagc tgagatcatg   11880
```

```
ccactgtact ccagcctggg tgacagagcg agactctgtc tcaaataaat aaatattaaa    11940
aaataaaata aaataaatta gccagatgtg gtggctcatg cctgtagtcc cagcagtgtg    12000
agaggctgag atgggaggat cacttgggag gttgagaccg cagtgagcca cgattgtaca    12060
actgtatcca gcctgggtga cagagcaaga ccctatctca aaaataaaac aaaaaaccaa    12120
aaaacttaga agtcaacaga tgcttattga attcttccta ggtgtcagac actgttaaag    12180
ttctggggat tcagcagtga acaaggctaa gcccctgttt tcttttaatt tttaatttta    12240
gttttttttt tagggacagt ctcactttgt cacttaggct gccaggctcg agtgcagtca    12300
tgcattctca gctcactgca acctctgact cctgggttca agttattctc gtgcctcagt    12360
ttcccatgta gctgggatta caggcactac cacacccagc taattttttgt atttttagta    12420
gacacaaggt ttcactatgt tggccaggct ggtctcaaac tcctgacctc aagtgatccg    12480
cctgcctctg cctcccaaag tgctgggatt acaggcacga gccaccgcac cccggcccac    12540
tggagtgttt tgagcagggt agtgacatta gtgatttgtg ctttagaaag atttatcgag    12600
gatggaatga ggcaggaatg aatagaggca ttcctgctgt ccccatggtc agtgatggga    12660
gagtagccag ggagatgatg attgttggtc aggttgggga tctgacttgg aggtaaaact    12720
gttgtaacca gctgtttcag atgtgggctt gttgtaggat gtttcctaaa ctttccgccg    12780
gaggaataaa cagggtagct agtggtataa ttaactgaga tggctgggaa agaacagcta    12840
ctgtggggaa atcaagaatt ctgttttttgg tcttgttaga tttgaagtgc ttattaggca    12900
tttgagtgga gataccaagt ggaaatagtg taaataagga gcttagggga gaggcttgag    12960
aggtgtgtat gtaagagaca tcagcaaaca gatgagaatt ggagccagga gtcaggctga    13020
gaagccctgg ggagaaaggg tagatgagga aagcaggcca ggaacaaagc ctatggggaa    13080
gcaggaaggg aggctgagaa gcacaacctt ctaggacatc agtagggaca tgatgtcact    13140
cacaactagg aaataagtag gtgttttcct ttctttctttt cttttttttt tttttttttt    13200
ttgagacgga gtttcgctct tattgcccag tctggggtgc aatggcgcga tcttggctca    13260
ctgcaacctc cgcctctcag gttcaagcga ttctcctgcc tcagcctcct gagtagctgg    13320
gattacaggc atgtgccacc acgcccggct aatttttttgt atttttagta gagacggggt    13380
ttcaccgtgt tagccaggat ggttgtaggc gtttctcatt tcagcatagt gtctttatgg    13440
tcagccctttt cagtggctgc ctctgatggt gtttgatcat aagtcataac tcatccatga    13500
aggtgtttta cagtctgtct tcaagcaggc aggtccttag attgaaagaa tggaggcttc    13560
actgcgtgtg cctttactac acagatagcc gatgggcag aggttgtata gctgatgggg    13620
cagaggctgt cagatgactg ttttacagaa aaacctttga caagttatat agtaaacttg    13680
ttaaaagaaa aagttgatct cctagctaag acaaaaggtt tcagtttagg aagataaaaa    13740
agatggatgg tggtgatggc tgcacaacaa tatgaatgta cttaatacca ctgaactgta    13800
cacttaaaag gggttaaaat gatgtttatg ttaataattt ttttttacca caaaacgaag    13860
tagaatactt tgtcactgat tatagtaaac atttaaatct gaatgctaga ttgcttttttt    13920
ttgagatgga gtctcactct gtcgcccagg ctggagtaca gcagtgtgat ctcagctcac    13980
tgcaaccttt gcctcctggg tttaagtgat tctcctgtct cagcctccca agtagctggg    14040
attataggtg cctgtcacca tgctcggcta atttttgtat ttttagtaga tagggttt     14100
caccgtgttg ctcacgctgg tctcaaactc ctgacctgaa gtgatctgtt tgcctcggcc    14160
tccgagagtc ctaggattat aagagtgagc caccgtgccc ggcctagact gctcttacat    14220
aggttaaaac acattatttt gttgggaggt gctggggaat caactctgtc atggaaatgt    14280
```

```
tccccgggct gggagttgga accagagtgt tgattgttgt catttgctac atgacctggg    14340
tcatctggca tgaccttccc taagcctcag tttcttcctt accaatagga tattgtgctg    14400
gaggatccca tctctcctag ctctgaaatc tggtagcttt ctgttccttt gtctctataa    14460
atgtctggaa ggcaagcaag ttccagtctg agaagtgact gtgaacattt ggaagaattg    14520
tgtggtccca gtgcatatca cagtccacag ttgtcctgtt agctggaaag ttttacttag    14580
taccagatta tagatatgaa aaagaagcaa ttaaaactta cagcaggcct tacaatttga    14640
gacagaaaca aaatctttgt tttttagact ttgaccaaat atttgggaat gagcaccatg    14700
tagatgtgat ttgtttatct gtgaggcttc acacattgtg acttgacaag aacccatagc    14760
acttaggttt gtgagcccag agtaccaccc tttgccttga agagtgtgga gggagtctta    14820
gggccagcgg tgagcaggat gaaaggttct tagaagctgg tgggcatgga ggggtacag     14880 aggggaggct ctcctgggag ataaggtggt ggaaggggcc ggtgaagtct ggtgtgctgg    14940
agagagctct aggggctcct ggaccctcac cccaaggaaa aggggcccag gtgagcctca    15000
tctcttggct ttcttctttg ccacatttct cctcacaaac tcctcccctc tttgcactgt    15060
ttggaaccct cttccatgca acgtttatat taagagttct tgctgggcgc agtggctcac    15120
gcctgtaatc ccagcacttt gggaggtcga ggcgggtgga tcacgaggtc aggagttcaa    15180
gaccagcctg gccaggatgg tgaaaccccca tatctactaa aaataagaaa attagctggg    15240
cacagtggca ggcacctgta atcccagcta cttgggaggc tgaggcagga gaatcgcttg    15300
aacctggggg cggggcaga ggttgcagtg agccgagatt gtgccactgc acttcagcct     15360
gggggacaga gtgagactct gtctcaaaaa gacaacaaca acaaaaaacc aaaaaacagt    15420
tcttgaagtg ttgtgggaag tcagggaccc cgaacggagg gactggctgg agccgcggca    15480
gaggaacata aatggtgaag atttcatttt aatatggaca tatatcagtt cccaaaatta    15540
atacttttat aatttcttac acctgtcttt acttcaatct ctgaacataa atcgttaata    15600 tttccttta atatggacat ttatcagttc ccaaaattaa tactttataa tttcttatgc     15660
ttgtcttact ttaatctctt aatcctgtta tcttcgtaag ctgaggatgt acgtcacctc    15720
aggaccacta ttgtgttagc tgtacaaatt gattgtaaaa cgtgtgtttg aacaatatga    15780
aatcagtgca tcttgaaaac agaataacag ctattttagg gaacaaggga agacaaccat    15840
aaggtctgac tgcctgtggg gtctggcaga atagagccat attttttcttc ttgcagagag    15900 cctataaatg gacatgcaag tagggaagat atcgctaaat tctttttccta gcaaggaata    15960 ttaataatta agaccctggg aaaggaatgc attcctggtg ggaggtctat aaatggccgc    16020
tctgggagtg tctgtcttat gcggttgaga taaggactga aatacgccct ggtctcctgc    16080
agtaccctca ggcttactag gattgggaaa ctccgccctg gtaaatttga ggtcagaccg    16140
gttctctgct cttgaaccct atttttctgtt gtttaagatg tttatcaaga caatacgtgc    16200
acagctgaac atagaccctt atcagtagtt ctgaatttgc ctttgtcctg tttcctcaga    16260
agcatgtgat ctttgttctc cttttttgccc tttgaagcat gtgatcttgt gacctactcc    16320
ctgttcttgc accccctccc cttttgaaat ccttaataaa acttgctggt tttgcagctc    16380
gggtgggtat cacggtccta ctcatatgtg atgtcaccc tggaggccca gctgtaaaat     16440
tcctctcttt gtactgtttc tctttatttc tcagccggcc gacacttacg gaaaatagaa    16500
agaacctatg ttgaaatatt gggggtgggt tcccctaata ttgaagtagt aacgcaacga    16560
gactcgtcac atctcccatt ttgggatttg attgtataaa actgtcaaga gctttgatgc    16620
```

-continued

```
cctccagcaa agcacgcttc ttgcaggaaa tcaggcaaag ggtgtttagc ctgtgtggcc    16680
tgatatgctc atgtgtagct ggtggcagga ggctggtcct ggctgtgctc ctacaagtac    16740
ctgctggagt ggaggctgag gacactctgt ccatgggcca agacattgtg tgaaatgaca    16800
aggctgcccc catgggctct caagttgttt ctagctttaa aacagattct tggctgggta    16860
cggtggctca cacctgtaat cccagtactt tgggaggcca aggcgggcag atcacctgag    16920
gtcaggagtt tgaaaccagc ctgaccaaca tggtgaaacc ccatctctac tgaaaataaa    16980
aaattagcca ggcatggtgg cacatacctg taatcccagc tacttgcgag gctgaggcaa    17040
gagaatcgct tgaacccagg aggctgaggt tgcagtgagc cgagatcacg ccgttgcacg    17100
tcagcctggg caacaagagc aaaactctgt ctcaaataaa gaaataaata aaaataaaac    17160
tgattcttag cagcagcagt tcagtcccct tgttagtcat tcctgaccag gtcaagaggg    17220
agtaagaatg taggtaactg gcattgtgga agaaaatctt taataggttt gttggtgttc    17280
tattgtaaag agggttgaca ttatgcacgt ggttatttgt gacaaccatt acaaccaact    17340
aatataattt ggtcttactt caatttgggt gttgctgtgc catcccaaca gttactctaa    17400
aatgtgccag tactcatctt cttgaatatg tgtgttttta ggctttaaat tctctgaaat    17460
cagctttcgt tcattaactg aaattccttt atttttttcaa tactatttaa ttattattat    17520
tttttttgaga cagagttttg cccctgttgc ccaggctgga gtgcagtggt gcaatctcag    17580
ctcactgcaa cctctgcctc cagggttcaa gcgattctcc tgcctcagcc tcctgagtag    17640
ctggaattac agacgcatgc caccacaccc agctaatttt tgtttttgag tagagacggg    17700
gtttcactgt gttggccagc tggtcttgaa ctcctgacct cgtgatccac ccgccttggc    17760
ctcccaaagt gctgggatta caggcatgag ccactgcgcc tggccacgcc ctgctaattt    17820
ttgtattttt agtagagacg gggtttcacc atgttgccca ggctggtctt gaactccaga    17880
cctcaggtga tctgcccacc tcagcctccc aaagttctgg gattacaggc gtgagccacc    17940
gtgcccgacc ttttttcaat actattaact tgatctgctg aaaattctcc caggttactg    18000
gctaattttg aagcttagag aagcaatttt cttttttattt atttattttg agacggagtc    18060
tcgctccatt gccaggctgg gagtgcagtg gcgccatctc agctcactgc aagctccgcc    18120
tcccgggttc atgccattct cctgcctcag cctcctgagt agctgggact acaggcaccc    18180
gccaccaggc ccagctaatt ttttgtattt ttagtagaga cggggtttca ctatgttagc    18240
caggatggtc tcgatctcct gacctcgtga cccacccacc tcggcctccc aaagtgctgg    18300
gattatagac gtgagccacc gtgcccggcc cagagaagta atttctgcc cttagcattg    18360
gtccgcttga caactttcag aaaaacatta tcccaagggg atgaattgtt tgcaccagtg    18420
gactagttta gctcagtgag cagacctata gtgactttct gctcagcacc aggtgaggtg    18480
ctgggtgctc tagggaacac aaggtgattc agttattccc ttctcctgaa ggggaacgca    18540
gtcaatccag gaggctgaga gagtcagaat gagcaaggtg gaagttcaca gttagagaag    18600
ctcagagaag agggctgctg cttccacagg aaactttgct cattattttt taatttcagc    18660
ttttcaatgt agaaatacat ttacatgaca caaaattgga aaggtaaact acatgggaaa    18720
gtttcccttc catcttgcac ctggctacca gatcctctcc ccagaggctg ctggtgctgc    18780
cacttctcat gtgtccattc ccaggtgttt tgtgcattta tagacaaata agcagagact    18840
tctgttctct tacatgaaag taggacactg ctcccttgct tttttctctg aatgtttctt    18900
tatgatagtt tatcattaat ttttgtattt ttagtagaga cagggtttca ccatgttggc    18960
caggctggtc tgaactcctg acctcaggtg atccacccgc ctcagcctcc caaagtgctg    19020
```

```
ggattgtagg tgtgagccat tgtgcctagc tgggctttgg tattttttaaa ttgattttgt   19080 caaaattgct tatatacgcg ggaatttagc accttgtcag cgatatgaat tgcagttgta   19140
tttttccaga tcttatttat cttttttttt tgagacggag tctcgctttg ttgcccagac   19200
tagagtacag tggcacgatc tcacacgatc tcggatgatc tcggctcact gcaacctccg   19260
cctcccaggt tcaagtgatt ctcctgtctc agcctcctga gtagctgaga ctacaggcgt   19320
gtaccaccac actggctaat ttttgtattt ttagtagaga cagggttttg ccatattggt   19380
cagactggtc tcaaactcct gacctcaggt gatccacctg tctcggcctc ccaaagtgct   19440
gggattacag gcatgagcca ctgcacctgg cctaaagtaa ttttttatatt tcatattttta  19500 cctttaaatc ttttctctat ttggaattta ttttttatttt ttatttttat gttgaggcag   19560
ggtcttattc tgttgcccat actggagcac agtagtgtga tcatggctca ctacagcctg   19620
gaccttgcca ggctcaggta atccacccgc ttcagcctcc tgaatagctg ggactacagg   19680
tgtgcatcac catgcccagc taattttttgt acttttggta gagaagggtt ttgccatgtt   19740
gcccaggctg gtcttgaact cctgggttca agtgatctgt ctgccttgac ttcccaaagt   19800
gctgggattg taggcctgag ccactgtgct ttttggaatt tattttgatg tgaagtgtta   19860
gatccagctt aattttttttc cgtggctacc catttgttgc aacaccttttt gttgcgcaat   19920 taatcttttct cctacttgtt tatcatttac tgtatatagt atactttgcc atatgtgtac   19980
attttggtct attcctggac attctgttct gttacattaa tctgtgtatt tatgtgttag   20040
gaccacactg ttttaattac tctagcatgt tttgttatttt ggtgaagtta gttccctttc   20100
atcatcttta ttttccagaa cttttcttggt tatatttgtt tttctgtata aacttgaagt   20160 ttgttttagtt aaagaagtcc tgtttttatt gggactgtta catttctaga tgaatgtagg   20220
aagagtgaca ctttggttac gttatattga cttttcctca ttaagaatgt ggcatgtttt   20280 tcttttttgtt gaagtcatct tttctgtctt tcggagtttc agagatttct tttggttttct   20340 tttttttttt tttttttttt tgaggtggag tcttgctctg tcacccaggc tggagtgcag   20400
tggtgcaatc ccggctcact gcaacctcca cctcccaggt tcaagtgatt ctcctgcctc   20460
agtttcctga gtagctagga ttacaggaac gtgccacaat gcccagctaa ttttttgtatt   20520 tttagtagag acgggggtttc accatgttgg ctaggctggt cttttaactcc tgacttcagg   20580 tgatctgccc atctcggcct cccaagttgc tgagattaca ggcgtgagcc actgtgtcct   20640
gctgggagtt tcagagattt cttacatttc ttttttaagtt tattttcaag ttttttggttt   20700 tgttatttat tttagtgtta atgaatcatt attataatca atattatcat tattttactt   20760
ctgcctgctt gttgttgatg tatgtgaagg cattgataca tattagtttt cactaccta    20820 tggtgattct tttatcaact gtaaaaggtt ttcagttgat tatatatata tatatatata   20880
tatatatata tatgtaattt ttttgtatat atatttggat tttgtacata atatcatttg   20940
caaataatga taatttaact ttttcctttc cagttgtata cctatgtttt ctttgtcttg   21000
actgattgtg ataactagta gttccacaat agtaataaat aatgatggtt aaatgcatag   21060
cctgtatggc ccctgacgtt agtgagaaca cttctagtgt gttcccattg ggcttgattt   21120
tagctttgag attgagaaag atgtaaacat ttagttgaag tctgtatttta ttttttatat   21180 atatatgtgt attttttttta ttattatttt ttgagacaga gtctctgtca tctgggctgg   21240
agtgcagtgg cacaatcttg gctcactgta acttctgcct cctgggttca agcgattctc   21300
ctgcgttcaa gcgattctcc tgcctcagcc acccaaatag ttgggattac aggtgcccgc   21360
```

-continued

```
caccatgcct gactaatttt tgtattttt agtggagacg ggggtttcac cttgttggcc    21420
aggctggtct cgaactcctg acctcaaacg atccaccagc cttggtctcc caaagtgcta    21480
ggattacagg tgtgagccac cgtgcctggc ctaatatgta tgtatttatg tatgtatgta    21540
aatcaacgta cacatatcta ctaagcatct gtctattctt ttttttttgt gacggagtct    21600
cactctttcg cccagatggg agtgcagtgg cgtgatctct gctcactgca ggctccgtcc    21660
cccggggttc acaccattct cctgcctcag cctcccgagt agctgggact acaggtgccc    21720
gccacctcgc ccggctaatt ttttgtattt ttagtagaga cagggtttca ctgtgttagc    21780
caggatggtc tcaatctcct gaccttgtga tccgcccgcc tcggccaccc aaagtgctgg    21840
gattacaggc atgagccacc gcacccggcc tgtctattct tatcttaaaa ggatgagggt    21900
tgaattttat cagatgtctt cagcattggc agagatgatc tctgttaata tgttgaacat    21960
aacattgttt taacattagt acttacatgt ttctggtaca aaatgaatag gatgatgttt    22020
agagaaggct tatggaggaa atagcatttt atctagtgcc tgaaggctga atggagaaaa    22080
ttagaggtgg gaaattagag tgggaagata ggaaaagggc attcagtaaa gagagagcct    22140
tgactgcaaa ggtgtggaaa gtgggaatgt aggttatttt ggggaagaat gccagcatcc    22200
caacattact gtgatattca tgagggcctt ctagatgggg aacatggggg cgtattacac    22260
ctctggactt cagattcttc ctttgtggaa ctgaaatagt aaaagtagtt attagtttaa    22320
gggttgttac aaggattcag gagataatgt aggcaaaagt cttaggccag aggctgacac    22380
atggtttata aatactagtt attttattt gacaagagaa taaagctgga aagaggtttc    22440
agtatatttt gagtgtacct gtataataag caaagaagta tggcctcaga tatgcaggca    22500
ctggagagcc attcagaact tttgtgcaag gggtgacata agcaggtctt ttttttttcc    22560
attaaaaatt ttttttaaag agatggggtc tcactatgtt gcccagactg gtctcgaact    22620
tctgggctca agcaatcctc ccatctcagc ctcccaaagt gccgggatta caggtgtgag    22680
ccactgtgcc tggccataag caggtctta ttttaggaag ctgtccatgc tgaccatgtg    22740
ggaagacaaa ccagaagtga agtgcaaatg caggtagcaa aatcaggtag gagactatta    22800 gaattttca ggctggtggt tttggatatc tatcactagt ccagttcatt ttttatttt    22860 tgagataggc cttgctcttc tgcccaggct agagtgcagt ggcggaatca cagcttactg    22920
tagccttgac ctcctgggct caagcagtcc ttcccactca ggcttccaag tagccaggac    22980
tacagtcatg agccaccaca attggctaat ttaaattttt tttttttttg tagagacagg    23040
atctctgtat gttgcccagg ctggtcttga actttcctgg cctcaagcag tcttcctgcc    23100
tcagtgtccc aaactgctgg gattacagac attagttagc tacgatgcct gccctgctcg    23160
tccagtttag acatatgttc aagatgtggg caccatagag ttgacttagg caactcttgg    23220
gctccaggtt tggtagggca gtgtttctca aatttgagca tatcactgtc agctggaggg    23280
tgtgttaaat agagatttct gggcctcacc gccagatttt ctgattcacc aggtctggga    23340
taggcccaat aatttgcatt tctaacaagg atttagattg ggacatttgt gaagaacagg    23400
atggatgaag tgttccttgt ttatgatttc attcagagag aggggattat agctctctt    23460 tcttccagaa tgcctgaggt gctttgtatc acagttagaa gttgagaaga tatgtactga    23520
gcactgtcct aataatatct gatcctggtt gggttggttg gtttgttcat cacttattca    23580
acaagtggtt tgttttcaga dacagggtct cactgtgttg cccaggctgg catcaaactc    23640
ctgggctcaa gggattgtcc cacctcagtc tcctgagtag ccgggattat aggtgcattt    23700
aataaaaatt taacatgcca agtgctatta aagaccctga agaacagaca gggagtttat    23760
```

```
ttatagtctt gacagaggac agatagtaaa ccagggaata agtcatttgt acaattacag    23820
agttttaaat gcactgaaaa agaagaaata ggctctgtaa ggaacaataa agagaactac    23880
tggaaaatat atggtcaagg gaggtctttt tgtagaagtg atatttcagc tgagacttga    23940
agaatgaaaa ggaaccagcc tataaagaga agagggaata gaggatggaa cagtatgtgc    24000
caggcccctg agatgggaat gaggttggca cacataaggc attggaagaa accagaacag    24060
ggagaggtga cacgaagtga agttgcagag gaccggggtg ggttgtgcag agccctgaga    24120
gctaggggga ggcatttggg ctttgttcta agtgcagaag ggtatccagc tcacagcatt    24180
agtagaatct gtgtccactc tgacctctga gataaagtga attgtaaagg gataggtagg    24240
aaggggtcta tgagggccag gcatggtggg tggctcagcc tgtaatccca actctttggg    24300
aggctgaggc aggaggattg ctggagtcta agagtttaag accagcctgg gcaacatggt    24360
aaaaccccat ctctattaaa aatacaaaca tttcgttggg tgtggtggtg cacgcctata    24420
gtcctagcta cttgggaggc tgaagtggga gaattgattg agcctgggag gtggaggctg    24480
cagtgagcca tgatcgtgcc actgcactcc agcctgggtg acagagtgag accctgtctc    24540
aaaaaaaaaa aaaaaaaaaa aggcattcca ggactgtttg aatatttgaa tataaacatg    24600
tatatttta cttttataat tgaaaaatag tcagcattgg ggctcataaa ggggaccttt    24660
ggggtaatgt tctgtttctt gatggaatgg tgtttaggtt acatggcttt gtttacttgg    24720
tggtaattca tggagctgtg tgcttataat ttgtgtgctt ttctgtgata tgttatacta    24780
aacttcaaaa gttatttaa aatagtcttg cacggtggct catgtctgta atcccaacac    24840
tttgggaggc tgaggcagga ggattgcttg aaaccaggag ttcaagacca acctgggcaa    24900
catattgaga ccctgtctcc ccacaacatt tttttttttt aattagctgg ccatggtggc    24960
acatgcctgt aatcctagct acacgggaag ctgagctggg aggactgcgt ccaggaattc    25020
aaggctacag taagacatga tagtgccact gtacccagc ctgggtgaca gagtgagacc    25080
ccatctctaa aaaagaaaa ataaataat gcttatagtg aaaaatgtaa agatactgag    25140
atttgagttt aaaaatttct ctgctgggtg tggtggctca cacctataat cagtttggga    25200
aattgaggca ggaggattgc ttgagcccag gagtttgaga ccagcctggg caacgtggca    25260
aaaccctgtc tctactaaaa ttaccaaaaa ttatctctca tggtggtacg tgcctatagg    25320
caggctaaag tgggaggatc acctgagcct gggagattga ggctgcagtg agctgtgatc    25380
ctgccactgc attccagcct gggtgacaga gtgagactct gtctcaagga aaaaaaaaa    25440
aaaccctgc atataatcac attacacaaa gacaagcaac cactactaac gtttccctct    25500
attctccttt tgtgcacttt ttgtatataa ttttattt ttcaaattgt aaaagtaatg    25560
tgtgcttttt gtagaaaact ttactacatg cttctcacaa tgaaatgatg tgattgacag    25620
aaaaatgcca gtaggcgtag tgtgaaaagt ttccttaggg ccaggagcag tggctcacac    25680
ctgtaatccc agcactttgg gaggctgagg caggcagatt cattgaggtc aggaattgga    25740
gaccagcctg gccaacatgg tgaaaccccg tttctaccaa aaatataaaa attagctggg    25800
tggggtggcg cacgcctgta actccagcta cttgggaggc tgaggcacaa gaattgcttg    25860
agcccaggag gcggaggttg cggtgagccg agatcacgcc actgcactcc agcctgggtg    25920
acagagcaag actccatctc aaaaaagaa aaaaagtttt ctttgaaggc aaagaatcct    25980
gaaatgtagg aagattatca cattaaaaaa atttaagagt tctgatgtga taagatgga    26040
gtaaacatac tccaccettt atgtctgaag agagcaactg aaatccctgg acagaatgca    26100
```

```
tggatcagtg gagtaacccc agaaagataa atgttagcat gcgaattgga gaaggaaacc    26160
agaactccaa ataccagtga actggtagtg agtttcccat aatttttttt cctccataca    26220
atattttcca gcctgcactt aaagtcagcc ccaaacctgg aaatgtgtgc tggatgtgca    26280
cagaaagagg tctaacagaa gccatctttc tagtttgagg agcaggaaag gggatcctca    26340
tgggtcagga atggggatgg aggaagaaat ctcgtgtgtt gtttgctttg tcttttctcc    26400
ttttctcttg ctctggccct ccacgtaatt gtgtagtggt ggagacagca gtgacattgg    26460
caaatggata ggagaggaag tcttctattt aaagggactg tggtcccagg agcatggagg    26520
gaatccttga ttttgttctt tcctttctct cattgctttt ccttggaggt agtcacagtt    26580
gtgggaggta ctcagcaggt tagggaaatt aaacccctga cttttagcca gaagaccagg    26640
aaaggggccc ttgggatctg gaaagtgtta ggaagattgt gtagaggaag gagctcaaca    26700
aattgaactc ataaagttgc atatgaactc ttgggctgtt cctcagaact aacatacgtg    26760
catctgaccc taaacagcat accaaaggct tgaggaccaa aactgtggag tacattactg    26820
ctcaagtagt tctgcactgg cccctggacg gtatgcttgg gaaaaatcaa aataatactt    26880
aaaaggcttt gaaaactgat atcatattgg taccacagcc cacagaaggt gggtaggaac    26940
ttgtggactg gacctaatta ggttgattgc tgcaaagaca aattcaaaat tttacgtggg    27000
acttaaacaa gagctagagt cacatagcat aatattcaaa atgtccagta attcagaatt    27060
acttcagcta tgaaaaatca ggaaaatcat aaggggaaaa gacagccaac agatggcaac    27120
cacaacatga cacagatgtt gaaattatca aaaattaaa agccaaagta taattaaagt    27180
attaattaaa accttgctat aacaagtaag ggtgaatgct cttgaaatga acagaaaatc    27240
agaaatttat ttactgcaaa atatgacaac ctaaatgaaa aattaattgg gtgggctcaa    27300
tagcagaatg gagaagacag aagagtcagt gaacatgaag gtagaataat agaaattatc    27360
cagtctgacc aacagagatc gaaataaaat gaaaaaaaaa aatgaacaga gcttcaggga    27420
cccatgggac aataacagaa agtttatctt ttatgttttt gaagtctcaa aaagagagga    27480
gaaagagtgg tgcagaaaaa aatttgaaga aattatggaa aggaataaat atgtttctgt    27540
tcacagataa catgataagt ctacgtagaa atttccaaag aatccacaca cacacacaca    27600
tgcagaaaga ctctggcact aataagtgat ttcaggacag ttgcaggata aaagattaac    27660
ataaaaaaat caatgtacta gcaatgaaca tgtgaaaatc aaaattgaaa acatagttgc    27720
taaaaagtga aatggtaggt ataaatctaa caaaacatgt acagtcatgt atgctgaaaa    27780
ctatacaatg ctgatgaaag aaatcaaaga tctaagtaga tggaaaaata taccatgttc    27840
atggattgga agactcaaca tgccagttct ttgcaaattt gataaacagg tttaatgcag    27900
tttctatcaa aattctatca agttttttt ttttttttt tttttttttt tttgagacgg    27960
agtctccctc ttgcccaggc tggagtgcag tggcactatc tcagcttact gcaacctctg    28020
cctcctgggt tcaagcgatt ctcctgcctc agcctccaga atagctggga ttacaggcac    28080
acgccaccat gcccggctat tttgtatttt tcatagagac ggggtttcac tgtgttggcc    28140
aggctggtct tgaactcctg acctcaggag atctgcctgc cctggcctcc caaagtgctg    28200
ggattacagg catgaaccac cacacctggc cttttttct tttttctttt cttttctttt    28260 ttttttgag tcagagtctc gctgtattgc ccaggctgga gtgcaatggc acagtctttg    28320
gctcactgtg gcctccgcct cccgggttta agcaattctc ctgtctccgc ctcccaagta    28380
gctggtatta caggcactcg ccaccacacc cagccaattt tggtattttt agtagagaag    28440
aggtttcacc atattggcta ggctggtctt gaacttctga ccttgtaatc cgcccacctt    28500
```

```
tgcctcacca agttctagga ttacaggcgt gagccaccgc gcctggcctt tttctccttt    28560
tttgagacgg agtcacagtc tgtcacctag gctggagtgc agtggcgtga tcttggcttg    28620
ctcaacctct gctttctggg ttcagtgat  tctcagcgta ccaagtagct gggattacaa    28680
gtgtgtgcca ccacacccag ctaatttttt ctgtttttag tagagaaggg gcttcactgt    28740
gttagccagg tctcacactc ctggcctcaa gcgatccgcc cacctcggtc tcccaaagtg    28800
ctgggactat aggcgtgagc cactgtgcct ggtccagaca actgcttttt gacaaagatg    28860
ccaagcaatt caatggagga aggatagtct tttcaccaaa tggtgctgga acaattggct    28920
atctttagac caaggggaa  aaaaaggaat ttatatctca caccttatct aaaaattaac    28980
tcaaatggat cacagatttt tatttttatt ttttgacaca gtctcgctct gttgcccagg    29040
ctagagtgca atggtgtggt catagctcat tgcagcctca aactctttgg ctcaagtgat    29100
cctcccactt cagcctccca agtagctagg actacaggca tgtgccaccc tgccctgcta    29160
attgttaatg tttttttttt tgtaaagaca cggtctcaca gtgtccaggc tggtctcaaa    29220
ctcctggttt caagtgattt cccacctcag cctcccaaag tgttgggatt acaggcatga    29280
gtcactgcac ccagctggat tacagactta aacaaatgtg aaactacaaa ttttaggag    29340
aagacattgg ggaaaattac cttatgacca agcaattcca ctcctaagaa tgaatatact    29400
caaaagaaaa caaaagaaaa aaaaatacaa aaacccccaac tgaagaacaa caacaacaaa    29460
aaaagtaaac ataagaattg agggggggcca ggcacggtgg ctcacgcctg taatcccagc    29520
cctttgggag gcgaaggagg gcagatcatg aggtcagtag ttcaagacaa gcctggccaa    29580
catagtgaaa cttcgtctct actaaaaata aaaaattagc cgggtgtggt ggtgagtgcc    29640
tgtagtccca gctacttggt aggctgaggc aggagaatca cttgaaccca ggaggtggag    29700
gttgcagtaa gctgagactg tgccactgca ctccagcctg ggcgacagag cgagactcca    29760
tctcaaaaaa aaaaaaaaag gttggccagg tgcagtggcc atgcctgtaa tctcagcact    29820
ttgggaggct gaggcggtca gatcacgagg tcaagagatt gagaccatcc tggccaagat    29880
ggtgaaaccc catctcttct aagaatgcaa aaattagctg ggcgtggtgg cgcgcatctg    29940
taattccagc tactcaggag gctgagacag gttaattgct tgaacccagg aggtggaggt    30000
tgcagtgagc tgagatcgca ccaccgcact ccagcctggt gacagagcaa gactctgtct    30060
caaaaaaaaa aaaaaaaaaa attgagacag ggtgtggtgg ctcacacctg taatcccagc    30120
actttgggag gccaggctgg caaatcatct aaggtcagga gttctagacc agtctggcca    30180
acatggtgaa accccatctc tactaaaaat acaaaaatta gccaagtgtg gtggtgtgca    30240
cctgtgctcc cagctacaag ggaggctgag gcacgaattg tttgaaccac cggaaggcgg    30300
agtttacagt gagctgagat cgcgctgctg cactccagcc tgggcgacaa agcaagattc    30360
cgtttcaaaa aaaaagttg  gagttcgaga ccaagtaaac aagaataatg tggcctggcg    30420
tggtggctca tgcctgtaat cccagcactt gggaggccg  aggcggtgga tcacctggtt    30480
aggagttcga gagcagcctg gccaacatga tgaaatccca tttctactaa aaatacgaaa    30540
aaatagctgg gcgtagtggc gggcacttgt aatcccagct actcaggaag ctgaggcaag    30600
agaatcgctt gaatctggga ggcagaggtt gcattgagtg gagattgtgc cacagcactc    30660
cagcctgggc aacaagagca aaactttatc tcaaaaaaaa aaaaaaaaa  aagaattgaa    30720
aacaggtatt caaacaaata caggaatgtt agaatgttca tcacagcact attcacaata    30780
ggcaaaacat agaaactgcc caaatgttta tcaactgatg aatggacaaa caaatgtgg    30840
```

```
catacccatt tgatgaaata ttcagccata aaaagtaatg aagtggctgg gctcggtgcc   30900
tcatgcctgt aatcccagca ctttgggagg ctgaggctgg cggatcactt gaggtcagga   30960
gtttgagacc agcctggcca acatggtgaa acttggtctc tatcaaaaat acaaaaatta   31020
gccaggtgtg gtggcgggca cctgtaatcc cagctacttg ggaggctgag tcaggagaat   31080
agcttaaacc caggagacag agatttcatt gagccaagat tgtgccactg cactccagcc   31140
tgggcaaccc catctcaaaa aaaaaaaagt aatgaagtac tggccgggtg tggtggttcg   31200
tgcctgtaat cccagcactt tgagaggctg aggcagctgg atcatttgag cccaggagtt   31260
tgagaccagc ctggaaaaca taatgagaac ctgtctctac aaaaaaatac aaaaattagc   31320
agggcatggt ggtgcacacc tgtaatccca gctacttgga aaactaggtg ggagaatcac   31380
ttgaacctgg gaggcagagg ttgcagtgag ccaagagagt gcccactgca ctccagcctg   31440
gtcgatagag tgagattcta tgtcaaaaaa aataaagggt tcctggattg gaaacttgca   31500
tgtgcgctta acgcttctgc tttcggaaag gtagaacgag caataggcat tccttttggc   31560
ttttgagttg gctgtggtgt gactcctttt gcttcttgtt tctgatcttg acacttatga   31620
ggagtcatct ttgagtctgg gttttcatca gtgagtacag tcaagccaag aaatgtgtct   31680
gggcaggttc cctctagcac agaccgaaga aaacagcaac atgaacaag agaagtaggt   31740 ttaaacttgg attccatcag agggctcagt agggaagata attctagatc cctgggcctc   31800
ctagagtttt ctattctgat tttattggtt taatgttatt tgtttgaaag caccagaaat   31860
taactttggc caacataagc aaaaagataa tttattagaa gggtatagaa tagcttacaa   31920
aacgaaaaaa aaagttgatg agccagtcct cagaaaggat gggagccaga acagcctggg   31980
gatcttggga gcaggaacct ctgtgggatg aataaacatc atgaatatcc aagttcctgt   32040
ttgtttgtgt ttagaagtca aagtccaggg agagaggccc aatttgtgta gcttgggtcg   32100
gcacggggca ccttgactca tagttaatcc aggttaaatc ctgtggagcg aggtggttcc   32160
cctgagccat accaggctgc tgttaactta tggaagggga cgggtactgg gcaggcagga   32220
acaggagctg ctctctgcct ttgcactccc aggaacaact ataggaccaa gagcagagag   32280
ttctaccaga gtgaattttg cttggtgacc attatgtcag agacctaagc ttttttagcgt   32340 tttatgttg agggctgacc tcgctagacc ttcttcacga gtgaatcact atttgtacaa   32400
cagtgtgttt tgaggaggcc atccctatgt aaagggtttc tctgtatccc tatgtaaagg   32460
acttttctca gtgggatttg tgcatagagg aggggggggga agaatgcctg tttgacagag   32520
agcagctgaa ggtgacgtct gttacacagg catggtttcg tgtgccacac atgagaaaaa   32580
tgcccttggg ggagtggcct tttagcattg cctaatatag gagggaggga gttgggcggg   32640
gagggagaga gagagagaga gagagagaga gagagagagt gtgtgtgtgt gtgtgtgtgt   32700
gtgtgtgtgt gtgtgtgtgt gtattttggg attgaggtca ctagaccttg catataggca   32760
ttctgaaacc attccccagc cacataacta tcgcctccct ccagcagccc tagtgtgcag   32820
agccaagtac tctttgttaa ctggcttttc tcccttctta ccaggtacct gcacatgttg   32880
ttctttgtca gtgctgtcaa gtgtgtgcca gggtgatcca tggtcacttt ccgggatggc   32940
agcaaggtga cttcggctga ggatgaccct gactgaaagg ctgcgtgaga agatatctcg   33000
ggccttctac aaccatgggc tcctctgtgc atcctatccc atccccatca tcctcttcac   33060
agggttctgc atcttagcct gctggtatgt ttttgggttg ccttggatat ggtgggccag   33120
tgtcttagga cagtaggttt tctaacccta accactatgg agcccttggc ctctgtatgc   33180
tttttacaca atgggagctt gggctcctta taactgtgag tggagaactc tagtcctggc   33240
```

```
ctggttagct aatataataa aatagtcctg gctggccctg acctactgat tcaccagatt    33300
tattcatatc actggtactc tatctcaaaa taatgtttag atacttctaa gacactgaaa    33360
taattgaaag atatgatact tcagttttct ttctcaatag tagtggtttc gttttagtac    33420
ctggttaagt gcaagagcct tttttgtgtg ttgcgaggca aagtccatta gaacagtatc    33480
ttggacaacc tgtggcaggc taacctcaga gacttgcttc tttgctctct agtcattttc    33540
ttgtgttcac atggagcttg cttcagactt cttgttgatt cttgtggcca gctgcacttg    33600
ccaaggacag ttgtgagagc tgtagctgcc cttgttcctg tctgtctttc tcaaggcctc    33660
atagaagcct gaaggctatg gctgacaatg acgtcgtaaa ggaggagttt gatatgagat    33720
gacatctgat gacccttta actctaaaat gctgacagct gtgaaaagag cccatcttat    33780
tcttttctct ggaaagaatt ctgttcttca gattcattgt ctaaacatt tatagatgtt    33840 ttcagtgcta tgctgaaggg aggatgagaa gtcaggaggg aactccctgt tcagttcagt    33900
tgctaatgat ctcaagctct tccctgatta tcagtaagaa agatgaactt tggccaggtg    33960
cagtgctcat acctgtaatt ccaacactgg gaggctgagg tgagagaatc acttgaggcc    34020
aggagttcag gatcagcctg gcaacatag caagaccaaa aaaaaaaaaa aaaaaaaaa    34080 agaaagatga acatcactga gagtttcttg ctgggtgctg tgttgatgct tcaggtataa    34140
cattaggaag tggtccagtt atgttccat ttaacaaaga ggggtaggga cttagagatt    34200
tgtctggtcc acataactaa taattaggga aactggggtt caaattcaaa tccaagccat    34260
agggactctg gtgcccgcct gcacctgtgt tactgtcacc tggtttcact ctggctcagt    34320
atgtttgtat tggtgtttaa actgctaaat tgtgttgtac aagataaaat acttatagct    34380
gtgtcccata agtgatgaat ttggagtgct ctaagaactc agctcttggg ttttttttc    34440 ctttaagtta attgacctt cttttttctt ctttaaaata agttttttga gacatggtct    34500
cactctgtca gccaggctgg aatgtagtgg cacaatcaca gctcacctca gcctcaacct    34560
cctaggctca agcgaccctc ccatctcagc ctcctaagaa gccacaacca caggtgtgcg    34620
ccaccacact tggctgtttt tcgtctttg tagagatggg gtctcattat gttgccctcc    34680
tttggtttta ctctctgatg gtactatggt ttcctctttt gtagtcaccc tgttttctt    34740 ttaagaggaa agacctggcc gggcgtggtg gctcacggct gtaatcccag cactttggga    34800
ggccgaggcg ggcagatcac gaggtcaggc gatcgagacc atcctggcca acatggtgaa    34860
acctcgtctc tactaaaaat gcaaaaatta gctaggtgtg gtggcctgca cctgtagtcc    34920 cgccactcg ggaggctgag gcaggagaat cacttgaacc cgggagacgg agattgcagt    34980
gagctgagat cgcgccactg cactctagcc tggcgaaaga gtgagactcc atctcaaaaa    35040 aaaaaagag gaggaaagac ccttctgtat tatcccattc ttttttttct tccttgagac    35100
agggtctcgc ttccgttgct caggctggag tgcagtggtg caatcactgc taattgcagt    35160
ctcgacttca tgggctcaag tgattctcct acctcagccc tctgagtagt tgggactata    35220
ggcgtgcacc actaattttt tgtattttta gtagagctgg ggtttcgcca tgttgcccag    35280
gctggtctca aactcctgag ctcgtgatcc cctcgccttg gcttcccaaa gtgtcgggat    35340
tacaggtgtg agccaccaaa cctggccttg tactgtcaca ttcttagtgc tgtgtactta    35400 tttttcccaaa tgagtatctt tgtcatgtga tcttaaagtt ttttttttaa ttttgttttt    35460
ttcttaaaac ctgattgact tgagaaaatt tttccaaggc tgggtgaagt ctctcagcct    35520
ccaaagacta ataaaaggtt gtataagaga atccatagat tctgggactt ggccagaaaa    35580
```

```
ccagagatca tggacccagg gacacaagcc tcaccattgt cttcaaccca ctgaagcttt    35640
tctgtccaga gcagcagagc agtgccccct tcttccagag cctgggattg cctgcagaaa    35700
ataaagtatg gatatagact gcttctagta gttttgctag acattcagtt tccatttaat    35760
tgcttacctt ttattgttcc tgggatgaaa gacttgtaca gccaaaccca aaggactgct    35820
gcacttaatt tccctattca gatctaacag ccacctgagc tgcagaaata cttttttgcac   35880 accactggct caccaccact gggtcacccc agggaaagta cagagcagta ctgggggat    35940 ggtgatcaat gacagcttgg gaatgtgcct gtctccatca ggcagaagaa tccagggagt    36000
gagagagggc atctgtatat gcatcaggct caccccaaac agcactgagg atgtgtgact    36060
ttcttctctg agctgctgtt gaggctgcag gtttcagtga ctgagagcca aggacactac    36120
ttcaaatgaa cccagtgctg agccttgcag gtgagctaga gttagctgtt cttcctgcct    36180
ggcccctggg tgcagtgact gttctttcct ctgggaaaat ctgatgaaat gtgtagcaaa    36240
taggcattat ggcaagaggt gtctgtttat aactcttgga ggttagacca ctgggcccag    36300
gatatgtccc agcagcagcc cagcaagaca gagggtactg ttaatctgaa cctgccctgg    36360
taagcagtgg gtgcgccatg ggataaaaag agcacccaga tgccatgtta gttggactgc    36420
cctatgtgca ggtcagagag tgatgtgaat cattgagaca tttgattcaa caagctgctg    36480
ctcatggtga gaggtggatt ttaatttgga gaggaaattg gaatcacatt gtgttgtttt    36540
tgattttgag acggggtctc actctgtcgc ccaggctgga gtgcaatggc acaatcatgg    36600
cttactgcaa cctctgcctc ccaggttcaa gtgattctct tgcctcagcc tcccgagtag    36660
ctgggattac aggtgtgagc caccacgtcc ggctatttt tgtattttta gtagagacgg    36720
ggtttcacca tgttggccag actggtgtca aactcctgac ctcaagtaac ctgcccactt    36780
cagcctccca aagtcctggg attataggca taagccacct tgctcagcct agtcatgcat    36840
ttttgactta ggatatttc aatttacgac agcgttatca ggacataacc ccatcgtaag    36900
tcaagatgta tctgtacata tcaagtgctt agaatagtgc ctggcacata ttaaatatca    36960
tgtatgagtt tttcattgtt attattcact gtcttcctag tcttctacct tcacagccag    37020
aaagcacaag cagaatccaa aaacatgtat agtctaaaca tagaacaaaa actgactata    37080
ctctgtgatt actatgcaaa cgctgtagcc acagcctaaa attttttttt ttttttttgag    37140 acagggtctc cctctgttgc ccaggctaga gtgcactggc atggcatgat cttggctcac    37200
tgcaacctcc acctcccggg ttcaagcgat tctcctgcct cagctgcccg agtagctagg    37260
attacaggcg tgtgccaccg cgtccggcca attttttgttt tttagtaaa gacggggttt    37320 caccatgttg gccaggctgg tcttgaactc ctgacctcac gtgacccacc cacctcggcc    37380
tcccaaagtg ctgggattac aggcgtgagc caccgtgccc agcctaaatt aactttttt    37440 taagtgaaag caagtttatt agaaaagtaa aggaataaag aatggctgct ccataggcag    37500
agcagcccta aatgaattct gatcacttgt agtcgtttct ctcttcctac ttagagcatc    37560
ttggaggcag accgtagtat tatctttgt attctcagtt cccagcatat aatacatact    37620
taataaatgg ttttttgagtg taggtaaaga tggaaaagcc agagaaaagt aaaaattgat    37680
ttttgtgaag gtaaggagat tgtgtaattg ttttctgtaa ttaacataat aaatgtattt    37740
aaaatattca aaacatggta ttgtcaaaag acttgaagag gcgtttcaca aaagttgcta    37800
tatccaagtg gccagtagta agtaaatgaa ataatttttt taattgtttc ttatcaggaa    37860
aatgtacatt aaaaccatgc tgagatacca ctgtctcttc ctctaaatgg ttaacattaa    37920
ttggactgac agtatcaaga ggtgacaagg atttggagaa actggaactc ctattacact    37980
```

```
ggtgatagtg ggaacataaa tttgtacaac cgctatggaa aactgtttgg tatcatctac   38040
taagctcaat gtgcatataa ctccatacce agccatttca tcctaggaat atacccgaca   38100
gaaataagtg cttatgaggc caccaaaaac caataaagga taatagttt attcttttt    38160 tttcttttt  ttaattaaaa acaattatcc agcccaaaat gttttgtttt tttgagacgg   38220
gggtctcact ctgtcaccta ggctggaatg cagtggcatg atcatggctt attgcagcct   38280
cagcctcccg gctcaagcga tcctcccact taagcctccc gagctgggac tacaggtgtg   38340
caccagcatg cctggctaac ttttgtattt ttttttttt  agggatggcg tttcaccatg   38400
ttgcccaggc tggtctcaaa ctcctgggct caagaaatcc ttctgccttg gcctcccaaa   38460
gtgctgggat tacaggcatg agccacctca cctggccaac tttattctcc tttttttt    38520 tttttttt   tttgagattg agtttcactc ttgttgccca ggctagagtg cagtggcgcc   38580
atctcagctc accggttcaa gtgattttcc tgcctcagcc ttctgagtag ctgggattac   38640
aggcatacgc caccacgccc ggctaatttt gaatttttag tagagacagg gtttctccct   38700
gttggtcagg ctggtctcga tctcccgatc tcaggtgatc cacctgcctc agcctcccaa   38760
agtgctggga ttacaggcgt gagccactgt gcctggccca actttattct taatagctca   38820
aaccagaaac agccaaatgt tcctcaacca gtggaataca caaatgcact atactttatt   38880
cattagtgga ctagtatgta tccaaaaagc aatgatctgc tatgtgcgcc agtgtggaga   38940
atctagcaga tagaatttga gtgaaagcag ccagtcacaa aagagtatat aagtagaatg   39000
aatggtttca tttatatgac attcaaaaat aggtaaaact aatttatggt gatagagatt   39060
ctaacagtta cctttggtgg tggggagtgg tatgctgttg actgggagtg ggcacaaggc   39120
tgccttctga ggctctggaa atattctata gcttgatcta gatagtagtt acacagatat   39180
acacatgtaa aaacttactg cactttatac ttaagatctg tgcattgtac tatatagaag   39240
ttatttctaa atttttaagaa agtgagatct gaaacaaaat gtacatctat ttgccaactt   39300
tttctttttt ttctttttt  ttcacttgag atggggtctc actgtgttgc ctaggctgga   39360
gtacagtggc atgatctcag ctcactgcag cctctacctc ccaggggttag atgatcctcc   39420 tgcctcagcc agtagctggg accacaggtg cacaccacca tgcccagcta atttttgta    39480 tttttggtag agatggggtt tcactgtgtt gctcagtctg gtctcaaact cctgagctca   39540
aatgatccgc ccgcttggcc tctcccaaag tgttgggatt acaggcttga ccaccgcac    39600 ccagcttatt tgccaacttt ttgatgaaag gtcagggctt ttccttgcgt atatcgggtc   39660
cattaactta actttcctca tgatcctagt ataaaccaca tccttagtta attatacata   39720
attttcatgg tctgtcccct taagtggaat agttgcttag ctatctgaat tggaatcctt   39780
ctggattttt aaaggtaccc ccacttttgt tttttattgt tccttatat  ctaatttggc   39840 aaggtgattt ttttttgttt gtttttagca tcttgctttt attaagtctc tgaaaacttt   39900 tttcttttcag agacaggggt cttatgttgc ccaggctgga gtgcagtggt ataatcatgg   39960
ctcactgcag cctctacctc taggcttaag cagtcctccc acctaagcct cctgagtagc   40020
tgggaccaca ggttcacatg gccatgcctg gctaattttt ttgattttct gtagagatga   40080
ggtctcacta tgttgtccag gctggtctca aacttctggg ctcaagcagc cctccagcct   40140
gggcctccca agtgctgggg ttacaggca  taacccactg cgcccagcct gaaaatatta   40200
atataatgtt atatattata acatgttggt gtttcctttc agtaaaagtt actcattaaa   40260 tgtataaaact agccaggcac ggttgcttac gcctgtaatc tcagcacttt gggaggctga   40320
```

```
ggtgggtgga tcacctgagg tcaggagttt aagaccagc  ctggtcaaca tgatgaaacc   40380
ccgtctccac taaaaataca aaaattacct ggatgtagtg gcaggcgcct atctatctgt   40440
gtgtgtgtgt gtgtgtgtgt gtgtgtgtgt gtgtgtgtgt gtgtgtatgt ttatattata   40500
tatgttaatg ttatatataa tgttataact aagtatattt atacatactt agcttataca   40560
gcctgaaaac atttaacaga acagtctatt ttaccagttg ggcttcttcg taaggtttat   40620
gtgactaaaa taagtttgaa aaattctaat ctagatgact tctgagtttc agctttgcaa   40680
ttttgtgatt ctaatatttt gcacatttgt acagtcctga cagaatttag ttattaactc   40740
cagtggctcc tgtgtcagtg ctgagagagg actgcctctc atagtgtcta attcttatct   40800
cctttttgta catcccagct acccactgct gaaactcccc ttgccaggaa caggacctgt   40860
ggaattcacc acccctgtga aggattactc gcccccacct gtggactctg accgcaaaca   40920
aggagagcct actgagcagc ctgagtgggt gggtactcgt catgttcctg aggccagcac   40980
agagcgttgg gtggagactg gctgaggcag gggtctgcca gtgagattga ggttggtcag   41040
cttctgattt gtgaattcat gtactttaac agctttatca gtgtaccata tagatactta   41100
gtttatacat ttttttttga gatggagttt tgctcctgtt gtccaggctg gagtgcaatg   41160
gcacaatctc ggctcactgc aacctccgcc tcccgggttc aagtgattct cctgcctcag   41220
cctcccgatt agctgggact gtaggtgtgc gccaccacgc ccaactaatt ttgtattttt   41280
attagagatg gagtttcact atgttggcca agctggtctc gaactcctga ccttgggtga   41340
tctacccgcc ttggcctccc aaagtgctgg gattacaggc gtgagccacc gcacctggcc   41400
agttatttag tttggaactc taggtctcct gaccccagcc cactcctcct tctggactgt   41460
actgttttca gttgactgtc tctgggccga acactgatat aaatgagaaa aaaggtcttc   41520
agttgagggg ctcagtcaag ggacctaact caccatcaca ccgcactcat tatttggagc   41580
tcattgaagc ttgactagct catctgtgta ccttttgcct gtcaggtgtg gacaaagtgc   41640
cctttcttct gtgttgttct gtggtccctg gattcgtgct ggacttgctg aatctgttgt   41700
tgaggaaaac caaagctcag cgaacagagc tctcctcccc cttctctctg acagtcatag   41760
catattccca tttcctttttt ggttaacgta gtagtcaggt aacttgttat gaacttgact   41820
ctgcggctga aatagaggca tatctggcaa gataggtctg tggcacaact atacatggtg   41880 tcagtggga gtgcaccacc ctggcttcat gaggctctgc ctatgaaggt caaggatgc    41940 atggtctgat gctggctgaa accagttttg tggtgaaacc agttttgtgg ctttatgtcc   42000
caggttggcc attggctcac tggctcattg tgggaccttc ttgcttaaac cttttacctt   42060
cattaaccat ttttttttta ttgttttgag atggagtctc actctgttgc ccagggtgga   42120
gtacagtggc gtgatctcag ctcattgcaa cctctgtctc ctgggttgaa agcgattctc   42180
ctgcctcagc ctcctgagta cctgggacta caggcatgtt gccaccacac ccggctaatt   42240
tttgtatttt tagtaggggt ggggtttcac catgttggcc aggctggtct caaactcctg   42300
acctcaggtg atccacctgc ctcagcctcc caaagtgctg ggattacagg cgtgagccat   42360
tgtgtccgga cttcattaac cttttaatgc aatgttagca cataagggaa tatttgtgtt   42420
tcctgactag gagagttcat ttggcccatt ggtgtggaat agatgtttaa tgatgaggcc   42480
gtaaggggtg tgatgtgttt gtgagctctt tgaatgatgg gatgatgata gaaagtgttg   42540
gtgcagaata actagagggc tcgggaatca ggagcattgt ccatttcctc tctctctgat   42600
tggagcgctc atccctgca ggattgagaa ggagatgggc ccagggcagt cacctggtgt    42660
cacacagctc agtggtcagt tatctcacct ccattggctg tccttgataa agatacaggc   42720
```

```
cagcgatact gaagtgggtg gtaaggactg ttttagttat gaagaacagg aaattcaacc   42780
caaatcagag taagtgaaag ggaatttttg gttcatataa ctcagccagg tgcagggctg   42840
acttaagcac gatatagttt gagcctcaaa aggagtccat ctcttgactt tgtcctctct   42900
gggtcagctt cacttttggt cttcccaaca gtggccctag cagcttcagc ccatgtttt   42960 tgcatcatcc aatccagtgg aggataaaag ggagcccagt tggctatgaa tagggttacc   43020
tgcctgtccc cttcccaagc cctatggcta aggcaggta tttcattgtt gttgtcagca   43080
ccttgctggg aatgagagag gatggtttcc aaagggacaa tagggccggg tgcagtggtg   43140
catacctgta atcccagtac tgaggcagga ggatcgcttg agcccaggag tttaaggctg   43200
cagtgagcca tgatcacacc attgcagtcc agctgggca atagagtgag accttgtctc   43260
taaaaaaata aaaataaat aaattttaaa aaagggaaaa taggagactc gggcagtaga   43320
cagtacattg caggcatctg ctgcctatac gaaggagcca aaacttcctt ccctactcga   43380
ctcactgctg agttcagcac tcgtttattg catacgcgtg gtgtgggatg atgtgggga   43440 cagatagagg ctcactgtcc ttgaggagat cctatactgt ttggaaagag aagacaaaga   43500
tttttcaaag tttaaagtaa atatagtgta tgtcaaagag acatagggg gcaatcgaaa   43560 gagctcccca gtggtcagtg ctagagcaat ttttttttct tttttttttt ccttttcttt   43620 ttctttttt tttttttttt tcaagacgga gtcttgcttt cgctaggctg gagtgcagtg   43680
gcgcgatctc agctcactgg aacctccgcc tcccgggttc aagtgattcc cctgcctcag   43740
cctcccgagt agctgggact acaggcacgc accaccacgc ctggctaatt ttttgtattt   43800
tagtagagac ggggttttcac catgttggcc aggatggtct tgatctcctg atcttgtgat   43860
tgatccatcc gcctcggcct cccaaagtgc tgggattaca ggcgtgagcc accatgcctg   43920
gcctagagca attttttgcaa caaataaac tggtattgaa ttaagaccca aaatataaaa   43980
taattctctg tgagtccatt cctgagtcca tatgcttgaa taaatataaa taatgaatg   44040 gatgacaata gacaaatctc ctgggcaaaa aaattctaag taatgtatcc taaagtgtgg   44100
actatgcatg atgactttct tccaaagagg acagtgtgac tgtgggaaaa agtaactta   44160 cagtgaagaa gcctgacaga cacctcctac agtaagtgat tggggttaaa gcagcagtga   44220
taaatcacat tgattgattg tgcccttgat atgtgaggag gaggaggaca ttttaccgct   44280
gatcttcctc tcccaaaccc ataaccgcag tataattaga agtaaaacat cagacaaatc   44340
ctagttgagg aacaccctac aaaatgcctg accagtaccc cttgaagctg ccaagatcat   44400
caaaagcaag ggaagtctga gaaactgtca caagctacaa gaagcctcag acactacagc   44460
taaacgtaac gtggtttcct ggatgggatc ctggaaaaga aaaggacat taggcaaaaa   44520 cttagaaaac ctgaatatac tttgactttt ggttaagaat ttcactgtgg actttggttt   44580
tcagaaggag gactacagag atgaaatgtc cttcttttta tatacctcag cctcctaaat   44640
tatttaaaaa ttcacgtaca ttaagattca gtctttgtgc tgtaaagtag ggattgtggg   44700
agttcactca gcacagtgag tgtgggccct gcccacatct tccttaccag ttagtgctc   44760 ctttcctgct cagacctgtg tgagcttctg ttctggtcat agcctgtggc agccagctcc   44820
atccaggtgc ctctgtgcct cccagcagct tctagtggct gagcgtgata cagaagacaa   44880
agtggatgag gccttctgtc cccagagccc tcactaaggc acagccacat aaagttcaca   44940
aaggctcaga cggttgcctc tggttgttcc tttgtgccca gggtcccagg aggcattaac   45000
ttgctgtgct tggtcagcat cttggccctt gcctatgctg taacctggag tactgcattg   45060
```

-continued

```
gtgagtggct ccatggcctc cctttcatcc acacgcatgc cccttggagt tcccgactgc   45120
agcccaggcg tggagacagc ccctcatccc tcagctgggc tgggccctgc cccctttcagt  45180
ccacacctcg cagtacaccg ctgtctaggg ccatgtttcc ttgtctccag ttgtcaccaa   45240
ctcccgggga gtcttttacag agcactgctt tcatcaggtt gcccctttcac ctcagagaca 45300
ctgggctttg ctttgtcaac tgattaaaat cctgacagct cagtcaggct tcagtctaag   45360
cctgcttgtc atcttcctcg taatttctgt tatcccctga caggtttcct tggtgcagat   45420
gtccaggcct tctgtgctct cagcatccct tgcaactcac attccctcct gctcctctcc   45480
tacctgttct tttctaacct tatggctcta ctcagcttct cctgggccat aactctgctg   45540
tggctgaccc agcatgtttt ggggtgctcc gcgacatgcc tgttactgag ggttgcatat   45600
gtgaacactc ttgtcattta catccctgtt aagctcttga aaggtagatg gcagattcta   45660
gtgagaaaag tatgtgatat ttagtgagga gaccttggtt tgagtccttta caccaccctg  45720
cctggagtgt gaagctctag gcaggcacaa tgcctgagcc tctccttgct tctcatcagg   45780
ctgttgtgag ggtcagatga agtgaaatgc ctgattgttc attgttaata tttctgctaa   45840
tctttcagac actgtttgta tgcgtgtgtg gtgtgtgcat acatcttgat gctgcagggt   45900
gaatgtcgtt attcctgttt cacaatgagg aaattgaaat ccagagatgt caaaagtgtt   45960
ttcaaggcca tatgtttgga aagctgtgat ttaaaattgg gtcctttgat cttcaaaacc   46020
cgctactctg ctgcaagtga caaaacctga atcagtaaga caggttacat gctttgggga   46080
gtgtagagtc tatagtgcgg tcagcagaca tgttccataa agggctagat agtaaacatt   46140
taggctttgc gggccagacg gcctctgttg cagccatttg accctgctgt tgtagagtga   46200
aagcagccat agacaatagt aatggtaggg gtgtggctgt gcttcagtaa aaattggaag   46260
tggaaaaaca ggcactaacc agcctgggca acatagtgag accccatctc tacagaaaat   46320
aaagaagtta gccaggtgtg gcacttcggg aggccaaaat gggaggatca cttgagccca   46380
ggagttcgag accagcctgg caacatagta tacccctgtc cctacaaaac attttttgaaa 46440
attaggcgtg gtggtggtgc acacacctct agtctcagct acttggtggg tgggggtgct   46500
gaggtgggag gatctcttga gcctgggaga ttgaggtttc agtgagccat gattgggcaa   46560
tagagcaaga ccctgtctca aaaagaaaaa caggcatggg ccctgatttg gcctacaggc   46620
catcgtttgc ctacacctgg tcccacagtg ctttgcccat agtagatgtg ttattgagca   46680
aaagaggctc gctgcccaat gtgctagaag ccaatactgt gacaccagga tttggggaaa   46740
agaaaagctt tatattgaag gttgactccc taggagaccg gagtccagct caaatctgtc   46800
tccctgtgct ggctttaagg cagtaatttt attaggaaag gtttagaggg tggatactag   46860
gattagcaga tgattgatgg aaggaagggt gatttctggg aagtctttga gcatgcccag   46920
ttatctcttg atgccacctc acaggtccca tgtgcaaatt ccgggggggag ttagtatgaa  46980
acatggcagt ggaaattcag gctgtgacat cggcaagctc attctgcaca actccagtcg   47040
gccatcttgg ttccagctta tttcagccag ttctttttatc tcataagcgg agggagttc    47100
tgggttccag caaattgttt cttttcttat ctgccatcct gcaaactcaa gaacttgtat   47160
tagtcattgg tttcttttaac tctgtggggc acggtttcca atgcccatta aatcccttga   47220
attggaccgt cttttcttctt cctgtgctca gctgcccttt ctgccctccc tcattttcttc  47280
tgcagtatgt gggtgccccg gtggcttatg tccagcagat atttgtgaag tcctcagtgt   47340
ttccctggca caagaacctc ctggcagtag atgtatttcg ttcacctttg tcccgggcat   47400
tccaactggt ggaggagatc cggaaccacg tgctgagaga caggtacccc tctcagggac   47460
```

```
cctggcctcc ctgaatccca ttctgtactg aagggagagt tacagtcctc agtgtaactg    47520
cagtgagcca gtcagctctg cagagataga acaagcaaga aggatggagg gtgagctagc    47580
cttgaatttc tcagcatcct tgtgggtcta cggtggctgc attccgcttg gacctatgca    47640
gatggcacac acatagcctt gagtctcatc cttacatctc agatggagtc agtgtccact    47700
gtgctaactc atgacccaca tggcttcctg cctgtgggtt atggtgtgaa tgtaatggtg    47760
gtgtctctgc cgacgagaag caagctctac ctgggggtac cttctgaagc cccagcccaa    47820
gtcgtgctcc cctgcctatc agtgggtccc tgggttatgc tggcttggca tacaatgtgt    47880
gtaattggca agctgcatca ctgccaggtt ttagttagct agtggcgttg acagatattt    47940
tggtgaacta aatgaagccc ctaatttacc ccggtccctg ctcatccact gaactggcca    48000
gggtgtttta gtgggtgggg ttgtgcatgc tcttatagta cacttgcccg tcctcagagc    48060
tgatgggctt ttgggcttca gatgcacttt gaaagtcaga cagccacatg tttaggttat    48120
tggccacctg gaagtacttc cccctgctgc cctagtggtc aggctctttg gcgataccag    48180
agagcaaata tggggcattg aagaacagac agaggatgtc ccctaagtac agcaggtctg    48240
ccctgtggtg gcagacacag caggtgcctt gtcctgtctc ctgtgcagct ctgggatcag    48300
gagcttggag gagttgtgtc tgcaagtgac cgacctgctg ccaggcctta ggaagctcag    48360
gaacctactc cctgagcatg gatgcctgct gctgtcccct gggaacttct ggcagaatga    48420
ctgggaacgc ttccatgctg atcctgacat cattgggacc atccaccagc acgagcctaa    48480
aaccctgcag acttcagcca cactcaaagg tagccccagt acaagttccc ttcagacctg    48540
taaaggtgcc cattggtcac cgtcttttg atgtgtgctt aggcagatca gggtttaccc    48600
tttgtttccc agggtggggg tgagaaaggg gtccttggtg gctctgcagt agctgtcatt    48660
tctgtgtcag tacctgctgg tttctgcttg cagacttgtt atttggtgtt cctgggaagt    48720
acagcggggt gagcctctac accaggaaga ggatggtctc ctacaccatc acctggtct     48780 tccagcacta ccatgccaag taagattgac agtaccctgg gctcttgact ggtctgctgg    48840
gtgacatgag gctttgagta gtccctcttc tggttagagt gttctgaatg cccctggaa     48900 acttgggaga gtttccaggc ctcctgttga atgtttacat ccctcagact agatgatgct    48960
gtctaccaca ttttaatggg gatgacctga cagctggtta agcatagggg actaaggtag    49020
ggctggcggt ctcagtgtcc tggtgcctcc tctggtctct cttgagccta gggcaggcat    49080
ccccagctgg ttactactga gcaccctata tggcctgtgt ccttcccagt ggggcactgc    49140
aggcagctcc ccaattggca agggcactcg aggtgcttct gatcggctct cctaggcctc    49200
tggcaatcaa gagtgttgga ggccgggcgc ggtggctcac gcctgtaatc ccagactttg    49260
ggaggccgag gcaggcggat catgaggtca ggagatcgag accatcctgg ctaacacggt    49320
gaaaccccgt ctctactaaa aatacaaaaa attagccggg cgtggtggtg ggacctgta     49380 gtcccagcta ctcgggaggc tgaggcagga ggatggtgtg aacccaggag gcggagcttg    49440
cagtgagccc agatggcgcc actgcactcc agcctgggcg acagcgagac tcttgtctca    49500
aaaaataaaa aataaaataa ataaataaat aaaaagaga gtgttggagt aggtccggaa    49560
agggagacaa agaaaggagc aggggagct cctgagaaaa ctttgtcccc tttgtgattt     49620
tcccagtgcc cctggagact atagagaagc tcaggcacca tagagaagtt ccctttcaac    49680
acaggggcag gagggaggtc ctgatggacc ctctgtccgg ggattgtctt tgtccccaga    49740
accaagagca acacttccat ttaccccac cctgctcctt gaccaggttc ctgggcagcc      49800
```

```
tgcgtgcccg cctgatgctt ctgcacccca gccccaactg cagccttcgg gcggagagcc   49860
tggtccacgt gcacttcaag gaggagattg gtgtcgctga gctcatcccc cttgtgacca   49920
cctacatcat cttgtttgcc tacatctact tctccacgcg taggttcatg gcagggaggc   49980
tgagggcttt ctccaagcta aacgggcatt tccatgtcac ctgcttccct ggctctggag   50040
gtggcttggg gtagagagat agaacacacc tggtggtcat cagagctagg gctttgtccc   50100
ccagcagggt cttaggagct tgggtggggc cggggctctt cccactttca gccccttcct   50160
gggttagggt tcctaaaagg tgtactgtgt ccatgacact gggaagtgct tgtgcctgtc   50220
cctttccttt ggtgaaacca ggagttttcc cttcctcgac tgtcagggca acctactccc   50280
gggagcccca gtgggccggg ggctggggga ggggccgccc tgatacgccc tctctgccct   50340
ccagggaaga tcgacatggt caagtccaag tgggggctgg ccctggctgc cgtggtcaca   50400
gtgctcagct cgctgctcat gtctgtggga ctctgcacac tcttcggcct gacgcccacc   50460
ctcaatggcg ggtaggtccc tagcaggctc cactgggcca cagggtgggc tcaggccaga   50520
gagccttgca cttctggggtt cttggccttc cctggacttt gctgtgacct cacgtcttca   50580
cattgttgtt tttgacattt aagaggtaca ttttcttcct cttctttgtc tggcttgtat   50640
tcatacttgt gtttgtatat agcatatcta gctatagtga gtgtccatat gtacaaaagt   50700
gcatatttgt gggctgggtg tgtatataag gggtgtgtgt tggtatgttt gtgtatacat   50760
gagtatgtat tgcatgtgtg tagtcggatt tgtgtgtctg tgtttatgta ttctatatac   50820
acacaccaca cacacactgc agcttgatgg cttaagccac tggaggtgtg agatagagaa   50880
gagaacattt ttttttttcat gattagaaca tttaaatgcc taatgaaata ggtcatttta   50940
gaggaagctc tttggaagat atgagcacac tgtaatttgt cgccttttc actgatgttt   51000 actttcccct tgccactcct ctctgaacct tagtctggaa gcccttccct cggcttgtcc   51060
tcaggctttg atcttggctc tggctaggcc cgcctgcctg tctattaatg gttattaatg   51120
gattatggat tggcctgtcc accactttgg cccatcaggc tggtcgtatg aaaagcgacg   51180 tcgtatttttg tttctggtag tttcgttgct cttagatacc tgctcccttt cctgagcttg   51240
acactgttaa acaccacccct cccccatacc gtctgccata cccttcacag ggccctccct   51300
tccttcggct ccaaagcaga ggtcctgcaa ggtataactt ggctggcgtt cctcgcacat   51360
agactttctt agggtttgct gcggggagtg tgggacagtg ggctcagata gctggtagag   51420
ctttgtgtag gaacagtcgt tcttctccac acacagcttc tcaacaaagg tgagtgggcc   51480
ttcaggatgt tttcatctcc ttgcatttag ctgtgatggg tccacccaga gttactggtg   51540
tgggtcttgg cagcagtcat tgtctttagc cagcagtctt ctcctgggaa gggccagcag   51600
aagtgtggtc tagcagtggc gctgcacagc tctccctgag gggcctcttc cagccctcct   51660
gtgctggatg gctagagaca ggatggctgc tggcccctct gcaaggctct ggagcctgcc   51720
tgaaagctga gtgctgtgta gatgcaggtc ttgttgggtg aggtggacaa gggagggttt   51780
ctgcccagca cctgtgggag tcactcagca gcccccatga caggctggaa acccacagc   51840 cttcctgagg gccccagtct gttgggaacc accacaacac tgtcctcacc ttctccttct   51900
ctgtccccag cgagattttc ccctaccttg gtggttat tgggttagag aatgtgttgg   51960
tgctcaccaa gtctgtggtc tcaaccccgg tagacctgga ggtgaagctg cggatcgccc   52020
aaggtaacgc agtgggagag ttgggcagag ggctgcagga ggggctgaa tggggcctgt   52080 tcctcttgct gttaacgctc tgtgagcaaa cagagccctt gaaatgtccc ttgctcttgc   52140
ctccggcata atatgcagtg ggccactggg ccctggcagc tcttgagtgt gtgccctggg   52200
```

```
gagccatggg gccattggac tgtacttcgt cctggttcat gtgtcagtaa gaaagtaaac   52260
caggctgggt gccatggctc acacctgtaa tcccagcact ttgggaggct gaggcaggtg   52320
gatcacttga gcccaggagt tcaagaccag cctgggcaac atggtgaaac cccatgtcta   52380
caaaagatag aaaaattagc agggcatatt ggcatgcacc tgtggtccca cctactcaag   52440
aggctgaggt gggaggattg cttgagcctg ggaggtcaaa gctgcagtga gccgtgatca   52500
caccactgca cttcagtgtg ggtggggctt tgtttggtg gtggctttct gtctggggag    52560
tttagcgcct agtattttct cttactgcct cactccagca cactaggccc aagccccggg   52620
ggctggccat ttcagagacg ctgccttcac ggctgccaga aaagctccct ctggccctgc   52680
tggtagaaac tggggatctg gggttctagg gaaaatgaga aaagggagag cctggccttg   52740
gaggcctggt cacttgagcc tcttcttcct cgtcacccca tgtctgtgag gaatgggct    52800 gtaggcagcc gtccattcat ccagacctct gtgagcctct gtgataagcc aggccctgtg   52860
ctggatatgg agttaggaag agatggggcg aaattgtcct tacccagtaa gagcacagag   52920
ccttagacat gcgacagtgt gatagcgtgg gatcagggct cactacagga aggggcttga   52980
ggaagaacgc agccaggtcc tctacccgcc gagtgcttct gccatgtggt tgatgggcac   53040
actgtcatgc tggcccgtgc agaccagaca agaaccacat gcggaggttg gatgtggttg   53100
ttgtgggtgg cacttggctt tccttgtgga ttttctcatc tccacactct gcttcttccc   53160
tcttttgatg attatagctc tcctctgcac cctccaggct gtgaacaccc gttccccgta   53220
gcagctgtgt ggtggtgatg gccccttaaa gtctgggcat tagcaggacc ctgagggttg   53280
gggtgctttg gtggaatggc tccttcaaag gctgggggg ccttgccatg cctctgccac    53340
tccgaggccc atgaggttgt gtgagtcatg tcgcagagtg gccatgtgtt gccctgtgcc   53400
ctgttgctgc cctctgcagg cctaagcagc gagagctggt ccatcatgaa gaacatggcc   53460
acggagctgg gcatcatcct catcggctac ttcaccctag tgcccgccat ccaggtaagg   53520
ccccaaggcc tgccacctgg atgagcatgg aagcaactgc tgtgctcccc agctgtgcag   53580
ccatgggcag ggtgctcccc tcttcagcac aggcatcctt gcttctgagg tgggacctct   53640
ttgcctggca agcagatcac tacagcaccc agatggcccc tggcatgcct ggctcagaag   53700
tgctcagcaa accctggctg ggttcccaga ttgagcacct agccaggcag actctgccct   53760
tgaccctgtc ttcctacccc tccctgcctg cttcccttc agccaagtgg caggaggagg    53820
ctgcaagggc atggcaggag ctggggactg gctgtgcagt ttgtcacacc tgtttcccat   53880
ttttgaggga gaagcaccgt gggttccta gacccttcct ccggtctcct cccttggccc    53940
tggcctgtgc cgcagtcgcc agacgcatgg ccttgcctgg cctgaccagt gggagggcca   54000
ccacccattg cccagagtga ccctgctctt ggcaaagtgc cctcactcag ctgtgggctg   54060
tgagcagagg tggaggtggc cctgcactga gctggaaccc cagactgatg ccagccattc   54120
cagaaggagt tgcaggaagg ggaggatgcc atctttctc gcccgtctt ccccagggc      54180 tggcaggcca gctgagggat gggggtgagc agagaacaga tgggctgtgg gctgcttctc   54240
ctggaaaaac agtagtatct gcaggatagg gtacagtctt gggacgttag agctgagaca   54300
accactgtgc cactatctgc actccatggt cttaccccag atcggagtag cactgtggtg   54360
atgtgctaga ggtctcaaca ccgacatctc agaaaatttt gtctgctgac agagcttggg   54420
gagcagagag ctcacccttt ttcagtttta gagaattaat ccctctctct ctctcttcat   54480
tgttccgggg cagttgctgg ctgggaacct ttctgagagc cctgaatca ggcctgggct    54540
```

```
ctagctgggt tggtgatgca tgagcagggc gggggctcag tggggaagga cttttggg     54600
agcaggctgg tggggcttag aggtttccgg gttggatcag gccttcagtc ccctctagag    54660
ggaccggaag attcagggaa ggtacttccc cttcccttc agccctttct gaagaaagtg    54720
tgagggtttc ttctgccccc tggtggagac ggggtgagct gctgctgta tgtgagctga    54780
ggaccaacca gcatctctca tctctgctgt gccctgcctg ctgctgccct gccggttatg    54840
aggtggctgc agtccgggta ctgctcctct tgggctggga cagtgaggtc acggcacccc    54900
cccatcccca tgtgctctga ttccaggagt tctgtctctt tgctgtcgtg gggctggtgt    54960
ctgacttctt ccttcagatg ctgttttca ccactgtcct gtccattgac attcgccgga    55020
tggaggtagg agtgggctga gccctgccct gcccgcctcc tcagccctgg ctgtactgag    55080
ggagtcctgg gtgagaaggg tgtagacctc gggcaggaca gcggtcctgt gcagcagcc    55140
tctggatggt ggactcaggc cctgaccact gtgcccccaa cagctagcag acctgaacaa    55200
gcgactgccc cctgaggcct gcctgccctc agccaagcca gtgggacagc caacgcgcta    55260
cgagcggcag ctggctgtga ggccgtccac accccacacc atcacgttgc agccgtcttc    55320
cttccgaaac ctgcggctcc ccaagaggct gcgtgttgtc tacttcctgg cccgcacccg    55380
cctggcacag cgcctcatca tggtacctgc caccccctgcc ctgccctgcc ctcttctgga    55440
gggccggtgc tccaggcccc ttgtggtgct gcacttggcc ttagagtggc aaagggtatt    55500
cctcaggccc tggtggcccc tggaagcctg gctctgggga gttgcccgtt gtgtcctccc    55560
tgcccagacc ctagtggctt ctgaggagat aagcctgtgg gagaagcagc tccagggttc    55620
tcaggtacag gagccatcct ctccccagag tggcccagga caggagcctg ttagttgagt    55680
gctctgggat ggacccactt gtggccacca cattgccctg gtcgggttc atcggccgct    55740
gcatggtgtg cagacactgg aaagtgctgg gcaaaatcat tcaccagccg ggctgggctg    55800
gccttggggc agcagtgcct cttccaggga gctgaactga gatgggagga aggctgaggc    55860
cccctgggac taggacctct gggggactct ggagcaggtc aggttgctgg ccctctgacc    55920
gtaggaatgg tagcagcttt ctggctccag ctgaggtgga gcttaggggt ggggacattc    55980
tgtgtcaaac ctcagggtgc ttcagtgtat ttccaggcca agaaactcag cccctaactg    56040
tggaaaggca agcaggcccc tccagcagca agtgttggca ggtgttagca ggaggacttg    56100
gagaggcagg agaaaaggac gcagtggggc ctgtgtcctc tctccatccc caggcctgag    56160
gtccctgtgc tgcttcctct cagcatgagg gctgaagctg ctgggggttg gggcccattc    56220
ctcccactga gtaccccctg ccccactgca ggctggcacc gttgtctgga ttggcatcct    56280
ggtatacaca gacccagcag ggctgcgcaa ctacctcgct gcccaggtga cggaacagag    56340
cccattgggt gagggagccc tggctcccat gcccgtgcct agtggcatgc tgcccccag    56400
ccacccggac cctgccttct ccatcttccc acctgatgcc cctaagctac ctgagaacca    56460
gacgtcgcca ggcgagtcac ctgagcgtgg aggtccagca gaggttgtcc atgacagccc    56520
agtcccagag gtaacctggg ggcctgagga tgaggaactt tggaggaaat tgtccttccg    56580
ccactggccg acgctcttca gctattacaa catcacactg gccaagaggt gagctgggcc    56640
gtgccaggtg ccacctcact cgatggtgtc aactcaccat ccccttccc caatgcagga    56700
ggcccacagg tttgaattat gcaaataatt aaaacagttc ataaggttgt gaggtgggaa    56760
ctggtggttt aggcagctat aacccaagag aggagtccca ggttgctctg aggagtcact    56820
ggtggctgcc agccctcacc agaatgagac ccacccacct gtgccaggag tggggaggga    56880
gatacccac acggccacca gggctgtttg ggtgctggta tctgggacag caagttggct    56940
```

| | |
|---|---|
| gctaagctgg gctggggagg gacctacctc tgtccccaac cccccatgct gggagagtct | 57000 |
| ggccggtgga gctgaggcct gcctggggag gagggagagg actggctggc gagcacagca | 57060 |
| ggaggaagcc ctgggaggcc ccccgctgag gctgcccact gtccgaatcc aggtacatca | 57120 |
| gcctgctgcc cgtcatccca gtcacgctcc gcctgaaccc gagggaggct ctggagggcc | 57180 |
| ggcaccctca ggacggccgc agtgcctggc ccccaccggg gcccatacct gctgggcact | 57240 |
| gggaagcagg acccaagggc ccaggtgggg tgcaggccca tggagacgtc acgctgtaca | 57300 |
| agtaaggctg ctgggtgggg tggggtggga aagagtgcgg ggaggggac gggtaggcaa | 57360 |
| gagtagggga gagggaggag gggagggac aggctgtgag gtgtgtctca cagcagtccg | 57420 |
| ccctcccgtg cagggtggcg cgctgggcc tggccaccgg catcgtcttg gtgctgctgc | 57480 |
| tgctctgcct ctaccgcgtg ctatgcccgc gcaactacgg gcagctgggt ggtgggcccg | 57540 |
| ggcggcggag gcgcggggag ctgccctgcg acgactacgg ctatgcgcca cccgagacgg | 57600 |
| agatcgtgcc gcttgtgctg cgcggccacc tcatggtgag caggggcaca gtggccgggt | 57660 |
| aggggagggc cggagcctgg cccataccaa caccgggctt ctgcaggaca tcgagtgcct | 57720 |
| ggccagcgac ggcatgctgc tggtgagctg ctgcctggca ggccacgtct gcgtgtggga | 57780 |
| cgcgcagacc ggggattgcc taacgcgcat tccgcgccca gggtaggtgc ggctgccctt | 57840 |
| tcctcctttg tgcccccaca accccccctca ccccacccc cgccgccacg tatctcccct | 57900 |
| cctttcttcc tccgaggtat ccccaaccc ctccaggccc cctctccccc cacccccgca | 57960 |
| cccctccca ccaccccgta ccccctctc cccacccgc accacctct ccccccaccc | 58020 |
| cctttccct tgcccttct cactcccacg ccccctctca ccccgtccc cgccccctc | 58080 |
| tcaccccct ccccgtgcc ccctctcact ccgccctcct ggccccagc aggcagcgcc | 58140 |
| gggacagtgg cgtgggcagc gggcttgagg ctcaggagag ctgggaacga ctttcagatg | 58200 |
| gtgggaaggc tggtccagag gagcctgggg acagccctcc cctgagacac cgcccccggg | 58260 |
| gccctccgcc gccttccctc ttcggggacc agcctgacct cacctgctta attgacacca | 58320 |
| acttttcagc gcagcctcgg tcctcacagc ccactcagcc cgagcccgg caccgggcgg | 58380 |
| tctgtggccg ctctcgggac tccccaggct atgacttcag ctgcctggtg cagcgggtgt | 58440 |
| accaggagga ggggctggcg gccgtctgca caccagccct gcgcccaccc tcgcctgggc | 58500 |
| cggtgctgtc ccaggcccct gaggacgagg gtggctcccc cgagaaaggc tcccttccc | 58560 |
| tcgcctgggc ccccagtgcc gagggttcca tctggagctt ggagctgcag ggcaacctca | 58620 |
| tcgtggtggg gcggagcagc ggccggctgg aggtgggcag aggggctaaa ggtgggcaga | 58680 |
| gcggctgtcc gccccgggga ttgtgggcct ttctggctgg caggtgctca cagcctctgg | 58740 |
| actcgtaggt gtgggacgcc attgaagggg tgctgtgctg cagcagcgag gaggtctcct | 58800 |
| caggcattac cgctctggtg ttcttggaca aaaggtgagc gtggcctgcc tcagccccag | 58860 |
| atgtccccag cctttgttgg ctaggccata ctctcttgag tcttgagttc tggttctctt | 58920 |
| caactgctgt actgtatgat tcgattgacc ttcttggtgc ccagctccac acctgtgagc | 58980 |
| agagggcagt ccacttggat gggaaggtaa caattaaaag cgttaggggt ggccgggcgc | 59040 |
| ggtggctcac gcctgtaatc ccagcacttt gggaggccga ggcgggcgga tcacgaggtc | 59100 |
| aggagatcga gaccatcccg gctaaaacgg tgaaacccg tctctactaa aaatacaaaa | 59160 |
| aattagccgg gcgtagtggc gggcgcctgt agtcccagct acttgggagg ctgaggcagg | 59220 |
| agaatggcgt gaacccggga ggcggagctt gcagtgagcc gagatcccgc cactgcactc | 59280 |

```
cagcctgggc gacagagcga gactccgtct caaaaaaaaa aaaaaaaaaa aaaaaaaaaa    59340
gcgttagggg tgtgacgtgc ttggaatagg gcatggcaca tggtgacctc ccagggcctt    59400
aagcagtgac agtggggagt gatatactcc tatcctttct cgcccttctc aatgaagcca    59460
gtttctctga ttagcttgtc aatattgagc ctttggggta tcttggttgc atttttagtt    59520
acagagtgcg cttgcagaac cctctcttct ccttggccgc tggcagctgt tctctgctct    59580
ccctgcctct gtcgtgcttg gcctcctcag caagcctgtt ggctgtgggc gtcccagta    59640 ctccgtctgc atgcacactc cttggggagt ctcagccacc tgggttctgg ccccacctcc    59700
aagctggtga acctgggtct ccacccagtg gccaggtgcc ttctgccgga cgcctttgcc    59760
tgcctgtccc acactggctc ctcctccaag gctccttgac tgttggtggc agcaccatct    59820
gacctagagc tggagtcttt ttccttgggg aggggcgtc ccttgcccttt agtgatgttg    59880 atttctgcca gtgggctgct gccgtcattc ctgtcaccac aggttctgca tgggctttgg    59940
ctgacatcct cccctccagc ctggccaatt tcaccaggcc cctccatgct tcttggaaat    60000
tctcctttgc tgcttgtttt agctttaagg aaagccccga tgtctcaacc tgaccatcag    60060
ggttcctggt gactgtggtc tctccttgtc cacccacttc caatcataaa actggcttcc    60120
ccagctctgg tgcaggccct tcaaattcat gggcagaggt tgtaggcaga catgcattgc    60180
ctttccctgc agtaagattt tgaaccccat ctgctttgag ctttggggt tactgggcaa    60240 atatacccat ccctgcctgt cagactgtac ctaggaattt tggagagcaa agaaaatcct    60300
tgtttcttta tggaaaaagg aattgatgtg agctgtgctt gggttgaagc tgcttttatg    60360
tggagaatgc aggcttccgc aacacccaac atagcccacc ctgcatcctg tttccctca    60420 gcagccctcc cttcagctcc aggctacatg gagccctctg cttgttttta atttacaaac    60480
ttacgtgata ttcaccaggt accacttac acgttagctc acttgattct catgaccacc    60540
ctgtgaggtg ggtactctta tccccatttt acggatgaag aaactgaggc acaaggtggt    60600
taatatttgg agttgccctc tggctccagc atctgttctg gcaccatgtg ctttcctctt    60660
ggccatgtcc ctcctgtgcc ttcttgaact ggcccttaac tctcatgtcc acatgctcag    60720
ccccagggct gggggctctaa gggagaggcc cctggcagct gttcttctct tccaggattg    60780
tggctgcacg gctcaacggt tcccttgatt tcttctcctt ggagacccac actgccctca    60840 gcccctgca gtttagaggt cggagggcct ggggtgggca ggtgttcaca cttggtggga    60900
cgggcagggg ccgtctaccc attgctttct cagagattct tcacttggcc ttttgtcctc    60960
agggacccca gggcggggca gttccctgc ctctccagtg tacagcagca gcgacacagt    61020
ggcctgtcac ctgacccaca cagtgccctg tgcacaccaa aaacccatca cagccctgaa    61080
agccgctgct gggcgcttgg tgactgggag ccaagaccac acactgagag tgagtattgt    61140
cttgtctctt gggtgctgga gtggcccggc acggggtggg agcctgatgc attcgtcagg    61200
gagaggctgg aagagtcctg atgaagaaca gagggcattt cccagccaaa gtataacttg    61260
gaaaatccca gagaccagaa cctgaggccc atccctgtcc caggtgttcc gtctggagga    61320
ctcgtgctgc ctcttcaccc ttcagggcca ctcaggggcc atcacgaccg tgtacattga    61380
ccaggtaagc ggcctgcagg tggggtaggg ggtacagagt ctgtggccca tgtttgctga    61440
ctcctgggag ctggtcccca ggggccttcc aggaagcagt cagggcccca cccactgggg    61500
cacagggaca ccactgttga cagaggtatt acaccatggt gaccccactc ccctggcctg    61560
tttccccaga ccatggtgct ggccagtgga ggacaagatg gggccatctg cctgtgggat    61620
gtactgactg gcagccgggt cagccatgtg tttgctcacc gtggggatgt cacctccctt    61680
```

| | |
|---|---:|
| acctgtacca cctcctgtgt catcagcagt ggcctggatg acctcatcag catctgggac | 61740 |
| cgcagcacag gcatcaagtt ctactccatt cagcaggtag aggggatggg gatcatagga | 61800 |
| ttcttgggat tttagggaag gactcaggac tgagcttgtc atgtccttgc ctccaggacc | 61860 |
| tgggctgtgg tgcaagcttg ggtgtcatct cagacaacct gctggtgact ggcggccagg | 61920 |
| gctgtgtctc cttttgggac ctaaactacg ggacctgtt acagacagtc tacctgggga | 61980 |
| agaacagtga ggcccagcct gcccgccaga tcctggtgct ggacaacgct gccattgtct | 62040 |
| gcaactttgg cagtgagctc agcctggtgt atgtgccctc tgtgctggag aagctggact | 62100 |
| gagcgcaggg cctccttgcc caggcaggag gctggggtgc tgtgtggggg ccaatgcact | 62160 |
| gaacctggac ttgggggaaa gagccgagta tcttccagcc gctgcctcct gactgtaata | 62220 |
| atattaaact ttttaaaaa accatatcat catctgtcag gcactttggg a | 62271 |

<210> SEQ ID NO 2
<211> LENGTH: 62267
<212> TYPE: DNA
<213> ORGANISM: homo sapien

<400> SEQUENCE: 2

| | |
|---|---:|
| agaggtgaag gggcgggcac ccggcggcca ggagagagag ggagggcgcc acgcaccgga | 60 |
| ctgcgggccg agagcgcgca cgccgcgctc cgcccctgct gccgccccg tcgccgccgc | 120 |
| cgccgccgcc gcagcttggg aggtgctgcc accacaggta ccgtcacgcg ggtgctcagg | 180 |
| gcgcctgccc gcgggcccca gctcgacccc agccgcgtgg agctgggagt tccggaatgg | 240 |
| gggccgctag gttcgggggt gcgtgggcat ggcgctgtcc agcagccgtg cgggccggcc | 300 |
| ctggagaccg caggccggca aggaggcagg gccgcgcgtc cccacccca acccggccgt | 360 |
| gtccctgcac cggccggccc ctggagctcc gcgtccccac cagacctccg cgggcccctg | 420 |
| gtgtgacggg gggagatgcg cggcgtcgca tcccctggcc tagttgctcc gggaagctgt | 480 |
| tgtagaacct gctttggtgc tgtttgggtt ttccggagtg cggggagag caggttctcc | 540 |
| actttgcctc ttttggaaga tcttattgag agacaacgct agttgctttg ctggttttgc | 600 |
| ttggtttcta gttttccgta ttgcttaaac ctcaactttg ctcactaatg ttgcttctgt | 660 |
| ttacttctga gtgggtttat gacctcagta tttaaccggc ttataatgtc acgatagcgt | 720 |
| tagttgcagg gagccctggc tccggactgt ttgaatcaca gaaagttgtg cagatgggaa | 780 |
| tgcggagggg ggggcagtga gtcgctgtgg gggctctggc aggggtcagc ccctggttcg | 840 |
| ggtcactcac tgctccacct tgtatggcga cagtcggagc taggtgaata aactcttttct | 900 |
| ggggattttg taatacttat cgtgaagcgg ccatagaaaa ggtttaatgt tagcgttgcg | 960 |
| tgtgtttctt ttatttggcc aaaaatttgt ggagtttggt tatgccgtgt ctttattggt | 1020 |
| ttgctgtcag gtcaggatat tgagcaaaag actgacgctt ttattaggga gtcagggtcg | 1080 |
| agggtgtcta gttagtgctg tatccatttt aggtgttcct cagtgatgcc taaagacttg | 1140 |
| tttttttgttt gtttgtttgg agacagggtc tcactctgtc tcccaggctg gagtgcagtg | 1200 |
| gcgcgatctc ggctcactgc agccttgatt tcctgggctc aggtgatcct cccacctcag | 1260 |
| cctccccagt agctgggaca gcaggtgtgt gccaccacgc ccggctaatt tttgtatttt | 1320 |
| tttgtagaga tgggggtctt gctgtgttgc ccaggctggt cttaactcc tgggctcaag | 1380 |
| cattatacaa gccttggcct cccaaagtgt tggtattaca ggcgtgaacc accgtgcccg | 1440 |
| gccaagacct gtatctttta aaatgtgtgt taatatagtt tacattttag gtgttttaca | 1500 |

```
catttgcagt attcccactg agcacatgat gtaaaaaaca ctatataaat atatttaaca    1560
ctgtataaat atatttccat atttattctt ttggtcataa attgaaatgg aaagaattag    1620 gcttttaaa  tttattatga actgatctga tgtttgaatg ctctctcttt tctttctttc    1680 ttttttttt  tgagatggag tctcgctctg tcgcccaggc tggagtgcag tggcgccatc    1740
tcggctcact gcaccctccg cctgccgggt tcaagcgatt ctcctgcctc agcctcccaa    1800
gtagctggga ctacaggcgc ccgccaccat gcccggctac ttttttgtat ttttagtaga    1860
gacggggttt caccgtgtta gccaggatcg tctctatctc ctgacctcat gatccgtccg    1920
cttcggcctc ccaaagtgct gggattacag gcgtgagcca ccgcgcctgg cttgaatgct    1980
ctctcttttc ttttgctgtt gcggcaaaaa cgcccctct  ctagagatct ccgtggactt    2040
tataatcact ggtttggggc cttcccccg  ttccctcagt cactgtcatt aggtgggtaa    2100
aaagtttact acaagtttat tactagaaaa atggaggcat atgcgattca ggaattaaat    2160
aaactaaaaa aggaaagaaa aagtgtgcct gtgggcttca ctgcaggtat gtatattaac    2220
atttggtggt agactttagg gatgttttct ctctcagaat ctagccatgc atgtgaatgt    2280
gcctcaggga tcctggaatg acaggttcat gtgctgtttg cttactctca ccattggtgg    2340
ttgccagtgt tttaccggct ctgacaggta cttcatatac agtttgtgtc atcaccccg    2400 ttgaacagat gagaggactc ctcatagaga gctgggttc  ttacaaggtc acccagcttg    2460
tcaagggtgg atcatccttc aaaccaggtc tgccacacct ctgccacctg agctccttcc    2520
gttagaactt gctaccttac tgagttggct aaagaaacaa ggttcaggtg tcgtcttttg    2580
ccactcagag taataattct gggtgatatc gagcacttgt gctgtttagg cagtgtccta    2640
ggtactgtaa tattagctta tctcacttag ttttcataat aaccaggtga gataacactg    2700
ttatcacccc ctttacggag agttttagaa aagttatttg actggccctg ggtcacctag    2760
cgaatttgag acggagtgtg ttgtgtgcaa actgagattt ggctgacaaa agagtccatc    2820
cttttatgct gttcttgtac ctgcttccac agtctgtttt ttttttttt  ttttgagat     2880 ggagtttcgc tcttcttgcc caggctggag tgcaatggcg tgatctcagc tcactgcaac    2940
ctccgcctcc caggttcaag cgattctcct gcctcagcct cctgagtagc tgggattaca    3000
ggcatgcact accacgcctg gctaattttg tattttagt  agaggcgagg tttctcccta    3060
ttggtcaggc tggtctcaga ctcccgatct caggtgatcc gcccgcctcg gcctcccaaa    3120
gtgctgggat tacaggcgtg agccactgca cgcagcccac agtctttct  gttgctcatt    3180 ggcaggtaag ggtagtggaa gaaggtggta ggggtggtgg gaggaagcca gcgtcactga    3240
ctctagtgtg gggatggtgg aactcagcaa gaaggtgaca gcaatttgac cactgccatt    3300
tgacagtttc tgcttaagca gtcaagggca ctaacctaga atggttgcag ggatgctaaa    3360
tcataaggaa gctttgcagt ggggtccaaa gttggtatgt aagcataaag atgcacgtgg    3420
atctcaggaa aaaataaaa  ctaatttcc  tgtttattc  agcttcattt aattattatt    3480
attattatta ttatttatt  ttattttttt ttttgagac  ggagtctcgc tctgtcgccc    3540
aggccggact gcggactgca gtggcgcaat ctcggctcac tgcaagctcc gcttcccggg    3600
tttacgccat tctcctgcct cagcctcccg agtagctggg actacaggcg cccgccaccg    3660
cgcccggcta atttttttgt attttagta  gagacggggt ttcaccttgt tagccaggat    3720
ggtctcgatc tcctgacctc atgatccact cgcctcggcc tcccaaagtg ctgggattac    3780
aggcgtgagc caccgcgccc ggccccattt aattattatt attatttttt tgagatggag    3840
tctcactcaa tctgttgccc aggctggagt gcattgatgc tatcttggtt tactgcaatc    3900
```

```
ttggtctcct gcctcagcct cccgagtagc tgggattaca gctgtgcacc accacacctg    3960
gctaattttg tattttttagt agagatgggg tttcaccata ttggttaggc tggtctcaaa   4020
ctcctggcct caagtgatcc acccacctta acctcccaaa gtgctgggat tacaggcatg   4080
aaccaccata ataatttta ttatgtactt tataatgtac actgtattat cactgtagta   4140
catatataat ttatatgtaa gtgtacatgt attgggagca tatacttgaa tttttgttgt   4200
tgggcattca tgatcaaaac atttgggaac cagtggctta tttgatattt agcatttca   4260
gaaagcataa aatatacaag gtgttggcca ggcacagtgg ctcatgcctg taatctcagc   4320
actttgggag gctgaggagg gtggatcacc tgaggtcagg agttcgagac cagcctgacc   4380
aacatgtgtg aaaccccgtc tccactataa atacaaaagt tagccaggtg tggtggcatg   4440
cgcctgtagt atacctctaa gtatactaga actatgttga tgttttcctc tctctgcctt   4500
ggccactagg aagctcagag tcaagtttgt atccagggtc ttccagcttg tgcttaagtg   4560
ttttaatcgt ctagattgtt tttaatggtt tctgctcttt gtctcaggtt ttactataaa   4620
atacataaca catttccttc ccgttctaaa tattactgtg attgtattct tatagccaaa   4680
tctttgttct tattcttatt ttattttatt ttttatactg ttgaatccct ctgagccttg   4740
cctttccctg cctcctcttc tgtactcatt tttgctaaaa tttgtaaggg gataaattct   4800
tgaaaagctt tgcacatttt gaagactgtt ttgtttttta atatttatta tagtaaaact   4860
caaatataca tccaaataga gagcaataag cccttgtgta cctatcactc agttatgtct   4920
gtcacttagt cattaacttg gggacactct tgtttcatct atatccttta atcctcatta   4980
tacttttttt tggggggaga agttttattaa ttgataggtg ttactttggg gtaaatgagg   5040
agggagccca ctagtatgct ggggaactgg taaggttttt ttgttttttt cttgaaacag   5100
agtcttgctc ttgtcgccca ggctggagtg cagtggtgcg atctcggctc actgcaacct   5160
tcgcccccct gggttcaagc gactctcctg cctcagcctc caagtagct gggattacag   5220
gcacctgcca ccacacctgg ctagttttg tactttttagt agatgggatt tcaccatgtt   5280
ggccaggcta gtcttgaact cctgacctcc ggtgatctgc ctgcctcggc ctcccaaagt   5340
gttgggatta taggcgtgag ccactgcgcc ccgcaaaggt tcttttcttt gggatccttt   5400
cctgtcctta gaagaccc tttagctttc tgcctgagga gctgatgcct agttgtcagg   5460
ctttcttctt gcccagataa gggtgttaac tcctgtgtac agatgttcac ttaatccttt   5520
ttaccagtcc cacatctcac tatagccta tgctacacct gggtttctcc atcccaagcc   5580
cctttagggt ctctagtgcc agtcttcttc ctcattggct atgtcccta ggttctttt   5640
tatttttccc aacggtgatg cacttactga gcagatgcag taatcttctt acctgagcct   5700
acatataacc attggcctaa atgtatgatg gtttgccagc atcagcaata agactggtaa   5760
tggggtaaaa aacaagttct cttaaggcta gctccttgatc ccctgttgta agctgaccaa   5820
cttaatctga aaataatttg cagcatgtaa atattttagg attagagcca tctgtataca   5880
cacttaaaag tagttttgct accattacat tagtctaaaa gagttaccta agaatgccaa   5940
acgatatttt gttcgaatgc cttggttatt ttaattttaaa agcatttctt tcaaaaccgc   6000
ttctctcttc acaatagtag agctgtggca gtgaactaag aggtcaagga ttcagtgaat   6060
ctgtggctaa tttcttgttc caatctgaga gctctctttg cactatgatc aaaatggagt   6120
cttgccaact gccagggta atagccttgc aagtctcttc cttgttgagc aatgaatata   6180
agttccacat ggctggggag gcctcacaat catggcagaa ggtgaaagag gagcaaaggc   6240
```

```
atgtcttaca tggtggcagg caagcctctt ctcattatac ttttaaaatt atttggtggc      6300
tgggtgcagt ggctcatgcc tgtaatccca gcactttggg aggccaaggt gggtggatca      6360
cttgaggtca gaagttcaag accagcttgg ccaacatggt gaaaccttgc ctgtactaaa      6420
aatacaaaaa ttagcaggt catggtggca cgcacctgta attctagcta cttgggaagc       6480
tgaggaagaa ttgtttggac ccagaggtaa aggttgcagt gagccaggat cgtgtcacag      6540
cactccagcc tgggtgaccg aacaagactc tcaaaacaaa caaacaaaaa ttatttggtg      6600 atttttttt tgagacggag tctccttgtc actcaagctg gaatgcaacg gcgtggtctc       6660
tgctcaccgc aacctttgcc tcccggttca agcgattctt ctgtctcagc ttaccaagta      6720
gctgggacta caggcatgtg ccaccacacc cggctaattt ttgtattttt tgtagagata      6780
gggtttcacc atgttggcca ggctggtctt gaactcctga cctcaagtga tctgcccacc      6840
ttggcatccc caagtgctgg gattgcaggt gtgagccaac gtgcctggcc cattttaacc      6900 attttaagt gtactattta gtgacattaa atgtattcac attgttatgc aaccatcatc       6960
actatccatt tccagaatgt tttcattatt ctacatagaa actatcgatc caggagccat      7020
atgtagaaag ctgaaactgg atcccttcct tacaccttat acaaaaatca attcaagatg      7080
gattaaagac ttaaatgtta gacctaaaac cataaaaacc ctagaagaaa acctaggcaa      7140
taccattcag gccataggca tgggcaagga cttcatgact aaaacaccaa agcaatggc       7200 aacaaaagcc aaaattgaca atgggatct aattaaacta aagagcttct acacagcaaa       7260
agaaactacc atcagactga acaggcaacc tacagagtgg gagaaaattt ttacaatcta      7320
cccatctgac aaagggctaa tatccagaat ctacaaagaa cttaaacaga tttacaagaa      7380
aaaaatcaaa caaccctatc aaaaagtggg tgaagcatat gaacagacac ttctcaaaag      7440
aagacattta tgcagccaac agacacatga aaaaatgctt gtcgtcactg gccatcagag      7500
aaatgcaaat caaaaccaca atgagatacc ctcacaccag ttagaatggg gatcattaaa      7560
aagtcaggaa acaacaggtg ctggagagga tgtggagaaa taggaaccct tttacactgt      7620
tggtgggact gtaaactagt tcaaccattg tggaagacag tgtggcgatt cctcaaggat      7680
ctagaactag aaataccatt tgacccagcc atcccattac tgggcatata cccaaaggat      7740
tataaatcat gctgctataa aggcacatgc acgtatgt ttattacggc actattcaca        7800
atagcaaaga cttggaacca acccaaatgt ccatcaatga tagactggat taagaaaatg      7860
tggcacatat acaccatgga atactatgca gccataaaaa aaggtgagtt catgtccttt      7920
ataggtacat ggatgaagct ggaaaccatc attctgagca aactatcgca aggacagaaa      7980
accaaacacc gcatgttctc actcataggt gggaattgaa caatgagaac acctggacat      8040
gggaacatca ctcaccaggg cctgccgggg gatgggggga ggggggaggg atagcattag      8100
gagataaacc taatgtaaat gacgagttaa cgggtgcagc acaccaacat ggcacatgta      8160
tgcatatgta acaaacctgt atgttgtgca catgtaccca agggccagtg ggtgggaatt      8220
ggtatctcat tgtgatttca atttgtattt tctaaggaat attgatgttg agcaattttt      8280
catatgttga ttggccattt gtatatcttc ttttttgttg ttgtttgggt ttttttttct      8340
ttttcttttt cttgagacgg ggtcttcttg ctctgttgcc cagactgcag tggcgcaatc      8400
acagttgact gcagcctcaa gcctctggtc ccaagtgatc ctcccacctc agtcttccaa      8460
gtagctggga ctgcaggcat gtgccccca gcctggctta tattcatatt ttttgtggag      8520
atgggggttc accatgttgc ctaggctggc cttgaactcc tgagctcaag tgacccatcc      8580
acctcagcct tccaaagtgg tgggattaca ggcatgagcc accccaccga gcctgtatat      8640
```

```
cttctttaga gaaatgttca ttcaagtcct tttctcactt tgagttatta attgttattt    8700
tgttgttatt gttgagttgt aggaattctt tacaaattct ggatattaaa cccttgttag    8760
atatatgatt tgtgaatagt ttctcccatt ctgttggtta gcatttcact ctctttattg    8820
tgtgatttgc acaatttta actttttttt tttttctttt tttaagacag agtctccctc     8880
agtcacccag ggtggagtgc agtgctacag tgttggctca ttgcagcctc cacttcctgg    8940
actcaagcag tcctcccacc tcagcctctc aagtagctga aactacaggt gcacaccacc    9000
atgcctggct aattttttt gtatttattt tttttaaga tatggggtct tgccatgttg      9060
tccaggctgg tctcaaactt ctgagctcaa gcagtccgct tgccttggct tcccaaagtg    9120
ctaggattaa ggcgtgagcc accacgcccg gccaaaagtt tttaatttt atgaattcca     9180
gtttatcaat tttttctt tgttgcctat acttttcaat ccttgctaaa ctcagcatca      9240
tgaagatctt tttcttatat ttcttctaa gggctttaca gttttagctc ttcttttttc    9300
atttatttga tctattttga gttaatttt gtgtataaga gtccaacttc acttttgcgt     9360
gtaactatcc agttttccca gtagcatttg ttgaagagac tgtcctttcc ccagtgactg    9420
gtcatggcat ctttgtcaaa aatcagttga ttatatttgt gagagtttat ttttgggttc   9480
tttttcttc ttcttttctt tttttcaggt tagatgggta gtgctgacat cataacaagg     9540
ttcaagaatg actcatctca catgtgtgtg aaacacccag gtatcatact gatgaactac    9600
agaagatctg ggctctctat tgttttatat gtctgacctt atgccagtac cacattgttc    9660
tgcttactgt agctttatag taagttttga aatcaggaag tgtgagtcct caacttagtt    9720
cttgttttc aagtttgttt tggctattca gggttcccac tttttctttt ggacaaagta    9780
atggggagaa tttctttctt tttttttttt tttttttttg gttttaagaa cagtctcact   9840
ctgttgtcag gctggagtgc agtgacgcaa tcttggctca ctgcaaactc cacctcctgg   9900
gttcaagcga ttctcctgcc tcagcctcct gagtagttga tattacaggc acctgccacc   9960
acgcccagct aattttgta tttttagtag agacggggtt tcaccatgtt ggccaagatg   10020
gtctcgatct cttgacctca tgacccacct gccttggcct cccaaagtgg tgggattaca  10080
ggcgtgggcc actgcaccca gcttttttt tttttgttttt ttaaacaagt aaatggaaag  10140
aaatcccacg ttcatggatt ggaagacaat attcttttt ttttttttgag acggagtctt  10200
gctctgtcac ctaggctgga atgcattggc gcagtcactg ctcactacag ccttgagctc   10260
ccaggctcaa gtgatcctcc cacctcagcc tgctaagtag gtgggactac aggaatgtac   10320
tactgtgcct ggctaattaa aaaattttt gtagagatgg agtctcactg tgttgcccag   10380
gctggtcttg aggactccag ggctcaagca gtcctcccca cttgacctcc caaagtgctg   10440
ggtttacagg catgggccac cgtgcctggc cagctgttag aattttgata gggattgcat   10500
tgcattttga tatggattgc gtttgtagat agctttggat aacgttgtca tttaaagaat   10560
attgtcttcc cagcctggcc aacatggtga accctgtctc tactaacaa tacaaaaatt    10620
atccaggtgt ggtggcatac acctgtaatc ccagttactc aggaggctga tacaggagaa   10680
tcgcttgaac ctgggaggcg gagattgcag tgaaccgaga ttgtgccact gcactccagc   10740
ctgggtgaca gagcaagact ctgtctaaaa aaagaaaaa aaaaaagaa tatcatcttc     10800
caatccatga aagtgggaaa gtgggatttc tttcccttta ttttacgtct ttaatttgtt   10860
tcagcaatgt ttcagtttat gtctttttgtc tcccttgctt aaatttattc ctaagtattt  10920
tattcttttt gatgctatta taaatggaat gttttcctaa ttttgttttt agattgttca  10980
```

-continued

```
ctgtcagtga acaatagaaa tgcaactgat ttttgcatgt tcattttgca tcctacaact   11040
ttgttgaatt catttattag ctgtgtgtgt gtgtaatctt tagggttttc tacatgtaag   11100
atcatgtcat ctaggaacgg aaataatttt actacttcct gtccagttga gatgcctgga   11160
gagaaagggt aaatgaggca gtgagaaggt tcttgcttaa tttctctggc taaaacttt    11220
cagtactgga ttaaatagaa gtggcatcct tgtcttgttc ctgattttag gggaaaagct   11280
tttagtcttt caccatcaag tgtgatgtaa gctgtgagat tttcatatat acccctttat   11340
tatgttgagg atattgcctt ctattcctat ttcattgagt attttttaat caaaaagtta   11400
tcttgaattt tgttaaatgc ttttttctgca tcagttggga tgatcattgt ttttctcctt  11460
cattctagta atgtggcata ttaccttaat tgattttgt taaaccatcc ttgcactttg    11520
ggaataaatt ccacttgtca tctgagatgt atgtttaata tctactttaa aaaaaaaaac   11580
acaaatcagt cccagcctgg gcaacatagt gagaccctca tctctacaaa aataaaaaa    11640
agcctggtgc agtggctcac gcctgtaatc ccagcacttt gagaggccga ggcaggcgga   11700
tcacctgaga tcaggagttc aagaccagcc tgactaacat ggtgaaaccc cgtctctact   11760
aaaaatagaa aaattagcca ggcttagtgg gaagcgcctg taatcccagc tactcaggag   11820
gctaaggcag gagaattgct tgaacctggg aggcggaggt tgcagtgagc tgagatcatg   11880
ccactgtact ccagcctggg tgacagagcg agactctgtc tcaaataaat aaatattaaa   11940
aaataaaata aaataaatta gccagatgtg gtggctcatg cctgtagtcc cagcagtgtg   12000
agaggctgag atgggaggat cacttgggag gttgagaccg cagtgagcca cgattgtaca   12060
actgtatcca gcctgggtga cagagcaaga ccctatctca aaaataaaac aaaaaaccaa   12120
aaaacttaga agtcaacaga tgcttattga attcttccta ggtgtcagac actgttaaag   12180
ttctggggat tcagcagtga acaaggctaa gcccctgttt tctttaatt tttaatttta    12240
gtttttttt tagggacagt ctcactttgt cacttaggct gccaggctcg agtgcagtca    12300
tgcattctca gctcactgca acctctgact cctgggttca agttattctc gtgcctcagt   12360
ttcccatgta gctgggatta caggcactac cacacccagc taattttgt atttttagta    12420
gacacaaggt ttcactatgt tggccaggct ggtctcaaac tcctgacctc aagtgatccg   12480
cctgcctctg cctcccaaag tgctgggatt acaggcacga gccaccgcac cccggcccac   12540
tggagtgttt tgagcagggt agtgacatta gtgatttgtg ctttagaaag atttatcgag   12600
gatggaatga ggcaggaatg aatagaggca ttcctgctgt ccccatggtc agtgatggga   12660
gagtagccag ggagatgatg attgttggtc aggttgggga tctgacttgg aggtaaaact   12720
gttgtaacca gctgtttcag atgtgggctt gttgtaggat gtttcctaaa ctttccgccg   12780
gaggaataaa cagggtagct agtggtataa ttaactgaga tggctgggaa agaacagcta   12840
ctgtggggaa atcaagaatt ctgttttgg tcttgttaga tttgaagtgc ttattaggca    12900
tttgagtgga gataccaagt ggaaatagtg taaataagga gcttagggga gaggcttgag   12960
aggtgtgtat gtaagagaca tcagcaaaca gatgagaatt ggagccagga gtcaggctga   13020
gaagccctgg ggagaaaggg tagatgagga aagcaggcca ggaacaaagc ctatggggaa   13080
gcaggaaggg aggctgagaa gcacaacctt ctaggacatc agtagggaca tgatgtcact   13140
cacaactagg aaataagtag gtgttttcct ttcttctt cttttttttt ttttttttt     13200
ttgagacgag gtttcgctct tattgcccag tctggggtgc aatggcgcga tcttggctca   13260
ctgcaacctc cgcctctcag gttcaagcga ttctcctgcc tcagcctcct gagtagctgg   13320
gattacaggc atgtgccacc acgcccggct aatttttgt atttttagta gagacggggt    13380
```

```
ttcaccgtgt tagccaggat ggttgtaggc gtttctcatt tcagcatagt gtctttatgg   13440
tcagcccttt cagtggctgc ctctgatggt gtttgatcat aagtcataac tcatccatga   13500
aggtgtttta cagtctgtct tcaagcaggc aggtccttag attgaaagaa tggaggcttc   13560
actgcgtgtg cctttactac acagatagcc gatgggcag aggttgtata gctgatgggg    13620
cagaggctgt cagatgactg ttttacagaa aaacctttga caagttatat agtaaacttg   13680
ttaaaagaaa aagttgatct cctagctaag acaaaaggtt tcagtttagg aagataaaaa   13740
agatggatgg tggtgatggc tgcacaacaa tatgaatgta cttaatacca ctgaactgta   13800
cacttaaaag gggttaaaat gatgtttatg ttaataattt ttttttacca caaaacgaag   13860
tagaatactt tgtcactgat tatagtaaac atttaaatct gaatgctaga ttgctttttt   13920
ttgagatgga gtctcactct gtcgcccagg ctggagtaca gcagtgtgat ctcagctcac   13980
tgcaaccttt gcctcctggg tttaagtgat tctcctgtct cagcctccca gtagctggg    14040 attataggtg cctgtcacca tgctcggcta atttttgtat ttttagtaga tagggtttt    14100 caccgtgttg ctcacgctgg tctcaaactc ctgacctgaa gtgatctgtt tgcctcggcc   14160
tccgagagtc ctaggattat aagagtgagc caccgtgccc ggcctagact gctcttacat   14220
aggttaaaac acattatttt gttgggaggt gctggggaat caactctgtc atggaaatgt   14280
tccccgggct gggagttgga accagagtgt tgattgttgt catttgctac atgacctggg   14340
tcatctggca tgaccttccc taagcctcag tttcttcctt accaatagga tattgtgctg   14400
gaggatccca tctctcctag ctctgaaatc tggtagcttt ctgttccttt gtctctataa   14460
atgtctggaa ggcaagcaag ttccagtctg agaagtgact gtgaacattt ggaagaattg   14520
tgtggtccca gtgcatatca cagtccacag ttgtcctgtt agctggaaag ttttacttag   14580
taccagatta tagatatgaa aaagaagcaa ttaaaactta cagcaggcct tacaatttga   14640
gacagaaaca aaatctttgt tttttagact ttgaccaaat atttgggaat gagcaccatg   14700
tagatgtgat ttgtttatct gtgaggcttc acacattgtg acttgacaag aacccatagc   14760
acttaggttt gtgagcccag agtaccaccc tttgccttga agagtgtgga gggagtctta   14820
gggccagcgg tgagcaggat gaaaggttct tagaagctgg tgggcatgga gggggtacag   14880
aggggaggct ctcctgggag ataaggtggt ggaaggggcc ggtgaagtct ggtgtgctgg   14940
agagagctct aggggctcct ggaccctcac cccaaggaaa aggggcccag gtgagcctca   15000
tctcttggct ttcttctttg ccacatttct cctcacaaac tcctcccctc tttgcactgt   15060
ttggaaccct cttccatgca acgtttatat taagagttct tgctgggcgc agtggctcac   15120
gcctgtaatc ccagcacttt gggaggtcga ggcggtgga tcacgaggtc aggagttcaa    15180
gaccagcctg gccaggatgg tgaaacccca tatctactaa aaataagaaa attagctggg   15240
cacagtggca ggcacctgta atcccagcta cttgggaggc tgaggcagga gaatcgcttg   15300 aacctgggg cggggcaga ggttgcagtg agccgagatt gtgccactgc acttcagcct     15360
gggggacaga gtgagactct gtctcaaaaa gacaacaaca acaaaaaacc aaaaaacagt   15420
tcttgaagtg ttgtgggaag tcagggaccc cgaacggagg gactggctgg agccgcggca   15480
gaggaacata aatggtgaag atttcatttt aatatggaca tatatcagtt cccaaaatta   15540
atacttttat aatttcttac acctgtcttt acttcaatct ctgaacataa atcgttaata   15600
tttcctttta atatggacat ttatcagttc ccaaaattaa tactttataa tttcttatgc   15660
ttgtcttact ttaatctctt aatcctgtta tcttcgtaag ctgaggatgt acgtcacctc   15720
```

```
aggaccacta ttgtgttagc tgtacaaatt gattgtaaaa cgtgtgtttg aacaatatga   15780
aatcagtgca tcttgaaaac agaataacag ctattttagg gaacaaggga agacaaccat   15840
aaggtctgac tgcctgtggg gtctggcaga atagagccat attttttcttc ttgcagagag   15900 cctataaatg gacatgcaag tagggaagat atcgctaaat tcttttccta gcaaggaata   15960
ttaataatta agaccctggg aaaggaatgc attcctggtg ggaggtctat aaatggccgc   16020
tctgggagtg tctgtcttat gcggttgaga taaggactga aatacgccct ggtctcctgc   16080
agtaccctca ggcttactag gattgggaaa ctccgccctg gtaaatttga ggtcagaccg   16140
gttctctgct cttgaaccct attttctgtt gtttaagatg tttatcaaga caatacgtgc   16200
acagctgaac atagacccctt atcagtagtt ctgaatttgc ctttgtcctg tttcctcaga   16260
agcatgtgat ctttgttctc cttttttgccc tttgaagcat gtgatcttgt gacctactcc   16320
ctgttcttgc acccccctccc cttttgaaat ccttaataaa acttgctggt tttgcagctc   16380
gggtgggtat cacggtccta ctcatatgtg atgtcacccc tggaggccca gctgtaaaat   16440
tcctctcttt gtactgtttc tctttatttc tcagccggcc gacacttacg gaaaatagaa   16500
agaacctatg ttgaaatatt gggggtgggt tcccctaata ttgaagtagt aacgcaacga   16560
gactcgtcac atctcccatt ttgggatttg attgtataaa actgtcaaga gctttgatgc   16620
cctccagcaa agcacgcttc ttgcaggaaa tcaggcaaag ggtgtttagc ctgtgtggcc   16680
tgatatgctc atgtgtagct ggtggcagga ggctggtcct ggctgtgctc ctacaagtac   16740
ctgctggagt ggaggctgag gacactctgt ccatgggcca agacattgtg tgaaatgaca   16800
aggctgcccc catgggctct caagttgttt ctagctttaa aacagattct tggctgggta   16860
cggtggctca cacctgtaat cccagtactt tgggaggcca aggcgggcag atcacctgag   16920
gtcaggagtt tgaaaccagc ctgaccaaca tggtgaaacc ccatctctac tgaaaataaa   16980
aaattagcca ggcatggtgg cacatacctg taatcccagc tacttgcgag gctgaggcaa   17040
gagaatcgct tgaacccagg aggctgaggt tgcagtgagc cgagatcacg ccgttgcacg   17100
tcagcctggg caacaagagc aaaactctgt ctcaaataaa gaaataaata aaaataaaac   17160
tgattcttag cagcagcagt tcagtcccctt tgttagtcat tcctgaccag gtcaagaggg   17220
agtaagaatg taggtaactg gcattgtgga agaaaatctt taataggttt gttggtgttc   17280
tattgtaaag agggttgaca ttatgcacgt ggttatttgt gacaaccatt acaaccaact   17340
aatataattt ggtcttactt caatttgggt gttgctgtgc catcccaaca gttactctaa   17400
aatgtgccag tactcatctt cttgaatatg tgtgttttta ggctttaaat tctctgaaat   17460
cagctttcgt tcattaactg aaattccttt attttttcaa tactatttaa ttattattat   17520
ttttttgaga cagagttttg cccctgttgc ccaggctgga gtgcagtggt gcaatctcag   17580
ctcactgcaa cctctgcctc cagggttcaa gcgattctcc tgcctcagcc tcctgagtag   17640
ctggaattac agacgcatgc caccacaccc agctaatttt tgttttttgag tagagacggg   17700 gtttcactgt gttggccagc tggtcttgaa ctcctgacct cgtgatccac ccgccttggc   17760
ctcccaaagt gctgggatta caggcatgag ccactgcgcc tggccacgcc ctgctaattt   17820
ttgtattttt agtagagacg gggtttcacc atgttgccca ggctggtctt gaactccaga   17880
cctcaggtga tctgcccacc tcagcctccc aaagttctgg gattacaggc gtgagccacc   17940
gtgcccgacc tttttttcaat actattaact tgatctgctg aaaattctcc caggttactg   18000
gctaattttg aagcttagag aagcaatttt ctttttattt atttatttttg agacggagtc   18060 tcgctccatt gcccaggctg gagtgcagtg gcgccatctc agctcactgc aagctccgcc   18120
```

```
tcccgggttc atgccattct cctgcctcag cctcctgagt agctgggact acaggcaccc    18180
gccaccaggc ccagctaatt ttttgtattt ttagtagaga cggggtttca ctatgttagc    18240
caggatggtc tcgatctcct gacctcgtga cccacccacc tcggcctccc aaagtgctgg    18300
gattatagac gtgagccacc gtgcccggcc cagagaagta attttctgcc cttagcattg    18360
gtccgcttga caactttcag aaaaacatta tcccaaaggg atgaattgtt tgcaccagtg    18420
gactagttta gctcagtgag cagacctata gtgactttct gctcagcacc aggtgaggtg    18480
ctgggtgctc tagggaacac aaggtgattc agttattccc ttctcctgaa ggggaacgca    18540
gtcaatccag gaggctgaga gagtcagaat gagcaaggtg gaagttcaca gttagagaag    18600
ctcagagaag agggctgctg cttccacagg aaactttgct cattattttt taatttcagc    18660
ttttcaatgt agaaatacat ttacatgaca caaaattgga aagtaaact acatgggaaa     18720 gtttcccttc catcttgcac ctggctacca gatcctctcc ccagaggctg ctggtgctgc    18780
cacttctcat gtgtccattc ccaggtgttt tgtgcattta tagacaaata agcagagact    18840
tctgttctct tacatgaaag taggacactg ctcccttgct ttttctctg aatgtttctt     18900 tatgatagtt tatcattaat ttttgtattt ttagtagaga cagggtttca ccatgttggc    18960
caggctggtc tgaactcctg acctcaggtg atccacccgc ctcagcctcc caaagtgctg    19020
ggattgtagg tgtgagccat gtgcctagc tgggctttgg tattttttaaa ttgattttgt    19080 caaaattgct tatatacgcg ggaatttagc accttgtcag cgatatgaat tgcagttgta    19140
tttttccaga tcttatttat cttttttttt tgagacggag tctcgctttg ttgcccagac    19200
tagagtacag tggcacgatc tcacacgatc tcggatgatc tcggctcact gcaacctccg    19260
cctcccaggt tcaagtgatt ctcctgtctc agcctcctga gtagctgaga ctacaggcgt    19320
gtaccaccac actggctaat ttttgtattt ttagtagaga cagggttttg ccatattggt    19380
cagactggtc tcaaactcct gacctcaggt gatccacctg tctcggcctc ccaaagtgct    19440
gggattacag gcatgagcca ctgcacctgg cctaaagtaa ttttatatt tcatatttta     19500 cctttaaatc ttttctctat ttggaattta ttttttatttt ttattttat gttgaggcag    19560 ggtcttattc tgttgcccat actggagcac agtagtgtga tcatggctca ctacagcctg    19620
gaccttgcca ggctcaggta atccacccgc ttcagcctcc tgaatagctg ggactacagg    19680
tgtgcatcac catgcccagc taattttgt acttttggta gagaagggtt ttgccatgtt     19740
gcccaggctg tcttgaact cctgggttca agtgatctgt ctgccttgac ttcccaaagt     19800
gctgggattg taggcctgag ccactgtgct ttttggaatt tattttgatg tgaagtgtta    19860
gatccagctt aattttttc cgtggctacc catttgttgc aacacctttt gttgcgcaat     19920
taatctttct cctacttgtt tatcatttac tgtatatagt atactttgcc atatgtgtac    19980
attttggtct attcctggac attctgttct gttacattaa tctgtgtatt tatgtgttag    20040
gaccacactg ttttaattac tctagcatgt tttgttattt ggtgaagtta gttccctttc    20100
atcatcttta ttttccagaa ctttcttggt tatatttgtt tttctgtata aacttgaagt    20160
ttgtttagtt aaagaagtcc tgttttatt gggactgtta catttctaga tgaatgtagg    20220
aagagtgaca ctttggttac gttatattga cttttcctca ttaagaatgt ggcatgtttt    20280 tcttttttgtt gaagtcatct tttctgtctt tcggagtttc agagatttct tttggtttct    20340
tttttttttt tttttttttt tgaggtggag tcttgctctg tcacccaggc tggagtgcag    20400
tggtgcaatc ccggctcact gcaacctcca cctcccaggt tcaagtgatt ctcctgcctc    20460
```

```
agtttcctga gtagctagga ttacaggaac gtgccacaat gcccagctaa ttttttgtatt   20520 tttagtagag acggggtttc accatgttgg ctaggctggt cttaactcc tgacttcagg     20580 tgatctgccc atctcggcct cccaagttgc tgagattaca ggcgtgagcc actgtgtcct    20640
gctgggagtt tcagagattt cttacatttc tttttaagtt tattttcaag tttttggttt    20700
tgttatttat tttagtgtta atgaatcatt attataatca atattatcat tattttactt    20760
ctgcctgctt gttgttgatg tatgtgaagg cattgatata tattagtttt cactacctta    20820
tggtgattct tttatcaact gtaaaaggtt ttcagttgat tatatatata tatatatata    20880
tatatatata tatgtaattt ttttgtatat atatttggat tttgtacata atatcatttg    20940
caaataatga taatttaact ttttcctttc cagttgtata cctatgtttt ctttgtcttg    21000
actgattgtg ataactagta gttccacaat agtaataaat aatgatggtt aaatgcatag    21060
cctgtatggc ccctgacgtt agtgagaaca cttctagtgt gttcccattg ggcttgattt    21120
tagctttgag attgagaaag atgtaaacat ttagttgaag tctgtattta ttttttatat    21180
atatatgtgt atttttttta ttattatttt ttgagacaga gtctctgtca tctgggctgg    21240
agtgcagtgg cacaatcttg gctcactgta acttctgcct cctgggttca gcgattctc     21300 ctgcgttcaa gcgattctcc tgcctcagcc acccaaatag ttgggattac aggtgcccgc    21360
caccatgcct gactaatttt tgtattttt agtggagacg gggtttcac cttgttggcc      21420 aggctggtct cgaactcctg acctcaaacg atccaccagc cttggtctcc caaagtgcta    21480
ggattacagg tgtgagccac cgtgcctggc ctaatatgta tgtatttatg tatgtatgta    21540
aatcaacgta cacatatcta ctaagcatct gtctattctt tttttttgt gacggagtct     21600 cactctttcg cccagatggg agtgcagtgg cgtgatctct gctcactgca ggctccgtcc    21660
cccggggttc acaccattct cctgcctcag cctcccgagt agctgggact acaggtgccc    21720
gccacctcgc ccggctaatt ttttgtattt ttagtagaga cagggtttca ctgtgttagc    21780
caggatggtc tcaatctcct gaccttgtga tccgcccgcc tcggccaccc aaagtgctgg    21840
gattacaggc atgagccacc gcacccggcc tgtctattct tatcttaaaa ggatgagggt    21900
tgaattttat cagatgtctt cagcattggc agagatgatc tctgttaata tgttgaacat    21960
aacattgttt taacattagt acttacatgt ttctggtaca aaatgaatag gatgatgttt    22020
agagaaggct tatggaggaa atagcatttt atctagtgcc tgaaggctga atggagaaaa    22080
ttagaggtgg gaaattagag tgggaagata ggaaaagggc attcagtaaa gagagagcct    22140
tgactgcaaa ggtgtggaaa gtgggaatgt aggttatttt ggggaagaat gccagcatcc    22200
caacattact gtgatattca tgagggcctt ctagatggg aacatggggg cgtattacac     22260
ctctggactt cagattcttc ctttgtggaa ctgaaatagt aaaagtagtt attagtttaa    22320
gggttgttac aaggattcag gagataatgt aggcaaaagt cttaggccag aggctgacac    22380
atggtttata aatactagtt atttttattt gacaagagaa taaagctgga aagaggtttc    22440
agtatatttt gagtgtacct gtataataag caaagaagta tggcctcaga tatgcaggca    22500
ctggagagcc attcagaact tttgtgcaag gggtgacata agcaggtctt ttttttttcc    22560
attaaaaatt tttttaaag atggggtc tcactatgtt gcccagactg gtctcgaact        22620
tctgggctca agcaatcctc ccatctcagc ctcccaaagt gccgggatta caggtgtgag    22680
ccactgtgcc tggccataag caggtcttta ttttaggaag ctgtccatgc tgaccatgtg    22740
ggaagacaaa ccagaagtga agtgcaaatg caggtagcaa aatcaggtag agactatta    22800 gaatttttca ggctggtggt tttggatatc tatcactagt ccagttcatt ttttatttt    22860
```

```
tgagataggc cttgctcttc tgcccaggct agagtgcagt ggcggaatca cagcttactg    22920
tagccttgac ctcctgggct caagcagtcc ttcccactca ggcttccaag tagccaggac    22980
tacagtcatg agccaccaca attggctaat ttaaatttt ttttttttg tagagacagg      23040 atctctgtat gttgcccagg ctggtcttga actttcctgg cctcaagcag tcttcctgcc    23100
tcagtgtccc aaactgctgg gattacagac attagttagc tacgatgcct gccctgctcg    23160
tccagtttag acatatgttc aagatgtggg caccatagag ttgacttagg caactcttgg    23220
gctccaggtt tggtagggca gtgtttctca aatttgagca tatcactgtc agctggaggg    23280
tgtgttaaat agagatttct gggcctcacc gccagatttt ctgattcacc aggtctggga    23340
taggcccaat aatttgcatt tctaacaagg atttagattg ggacatttgt gaagaacagg    23400
atggatgaag tgttccttgt ttatgatttc attcagagag aggggattat tagctctctt    23460
tcttccagaa tgcctgaggt gctttgtatc acagttagaa gttgagaaga tatgtactga    23520
gcactgtcct aataatatct gatcctggtt gggttggttg gtttgttcat cacttattca    23580
acaagtggtt tgttttcaga gacagggtct cactgtgttg cccaggctgg catcaaactc    23640
ctgggctcaa gggattgtcc cacctcagtc tcctgagtag ccgggattat aggtgcattt    23700
aataaaaatt taacatgcca agtgctatta aagaccctga agaacagaca gggagtttat    23760
ttatagtctt gacagaggac agatagtaaa ccagggaata agtcatttgt acaattacag    23820
agttttaaat gcactgaaaa agaagaaata ggctctgtaa ggaacaataa agagaactac    23880
tggaaaatat atggtcaagg gaggtctttt tgtagaagtg atatttcagc tgagacttga    23940
agaatgaaaa ggaaccagcc tataaagaga agagggaata gaggatggaa cagtatgtgc    24000 caggccctg agatgggaat gaggttggca cacataaggc attggaagaa accagaacag     24060
ggagaggtga cacgaagtga agttgcagag gaccggggtg ggttgtgcag agccctgaga    24120
gctaggggga ggcatttggg ctttgttcta agtgcagaag ggtatccagc tcacagcatt    24180
agtagaatct gtgtccactc tgacctctga gataaagtga attgtaaagg gataggtagg    24240
aaggggtcta tgagggccag gcatggtggg tggctcagcc tgtaatccca actctttggg    24300
aggctgaggc aggaggattg ctggagtcta agagtttaag accagcctgg gcaacatggt    24360
aaaaccccat ctctattaaa aatacaaaca tttcgttggg tgtggtggtg cacgcctata    24420
gtcctagcta cttgggaggc tgaagtggga gaattgattg agcctgggag gtggaggctg    24480
cagtgagcca tgatcgtgcc actgcactcc agcctgggtg acagagtgag accctgtctc    24540
aaaaaaaaaa aaaaaaaaaa aggcattcca ggactgtttg aatatttgaa tataaacatg    24600
tatattttta ctttttataat tgaaaaatag tcagcattgg ggctcataaa ggggacctttt   24660 ggggtaatgt tctgtttctt gatggaatgg tgtttaggtt acatggcttt gtttacttgg    24720
tggtaattca tggagctgtg tgcttataat ttgtgtgctt ttctgtgata tgttatacta    24780
aacttcaaaa gttatttaa aatagtcttg cacggtggct catgtctgta atcccaacac     24840
tttgggaggc tgaggcagga ggattgcttg aaaccaggag ttcaagacca acctgggcaa    24900
catattgaga ccctgtctcc ccacaacatt tttttttt aattagctgg ccatggtggc       24960
acatgcctgt aatcctagct acacgggaag ctgagctggg aggactgcgt ccaggaattc    25020
aaggctacag taagacatga tagtgccact gtaccccagc ctgggtgaca gagtgagacc    25080
ccatctctaa aaaagaaaa ataaataaat gctatagtg aaaaatgtaa agatactgag       25140
atttgagttt aaaaatttct ctgctggtg tggtggctca cacctataat cagtttggga     25200
```

```
aattgaggca ggaggattgc ttgagcccag gagtttgaga ccagcctggg caacgtggca   25260
aaaccctgtc tctactaaaa ttaccaaaaa ttatctctca tggtggtacg tgcctatagg   25320
caggctaaag tgggaggatc acctgagcct gggagattga ggctgcagtg agctgtgatc   25380
ctgccactgc attccagcct gggtgacaga gtgagactct gtctcaagga aaaaaaaaa    25440 aaaaccctgc atataatcac attacacaaa gacaagcaac cactactaac gtttccctct   25500
attctccttt tgtgcacttt ttgtatataa ttttttatttt ttcaaattgt aaaagtaatg   25560
tgtgcttttt gtagaaaact ttactacatg cttctcacaa tgaaatgatg tgattgacag   25620
aaaaatgcca gtaggcgtag tgtgaaaagt ttccttaggg ccaggagcag tggctcacac   25680
ctgtaatccc agcactttgg gaggctgagg caggcagatt cattgaggtc aggaattgga   25740
gaccagcctg gccaacatgg tgaaaccccg tttctaccaa aaatataaaa attagctggg   25800
tggggtggcg cacgcctgta actccagcta cttgggaggc tgaggcacaa gaattgcttg   25860
agcccaggag gcggaggttg cggtgagccg agatcacgcc actgcactcc agcctgggtg   25920
acagagcaag actccatctc aaaaaaagaa aaaaagttt ctttgaaggc aaagaatcct    25980
gaaatgtagg aagattatca cattaaaaaa atttaagagt tctgatgtga taaagatgga   26040
gtaaacatac tccacccttt atgtctgaag agagcaactg aaatccctgg acagaatgca   26100
tggatcagtg gagtaacccc agaaagataa atgttagcat gcgaattgga gaaggaaacc   26160
agaactccaa ataccagtga actggtagtg agtttcccat aattttttt cctccataca    26220 atattttcca gcctgcactt aaagtcagcc ccaaacctgg aaatgtgtgc tggatgtgca   26280
cagaaagagg tctaacagaa gccatctttc tagtttgagg agcaggaaag gggatcctca   26340
tgggtcagga atggggatgg aggaagaaat ctcgtgtgtt gtttgctttg tcttttctcc   26400
ttttctcttg ctctggccct ccacgtaatt gtgtagtggt ggagacagca gtgacattgg   26460
caaatggata ggagaggaag tcttctattt aaagggactg tggtcccagg agcatggagg   26520
gaatccttga ttttgttctt tcctttctct cattgctttt ccttggaggt agtcacagtt   26580
gtgggaggta ctcagcaggt tagggaaatt aaacccctga cttttagcca gaagaccagg   26640
aaaggggccc ttgggatctg gaaagtgtta ggaagattgt gtagaggaag gagctcaaca   26700
aattgaactc ataaagttgc atatgaactc ttgggctgtt cctcagaact aacatacgtg   26760
catctgaccc taaacagcat accaaaggct ttgaggacca aactgtggag tacattactg   26820
ctcaagtagt tctgcactgg cccctggacg gtatgcttgg gaaaaatcaa aataatactt   26880
aaaaggcttt gaaactgat atcatattgg taccacagcc cacagaaggt gggtaggaac    26940
ttgtggactg gacctaatta ggttgattgc tgcaaagaca aattcaaaat tttacgtggg   27000
acttaaacaa gagctagagt cacatagcat aatattcaaa atgtccagta attcagaatt   27060
acttcagcta tgaaaaatca ggaaaatcat aaggggaaaa gacagccaac agatggcaac   27120
cacaacatga cacagatgtt gaaattatca aaaaattaaa agccaaagta taattaaagt   27180
attaattaaa accttgctat aacaagtaag ggtgaatgct cttgaaatga acagaaaatc   27240
agaaatttat ttactgcaaa atatgacaac ctaaatgaaa aattaattgg gtgggctcaa   27300
tagcagaatg gagaagacag aagagtcagt gaacatgaag gtagaataat agaaattatc   27360
cagtctgacc aacagagatc gaaataaaat gaaaaaaaaa aatgaacaga gcttcaggga   27420
cccatgggac aataacagaa agtttatctt ttatgttttt gaagtctcaa aagagagga    27480 gaaagagtgg tgcagaaaaa aatttgaaga aattatggaa aggaataaat atgtttctgt   27540
tcacagataa catgataagt ctacgtagaa atttccaaag aatccacaca cacacacaca   27600
```

```
tgcagaaaga ctctggcact aataagtgat ttcaggacag ttgcaggata aaagattaac  27660
ataaaaaaat caatgtacta gcaatgaaca tgtgaaaatc aaaattgaaa acatagttgc  27720
taaaaagtga aatggtaggt ataaatctaa caaaacatgt acagtcatgt atgctgaaaa  27780
ctatacaatg ctgatgaaag aaatcaaaga tctaagtaga tggaaaaata taccatgttc  27840
atggattgga agactcaaca tgccagttct ttgcaaattt gataaacagg tttaatgcag  27900
tttctatcaa aattctatca agttttttt ttttttttt tttttttttt tttgagacgg  27960
agtctccctc ttgcccaggc tggagtgcag tggcactatc tcagcttact gcaacctctg  28020
cctcctgggt tcaagcgatt ctcctgcctc agcctccaga atagctggga ttacaggcac  28080
acgccaccat gcccggctat tttgtatttt tcatagagac ggggtttcac tgtgttggcc  28140
aggctggtct tgaactcctg acctcaggag atctgcctgc cctggcctcc caaagtgctg  28200
ggattacagg catgaaccac cacacctggc cttttttct ttttctttt ctttctttt  28260 ttttttgag tcagagtctc gctgtattgc ccaggctgga gtgcaatggc acagtctttg  28320
gctcactgtg gcctccgcct cccgggttta agcaattctc ctgtctccgc ctcccaagta  28380
gctggtatta caggcactcg ccaccacacc cagccaattt tggtattttt agtagagaag  28440
aggtttcacc atattggcta ggctggtctt gaacttctga ccttgtaatc cgcccacctt  28500
tgcctcacca agttctagga ttacaggcgt gagccaccgc gcctggcctt tttctccttt  28560
tttgagacgg agtcacagtc tgtcacctag gctggagtgc agtggcgtga tcttggcttg  28620
ctcaacctct gctttctggg ttcaggtgat tctcagcgta ccaagtagct gggattacaa  28680
gtgtgtgcca ccacacccag ctaatttttt ctgttttag tagagaaggg gcttcactgt  28740
gttagccagg tctcacactc ctggcctcaa gcgatccgcc cacctcggtc tcccaaagtg  28800
ctgggactat aggcgtgagc cactgtgcct ggtccagaca actgcttttt gacaaagatg  28860
ccaagcaatt caatggagga aggatagtct tttcaccaaa tggtgctgga acaattggct  28920
atctttagac caaggggaa aaaaggaat ttatatctca caccttatct aaaaattaac  28980
tcaaatggat cacagatttt tatttttatt ttttgacaca gtctcgctct gttgcccagg  29040
ctagagtgca atggtgtggt catagctcat tgcagcctca aactctttgg ctcaagtgat  29100
cctcccactt cagcctccca agtagctagg actacaggca tgtgccaccc tgccctgcta  29160
attgttaatg ttttttttt tgtaaagaca cggtctcaca gtgtccaggc tggtctcaaa  29220
ctcctggttt caagtgattt cccacctcag cctcccaaag tgttgggatt acaggcatga  29280
gtcactgcac ccagctggat tacagactta aacaaatgtg aaactacaaa tttttaggag  29340
aagacattgg ggaaaattac cttatgacca agcaattcca ctcctaagaa tgaatatact  29400
caaaagaaaa caaaaagaaa aaaaatacaa aaacccaac tgaagaacaa caacaacaaa  29460
aaaagtaaac ataagaattg agggggccca ggcacggtgg ctcacgcctg taatcccagc  29520
cctttgggag gcgaaggagg gcagatcatg aggtcagtag ttcaagacaa gcctggccaa  29580
catagtgaaa cttcgtctct actaaaaata aaaaattagc cgggtgtggt ggtgagtgcc  29640
tgtagtccca gctacttggt aggctgaggc aggagaatca cttgaaccca ggaggtggag  29700
gttgcagtaa gctgagactg tgccactgca ctccagcctg ggcgacagag cgagactcca  29760
tctcaaaaaa aaaaaaaag gttggccagg tgcagtggcc atgcctgtaa tctcagcact  29820
ttgggaggct gaggcggtca gatcacgagg tcaagagatt gagaccatcc tggccaagat  29880
ggtgaaaccc catctcttct aagaatgcaa aaattagctg ggcgtggtgg cgcgcatctg  29940
```

```
taattccagc tactcaggag gctgagacag gttaattgct tgaacccagg aggtggaggt   30000
tgcagtgagc tgagatcgca ccaccgcact ccagcctggt gacagagcaa gactctgtct   30060
caaaaaaaaa aaaaaaaaaa attgagacag ggtgtggtgg ctcacacctg taatcccagc   30120
actttgggag gccaggctgg caaatcatct aaggtcagga gttctagacc agtctggcca   30180
acatggtgaa accccatctc tactaaaaat acaaaaatta gccaagtgtg gtggtgtgca   30240
cctgtgctcc cagctacaag ggaggctgag gcacgaattg tttgaaccac cggaaggcgg   30300
agtttacagt gagctgagat cgcgctgctg cactccagcc tgggcgacaa agcaagattc   30360
cgtttcaaaa aaaaaagttg gagttcgaga ccaagtaaac aagaataatg tggcctggcg   30420
tggtggctca tgcctgtaat cccagcactt tgggaggccg aggcggtgga tcacctggtt   30480
aggagttcga gagcagcctg gccaacatga tgaaatccca tttctactaa aaatacgaaa   30540
aaatagctgg gcgtagtggc gggcacttgt aatcccagct actcaggaag ctgaggcaag   30600
agaatcgctt gaatctggga ggcagaggtt gcattgagtg gagattgtgc cacagcactc   30660
cagcctgggc aacaagagca aaactttatc tcaaaaaaaa aaaaaaaaaa aagaattgaa   30720
aacaggtatt caaacaaata caggaatgtt agaatgttca tcacagcact attcacaata   30780
ggcaaaacat agaaactgcc caaatgttta tcaactgatg aatggacaaa caaatgtgg   30840
catacccatt tgatgaaata ttcagccata aaagtaatg aagtggctgg gctcggtgcc   30900
tcatgcctgt aatcccagca ctttgggagg ctgaggctgg cggatcactt gaggtcagga   30960
gtttgagacc agcctggcca acatggtgaa acttggtctc tatcaaaaat acaaaaatta   31020
gccaggtgtg gtggcgggca cctgtaatcc cagctacttg ggaggctgag tcaggagaat   31080
agcttaaacc caggagacag agatttcatt gagccaagat tgtgccactg cactccagcc   31140
tgggcaaccc catctcaaaa aaaaaaagt aatgaagtac tggccgggtg tggtggttcg   31200
tgcctgtaat cccagcactt tgagaggctg aggcagctgg atcatttgag cccaggagtt   31260
tgagaccagc ctgaaaaaca taatgagaac ctgtctctac aaaaaaatac aaaaattagc   31320
agggcatggt ggtgcacacc tgtaatccca gctacttgga aaactaggtg ggagaatcac   31380
ttgaacctgg gaggcagagg ttgcagtgag ccaagagagt gcccactgca ctccagcctg   31440
gtcgatagag tgagattcta tgtcaaaaaa aataaagggt tcctggattg gaaacttgca   31500
tgtgcgctta acgcttctgc tttcggaaag gtagaacgag caataggcat tccttttggc   31560
ttttgagttg gctgtggtgt gactcctttt gcttcttgtt tctgatcttg acacttatga   31620
ggagtcatct ttgagtctgg gttttcatca gtgagtacag tcaagccaag aaatgtgtct   31680
gggcaggttc cctctagcac agaccgaaga aaacagcaac atggaacaag agaagtaggt   31740
ttaaacttgg attccatcag agggctcagt agggaagata attctagatc cctgggcctc   31800
ctagagtttt ctattctgat tttattggtt taatgttatt tgtttgaaag caccagaaat   31860
taactttggc caacataagc aaaaagataa tttattagaa gggtatagaa tagcttacaa   31920
aacggaaaaa aaagttgatg agccagtcct cagaaaggat gggagccaga acagcctggg   31980
gatcttggga gcaggaacct ctgtgggatg aataaacatc atgaatatcc aagttcctgt   32040
ttgtttgtgt ttagaagtca aagtccaggg agagaggccc aatttgtgta gcttgggtcg   32100
gcacggggca ccttgactca tagttaatcc aggttaaatc ctgtggagcg aggtggttcc   32160
cctgagccat accaggctgc tgttaactta tggaagggga cgggtactgg gcaggcagga   32220
acaggagctg ctctctgcct ttgcactccc aggaacaact ataggaccaa gagcagagag   32280
ttctaccaga gtgaattttg cttggtgacc attatgtcag agacctaagc ttttagcgt   32340
```

```
ttttatgttg agggctgacc tcgctagacc ttcttcacga gtgaatcact atttgtacaa   32400
cagtgtgttt tgaggaggcc atccctatgt aaagggtttc tctgtatccc tatgtaaagg   32460
acttttctca gtgggatttg tgcatagagg agggggggga agaatgcctg tttgacagag   32520
agcagctgaa ggtgacgtct gttacacagg catggtttcg tgtgccacac atgagaaaaa   32580
tgccctttgg ggagtggcct tttagcattg cctaatatag gagggaggga gttgggcggg   32640
gagggagaga gagagagaga gagagagaga gagagagagt gtgtgtgtgt gtgtgtgtgt   32700
gtgtgtgtgt gtgtgtgtgt gtattttggg attgaggtca ctagaccttg catataggca   32760
ttctgaaacc attccccagc cacataacta tcgcctccct ccagcagccc tagtgtgcag   32820
agccaagtac tctttgttaa ctggcttttc tcccttctta ccaggtacct gcacatgttg   32880
ttctttgtca gtgctgtcaa gtgtgtgcca gggtgatcca tggtcacttt ccgggatggc   32940
agcaaggtga cttcggctga ggatgaccct gactgaaagg ctgcgtgaga agatatctcg   33000
ggccttctac aaccatgggc tcctctgtgc atcctatccc atcccatcca tcctcttcac   33060
agggttctgc atcttagcct gctggtatgt ttttgggttg ccttggatat ggtgggccag   33120
tgtcttagga cagtaggttt tctaacccta accactatgg agcccttggc ctctgtatgc   33180
tttttacaca atgggagctt gggctcctta taactgtgag tggagaactc tagtcctggc   33240
ctggttagct aatataataa aatagtcctg gctggccctg acctactgat tcaccagatt   33300
tattcatatc actggtactc tatctcaaaa taatgtttag atacttctaa gacactgaaa   33360
taattgaaag atatgatact tcagttttct ttctcaatag tagtggtttc gttttagtac   33420
ctggttaagt gcaagagcct ttttttgtgtg ttgcgaggca aagtccatta gaacagtatc   33480
ttggacaacc tgtggcaggc taacctcaga gacttgcttc tttgctctct agtcattttc   33540
ttgtgttcac atggagcttg cttcagactt cttgttgatt cttgtggcca gctgcacttg   33600
ccaaggacag ttgtgagagc tgtagctgcc cttgttcctg tctgtctttc tcaaggcctc   33660
atagaagcct gaaggctatg gctgacaatg acgtcgtaaa ggaggagttt gatatgagat   33720
gacatctgat gacccttta actctaaaat gctgacagct gtgaaaagag cccatcttat   33780
tcttttctct ggaaagaatt ctgttcttca gattcattgt ctaaacatt tatagatgtt   33840 ttcagtgcta tgctgaaggg aggatgagaa gtcaggaggg aactccctgt tcagttcagt   33900
tgctaatgat ctcaagctct tccctgatta tcagtaagaa agatgaactt tggccaggtg   33960
cagtgctcat acctgtaatt ccaacactgg gaggctgagg tgagagaatc acttgaggcc   34020
aggagttcag gatcagcctg ggcaacatag caagaccaaa aaaaaaaaa aaaaaaaaa   34080 agaaagatga acatcactga gagtttcttg ctgggtgctg tgttgatgct tcaggtataa   34140
cattaggaag tggtccagtt atgtttccat ttaacaaaga ggggtaggga cttagagatt   34200
tgtctggtcc acataactaa taattaggga aactggggtt caaattcaaa tccaagccat   34260
agggactctg gtgcccgcct gcacctgtgt tactgtcacc tggttcact ctggctcagt   34320 atgtttgtat tggtgtttaa actgctaaat tgtgttgtac aagataaaat acttatagct   34380
gtgtcccata agtgatgaat ttggagtgct ctaagaactc agctcttggg ttttttttc   34440 ctttaagtta attgaccttt cttttttctt ctttaaaata agtttttga gacatggtct   34500 cactctgtca gccaggctgg aatgtagtgg cacaatcaca gctcacctca gcctcaacct   34560
cctaggctca agcgaccctc ccatctcagc ctcctaagaa gccacaacca caggtgtgcg   34620
ccaccacact tggctgtttt tcgtcttttg tagagatggg gtctcattat gttgccctcc   34680
```

```
tttggtttta ctctctgatg gtactatggt ttcctctttt gtagtcaccc tgttttttctt   34740 ttaagaggaa agacctggcc gggcgtggtg gctcacggct gtaatcccag cactttggga   34800
ggccgaggcg ggcagatcac gaggtcaggc gatcgagacc atcctggcca acatggtgaa   34860
acctcgtctc tactaaaaat gcaaaaatta gctaggtgtg gtggcctgca cctgtagtcc   34920
ccgccactcg ggaggctgag gcaggagaat cacttgaacc cgggagacgg agattgcagt   34980
gagctgagat cgcgccactg cactctagcc tggcgaaaga gtgagactcc atctcaaaaa   35040
aaaaaaagag gaggaaagac ccttctgtat tatcccattc ttttttttct tccttgagac   35100
agggtctcgc ttccgttgct caggctgag tgcagtggtg caatcactgc taattgcagt    35160
ctcgacttca tgggctcaag tgattctcct acctcagccc tctgagtagt tgggactata   35220
ggcgtgcacc actaatttt tgtatttta gtagagctgg ggtttcgcca tgttgcccag     35280
gctggtctca aactcctgag ctcgtgatcc cctcgccttg gcttcccaaa gtgtcgggat   35340
tacaggtgtg agccaccaaa cctggccttg tactgtcaca ttcttagtgc tgtgtactta   35400
ttttcccaaa tgagtatctt tgtcatgtga tcttaaagtt ttttttttaa ttttgttttt   35460
ttcttaaaac ctgattgact tgagaaaatt tttccaaggc tgggtgaagt ctctcagcct   35520
ccaaagacta ataaaaggtt gtataagaga atccatagat tctgggactt ggccagaaaa   35580
ccagagatca tggacccagg gacacaagcc tcaccattgt cttcaaccca ctgaagcttt   35640
tctgtccaga gcagcagagc agtgcccccc tcttccagag cctgggattg cctgcagaaa   35700
ataaagtatg gatatagact gcttctagta gttttgctag acattcagtt tccattaat   35760 tgcttaccct ttattgttcc tgggatgaaa gacttgtaca gccaaaccca aaggactgct   35820
gcacttaatt tccctattca gatctaacag ccacctgagc tgcagaaata cttttgcac   35880 accactggct caccaccact gggtcacccc agggaaagta cagagcagta ctgggggat   35940 ggtgatcaat gacagcttgg gaatgtgcct gtctccatca ggcagaagaa tccagggagt   36000
gagagagggc atctgtatat gcatcaggct caccccaaac agcactgagg atgtgtgact   36060
ttcttctctg agctgctgtt gaggctgcag gtttcagtga ctgagagcca aggacactac   36120
ttcaaatgaa cccagtgctg agccttgcag gtgagctaga gttagctgtt cttcctgcct   36180
ggcccctggg tgcagtgact gttctttcct ctgggaaaat ctgatgaaat gtgtagcaaa   36240
taggcattat ggcaagaggt gtctgtttat aactcttgga ggttagacca ctgggcccag   36300
gatatgtccc agcagcagcc cagcaagaca gagggtactg ttaatctgaa cctgccctgg   36360
taagcagtgg gtgcgccatg ggataaaaag agcacccaga tgccatgtta gttgactgc    36420 cctatgtgca ggtcagagag tgatgtgaat cattgagaca tttgattcaa caagctgctg   36480
ctcatggtga gaggtggatt ttaatttgga gaggaaattg gaatcacatt gtgttgtttt   36540
tgattttgag acgggtctc actctgtcgc ccaggctgga gtgcaatggc acaatcatgg    36600
cttactgcaa cctctgcctc ccaggttcaa gtgattctct tgcctcagcc tcccgagtag   36660
ctgggattac aggtgtgagc caccacgtcc ggctatttt tgtattttta gtagagacgg    36720
ggtttcacca tgttggccag actggtgtca aactcctgac ctcaagtaac ctgcccactt   36780
cagcctccca aagtcctggg attataggca taagccacct tgctcagcct agtcatgcat   36840
ttttgactta ggatattttc aatttacgac agcgttatca ggacataacc ccatcgtaag   36900
tcaagatgta tctgtacata tcaagtgctt agaatagtgc ctggcacata ttaaatatca   36960
tgtatgagtt tttcattgtt attattcact gtcttcctag tcttctacct tcacagccag   37020
aaagcacaag cagaatccaa aaacatgtat agtctaaaca tagaacaaaa actgactata   37080
```

```
ctctgtgatt actatgcaaa cgctgtagcc acagcctaaa attttttttt tttttttgag  37140
acagggtctc cctctgttgc ccaggctaga gtgcactggc atggcatgat cttggctcac  37200
tgcaacctcc acctcccggg ttcaagcgat tctcctgcct cagctgcccg agtagctagg  37260
attacaggcg tgtgccaccg cgtccggcca attttttgttt tttagtaaa gacggggttt  37320 caccatgttg gccaggctgg tcttgaactc ctgacctcac gtgacccacc cacctcggcc  37380
tcccaaagtg ctgggattac aggcgtgagc caccgtgccc agcctaaatt aactttttt  37440 taagtgaaag caagtttatt agaaaagtaa aggaataaag aatggctgct ccataggcag  37500
agcagcccta aatgaattct gatcacttgt agtcgtttct ctcttcctac ttagagcatc  37560
ttggaggcag accgtagtat tatcttttgt attctcagtt cccagcatat aatacatact  37620
taataaatgg ttttgagtg taggtaaaga tggaaaagcc agagaaaagt aaaaattgat  37680
ttttgtgaag gtaaggagat tgtgtaattg ttttctgtaa ttaacataat aaatgtattt  37740
aaaatattca aaacatggta ttgtcaaaag acttgaagag gcgtttcaca aaagttgcta  37800
tatccaagtg gccagtagta agtaaatgaa ataatttttt taattgtttc ttatcaggaa  37860
aatgtacatt aaaaccatgc tgagatacca ctgtctcttc ctctaaatgg ttaacattaa  37920
ttggactgac agtatcaaga ggtgacaagg atttggagaa actggaactc ctattacact  37980
ggtgatagtg ggaacataaa tttgtacaac cgctatggaa aactgtttgg tatcatctac  38040
taagctcaat gtgcatataa ctccataccc agccatttca tcctaggaat atcccgaca  38100 gaaataagtg cttatgaggc caccaaaaac caataaagga taatagtttt attcttttt  38160 tttcttttt ttaattaaaa acaattatcc agcccaaaat gttttgtttt tttgagacgg  38220
gggtctcact ctgtcaccta ggctggaatg cagtggcatg atcatggctt attgcagcct  38280
cagcctcccg gctcaagcga tcctcccact taagcctccc gagctgggac tacaggtgtg  38340
caccagcatg cctggctaac ttttgtattt tttttttttt agggatggcg tttcaccatg  38400
ttgcccaggc tggtctcaaa ctcctgggct caagaaatcc ttctgccttg gcctcccaaa  38460
gtgctgggat tacaggcatg agccacctca cctggccaac tttattctcc tttttttt  38520 tttttttttt tttgagattg agtttcactc ttgttgccca ggctagagtg cagtggcgcc  38580
atctcagctc accggttcaa gtgatttcc tgcctcagcc ttctgagtag ctgggattac  38640
aggcatacgc caccacgccc ggctaatttt gaattttag tagagacagg gtttctcctt  38700
gttggtcagg ctggtctcga tctcccgatc tcaggtgatc cacctgcctc agcctcccaa  38760
agtgctggga ttacaggcgt gagccactgt gcctggccca actttattct taatagctca  38820
aaccagaaac agccaaatgt tcctcaacca gtggaataca caaatgcact atactttatt  38880
cattagtgga ctagtatgta tccaaaaagc aatgatctgc tatgtgcgcc agtgtggaga  38940
atctagcaga tagaatttga gtgaaagcag ccagtcacaa aagagtatat aagtagaatg  39000
aatggtttca tttatatgac attcaaaaat aggtaaaact aatttatggt gatagagatt  39060
ctaacagtta cctttggtgg tggggagtgg tatgctgttg actgggagtg ggcacaaggc  39120
tgccttctga ggctctggaa atattctata gcttgatcta gatagtagtt acacagatat  39180
acacatgtaa aaacttactg cactttatac ttaagatctg tgcattgtac tatatagaag  39240
ttatttctaa attttaagaa agtgagatct gaaacaaaat gtacatctat ttgccaactt  39300 tttcttttt ttcttttttt ttcacttgag atggggtctc actgtgttgc ctaggctgga  39360
gtacagtggc atgatctcag ctcactgcag cctctacctc ccagggttag atgatcctcc  39420
```

```
tgcctcagcc agtagctggg accacaggtg cacaccacca tgcccagcta atttttgta    39480 ttttggtag  agatggggtt tcactgtgtt gctcagtctg gtctcaaact cctgagctca   39540
aatgatccgc ccgcttggcc tctcccaaag tgttgggatt acaggcttga gccaccgcac   39600
ccagcttatt tgccaacttt ttgatgaaag gtcaggggct ttccttgcgt atatcgggtc   39660
cattaactta actttcctca tgatcctagt ataaaccaca tccttagtta attatacata   39720
attttcatgg tctgtccctt taagtggaat agttgcttag ctatctgaat tggaatcctt   39780 ctggatttt  aaaggtaccc ccacttttgt tttttattgt tcccttatat ctaatttggc   39840
aaggtgattt tttttgttt  gtttttagca tcttgctttt attaagtctc tgaaaacttt   39900
tttctttcag agacagggt  cttatgttgc ccaggctgga gtgcagtggt ataatcatgg   39960
ctcactgcag cctctacctc taggcttaag cagtcctccc acctaagcct cctgagtagc   40020
tgggaccaca ggttcacatg ccatgcctg  gctaatttt  ttgattttct gtagagatga   40080
ggtctcacta tgttgtccag gctggtctca aacttctggg ctcaagcagc cctccagcct   40140
gggcctccca aagtgctggg gttacaggca taacccactg cgcccagcct gaaaatatta   40200
atataatgtt atatattata acatgttggt gtttcctttc agtaaaagtt actcattaaa   40260
tgtataaact agccaggcac ggttgcttac gcctgtaatc tcagcacttt gggaggctga   40320
ggtgggtgga tcacctgagg tcaggagttt aagaccagc  ctggtcaaca tgatgaaacc   40380
ccgtctccac taaaaataca aaaattacct ggatgtagtg gcaggcgcct atctatctgt   40440
gtgtgtgtgt gtgtgtgtgt gtgtgtgtgt gtgtgtgtgt gtgtgtatgt ttatattata   40500
tatgttaatg ttatatataa tgttataact aagtatattt atacatactt agcttataca   40560
gcctgaaaac atttaacaga acagtctatt ttaccagttg ggcttcttcg taaggtttat   40620
gtgactaaaa taagttttgaa aaattctaat ctagatgact tctgagtttc agctttgcaa  40680
ttttgtgatt ctaatatttt gcacatttgt acagtcctga cagaatttag ttattaactc   40740
cagtggctcc tgtgtcagtg ctgagagagg actgcctctc atagtgtcta attcttatct   40800
cctttttgta catcccagct acccactgct gaaactcccc ttgccaggaa caggacctgt   40860
ggaattcacc accccgtgtga aggattactc gcccccacct gtggactctg accgcaaaca   40920
aggagagcct actgagcagc ctgagtgggt gggtactcgt catgttcctg aggccagcac   40980
agagcgttgg gtggagactg gctgaggcag gggtctgcca gtgagattga ggttggtcag   41040
cttctgattt gtgaattcat gtactttaac agctttatca gtgtaccata tagatactta   41100
gtttatacat ttttttttga gatggagttt tgctcctgtt gtccaggctg gagtgcaatg   41160
gcacaatctc ggctcactgc aacctccgcc tcccgggttc aagtgattct cctgcctcag   41220
cctcccgatt agctgggact gtaggtgtgc gccaccacgc ccaactaatt ttgtattttt   41280
attagagatg gagtttcact atgttggcca agctggtctc gaactcctga ccttgggtga   41340
tctacccgcc ttggcctccc aaagtgctgg gattacaggc gtgagccacc gcacctggcc   41400
agttatttag tttggaactc taggtctcct gaccccagcc cactcctcct tctgactgt    41460 actgttttca gttgactgtc tctgggccga acactgatat aaatgagaaa aaggtcttc    41520 agttgagggg ctcagtcaag ggacctaact caccatcaca ccgcactcat tatttggagc   41580
tcattgaagc ttgactagct catctgtgta ccttttgcct gtcaggtgtg acaaagtgc    41640 cctttcttct gtgttgttct gtggtccctg gattcgtgct ggacttgctg aatctgttgt   41700
tgaggaaaac caaagctcag cgaacagagc tctcctcccc cttctctctg acagtcatag   41760
catattccca tttccttttt ggttaacgta gtagtcaggt aacttgttat gaacttgact   41820
```

```
ctgcggctga aatagaggca tatctggcaa gataggtctg tggcacaact atacatggtg   41880
tcagtgggga gtgcaccacc ctggcttcat gaggctctgc ctatgaaggt caaaggatgc   41940
atggtctgat gctggctgaa accagttttg tggtgaaacc agttttgtgg ctttatgtcc   42000
caggttggcc attggctcac tggctcattg tgggaccttc ttgcttaaac cttttacctt   42060
cattaaccat ttttttttta ttgttttgag atggagtctc actctgttgc ccagggtgga   42120
gtacagtggc gtgatctcag ctcattgcaa cctctgtctc ctgggttgaa agcgattctc   42180
ctgcctcagc ctcctgagta cctgggacta caggcatgtt gccaccacac ccggctaatt   42240
tttgtatttt tagtaggggt ggggtttcac catgttggcc aggctggtct caaactcctg   42300
acctcaggtg atccacctgc ctcagcctcc caaagtgctg ggattacagg cgtgagccat   42360
tgtgtccgga cttcattaac cttttaatgc aatgttagca cataagggaa tatttgtgtt   42420
tcctgactag gagagttcat ttggcccatt ggtgtggaat agatgtttaa tgatgaggcc   42480
gtaaggggtg tgatgtgttt gtgagctctt tgaatgatgg gatgatgata gaaagtgttg   42540
gtgcagaata actagagggc tcgggaatca ggagcattgt ccatttcctc tctctctgat   42600
tggagcgctc atcccctgca ggattgagaa ggagatgggc ccagggcagt cacctggtgt   42660
cacacagctc agtggtcagt tatctcacct ccattggctg tccttgataa agatacaggc   42720
cagcgatact gaagtgggtg gtaaggactg ttttagttat gaagaacagg aaattcaacc   42780
caaatcagag taagtgaaag ggaattttg gttcatataa ctcagccagg tgcagggctg   42840
acttaagcac gatatagttt gagcctcaaa aggagtccat ctcttgactt tgtcctctct   42900
gggtcagctt cacttttggt cttcccaaca gtggccctag cagcttcagc cccatgtttt   42960
tgcatcatcc aatccagtgg aggataaaag ggagcccagt tggctatgaa tagggttacc   43020
tgcctgtccc cttcccaagc cctatggcta aaggcaggta tttcattgtt gttgtcagca   43080
ccttgctggg aatgagagag gatggtttcc aaagggacaa tagggccggg tgcagtggtg   43140
catacctgta atcccagtac tgaggcagga ggatcgcttg agcccaggag tttaaggctg   43200
cagtgagcca tgatcacacc attgcagtcc agctggggca atagagtgag accttgtctc   43260
taaaaaaata aaaataaat aaattttaaa aagggaaaa taggagactc gggcagtaga   43320
cagtacattg caggcatctg ctgcctatac gaaggagcca aaacttcctt ccctactcga   43380
ctcactgctg agttcagcac tcgtttattg catacgcgtg gtgtgggatg atgtggggaa   43440
cagatagagg ctcactgtcc ttgaggagat cctatactgt ttggaaagag aagacaaaga   43500
tttttcaaag tttaaagtaa atatagtgta tgtcaaagag acatagggg gcaatcgaaa   43560 gagctcccca gtggtcagtg ctagagcaat tttttttct ttttttttt ccttttcttt   43620 ttcttttttt ttttttttttt tcaagacgga gtcttgcttt cgctaggctg gagtgcagtg   43680
gcgcgatctc agctcactgg aacctccgcc tcccgggttc aagtgattcc cctgcctcag   43740
cctcccgagt agctgggact acaggcacgc accaccacgc ctggctaatt ttttgtattt   43800
tagtagagac ggggtttcac catgttggcc aggatggtct tgatctcctg atcttgtgat   43860
tgatccatcc gcctcggcct cccaaagtgc tgggattaca ggcgtgagcc accatgcctg   43920 gcctagcagca atttttgcaa caaaataaac tggtattgaa ttaagaccca aaatataaaa   43980
taattctctg tgagtccatt cctgagtcca tatgcttgaa taaatataaa taaatgaatg   44040
gatgacaata gacaaatctc ctgggcaaaa aaattctaag taatgtatcc taaagtgtgg   44100
actatgcatg atgactttct tccaaagagg acagtgtgac tgtgggaaaa agtaacttta   44160
```

```
cagtgaagaa gcctgacaga cacctcctac agtaagtgat tggggttaaa gcagcagtga    44220
taaatcacat tgattgattg tgcccttgat atgtgaggag gaggaggaca ttttaccgct    44280
gatcttcctc tcccaaaccc ataaccgcag tataattaga agtaaaacat cagacaaatc    44340
ctagttgagg aacaccctac aaaatgcctg accagtaccc cttgaagctg ccaagatcat    44400
caaaagcaag ggaagtctga gaaactgtca caagctacaa gaagcctcag acactacagc    44460
taaacgtaac gtggtttcct ggatgggatc ctggaaaaga aaaggacat  taggcaaaaa    44520 cttagaaaac ctgaatatac tttggacttt ggttaagaat ttcactgtgg actttggttt    44580
tcagaaggag gactcagag  atgaaatgtc cttcttttta tatacctcag cctcctaaat    44640
tatttaaaaa ttcacgtaca ttaagattca gtctttgtgc tgtaaagtag ggattgtggg    44700
agttcactca gcacagtgag tgtgggccct gcccacatct tccttaccag gttagtgctc    44760 cttcctgct  cagacctgtg tgagcttctg ttctggtcat agcctgtggc agccagctcc    44820
atccaggtgc ctctgtgcct cccagcagct tctagtggct gagcgtgata cagaagacaa    44880
agtggatgag gccttctgtc cccagagccc tcactaaggc acagccacat aaagttcaca    44940
aaggctcaga cggttgcctc tggttgttcc tttgtgccca gggtcccagg aggcattaac    45000
ttgctgtgct tggtcagcat cttggccctt gcctatgctg taacctggag tactgcattg    45060
gtgagtggct ccatggcctc cctttcatcc acacgcatgc cccttggagt tcccgactgc    45120
agcccaggcg tggagacagc ccctcatccc tcagctgggc tgggccctgc ccccttcagt    45180
ccacacctcg cagtacaccg ctgtctaggg ccatgtttcc ttgtctccag ttgtcaccaa    45240
ctcccgggga gtctttacag agcactgctt tcatcaggtt gcccctt cac ctcagagaca    45300 ctgggctttg ctttgtcaac tgattaaaat cctgacagct cagtcaggct tcagtctaag    45360
cctgcttgtc atcttcctcg taatttctgt tatcccctga caggttt cct tggtgcagat    45420 gtccaggcct tctgtgctct cagcatccct tgcaactcac attccctcct gctcctctcc    45480
tacctgttct tttctaacct tatggctcta ctcagcttct cctgggccat aactctgctg    45540
tggctgaccc agcatgtttt ggggtgctcc gcgacatgcc tgttactgag ggttgcatat    45600
gtgaacactc ttgtcattta catccctgtt aagctcttga aaggtagatg gcagattcta    45660
gtgagaaaag tatgtgatat ttagtgagga gaccttggtt tgagtcctta caccaccctg    45720
cctggagtgt gaagctctag gcaggcacaa tgcctgagcc tctccttgct tctcatcagg    45780
ctgttgtgag ggtcagatga agtgaaatgc ctgattgttc attgttaata tttctgctaa    45840
tctttcagac actgttt gta tgcgtgtgtg tgtgtgcat  acatcttgat gctgcagggt    45900
gaatgtcgtt attcctgttt cacaatgagg aaattgaaat ccagagatgt caaaagtgtt    45960
ttcaaggcca tatgtttgga aagctgtgat ttaaaattgg gtcctttgat cttcaaaacc    46020
cgctactctg ctgcaagtga caaaacctga atcagtaaga caggttacat gctttgggga    46080
gtgtagagtc tatagtgcgg tcagcagaca tgttccataa agggctagat agtaaacatt    46140
taggctttgc gggccagacg gcctctgttg cagcccatttg accctgctgt tgtagagtga    46200
aagcagccat agacaatagt aatggtaggg gtgtggctgt gcttcagtaa aaattggaag    46260
tggaaaaaca ggcactaacc agcctgggca acatagtgag accccatctc tacagaaaat    46320
aaagaagtta gccaggtgtg gcacttcggg aggccaaaat gggaggatca cttgagccca    46380
ggagttcgag accagcctgg caacatagtg atacccgtc  cctacaaaac atttttgaaa    46440
attaggcgtg gtggtggtgc acacctct  agtctcagct acttggtggg tggggtgct    46500 gaggtgggag gatctcttga gcctgggaga ttgaggtttc agtgagccat gattgggcaa    46560
```

```
tagagcaaga ccctgtctca aaaagaaaaa caggcatggg ccctgatttg gcctacaggc   46620
catcgtttgc ctacacctgg tcccacagtg ctttgcccat agtagatgtg ttattgagca   46680
aaagaggctc gctgcccaat gtgctagaag ccaatactgt gacaccagga tttggggaaa   46740
agaaaagctt tatattgaag gttgactccc taggagaccg gagtccagct caaatctgtc   46800
tccctgtgct ggctttaagg cagtaatttt attaggaaag gtttagaggg tggatactag   46860
gattagcaga tgattgatgg aaggaagggt gatttctggg aagtctttga gcatgccag    46920 ttatctcttg atgccacctc acaggtccca tgtgcaaatt ccggggggag ttagtatgaa   46980
acatggcagt ggaaattcag gctgtgacat cggcaagctc attctgcaca actccagtcg   47040
gccatcttgg ttccagctta tttcagccag ttcttttatc tcataagcgg agggagtttc   47100
tgggtttcag caaattgttt cttttcttat ctgccatcct gcaaactcaa gaacttgtat   47160
tagtcattgg tttctttaac tctgtggggc acggtttcca atgcccatta aatcccttga   47220
attggaccgt ctttcttctt cctgtgctca gctgcccttt ctgccctccc tcatttcttc   47280
tgcagtatgt gggtgccccg gtggcttatg tccagcagat atttgtgaag tcctcagtgt   47340
ttccctggca caagaacctc ctggcagtag atgtatttcg ttcacctttg tcccgggcat   47400
tccaactggt ggaggagatc cggaaccacg tgctgagaga caggtacccc tctcagggac   47460
cctggcctcc ctgaatccca ttctgtactg aagggagagt tacagtcctc agtgtaactg   47520
cagtgagcca gtcagctctg cagagataga acaagcaaga aggatggagg gtgagctagc   47580
cttgaatttc tcagcatcct tgtgggtcta cggtggctgc attccgcttg gacctatgca   47640
gatggcacac acatagcctt gagtctcatc cttacatctc agatggagtc agtgtccact   47700
gtgctaactc atgacccaca tggcttcctg cctgtgggtt atggtgtgaa tgtaatggtg   47760
gtgtctctgc cgacgagaag caagctctac ctgggggtac cttctgaagc cccagcccaa   47820
gtcgtgctcc cctgcctatc agtgggtccc tgggttatgc tggcttggca tacaatgtgt   47880
gtaattggca agctgcatca ctgccaggtt ttagttagct agtggcgttg acagatattt   47940
tggtgaacta aatgaagccc ctaatttacc ccggtccctg ctcatccact gaactggcca   48000
gggtgtttta gtgggtgggg ttgtgcatgc tcttatagta cacttgcccg tcctcagagc   48060
tgatgggctt ttgggcttca gatgcacttt gaaagtcaga cagccacatg tttaggttat   48120
tggccacctg gaagtacttc cccctgctgc cctagtggtc aggctctttg gcgataccag   48180
agagcaaata tggggcattg aagaacagac agaggatgtc ccctaagtac agcaggtctg   48240
ccctgtggtg gcagacacag caggtgcctt gtcctgtctc ctgtgcagct ctgggatcag   48300
gagcttggag gagttgtgtc tgcaagtgac cgacctgctg ccaggcctta ggaagctcag   48360
gaacctactc cctgagcatg gatgcctgct gctgtcccct gggaacttct ggcagaatga   48420
ctgggaacgc ttccatgctg atcctgacat cattgggacc atccaccagc acgagcctaa   48480
aaccctgcag acttcagcca cactcaaagg tagccccagt acaagttccc ttcagacctg   48540
taaaggtgcc cattggtcac cgtcttttg atgtgtgctt aggcagatca gggtttaccc    48600
tttgtttccc agggtggggg tgagaaaggg gtccttggtg gctctgcagt agctgtcatt   48660
tctgtgtcag tacctgctgg tttctgcttg cagacttgtt atttggtgtt cctgggaagt   48720
acagcggggt gagcctctac accaggaaga ggatggtctc ctacaccatc accctggtct   48780
tccagcacta ccatgccaag taagattgac agtaccctgg gctcttgact ggtctgctgg   48840
gtgacatgag gctttgagta gtccctcttc tggttagagt gttctgaatg cccctggaa    48900
```

```
acttgggaga gtttccaggc ctcctgttga atgtttacat ccctcagact agatgatgct    48960
gtctaccaca ttttaatggg gatgacctga cagctggtta agcataggg  actaaggtag    49020
ggctggcggt ctcagtgtcc tggtgcctcc tctggtctct cttgagccta gggcaggcat    49080
ccccagctgg ttactactga gcaccctata tggcctgtgt ccttcccagt ggggcactgc    49140
aggcagctcc ccaattggca agggcactcg aggtgcttct gatcggctct cctaggcctc    49200
tggcaatcaa gagtgttgga ggccgggcgc ggtggctcac gcctgtaatc ccagactttg    49260
ggaggccgag gcaggcggat catgaggtca ggagatcgag accatcctgg ctaacacggt    49320
gaaaccccgt ctctactaaa aatacaaaaa attagccggg cgtggtggtg ggcacctgta    49380
gtcccagcta ctcgggaggc tgaggcagga ggatggtgtg aacccaggag gcggagcttg    49440
cagtgagccc agatggcgcc actgcactcc agcctgggcg acagcgagac tcttgtctca    49500
aaaaataaaa aataaaataa ataaataaat aaaaagaga gtgttggagt aggtccggaa    49560
agggagacaa agaaggagc aggggagct cctgagaaaa cttttgtcccc tttgtgattt    49620
tcccagtgcc cctggagact atagagaagc tcaggcacca tagagaagtt ccctttcaac    49680
acaggggcag gagggaggtc ctgatggacc ctctgtccgg ggattgtctt tgtccccaga    49740
accaagagca acacttccat ttaccccac cctgctcctt gaccaggttc ctgggcagcc    49800
tgcgtgcccg cctgatgctt ctgcacccca gccccaactg cagccttcgg gcggagagcc    49860
tggtccacgt gcacttcaag gaggagattg tgtcgctga gctcatcccc cttgtgacca    49920
cctacatcat cttgtttgcc tacatctact tctccacgcg taggttcatg gcagggaggc    49980
tgagggcttt ctccaagcta acgggcatt tccatgtcac ctgcttccct ggctctggag    50040
gtggcttggg gtagagagat agaacacacc tggtggtcat cagagctagg gctttgtccc    50100
ccagcagggt cttaggagct tgggtgggc cgggctctt cccactttca gccccttcct    50160
gggttagggt tcctaaaagg tgtactgtgt ccatgacact gggaagtgct tgtgcctgtc    50220
cctttccttt ggtgaaacca ggagttttcc cttcctcgac tgtcagggca acctactccc    50280
gggagcccca gtgggccggg ggctggggga ggggccgccc tgatacgccc tctctgccct    50340
ccagggaaga tcgacatggt caagtccaag tgggggctgg ccctggctgc cgtggtcaca    50400
gtgctcagct cgctgctcat gtctgtggga ctctgcacac tcttcggcct gacgcccacc    50460
ctcaatggcg ggtaggtccc tagcaggctc cactgggcca cagggtgggc tcaggccaga    50520
gagccttgca cttctgggtt cttggccttc cctggacttt gctgtgacct cacgtcttca    50580
cattgttgtt tttgacattt aagaggtaca ttttcttcct cttctttgtc tggcttgtat    50640
tcatacttgt gtttgtatat agcatatcta gctatagtga gtgtccatat gtacaaagt     50700
gcatatttgt gggctgggtg tgtatataag gggtgtgtgt tggtatgttt gtgtatacat    50760
gagtatgtat tgcatgtgtg tagtcggatt tgtgtgtctg tgtttatgta ttctatatac    50820
acacaccaca cacacactgc agcttgatgg cttaagccac tggaggtgtg agatagagaa    50880
gagaacattt tttttttcat gattagaaca tttaaatgcc taatgaaata ggtcattta     50940
gaggaagctc tttggaagat atgagcacac tgtaatttgt cgccttttc  actgatgttt    51000
actttcccct tgccactcct ctctgaacct tagtctggaa gccttccct  cggcttgtcc    51060
tcaggctttg atcttggctc tggctaggcc cgcctgcctg tctattaatg gttattaatg    51120
gattatggat tggcctgtcc accactttgg cccatcaggc tggtcgtatg aaaagcgacg    51180
tcgtatttg tttctggtag tttcgttgct cttagatacc tgctcccttt cctgagcttg    51240
acactgttaa acaccaccct cccccatacc gtctgccata cccttcacag ggccctccct    51300
```

```
tccttcggct ccaaagcaga ggtcctgcaa ggtataactt ggctggcgtt cctcgcacat    51360
agactttctt agggtttgct gcggggagtg tgggacagtg ggctcagata gctggtagag    51420
ctttgtgtag gaacagtcgt tcttctccac acacagcttc tcaacaaagg tgagtgggcc    51480
ttcaggatgg tttcatctcc ttgcatttag ctgtgatggg tccacccaga gttactggtg    51540
tgggtcttgg cagcagtcat tgtctttagc cagcagtctt ctcctgggaa gggccagcag    51600
aagtgtggtc tagcagtggc gctgcacagc tctccctgag gggcctcttc cagccctcct    51660
gtgctggatg gctagagaca ggatggctgc tggcccctct gcaaggctct ggagcctgcc    51720
tgaaagctga gtgctgtgta gatgcaggtc ttgttgggtg aggtggacaa gggagggttt    51780
ctgcccagca cctgtgggag tcactcagca gcccccatga caggctggaa accccacagc    51840
cttcctgagg gccccagtct gttgggaacc accacaacac tgtcctcacc ttctccttct    51900
ctgtccccag cgagattttc ccctaccttg tggtggttat tgggttagag aatgtgttgg    51960
tgctcaccaa gtctgtggtc tcaaccccgg tagacctgga ggtgaagctg cggatcgccc    52020
aaggtaacgc agtgggagag ttgggcagag ggctgcagga ggggctggaa tggggcctgt    52080
tcctcttgct gttaacgctc tgtgagcaaa cagagccctt gaaatgtccc ttgctcttgc    52140
ctccggcata atatgcagtg ggccactggg ccctggcagc tcttgagtgt gtgccctggg    52200
gagccatggg gccattggac tgtacttcgt cctggttcat gtgtcagtaa gaaagtaaac    52260
caggctgggt gccatggctc acacctgtaa tcccagcact ttgggaggct gaggcaggtg    52320
gatcacttga gcccaggagt tcaagaccag cctgggcaac atggtgaaac ccatgtcta    52380 caaaagatag aaaaattagc agggcatatt ggcatgcacc tgtggtccca cctactcaag    52440
aggctgaggt gggaggattg cttgagcctg ggaggtcaaa gctgcagtga gccgtgatca    52500
caccactgca cttcagtgtg ggtggggctt gtgtttggtg gtggctttct gtctggggag    52560
tttagcgcct agtattttct cttactgcct cactccagca cactaggccc aagcccgggg    52620
ggctggccat ttcagagacg ctgccttcac ggctgccaga aaagctccct ctggccctgc    52680
tggtagaaac tggggatctg gggttctagg gaaaatgaga aaaggagag cctggccttg    52740 gaggcctggt cacttgagcc tcttcttcct cgtcacccca tgtctgtgag gaatggggct    52800
gtaggcagcc gtccattcat ccagacctct gtgagcctct gtgataagcc aggccctgtg    52860
ctggatatgg agttaggaag agatgggcg aaattgtcct tacccagtaa gagcacagag    52920
ccttagacat gcgacagtgt gatagcgtgg gatcagggct cactacagga aggggcttga    52980
ggaagaacgc agccaggtcc tctacccgcc gagtgcttct gccatgtggt tgatgggcac    53040
actgtcatgc tggcccgtgc agaccagaca agaaccacat gcggaggttg gatgtggttg    53100
ttgtgggtgg cacttggctt tccttgtgga ttttctcatc tccacactct gcttcttccc    53160
tcttttgatg attatagctc tcctctgcac cctccaggct gtgaacaccc gttccccgta    53220
gcagctgtgt ggtggtgatg gccccttaaa gtctgggcat tagcaggacc tgagggttg    53280 gggtgctttg gtggaatggc tccttcaaag ggctggggg ccttgccatg cctctgccac    53340
tccgaggccc atgaggttgt gtgagtcatg tcgcagagtg gccatgtgtt gccctgtgcc    53400
ctgttgctgc cctctgcagg cctaagcagc gagagctggg ccatcatgaa gaacatggcc    53460
acggagctgg gcatcatcct catcggctac ttcaccctag tgcccgccat ccaggtaagg    53520
ccccaaggcc tgccacctgg atgagcatgg aagcaactgc tgtgctcccc agctgtgcag    53580
ccatgggcag ggtgctcccc tcttcagcac aggcatcctt gcttctgagg tgggacctct    53640
```

```
ttgcctggca agcagatcac tacagcaccc agatggcccc tggcatgcct ggctcagaag    53700
tgctcagcaa accctggctg ggttcccaga ttgagcacct agccaggcag actctgccct    53760
tgaccctgtc ttcctacccc tccctgcctg cttcccttc agccaagtgg caggaggagg     53820
ctgcaagggc atggcaggag ctggggactg gctgtgcagt ttgtcacacc tgtttcccat    53880
ttttgaggga gaagcaccgt ggggttccta gaccttcct ccggtctcct cccttggccc     53940
tggcctgtgc cgcagtcgcc agacgcatgg ccttgcctgg cctgaccagt gggagggcca    54000
ccacccattg cccagagtga ccctgctctt ggcaaagtgc cctcactcag ctgtgggctg    54060
tgagcagagg tggaggtggc cctgcactga gctggaaccc cagactgatg ccagccattc    54120
cagaaggagt tgcaggaagg ggaggatgcc atctttctc gcccgtcttt cccccagggc     54180
tggcaggcca gctgagggat gggggtgagc agagaacaga tggctgtgg gctgcttctc     54240 ctggaaaaac agtagtatct gcaggatagg gtacagtctt gggacgttag agctgagaca    54300
accactgtgc cactatctgc actccatggt cttaccccag atcggagtag cactgtggtg    54360
atgtgctaga ggtctcaaca ccgacatctc agaaaatttt gtctgctgac agagcttggg    54420
gagcagagag ctcacccttt ttcagtttta gagaattaat ccctctctct ctctcttcat    54480
tgttccgggg cagttgctgg ctgggaacct ttctgagagc ccctgaatca ggcctgggct    54540
ctagctgggt tggtgatgca tgagcagggc ggggggctcag tggggaagga ctttttgggg    54600
agcaggctgc tggggcttag aggtttccgg gttggatcag gccttcagtc ccctctagag    54660
ggaccggaag attcagggaa ggtacttccc cttcccttc agcccttct gaagaaagtg       54720 tgagggtttc ttctgccccc tggtggagac ggggtgagct gctgctggta tgtgagctga    54780
ggaccaacca gcatctctca tctctgctgt gccctgcctg ctgctgccct gccggttatg    54840
aggtggctgc agtccgggta ctgctcctct tgggctggga cagtgaggtc acggcacccc    54900
cccatcccca tgtgctctga ttccaggagt tctgtctctt tgctgtcgtg gggctggtgt    54960
ctgacttctt ccttcagatg ctgtttttca ccactgtcct gtccattgac attgccggga    55020
tggaggtagg agtgggctga gccctgccct gcccgcctcc tcagccctgg ctgtactgag    55080
ggagtcctgg gtgagaaggg tgtagacctc gggcaggaca gcggtcctgt gcgagcagcc    55140
tctggatggt ggactcaggc cctgaccact gtgcccccaa cagctagcag acctgaacaa    55200
gcgactgccc cctgaggcct gcctgccctc agccaagcca gtgggacagc caacgcgcta    55260
cgagcggcag ctggctgtga ggccgtccac accccacacc atcacgttgc agccgtcttc    55320
cttccgaaac ctgcggctcc ccaagaggct gcgtgttgtc tacttcctgg cccgcacccg    55380
cctggcacag cgcctcatca tggtacctgc caccctgcc ctgccctgcc tcttctgga     55440 gggccggtgc tccaggcccc ttgtggtgct gcacttggcc ttagagtggc aaagggtatt    55500
cctcaggccc tggtggcccc tggaagcctg gctctgggga gttgcccgtt gtgtcctccc    55560
tgcccagacc ctagtggctt ctgaggagat aagcctgtgg gagaagcagc tccagggttc    55620
tcaggtacag gagccatcct ctccccagag tggcccagga caggagcctg ttagttgagt    55680
gctctgggat ggacccactt gtggccacca cattgccctg ggtcgggttc atcggccgct    55740
gcatggtgtg cagacactgg aaagtgctgg gcaaaatcat tcaccagccg ggctgggctg    55800 gccttgggc agcagtgcct cttccaggga gctgaactga gatgggagga aggctgaggc     55860
cccctgggac taggacctct gggggactct ggagcaggtc aggttgctgg ccctctgacc    55920
gtaggaatgg tagcagcttt ctggctccag ctgaggtgga gcttaggggt ggggacattc    55980
tgtgtcaaac ctcagggtgc ttcagtgtat ttccaggcca agaaactcag cccctaactg    56040
```

| | | | | |
|---|---|---|---|---|
| tggaaaggca | agcaggcccc | tccagcagca | agtgttggca | ggtgttagca ggaggacttg | 56100 |
| gagaggcagg | agaaaaggac | gcagtggggc | ctgtgtcctc | tctccatccc caggcctgag | 56160 |
| gtccctgtgc | tgcttcctct | cagcatgagg | gctgaagctg | ctgggggttg gggcccattc | 56220 |
| ctcccactga | gtacccoctg | ccccactgca | ggctggcacc | gttgtctgga ttggcatcct | 56280 |
| ggtatacaca | gacccagcag | ggctgcgcaa | ctacctcgct | gcccaggtga cggaacagag | 56340 |
| cccattgggt | gagggagccc | tggctcccat | gcccgtgcct | agtggcatgc tgcccccag | 56400 |
| ccacccggac | cctgccttct | ccatcttccc | acctgatgcc | cctaagctac ctgagaacca | 56460 |
| gacgtcgcca | ggcgagtcac | ctgagcgtgg | aggtccagca | gaggttgtcc atgacagccc | 56520 |
| agtcccagag | gtaacctggg | ggcctgagga | tgaggaactt | tggaggaaat tgtccttccg | 56580 |
| ccactggccg | acgctcttca | gctattacaa | catcacactg | gccaagaggt gagctgggcc | 56640 |
| gtgccaggtg | ccacctcact | cgatggtgtc | aactcaccat | ccccttccc caatgcagga | 56700 |
| ggcccacagg | tttgaattat | gcaaataatt | aaaacagttc | ataaggttgt gaggtgggaa | 56760 |
| ctggtggttt | aggcagctat | aacccaagag | aggagtccca | ggttgctctg aggagtcact | 56820 |
| ggtggctgcc | agccctcacc | agaatgagac | ccacccacct | gtgccaggag tgggaggga | 56880 |
| gatacccoac | acggccacca | gggctgtttg | ggtgctggta | tctgggacag caagttggct | 56940 |
| gctaagctgg | gctggggagg | gacctacctc | tgtcccoaac | cccccatgct gggagagtct | 57000 |
| ggccggtgga | gctgaggcct | gcctggggag | gagggagagg | actggctggc gagcacagca | 57060 |
| ggaggaagcc | ctgggaggcc | cccgctgag | gctgcccact | gtccgaatcc aggtacatca | 57120 |
| gcctgctgcc | cgtcatccca | gtcacgctcc | gcctgaaccc | gagggaggct ctggagggcc | 57180 |
| ggcaccctca | ggacggccgc | agtgcctggc | ccccaccggg | gcccatacct gctgggcact | 57240 |
| gggaagcagg | acccaagggc | ccaggtgggg | tgcaggccca | tggagacgtc acgctgtaca | 57300 |
| agtaaggctg | ctgggtgggg | tggggtggga | aagagtgcgg | ggaggggac gggtaggcaa | 57360 |
| gagtagggga | gagggaggag | gggaggggac | aggctgtgag | gtgtgtctca cagcagtccg | 57420 |
| ccctcccgtg | cagggtggcg | gcgctggcc | tggccaccgg | catcgtcttg gtgctgctgc | 57480 |
| tgctctgcct | ctaccgcgtg | ctatgcccgc | gcaactacgg | gcagctgggt ggtgggcccg | 57540 |
| ggcggcggag | gcgcgggag | ctgccctgcg | acgactacgg | ctatgcgcca cccgagacgg | 57600 |
| agatcgtgcc | gcttgtgctg | cgcggccacc | tcatggtgag | caggggcaca gtggccgggt | 57660 |
| aggggagggc | cggagcctgg | cccataccaa | caccgggctt | ctgcaggaca tcgagtgcct | 57720 |
| ggccagcgac | ggcatgctgc | tggtgagctg | ctgcctggca | ggccacgtct gcgtgtggga | 57780 |
| cgcgcagacc | ggggattgcc | taacgcgcat | tccgcgccca | gggtaggtgc ggctgccctt | 57840 |
| tcctcctttg | tgccccaca | accccoctca | ccccaccccc | cgccgccacg tatctccoct | 57900 |
| cctttcttcc | tccgaggtat | ccccoaaccc | ctccaggccc | cctctccccc cacccccgca | 57960 |
| cccoctccca | ccacccogta | cccccoctctc | cccacccogc | accaccctct cccccacccc | 58020 |
| ccttttccct | tgcccoттct | cactcccacg | ccccctctca | ccccogtccc ccgcccoctc | 58080 |
| tcaccccoct | ccccogtgcc | ccctctcact | ccgccctcct | ggccccoagc aggcagcgcc | 58140 |
| gggacagtgg | cgtgggcagc | gggcttgagg | ctcaggagag | ctgggaacga ctttcagatg | 58200 |
| gtgggaaggc | tggtccagag | gagcctgggg | acagccctcc | cctgagacac cgccocggg | 58260 |
| gcctccgcc | gccttccctc | ttcggggacc | agcctgacct | cacctgctta attgacacca | 58320 |
| acttttcagc | gcagcctcgg | tcctcacagc | ccactcagcc | cgagcccogg caccgggcgg | 58380 |

```
tctgtggccg ctctcgggac tccccaggct atgacttcag ctgcctggtg cagcgggtgt   58440
accaggagga ggggctggcg gccgtctgca caccagccct gcgcccaccc tcgcctgggc   58500
cggtgctgtc ccaggcccct gaggacgagg gtggctcccc cgagaaaggc tcccttccc    58560 tcgcctgggc ccccagtgcc gagggttcca tctggagctt ggagctgcag gcaacctca    58620 tcgtggtggg gcggagcagc ggccggctgg aggtgggcag aggggctaaa ggtgggcaga   58680
gcggctgtcc gccccgggga ttgtgggcct ttctggctgg caggtgctca cagcctctgg   58740
actcgtaggt gtgggacgcc attgaagggg tgctgtgctg cagcagcgag gaggtctcct   58800
caggcattac cgctctggtg ttcttggaca aaaggtgagc gtggcctgcc tcagccccag   58860
atgtccccag cctttgttgg ctaggccata ctctcttgag tcttgagttc tggttctctt   58920
caactgctgt actgtatgat tcgattgacc ttcttggtgc ccagctccac acctgtgagc   58980
agagggcagt ccacttggat gggaaggtaa caattaaaag cgttaggggt ggccgggcgc   59040
ggtggctcac gcctgtaatc ccagcacttt gggaggccga ggcgggcgga tcacgaggtc   59100
aggagatcga gaccatcccg gctaaaacgg tgaaaccccg tctctactaa aaatacaaaa   59160
aattagccgg gcgtagtggc gggcgcctgt agtcccagct acttgggagg ctgaggcagg   59220
agaatggcgt gaacccggga ggcggagctt gcagtgagcc gagatcccgc cactgcactc   59280
cagcctgggc gacagagcga gactccgtct caaaaaaaaa aaaaaaaaaa aaaaaaaaa    59340 gcgttagggg tgtgacgtgc ttggaatagg catggcaca tggtgacctc ccagggcctt    59400
aagcagtgac agtggggagt gatatactcc tatcctttct cgcccttctc aatgaagcca   59460
gtttctctga ttagcttgtc aatattgagc ctttggggta tcttggttgc atttttagtt   59520
acagagtgcg cttgcagaac cctctcttct ccttggccgc tggcagctgt tctctgctct   59580
ccctgcctct gtcgtgcttg gcctcctcag caagcctgtt ggctgtgggc gtccccagta   59640
ctccgtctgc atgcacactc cttggggagt ctcagccacc tgggttctgg ccccacctcc   59700
aagctggtga acctgggtct ccacccagtg gccaggtgcc ttctgccgga cgcctttgcc   59760
tgcctgtccc acactggctc ctcctccaag gctccttgac tgttggtggc agcaccatct   59820
gacctagagc tggagtcttt ttccttgggg aggggcgtc ccttgccctt agtgatgttg    59880
atttctgcca gtgggctgct gccgtcattc ctgtcaccac aggttctgca tgggctttgg   59940
ctgacatcct cccctccagc ctggccaatt tcaccaggcc cctccatgct tcttggaaat   60000
tctcctttgc tgcttgtttt agctttaagg aaagcccga tgtctcaacc tgaccatcag    60060
ggttcctggt gactgtggtc tctccttgtc cacccacttc caatcataaa actggcttcc   60120
ccagctctgg tgcaggccct tcaaattcat gggcagaggt tgtaggcaga catgcattgc   60180 ctttcccctgc agtaagattt tgaacccat ctgctttgag gctttggggt tactgggcaa    60240
atatacccat ccctgcctgt cagactgtac ctaggaattt tggagagcaa agaaaatcct   60300
tgtttcttta tggaaaaagg aattgatgtg agctgtgctt gggttgaagc tgcttttatg   60360
tggagaatgc aggcttccgc aacacccaac atagcccacc ctgcatcctg tttcccctca   60420
gcagccctcc cttcagctcc aggctacatg gagccctctg cttgttttta atttacaaac   60480
ttacgtgata ttcaccaggt accacctac acgttagctc acttgattct catgaccacc    60540
ctgtgaggtg ggtactctta tccccatttt acggatgaag aaactgaggc acaaggtggt   60600
taatatttgg agttgccctc tggctccagc atctgttctg gcaccatgtg ctttcctctt   60660
ggccatgtcc ctcctgtgcc ttcttgaact ggcccttaac tctcatgtcc acatgctcag   60720
ccccagggct ggggctctaa gggagaggcc cctggcagct gttcttctct tccaggattg   60780
```

```
tggctgcacg gctcaacggt tcccttgatt tcttctcctt ggagacccac actgccctca    60840
gcccctgca gtttagaggt cggagggcct ggggtgggca ggtgttcaca cttggtggga    60900
cgggcagggg ccgtctaccc attgctttct cagagattct tcacttggcc ttttgtcctc    60960
agggacccca gggcggggca gttccctgc ctctccagtg tacagcagca gcgacacagt    61020
ggcctgtcac ctgacccaca cagtgccctg tgcacaccaa aaacccatca cagccctgaa    61080
agccgctgct gggcgcttgg tgactgggag ccaagaccac acactgagag tgagtattgt    61140
cttgtctctt gggtgctgga gtggcccggc acggggtggg agcctgatgc attcgtcagg    61200
gagaggctgg aagagtcctg atgaagaaca gagggcattt cccagccaaa gtataacttg    61260
gaaaatccca gagaccagaa cctgaggccc atccctgtcc caggtgttcc gtctggagga    61320
ctcgtgctgc ctcttcaccc ttcagggcca ctcaggggcc atcacgaccg tgtacattga    61380
ccaggtaagc ggcctgcagg tggggtaggg ggtacagagt ctgtggccca tgtttgctga    61440
ctcctgggag ctggtcccca ggggccttcc aggaagcagt cagggcccca cccactgggg    61500
cacagggaca ccactgttga cagaggtatt acaccatggt gaccccactc ccctggcctg    61560
tttccccaga ccatggtgct ggccagtgga ggacaagatg gggccatctg cctgtgggat    61620
gtactgactg gcagccgggt cagccatgtg tttgctcacc gtggggatgt cacctcccttt    61680
acctgtacca cctcctgtgt catcagcagt ggcctggatg acctcatcag catctgggac    61740
cgcagcacag gcatcaagtt ctactccatt cagcaggtag aggggatggg gatcatagga    61800
ttcttgggat tttagggaag gactcaggac tgagcttgtc atgtccttgc ctccaggacc    61860
tgggctgtgg tgcaagcttg ggtgtcatct cagacaacct gctggtgact ggcggccagg    61920
gctgtgtctc cttttgggac ctaaactacg gggacctgtt acagtctacc tggggaagaa    61980
cagtgaggcc cagcctgccc gccagatcct ggtgctggac aacgctgcca ttgtctgcaa    62040
ctttggcagt gagctcagcc tggtgtatgt gccctctgtg ctggagaagc tggactgagc    62100
gcagggcctc cttcccagg caggaggctg gggtgctgtg tgggggccaa tgcactgaac    62160
ctggacttgg gggaaagagc cgagtatctt ccagccgctg cctcctgact gtaataatat    62220
taaactttt taaaaaacca tatcatcatc tgtcaggcac tttggga                    62267

<210> SEQ ID NO 3
<211> LENGTH: 4421
<212> TYPE: DNA
<213> ORGANISM: homo sapien

<400> SEQUENCE: 3
acgcuccgcc cggcccggcc cggcccggcc guccauacuu cccuccggug uccaccagag      60
ggcgaacggg agacgcgaau gugguucgac uacgcaugcg cacgccgcug ggcgcacgug     120
cggagggcgg cggggcggga ggguaaaggu aggaggugag aggugaaggg gcgggcaccc     180
ggcggccagg agagagaggg agggcgccac gcaccggacu gcgggccgag agcgcgcacg     240
ccgcgcuccg ccccugcugc cgccccguc gccgccgccg ccgccgccgc agcuugggag     300
gugcugccac cacaggguacc ugcacauguu guucuuugc agugcugucaa gugugugcc     360
agggugaucc auggucacuu uccgggaugg cagcaaggug acuucggcug aggaugaccc     420
ugacugaaag gcugcgugag aagauaucuc gggccuucua caaccauggg cuccucugug    480
cauccuaucc cauccccauc auccucuuca cagggucug cauucuuagcc ugcugcuacc    540
cacugcugaa acuccccuug ccaggaacag gaccugugga auucaccacc ccugugaagg    600
```

```
auuacucgcc cccaccugug gacucugacc gcaaacaagg agagccuacu gagcagccug    660
agugguaugu gggugccccg guggcuuaug uccagcagau auuugugaag uccucagugu    720
uucccuggca caagaaccuc cuggcaguag auguauuucg uucaccuuug ucccgggcau    780
uccaacuggu ggaggagauc cggaaccacg ugcugagaga cagcucuggg aucaggagcu    840
uggaggaguu gugucugcaa ugaccgaccu gcugccaggc ccuuaggaag cucaggaacc    900
uacucccuga gcauggaugc cugcugcugu ccccugggaa cuucggcag aaugacuggg     960 aacgcuucca ugcugauccu gacaucauug ggaccaucca ccagcacgag ccuaaaaccc   1020
ugcagacuuc agccacacuc aaagacuugu auuuggugu uccugggaag uacagcgggg    1080
ugagccucua caccaggaag aggauggucu ccuacaccau cacccugguc uuccagcacu   1140
accaugccaa guuccugggc agccugcgug cccgccugau gcuucugcac cccagcccca   1200
acugcagccu ucgggcggag agccugguac acgugcacuu caaggaggag auuggugucg   1260
cugagcucau cccccuugug accaccuaca ucaucuuguu ugccuacauc uacuucucca   1320
cgcggaagau cgacauggu c aaguccaagu gggggcuggc ccuggcugcc guggucacag   1380
ugcucagcuc gcugcucaug ucuguggga c ucugcacacu cuucggccug acgcccaccc   1440
ucaauggcgg cgagauuuuc cccuaccuug uggugguuau ugggui1agag aaugucuugg   1500 ugcucaccaa gucugugguc ucaacccggg uagaccugga ggugaagcug cggaucgccc   1560
aaggccuaag cagcgagagc uggu.ccauca ugaagaacau ggccacgagc cugggcauca   1620
uccucaucgg cuacuucacc cuagugcccg ccauccagga guucugucuc uuugcugucg   1680
uggggcuggu gucugacuuc uuccuucaga ugcuguuuuu caccacuguc cugucccauug   1740 acauucgccg gauggagcua gcagaccuga acaagcgacu gccccccugag gccugccugc   1800 ccucagccaa gccagggga cagccaacgc gcuacgagcg cagcuggcu gugaggccgu     1860 ccacaccccg caccaucacg uugcagccgu cuuccuuccg aaaccugcgg cucccaagaa   1920
ggcugcgugu ugucuacuuc cuggcccgca cccgccuggc acagcgccuc aucauggcug   1980
gcaccguugu cuggauuggc auccugguau acacagaccc agcagggcug cgcaacuacc   2040
ucgcugccca ggugacggaa cagagcccau ugggugaggg agcccuggcu cccaugcccg   2100
ugccuagugg caugcugccc cccagccacc cggacccugc cuucuccauc uucccaccug   2160 augcccuaa gcuaccugag aaccagacgc cgccaggcga gucaccugag cgugggauc   2220 cagcagaggu uguccaugac agcccagucc cagagguaac cuggggggccu gaggaugagg   2280 aacuuuggag gaaauugucc uuccgccacu ggccgacgcu cuucagcuau acaacauca    2340 cacuggccaa gagguacauc agccugcugc ccguucuccc agcacgcuc cgccugaacc    2400 cgagggaggc ucuggaggc cggcaccccuc aggacgccg cagugccugg ccccaccgg    2460 ggcccauacc ugcugggcac ugggaagcag gacccaaggg cccagguggg gugcaggccc   2520
auggagacgu cacgcuguac aaggugggcg cgcugggccu ggccaccggc aucgucuugg   2580
ugcugcugcu gcucugccuc uaccgcgugc uaugcccgcg caacuacggg cagcggggug   2640 gugggccgg gcggcggagg cgcggggagc ugcccugcga cgacacggc uaugcgccac    2700 ccgagacgga gaucgugccg cuugugcugc gcggccaccu cauggacauc gagugccugg   2760
ccagcgacgg caugcugcug gugagcugcu ccugggcagg ccacgucugc gugugggacg   2820
cgcagaccgg ggauugccua acgcgcauuc gcgcccagg caggcagcgc cgggacagug   2880 gcguggggcag cgggcuugag gcucaggaga gcugggaacg acuuucagau gguggaaggg   2940
cugguccaga ggagccuggg gacagcccuc cccugagaca ccgcccccgg ggcccuccgc   3000
```

| | |
|---|---|
| cgccuucccu cuucggggac cagccugacc ucaccugcuu aauugacacc aacuuuucag | 3060 |
| cgcagccucg guccucacag cccacucagc ccgagccccg gcaccgggcg ucuguggcc | 3120 |
| gcucucggga cuccccaggc uaugacuuca gcugccuggu gcagcgggug uaccaggagg | 3180 |
| aggggcuggc ggccgucugc acaccagccc ugcgcccacc cucgccuggg ccggugcugu | 3240 |
| cccaggcccc ugaggacgag gguggcuccc ccgagaaagg cuccccuucc cucgccuggg | 3300 |
| cccccagugc cgaggguucc aucuggagcu uggagcugca gggcaaccuc aucguggugg | 3360 |
| ggcggagcag cggccggcug gaggugugg acgccauuga aggggugcug ugcugcagca | 3420 |
| gcgaggaggu cuccucaggc auuaccgcuc uggguguucu ggacaaaagg auuguggcug | 3480 |
| cacggcucaa cgguucccuu gauuucuucu ccuuggagac ccacacugcc cucagccccc | 3540 |
| ugcaguuuag agggacccca gggcggggca guucccccugc cucuccagug uacagcagca | 3600 |
| gcgacacagu ggccugucac cugacccaca cagugcccug ugcacaccaa aaacccauca | 3660 |
| cagcccugaa agccgcugcu gggcgcuugg ugacugggag ccaagaccac acacugagag | 3720 |
| uguccgucu ggaggacucg cugcugccucu ucacccuuca gggccacuca ggggccauca | 3780 |
| cgaccgugua cauugaccag accauggugc uggccagugg aggacaagau gggggccaucu | 3840 |
| gccugugggga uguacugacu ggcagccggg ucagccaugu guuugcucac cgugggaug | 3900 |
| ucaccucccu uaccguacc accuccugug uaucagcag uggccuggau gaccucauca | 3960 |
| gcaucuggga ccgcagcaca ggcaucaagu ucuaucccau ucagcaggac cugggcugug | 4020 |
| gugcaagcuu gggugucauc ucagacaacc ugcggugac uggcggccag ggcugugucu | 4080 |
| ccuuuuggga ccuaaacuac ggggaccugu uacagacagu cuaccggggg aagaacagug | 4140 |
| aggcccagcc ugcccgccag auccuggugc uggacaacgc ugccauugc ugcaacuuug | 4200 |
| gcagugagcu cagccuggug uaugugcccu cugugcugga aagcuggac ugagcgcagg | 4260 |
| gccuccuugc ccaggcagga ggcuggggu cugugugggg gccaaugcac ugaaccugga | 4320 |
| cuuggggggaa agagccgagu aucuuccagc cgcugccucc ugacuguaau aauauuaaac | 4380 |
| uuuuuuaaaa aacctaucau caucugucag gcacuuuggg a | 4421 |

<210> SEQ ID NO 4
<211> LENGTH: 4417
<212> TYPE: DNA
<213> ORGANISM: homo sapien

<400> SEQUENCE: 4

| | |
|---|---|
| acgcuccgcc cggcccggcc cggcccggcc guccauacuu ccuccggug uccaccagag | 60 |
| ggcgaacggg agacgcgaau gugguucgac uacgcaugcg cacgccgcug ggcgcacgug | 120 |
| cggagggcg cggggcggga ggguaaaggu aggaggugag aggugaaggg gcgggcaccc | 180 |
| ggcggccagg agagagaggg agggcgccac gcaccggacu gcgggccgag agcgcgcacg | 240 |
| ccgcgcuccg ccccugcugc cgccccguc gccgccgccg ccgccgccgc agcuugggag | 300 |
| gugcugccac cacagguacc ugcacauguu guucuuuguc agugcugucu agugugugcc | 360 |
| agggugaucc auggucacuu uccgggaugg cagcaaggug acuucggcug aggaugaccc | 420 |
| ugacugaaag gcugcgugag aagauaucuc gggccuucua caaccauggg cucucucugu | 480 |
| cauccuaucc cauccccauc auccucuuca cagggauucug caucuuagcc ugcugcuacc | 540 |
| cacugcugaa acuccccuug ccaggaacag gaccugugga auucaccacc ccugugaagg | 600 |
| auuacucgcc cccaccugug gacucugacc gcaaacaagg agagccuacu gagcagccug | 660 |

-continued

| | |
|---|---|
| agugguaugu ggguglcccg guggcuuaug uccagcagau auuugugaag uccucagugu | 720 |
| uccccuggca caagaaccuc cuggcaguag auguauuucg ucaccuuug ucccgggcau | 780 |
| uccaacuggu ggaggagauc cggaaccacg ugcugagaga cagcucuggg aucaggagcu | 840 |
| uggaggaguu gugucugcaa ugaccgacc ugcugccagg ccuuaggaag cucaggaacc | 900 |
| uacucccuga gcauggaugc cugcugcugu ccccugggaa cuucuggcag aaugacuggg | 960 |
| aacgcuucca ugcugauccu gacaucauug ggaccaucca ccagcacgag ccuaaaaccc | 1020 |
| ugcagacuuc agccacacuc aaagacuugu auuugugugu uccugggaag uacagcgggg | 1080 |
| ugagccucua caccaggaag aggauggucu ccuacaccau cacccuggguc uuccagcacu | 1140 |
| accaugccaa guuccugggc agccugcgug cccgccugau gcuucugcac cccagcccca | 1200 |
| acugcagccu ucgggcggag agccuggucc acgugcacuu caaggaggag auugugucg | 1260 |
| cugagcucau cccccuugug accaccuaca ucaucuuguu ugccuacauc uacuucucca | 1320 |
| cgcggaagau cgacauggguc aaguccaagu gggggcuggc ccuggcugcc ggugucacag | 1380 |
| ugcucagcuc gcugcucaug ucuguggggac ucugcacacu cuucggccug acgcccaccc | 1440 |
| ucaauggcgg cgagauuuuc cccuaccuug ugguguuau uggguuagag aaugguguugg | 1500 |
| ugcucaccaa gucuguggguc ucaaccccgg uagaccugga ggugaagcug cggaucgccc | 1560 |
| aaggccuaag cagcgagagc uggucccauca ugaagaacau ggccacggag cugggcauca | 1620 |
| uccucaucgg cuacuuccacc cuagugcccg ccauccagga guucugucuc uuugcugucg | 1680 |
| uggggcuggu gucugacuuc uuccuucaga ugcuguuuuu caccacuguc cuguccauug | 1740 |
| acauucgccg gauggagcua gcagaccuga acaagcgacu gccccccugag gccugccugc | 1800 |
| ccucagccaa gccaguggga cagccaacgc gcuacgagcg cagcuggcu gugaggccgu | 1860 |
| ccacaccccca caccaucacg uugcagccgu cuuccuuccg aaaccugcgg cuccccaaga | 1920 |
| ggcugcgugu ugucuacuuc cuggcccgca cccgccuggc acagcgccuc aucauggcug | 1980 |
| gcaccguugu cuggauugggc auccugguau acacagaccc agcagggcug cgcaacuacc | 2040 |
| ucgcugccca ggugacggaa cagagcccau ugggugaggg agcccuggcu cccaugcccg | 2100 |
| ugccuagugg caugcugccc cccagccacc cggacccugc cuucuccauc uucccaccug | 2160 |
| augcccccuaa gcuaccugag aaccagacgu cgccaggcga gucaccugag cguggaugguc | 2220 |
| cagcagaggu ugucccaugac agccccaguccc cagagguaac cugggggccu gaggaugagg | 2280 |
| aacuuuggag gaaauugucc uuccgccacu ggccgacgcu cuucagcuau acaacauca | 2340 |
| cacuggccaa gagguacauc agccugcugc ccgucauccc agucacgcuc cgccugaacc | 2400 |
| cgagggaggc ucuggagggc cggcacccuc aggacggccg cagugccugg ccccaccgg | 2460 |
| ggcccauacc ugcugggcac ugggaagcag gacccaaggg cccaggugggg gugcaggccc | 2520 |
| auggagacgu cacgcuguac aagguggcgg cgcugggccu ggccaccggc aucgucuugg | 2580 |
| ugcugcugcu gcucugccuc uaccgcgugc uaugcccgcg caacuacggg cagcuggguug | 2640 |
| gugggcccgg gcgcggagg cgcggggagc ugcccgcga cgacuacggc uaugcgccac | 2700 |
| ccgagacgga gaucgugccg cuugugcugc gcggccaccu caugggacauc gagugccugg | 2760 |
| ccagcgacgg caugcugcug gugagcugcu ccuggcagg ccacgucugc guguggggacg | 2820 |
| cgcagaccgg ggauugccua acgcgcauuc cgcgcccagg caggcagcgc cgggacagug | 2880 |
| gcguggggcag cgggcuugag gcucaggaga gcugggaacg acuucagau ggugggaagg | 2940 |
| cugguccaga ggagccuggg gacagcccuc cccgagaca ccgcccccgg ggcccuccgc | 3000 |
| cgccuucccu cuucggggac cagccugacc ucaccugcuu aauugacacc aacuuuucag | 3060 |

| | | | | | |
|---|---|---|---|---|---|
| cgcagccucg | guccucacag | cccacucagc | ccgagccccg | gcaccgggcg | gucuguggcc | 3120 |
| gcucucggga | cuccccaggc | uaugacuuca | gcugccuggu | gcagcgggug | uaccaggagg | 3180 |
| aggggcuggc | ggccgucugc | acaccagccc | ugcgcccacc | cucgccuggg | ccggugcugu | 3240 |
| cccaggcccc | ugaggacgag | gguggcuccc | ccgagaaagg | cuccccuucc | cucgccuggg | 3300 |
| cccccagugc | cgagggguucc | aucuggagcu | uggagcugca | gggcaaccuc | aucgguggug | 3360 |
| ggcggagcag | cggccggcug | gaggugugggg | acgccauuga | aggggugcug | ugcugcagca | 3420 |
| gcgaggaggu | cuccucaggc | auuaccgcuc | uggguguucuu | ggacaaaagg | auuguggcug | 3480 |
| cacggcucaa | cgguucccuu | gauuucuucu | ccuuggagac | ccacacugcc | cucagccccc | 3540 |
| ugcaguuuag | agggaccccca | gggcggggca | guuccccugc | cucuccagug | uacagcagca | 3600 |
| gcgacacagu | ggccugucac | cugacccaca | cagugcccug | ugcacaccaa | aaacccauca | 3660 |
| cagcccugaa | agccgcugcu | gggcgcuugg | ugacugggag | ccaagaccac | acacugagag | 3720 |
| uguuccgucu | ggaggacucg | ugcugccucu | ucacccuuca | gggccacuca | ggggccauca | 3780 |
| cgaccgugua | cauugaccag | accauggugc | uggccagugg | aggacaagau | ggggccaucu | 3840 |
| gccugugggga | uguacugacu | ggcagccggg | ucagccaugu | guuugcucac | cguggggaug | 3900 |
| ucaccucccu | uaccuguacc | accuccugug | ucaucagcag | uggccuggau | gaccucauca | 3960 |
| gcaucuggga | ccgcagcaca | ggcaucaagu | ucuauuccau | ucagcaggac | cugggcugug | 4020 |
| gugcaagcuu | ggggucauc | ucagacaacc | ugcuggugac | uggcggccag | ggcuguguucu | 4080 |
| ccuuuuggga | ccuaaacuac | ggggaccugu | uacagucuac | cugggggaaga | acagugaggc | 4140 |
| ccagccugcc | cgccagaucc | uggugcugga | caacgcugcc | auugucugca | acuuuggcag | 4200 |
| ugagcucagc | cugguguaug | ugcccucugu | gcugagaaag | cuggacugag | cgcagggccu | 4260 |
| ccuugcccag | gcaggaggcu | ggggugcugu | gugggggcca | augcacugaa | ccuggacuug | 4320 |
| ggggaaagag | ccgaguaucu | uccagccgcu | gccuccugac | uguaauaaua | uuaaacuuuu | 4380 |
| uuaaaaaacc | uaucaucauc | ugucaggcac | uuuggga | | | 4417 |

<210> SEQ ID NO 5
<211> LENGTH: 4422
<212> TYPE: DNA
<213> ORGANISM: homo sapien

<400> SEQUENCE: 5

| | | | | | |
|---|---|---|---|---|---|
| acgctccgcc | cggcccggcc | cggcccggcc | gtccatactt | ccctccggtg | tccaccagag | 60 |
| ggcgaacggg | agacgcgaat | gtggttcgac | tacgcatgcg | cacgccgctg | ggcgcacgtg | 120 |
| cggagggcgg | cggggcggga | gggtaaaggt | aggaggtgag | aggtgaaggg | gcgggcaccc | 180 |
| ggcggccagg | agagagaggg | agggcgccac | gcaccggact | gcgggccgag | agcgcgcacg | 240 |
| ccgcgctccg | ccccctgctgc | cgccccgtc | gccgccgccg | ccgccgccgc | agcttgggag | 300 |
| gtgctgccac | cacaggtacc | tgcacatgtt | gttctttgtc | agtgctgtca | agtgtgtgcc | 360 |
| agggtgatcc | atggtcactt | tccgggatgg | cagcaaggtg | acttcggctg | aggatgaccc | 420 |
| tgactgaaag | gctgcgtgag | aagatatctc | gggccttcta | caaccatggg | ctcctctgtg | 480 |
| catcctatcc | catccccatc | atcctcttca | cagggttctg | catcttagcc | tgctgctacc | 540 |
| cactgctgaa | actccccttg | ccaggaacag | gacctgtgga | attcaccacc | cctgtgaagg | 600 |
| attactcgcc | cccacctgtg | gactctgacc | gcaaacaagg | agagcctact | gagcagcctg | 660 |
| agtggtatgt | gggtgccccg | gtggcttatg | tccagcagat | atttgtgaag | tcctcagtgt | 720 |

```
ttccctggca caagaacctc ctggcagtag atgtatttcg ttcacctttg tcccgggcat    780
tccaactggt ggaggagatc cggaaccacg tgctgagaga cagctctggg atcaggagct    840
tggaggagtt gtgtctgcaa gtgaccgacc tgctgccagg ccttaggaag ctcaggaacc    900
tactccctga gcatggatgc ctgctgctgt cccctgggaa cttctggcag aatgactggg    960
aacgcttcca tgctgatcct gacatcattg ggaccatcca ccagcacgag cctaaaaccc   1020
tgcagacttc agccacactc aaagacttgt tatttggtgt tcctgggaag tacagcgggg   1080
tgagcctcta caccaggaag aggatggtct cctacaccat caccctggtc ttccagcact   1140
accatgccaa gttcctgggc agcctgcgtg cccgcctgat gcttctgcac cccagcccca   1200
actgcagcct tcgggcggag agcctggtcc acgtgcactt caaggaggag attggtgtcg   1260
ctgagctcat ccccttgtg accacctaca tcatcttgtt tgcctacatc tacttctcca   1320
cgcggaagat cgacatggtc aagtccaagt gggggctggc cctggctgcc gtggtcacag   1380
tgctcagctc gctgctcatg tctgtgggac tctgcacact cttcggcctg acgcccaccc   1440
tcaatggcgg cgagattttc ccctaccttg tggtggttat tgggttagag aatgtgttgg   1500
tgctcaccaa gtctgtggtc tcaaccccgg tagacctgga ggtgaagctg cggatcgccc   1560
aaggcctaag cagcgagagc tggtccatca tgaagaacat ggccacgag ctgggcatca   1620
tcctcatcgg ctacttcacc ctagtgcccg ccatccagga gttctgtctc tttgctgtcg   1680
tggggctggt gtctgacttc ttccttcaga tgctgttttt caccactgtc ctgtccattg   1740
acattcgccg gatggagcta gcagacctga acaagcgact gccccctgag gcctgcctgc   1800
cctcagccaa gccagtggga cagccaacgc gctacgagcg gcagctggct gtgaggccgt   1860
ccacacccca caccatcacg ttgcagccgt ctttccttccg aaacctgcgg ctccccaaga   1920
ggctgcgtgt tgtctacttc ctggcccgca cccgcctggc acagcgcctc atcatggctg   1980
gcaccgttgt ctggattggc atcctggtat acacagaccc agcagggctg cgcaactacc   2040
tcgctgccca ggtgacggaa cagagcccat gggtgaggg agccctggct cccatgcccg   2100
tgcctagtgg catgctgccc cccagccacc cggaccctgc cttctccatc ttcccacctg   2160
atgcccctaa gctacctgag aaccagacgt cgccaggcga gtcacctgag cgtggaggtc   2220
cagcagaggt tgtccatgac agcccagtcc cagaggtaac ctgggggcct gaggatgagg   2280
aactttggag gaaattgtcc ttccgccact ggccgacgct cttcagctat acaacatca    2340
cactggccaa gaggtacatc agcctgctgc ccgtcatccc agtcacgctc cgcctgaacc    2400
cgagggaggc tctggagggc cggcaccctc aggacggccg cagtgcctgg cccccaccgg    2460
ggcccatacc tgctgggcac tgggaagcag gacccaaggg cccaggtggg gtgcaggccc    2520
atggagacgt cacgctgtac aaggtggcgg cgctgggcct ggccaccggc atcgtcttgg    2580
tgctgctgct gctctgcctc taccgcgtgc tatgcccgcg caactacggg cagctgggtg    2640
gtgggcccgg gcggcggagg cgcggggagc tgccctgcga cgactacggc tatgcgccac    2700
ccgagacgga gatcgtgccg cttgtgctgc gcggccacct catggacatc gagtgcctgg    2760
ccagcgacgg catgctgctg gtgagctgct gcctggcagg ccacgtctgc gtgtgggacg    2820
cgcagaccgg ggattgccta acgcgcattc gcgcccagg caggcagcgc cgggacagtg    2880
gcgtgggcag cgggcttgag gctcaggaga gctgggaacg actttcagat ggtgggaagg    2940
ctggtccaga ggagcctggg gacagccctc ccctgagaca ccgccccgg ggccctccgc    3000
cgccttccct cttcggggac cagcctgacc tcacctgctt aattgacacc aacttttcag    3060
cgcagcctcg gtcctcacag cccactcagc ccgagcccg gcaccgggcg gtctgtggcc    3120
```

```
gctctcggga ctccccaggc tatgacttca gctgcctggt gcagcgggtg taccaggagg    3180 agggggctggc ggccgtctgc acaccagccc tgcgcccacc ctcgcctggg ccggtgctgt    3240
cccaggcccc tgaggacgag ggtggctccc ccgagaaagg ctccccttcc ctcgcctggg    3300
cccccagtgc cgagggttcc atctggagct tggagctgca gggcaacctc atcgtggtgg    3360
ggcggagcag cggccggctg gaggtgtggg acgccattga aggggtgctg tgctgcagca    3420
gcgaggaggt ctcctcaggc attaccgctc tggtgttctt ggacaaaagg attgtggctg    3480
cacggctcaa cggttccctt gatttcttct ccttggagac ccacactgcc ctcagccccc    3540
tgcagtttag agggacccca gggcggggca gttcccctgc ctctccagtg tacagcagca    3600
gcgacacagt ggcctgtcac ctgacccaca cagtgccctg tgcacaccaa aaacccatca    3660
cagccctgaa agccgctgct gggcgcttgg tgactgggag ccaagaccac acactgagag    3720
tgttccgtct ggaggactcg tgctgcctct tcacccttca gggccactca ggggccatca    3780
cgaccgtgta cattgaccag accatggtgc tggccagtgg aggacaagat ggggccatct    3840
gcctgtggga tgtactgact ggcagccggg tcagccatgt gtttgctcac cgtggggatg    3900
tcacctccct tacctgtacc acctcctgtg tcatcagcag tggcctggat gacctcatca    3960
gcatctggga ccgcagcaca ggcatcaagt tctactccat tcagcaggac ctgggctgtg    4020
gtgcaagctt gggtgtcatc tcagacaacc tgctggtgac tggcggccag ggctgtgtct    4080 cctttttggga cctaaactac ggggacctgt tacagacagt ctacctgggg aagaacagtg    4140
aggcccagcc tgcccgccag atcctggtgc tggacaacgc tgccattgtc tgcaactttg    4200
gcagtgagct cagcctggtg tatgtgccct ctgtgctgga gaagctggac tgagcgcagg    4260
gcctccttgc ccaggcagga ggctggggtg ctgtgtgggg gccaatgcac tgaacctgga    4320
cttgggggaa agagccgagt atcttccagc cgctgcctcc tgactgtaat aatattaaac    4380
ttttttaaaa aaccatatca tcatctgtca ggcacttggg ga    4422

<210> SEQ ID NO 6
<211> LENGTH: 4418
<212> TYPE: DNA
<213> ORGANISM: homo sapien

<400> SEQUENCE: 6
acgctccgcc cggcccggcc cggcccggcc gtccatactt ccctccggtg tccaccagag      60
ggcgaacggg agacgcgaat gtggttcgac tacgcatgcg cacgccgctg ggcgcacgtg     120
cggagggcgc cggggcggga gggtaaaggt aggaggtgag aggtgaaggg gcgggcaccc     180
ggcggccagg agagagaggg agggcgccac gcaccggact gcgggccgag agcgcgcacg     240
ccgcgctccg ccctgctgc cgccccgtc gccgccgccg ccgccgccgc agcttgggag     300
gtgctgccac cacaggtacc tgcacatgtt gttcttgtc agtgctgtca agtgtgtgcc     360
agggtgatcc atggtcactt tccgggatgg cagcaaggtg acttcggctg aggatgaccc    420
tgactgaaag gctgcgtgag aagatatctc gggccttcta caaccatggg ctcctctgtg     480
catcctatcc catccccatc atcctcttca cagggttctg catcttagcc tgctgctacc     540
cactgctgaa actcccctttg ccaggaacag gacctgtgga attcaccacc cctgtgaagg     600
attactcgcc cccacctgtg gactctgacc gcaaacaagg agagcctact gagcagcctg     660
agtggtatgt gggtgccccg gtggcttatg tccagcagat atttgtgaag tcctcagtgt     720
ttccctggca caagaacctc ctggcagtag atgtatttcg ttcacctttg tcccgggcat     780
```

```
tccaactggt ggaggagatc cggaaccacg tgctgagaga cagctctggg atcaggagct    840
tggaggagtt gtgtctgcaa gtgaccgacc tgctgccagg ccttaggaag ctcaggaacc    900
tactccctga gcatggatgc ctgctgctgt cccctgggaa cttctggcag aatgactggg    960
aacgcttcca tgctgatcct gacatcattg ggaccatcca ccagcacgag cctaaaaccc   1020
tgcagacttc agccacactc aaagacttgt tatttggtgt tcctgggaag tacagcgggg   1080
tgagcctcta caccaggaag aggatggtct cctacaccat caccctggtc ttccagcact   1140
accatgccaa gttcctgggc agcctgcgtg cccgcctgat gcttctgcac cccagcccca   1200
actgcagcct tcgggcggag agcctggtcc acgtgcactt caaggaggag attggtgtcg   1260
ctgagctcat cccccttgtg accacctaca tcatcttgtt tgcctacatc tacttctcca   1320
cgcggaagat cgacatggtc aagtccaagt ggggctggc cctggctgcc gtggtcacag   1380
tgctcagctc gctgctcatg tctgtgggac tctgcacact cttcggcctg acgcccaccc   1440
tcaatggcgg cgagatttc ccctaccttg tggtggttat tgggttagag aatgtgttgg   1500
tgctcaccaa gtctgtggtc tcaaccccgg tagacctgga ggtgaagctg cggatcgccc   1560
aaggcctaag cagcgagagc tggtccatca tgaagaacat ggccacggag ctgggcatca   1620
tcctcatcgg ctacttcacc ctagtgcccg ccatccagga gttctgtctc tttgctgtcg   1680
tggggctggt gtctgacttc ttccttcaga tgctgttttt caccactgtc ctgtccattg   1740
acattcgccg gatggagcta gcagacctga caagcgact gccccctgag gcctgcctgc   1800
cctcagccaa gccagtggga cagccaacgc gctacgagcg gcagctggct gtgaggccgt   1860
ccacacccca caccatcacg ttgcagccgt cttccttccg aaacctgcgg ctccccaaga   1920
ggctgcgtgt tgtctacttc ctggcccgca cccgcctggc acagcgcctc atcatggctg   1980
gcaccgttgt ctggattggc atcctggtat acacagaccc agcagggctg cgcaactacc   2040
tcgctgccca ggtgacggaa cagagcccat gggtgaggg agccctggct cccatgcccg   2100
tgcctagtgg catgctgccc ccagccacc cggaccctgc cttctccatc ttcccacctg   2160
atgcccctaa gctacctgag aaccagacgt cgccaggcga gtcacctgag cgtggaggtc   2220
cagcagaggt tgtccatgac agcccagtcc cagaggtaac ctgggggcct gaggatgagg   2280
aactttggag gaaattgtcc ttccgccact ggccgacgct cttcagctat tacaacatca   2340
cactggccaa gaggtacatc agcctgctgc ccgtcatccc agtcacgctc cgcctgaacc   2400
cgagggaggc tctggagggc cggcaccctc aggacggccg cagtgcctgg cccccaccgg   2460
ggcccatacc tgctgggcac tgggaagcag gacccaaggg cccaggtggg gtgcaggccc   2520
atggagacgt cacgctgtac aaggtggcgg cgctgggcct ggccaccggc atcgtcttgg   2580
tgctgctgct gctctgcctc taccgcgtgc tatgcccgcg caactacggg cagctgggtg   2640
gtgggcccgg gcggcggagg cgcggggagc tgccctgcga cgactacggc tatgcgccac   2700
ccgagacgga gatcgtgccg cttgtgctgc gcggccacct catggacatc gagtgcctgg   2760
ccagcgacgg catgctgctg gtgagctgct gcctggcagg ccacgtctgc gtgtgggacg   2820
cgcagaccgg ggattgccta acgcgcattc gcgcccagg caggcagcgc cgggacagtg   2880
gcgtgggcag cgggcttgag gctcaggaga gctgggaacg actttcagat ggtgggaagg   2940
ctggtccaga ggagcctggg gacagccctc ccctgagaca ccgcccccgg ggccctccgc   3000
cgccttccct cttcggggac cagcctgacc tcacctgctt aattgacacc aactttttcag   3060 cgcagcctcg gtcctcacag cccactcagc ccgagcccg gcaccgggcg gtctgtggcc   3120
gctctcggga ctccccaggc tatgacttca gctgcctggt gcagcgggtg taccaggagg   3180
```

-continued

```
agggctggc ggccgtctgc acaccagccc tgcgcccacc ctcgcctggg ccggtgctgt   3240
cccaggcccc tgaggacgag ggtggctccc ccgagaaagg ctccccttcc ctcgcctggg   3300 ccccagtgc cgagggttcc atctggagct ggagctgca gggcaacctc atcgtggtgg    3360
ggcggagcag cggccggctg gaggtgtggg acgccattga aggggtgctg tgctgcagca   3420
gcgaggaggt ctcctcaggc attaccgctc tggtgttctt ggacaaaagg attgtggctg   3480
cacggctcaa cggttcccctt gatttcttct ccttggagac ccacactgcc ctcagccccc   3540
tgcagtttag agggaccca gggcggggca gttccctgc ctctccagtg tacagcagca    3600
gcgacacagt ggcctgtcac ctgacccaca cagtgccctg tgcacaccaa aaacccatca   3660
cagccctgaa agccgctgct gggcgcttgg tgactgggag ccaagaccac acactgagag   3720
tgttccgtct ggaggactcg tgctgcctct tcacccttca ggggccactca ggggccatca   3780 cgaccgtgta cattgaccag accatggtgc tggccagtgg aggacaagat ggggccatct   3840
gcctgtggga tgtactgact ggcagccggg tcagccatgt gtttgctcac cgtggggatg   3900
tcacctccct tacctgtacc acctcctgtg tcatcagcag tggcctggat gacctcatca   3960
gcatctggga ccgcagcaca ggcatcaagt tctactccat tcagcaggac ctgggctgtg   4020
gtgcaagctt gggtgtcatc tcagacaacc tgctggtgac tggcggccag ggctgtgtct   4080
ccttttggga cctaaactac ggggacctgt acagtctac ctggggaaga acagtgaggc    4140
ccagcctgcc cgccagatcc tggtgctgga caacgctgcc attgtctgca actttggcag   4200
tgagctcagc ctggtgtatg tgccctctgt gctggagaag ctggactgag cgcagggcct   4260
ccttgcccag gcaggaggct ggggtgctgt gtgggggcca atgcactgaa cctggacttg   4320
ggggaaagag ccgagtatct tccagccgct gcctcctgac tgtaataata ttaaactttt   4380
ttaaaaaacc atatcatcat ctgtcaggca ctttggga                          4418
```

<210> SEQ ID NO 7
<211> LENGTH: 1279
<212> TYPE: PRT
<213> ORGANISM: homo sapien

<400> SEQUENCE: 7

```
Met Thr Leu Thr Glu Arg Leu Arg Glu Lys Ile Ser Arg Ala Phe Tyr
1               5                   10                  15

Asn His Gly Leu Leu Cys Ala Ser Tyr Pro Ile Pro Ile Ile Leu Phe
                20                  25                  30

Thr Gly Phe Cys Ile Leu Ala Cys Cys Tyr Pro Leu Leu Lys Leu Pro
            35                  40                  45

Leu Pro Gly Thr Gly Pro Val Glu Phe Thr Thr Pro Val Lys Asp Tyr
        50                  55                  60

Ser Pro Pro Pro Val Asp Ser Asp Arg Lys Gln Gly Glu Pro Thr Glu
65                  70                  75                  80

Gln Pro Glu Trp Tyr Val Gly Ala Pro Val Ala Tyr Val Gln Gln Ile
                85                  90                  95

Phe Val Lys Ser Ser Val Phe Pro Trp His Lys Asn Leu Leu Ala Val
                100                 105                 110

Asp Val Phe Arg Ser Pro Leu Ser Arg Ala Phe Gln Leu Val Glu Glu
            115                 120                 125

Ile Arg Asn His Val Leu Arg Asp Ser Ser Gly Ile Arg Ser Leu Glu
        130                 135                 140

Glu Leu Cys Leu Gln Val Thr Asp Leu Leu Pro Gly Leu Arg Lys Leu
```

```
        145                 150                 155                 160
Arg Asn Leu Leu Pro Glu His Gly Cys Leu Leu Ser Pro Gly Asn
                165                 170                 175

Phe Trp Gln Asn Asp Trp Glu Arg Phe His Ala Asp Pro Asp Ile Ile
                180                 185                 190

Gly Thr Ile His Gln His Glu Pro Lys Thr Leu Gln Thr Ser Ala Thr
                195                 200                 205

Leu Lys Asp Leu Leu Phe Gly Val Pro Gly Lys Tyr Ser Gly Val Ser
    210                 215                 220

Leu Tyr Thr Arg Lys Arg Met Val Ser Tyr Thr Ile Thr Leu Val Phe
225                 230                 235                 240

Gln His Tyr His Ala Lys Phe Leu Gly Ser Leu Arg Ala Arg Leu Met
                245                 250                 255

Leu Leu His Pro Ser Pro Asn Cys Ser Leu Arg Ala Glu Ser Leu Val
                260                 265                 270

His Val His Phe Lys Glu Glu Ile Gly Val Ala Glu Leu Ile Pro Leu
                275                 280                 285

Val Thr Thr Tyr Ile Ile Leu Phe Ala Tyr Ile Tyr Phe Ser Thr Arg
    290                 295                 300

Lys Ile Asp Met Val Lys Ser Lys Trp Gly Leu Ala Leu Ala Ala Val
305                 310                 315                 320

Val Thr Val Leu Ser Ser Leu Leu Met Ser Val Gly Leu Cys Thr Leu
                325                 330                 335

Phe Gly Leu Thr Pro Thr Leu Asn Gly Gly Glu Ile Phe Pro Tyr Leu
                340                 345                 350

Val Val Val Ile Gly Leu Glu Asn Val Leu Val Leu Thr Lys Ser Val
                355                 360                 365

Val Ser Thr Pro Val Asp Leu Glu Val Lys Leu Arg Ile Ala Gln Gly
                370                 375                 380

Leu Ser Ser Glu Ser Trp Ser Ile Met Lys Asn Met Ala Thr Glu Leu
385                 390                 395                 400

Gly Ile Ile Leu Ile Gly Tyr Phe Thr Leu Val Pro Ala Ile Gln Glu
                        405                 410                 415

Phe Cys Leu Phe Ala Val Val Gly Leu Val Ser Asp Phe Phe Leu Gln
                420                 425                 430

Met Leu Phe Phe Thr Thr Val Leu Ser Ile Asp Ile Arg Arg Met Glu
                435                 440                 445

Leu Ala Asp Leu Asn Lys Arg Leu Pro Pro Glu Ala Cys Leu Pro Ser
    450                 455                 460

Ala Lys Pro Val Gly Gln Pro Thr Arg Tyr Glu Arg Gln Leu Ala Val
465                 470                 475                 480

Arg Pro Ser Thr Pro His Thr Ile Thr Leu Gln Pro Ser Ser Phe Arg
                485                 490                 495

Asn Leu Arg Leu Pro Lys Arg Leu Arg Val Val Tyr Phe Leu Ala Arg
                500                 505                 510

Thr Arg Leu Ala Gln Arg Leu Ile Met Ala Gly Thr Val Val Trp Ile
                515                 520                 525

Gly Ile Leu Val Tyr Thr Asp Pro Ala Gly Leu Arg Asn Tyr Leu Ala
                530                 535                 540

Ala Gln Val Thr Glu Gln Ser Pro Leu Gly Glu Gly Ala Leu Ala Pro
545                 550                 555                 560

Met Pro Val Pro Ser Gly Met Leu Pro Pro Ser His Pro Asp Pro Ala
                565                 570                 575
```

```
Phe Ser Ile Phe Pro Pro Asp Ala Pro Lys Leu Pro Glu Asn Gln Thr
            580                 585                 590

Ser Pro Gly Glu Ser Pro Glu Arg Gly Pro Ala Glu Val Val His
        595                 600                 605

Asp Ser Pro Val Pro Glu Val Thr Trp Gly Pro Glu Asp Glu Leu
610                 615                 620

Trp Arg Lys Leu Ser Phe Arg His Trp Pro Thr Leu Phe Ser Tyr Tyr
625                 630                 635                 640

Asn Ile Thr Leu Ala Lys Arg Tyr Ile Ser Leu Leu Pro Val Ile Pro
                645                 650                 655

Val Thr Leu Arg Leu Asn Pro Arg Glu Ala Leu Glu Gly Arg His Pro
            660                 665                 670

Gln Asp Gly Arg Ser Ala Trp Pro Pro Gly Pro Ile Pro Ala Gly
        675                 680                 685

His Trp Glu Ala Gly Pro Lys Gly Pro Gly Val Gln Ala His Gly
        690                 695                 700

Asp Val Thr Leu Tyr Lys Val Ala Ala Leu Gly Leu Ala Thr Gly Ile
705                 710                 715                 720

Val Leu Val Leu Leu Leu Cys Leu Tyr Arg Val Leu Cys Pro Arg
            725                 730                 735

Asn Tyr Gly Gln Leu Gly Gly Pro Gly Arg Arg Arg Gly Glu
        740                 745                 750

Leu Pro Cys Asp Asp Tyr Gly Tyr Ala Pro Pro Glu Thr Glu Ile Val
        755                 760                 765

Pro Leu Val Leu Arg Gly His Leu Met Asp Ile Glu Cys Leu Ala Ser
770                 775                 780

Asp Gly Met Leu Leu Val Ser Cys Cys Leu Ala Gly His Val Cys Val
785                 790                 795                 800

Trp Asp Ala Gln Thr Gly Asp Cys Leu Thr Arg Ile Pro Arg Pro Gly
                805                 810                 815

Arg Gln Arg Arg Asp Ser Gly Val Gly Ser Gly Leu Glu Ala Gln Glu
                820                 825                 830

Ser Trp Glu Arg Leu Ser Asp Gly Gly Lys Ala Gly Pro Glu Pro
        835                 840                 845

Gly Asp Ser Pro Pro Leu Arg His Arg Pro Arg Gly Pro Pro Pro
850                 855                 860

Ser Leu Phe Gly Asp Gln Pro Asp Leu Thr Cys Leu Ile Asp Thr Asn
865                 870                 875                 880

Phe Ser Ala Gln Pro Arg Ser Ser Gln Pro Thr Gln Pro Glu Pro Arg
                885                 890                 895

His Arg Ala Val Cys Gly Arg Ser Arg Asp Ser Pro Gly Tyr Asp Phe
                900                 905                 910

Ser Cys Leu Val Gln Arg Val Tyr Gln Glu Glu Gly Leu Ala Ala Val
            915                 920                 925

Cys Thr Pro Ala Leu Arg Pro Pro Ser Pro Gly Pro Val Leu Ser Gln
            930                 935                 940

Ala Pro Glu Asp Glu Gly Gly Ser Pro Glu Lys Gly Ser Pro Ser Leu
945                 950                 955                 960

Ala Trp Ala Pro Ser Ala Glu Gly Ser Ile Trp Ser Leu Glu Leu Gln
                965                 970                 975

Gly Asn Leu Ile Val Val Gly Arg Ser Ser Gly Arg Leu Glu Val Trp
            980                 985                 990
```

Asp Ala Ile Glu Gly Val Leu Cys Cys Ser Ser Glu Glu Val Ser Ser
               995                1000                1005

Gly Ile Thr Ala Leu Val Phe Leu Asp Lys Arg Ile Val Ala Ala
        1010                1015                1020

Arg Leu Asn Gly Ser Leu Asp Phe Phe Ser Leu Glu Thr His Thr
        1025                1030                1035

Ala Leu Ser Pro Leu Gln Phe Arg Gly Thr Pro Gly Arg Gly Ser
        1040                1045                1050

Ser Pro Ala Ser Pro Val Tyr Ser Ser Ser Asp Thr Val Ala Cys
        1055                1060                1065

His Leu Thr His Thr Val Pro Cys Ala His Gln Lys Pro Ile Thr
        1070                1075                1080

Ala Leu Lys Ala Ala Ala Gly Arg Leu Val Thr Gly Ser Gln Asp
        1085                1090                1095

His Thr Leu Arg Val Phe Arg Leu Glu Asp Ser Cys Cys Leu Phe
        1100                1105                1110

Thr Leu Gln Gly His Ser Gly Ala Ile Thr Thr Val Tyr Ile Asp
        1115                1120                1125

Gln Thr Met Val Leu Ala Ser Gly Gly Gln Asp Gly Ala Ile Cys
        1130                1135                1140

Leu Trp Asp Val Leu Thr Gly Ser Arg Val Ser His Val Phe Ala
        1145                1150                1155

His Arg Gly Asp Val Thr Ser Leu Thr Cys Thr Thr Ser Cys Val
        1160                1165                1170

Ile Ser Ser Gly Leu Asp Asp Leu Ile Ser Ile Trp Asp Arg Ser
        1175                1180                1185

Thr Gly Ile Lys Phe Tyr Ser Ile Gln Gln Asp Leu Gly Cys Gly
        1190                1195                1200

Ala Ser Leu Gly Val Ile Ser Asp Asn Leu Leu Val Thr Gly Gly
        1205                1210                1215

Gln Gly Cys Val Ser Phe Trp Asp Leu Asn Tyr Gly Asp Leu Leu
        1220                1225                1230

Gln Thr Val Tyr Leu Gly Lys Asn Ser Glu Ala Gln Pro Ala Arg
        1235                1240                1245

Gln Ile Leu Val Leu Asp Asn Ala Ala Ile Val Cys Asn Phe Gly
        1250                1255                1260

Ser Glu Leu Ser Leu Val Tyr Val Pro Ser Val Leu Glu Lys Leu
        1265                1270                1275

Asp

<210> SEQ ID NO 8
<211> LENGTH: 1335
<212> TYPE: PRT
<213> ORGANISM: homo sapien

<400> SEQUENCE: 8

Met Thr Leu Thr Glu Arg Leu Arg Glu Lys Ile Ser Arg Ala Phe Tyr
1               5                   10                  15

Asn His Gly Leu Leu Cys Ala Ser Tyr Pro Ile Pro Ile Ile Leu Phe
                20                  25                  30

Thr Gly Phe Cys Ile Leu Ala Cys Cys Tyr Pro Leu Leu Lys Leu Pro
            35                  40                  45

Leu Pro Gly Thr Gly Pro Val Glu Phe Thr Thr Pro Val Lys Asp Tyr
        50                  55                  60

```
Ser Pro Pro Val Asp Ser Asp Arg Lys Gln Gly Glu Pro Thr Glu
 65              70                  75                  80

Gln Pro Glu Trp Tyr Val Gly Ala Pro Val Ala Tyr Val Gln Gln Ile
                 85                  90                  95

Phe Val Lys Ser Ser Val Phe Pro Trp His Lys Asn Leu Leu Ala Val
            100                 105                 110

Asp Val Phe Arg Ser Pro Leu Ser Arg Ala Phe Gln Leu Val Glu Glu
            115                 120                 125

Ile Arg Asn His Val Leu Arg Asp Ser Ser Gly Ile Arg Ser Leu Glu
    130                 135                 140

Glu Leu Cys Leu Gln Val Thr Asp Leu Leu Pro Gly Leu Arg Lys Leu
145                 150                 155                 160

Arg Asn Leu Leu Pro Glu His Gly Cys Leu Leu Ser Pro Gly Asn
                165                 170                 175

Phe Trp Gln Asn Asp Trp Glu Arg Phe His Ala Asp Pro Asp Ile Ile
            180                 185                 190

Gly Thr Ile His Gln His Glu Pro Lys Thr Leu Gln Thr Ser Ala Thr
            195                 200                 205

Leu Lys Asp Leu Leu Phe Gly Val Pro Gly Lys Tyr Ser Gly Val Ser
    210                 215                 220

Leu Tyr Thr Arg Lys Arg Met Val Ser Tyr Thr Ile Thr Leu Val Phe
225                 230                 235                 240

Gln His Tyr His Ala Lys Phe Leu Gly Ser Leu Arg Ala Arg Leu Met
            245                 250                 255

Leu Leu His Pro Ser Pro Asn Cys Ser Leu Arg Ala Glu Ser Leu Val
            260                 265                 270

His Val His Phe Lys Glu Glu Ile Gly Val Ala Glu Leu Ile Pro Leu
            275                 280                 285

Val Thr Thr Tyr Ile Ile Leu Phe Ala Tyr Ile Tyr Phe Ser Thr Arg
    290                 295                 300

Lys Ile Asp Met Val Lys Ser Lys Trp Gly Leu Ala Leu Ala Ala Val
305                 310                 315                 320

Val Thr Val Leu Ser Ser Leu Leu Met Ser Val Gly Leu Cys Thr Leu
            325                 330                 335

Phe Gly Leu Thr Pro Thr Leu Asn Gly Gly Glu Ile Phe Pro Tyr Leu
            340                 345                 350

Val Val Val Ile Gly Leu Glu Asn Val Leu Val Leu Thr Lys Ser Val
    355                 360                 365

Val Ser Thr Pro Val Asp Leu Glu Val Lys Leu Arg Ile Ala Gln Gly
    370                 375                 380

Leu Ser Ser Glu Ser Trp Ser Ile Met Lys Asn Met Ala Thr Glu Leu
385                 390                 395                 400

Gly Ile Ile Leu Ile Gly Tyr Phe Thr Leu Val Pro Ala Ile Gln Glu
            405                 410                 415

Phe Cys Leu Phe Ala Val Val Gly Leu Val Ser Asp Phe Phe Leu Gln
            420                 425                 430

Met Leu Phe Phe Thr Thr Val Leu Ser Ile Asp Ile Arg Arg Met Glu
            435                 440                 445

Leu Ala Asp Leu Asn Lys Arg Leu Pro Pro Glu Ala Cys Leu Pro Ser
    450                 455                 460

Ala Lys Pro Val Gly Gln Pro Thr Arg Tyr Glu Arg Gln Leu Ala Val
465                 470                 475                 480

Arg Pro Ser Thr Pro His Thr Ile Thr Leu Gln Pro Ser Ser Phe Arg
```

```
                485                 490                 495
Asn Leu Arg Leu Pro Lys Arg Leu Arg Val Val Tyr Phe Leu Ala Arg
            500                 505                 510
Thr Arg Leu Ala Gln Arg Leu Ile Met Ala Gly Thr Val Val Trp Ile
            515                 520                 525
Gly Ile Leu Val Tyr Thr Asp Pro Ala Gly Leu Arg Asn Tyr Leu Ala
            530                 535                 540
Ala Gln Val Thr Glu Gln Ser Pro Leu Gly Glu Gly Ala Leu Ala Pro
545                 550                 555                 560
Met Pro Val Pro Ser Gly Met Leu Pro Pro Ser His Pro Asp Pro Ala
                565                 570                 575
Phe Ser Ile Phe Pro Pro Asp Ala Pro Lys Leu Pro Glu Asn Gln Thr
            580                 585                 590
Ser Pro Gly Glu Ser Pro Glu Arg Gly Gly Pro Ala Glu Val Val His
            595                 600                 605
Asp Ser Pro Val Pro Glu Val Thr Trp Gly Pro Glu Asp Glu Glu Leu
            610                 615                 620
Trp Arg Lys Leu Ser Phe Arg His Trp Pro Thr Leu Phe Ser Tyr Tyr
625                 630                 635                 640
Asn Ile Thr Leu Ala Lys Arg Tyr Ile Ser Leu Leu Pro Val Ile Pro
                645                 650                 655
Val Thr Leu Arg Leu Asn Pro Arg Glu Ala Leu Glu Gly Arg His Pro
            660                 665                 670
Gln Asp Gly Arg Ser Ala Trp Pro Pro Gly Pro Ile Pro Ala Gly
            675                 680                 685
His Trp Glu Ala Gly Pro Lys Gly Pro Gly Gly Val Gln Ala His Gly
            690                 695                 700
Asp Val Thr Leu Tyr Lys Val Ala Ala Leu Gly Leu Ala Thr Gly Ile
705                 710                 715                 720
Val Leu Val Leu Leu Leu Leu Cys Leu Tyr Arg Val Leu Cys Pro Arg
                725                 730                 735
Asn Tyr Gly Gln Leu Gly Gly Pro Gly Arg Arg Arg Gly Glu
            740                 745                 750
Leu Pro Cys Asp Asp Tyr Gly Tyr Ala Pro Pro Glu Thr Glu Ile Val
            755                 760                 765
Pro Leu Val Leu Arg Gly His Leu Met Asp Ile Glu Cys Leu Ala Ser
            770                 775                 780
Asp Gly Met Leu Leu Val Ser Cys Cys Leu Ala Gly His Val Cys Val
785                 790                 795                 800
Trp Asp Ala Gln Thr Gly Asp Cys Leu Thr Arg Ile Pro Arg Pro Gly
                805                 810                 815
Arg Gln Arg Arg Asp Ser Gly Val Gly Ser Gly Leu Glu Ala Gln Glu
            820                 825                 830
Ser Trp Glu Arg Leu Ser Asp Gly Gly Lys Ala Gly Pro Glu Pro
            835                 840                 845
Gly Asp Ser Pro Pro Leu Arg His Arg Pro Gly Pro Pro Pro
            850                 855                 860
Ser Leu Phe Gly Asp Gln Pro Asp Leu Thr Cys Leu Ile Asp Thr Asn
865                 870                 875                 880
Phe Ser Ala Gln Pro Arg Ser Ser Gln Pro Thr Gln Pro Glu Pro Arg
                885                 890                 895
His Arg Ala Val Cys Gly Arg Ser Arg Asp Ser Pro Gly Tyr Asp Phe
            900                 905                 910
```

Ser Cys Leu Val Gln Arg Val Tyr Gln Glu Glu Gly Leu Ala Ala Val
        915                 920                 925

Cys Thr Pro Ala Leu Arg Pro Pro Ser Pro Gly Pro Val Leu Ser Gln
930                 935                 940

Ala Pro Glu Asp Glu Gly Gly Ser Pro Glu Lys Gly Ser Pro Ser Leu
945                 950                 955                 960

Ala Trp Ala Pro Ser Ala Glu Gly Ser Ile Trp Ser Leu Glu Leu Gln
            965                 970                 975

Gly Asn Leu Ile Val Val Gly Arg Ser Ser Gly Arg Leu Glu Val Trp
            980                 985                 990

Asp Ala Ile Glu Gly Val Leu Cys Cys Ser Ser Glu Glu Val Ser Ser
            995                 1000                1005

Gly Ile Thr Ala Leu Val Phe Leu Asp Lys Arg Ile Val Ala Ala
    1010                1015                1020

Arg Leu Asn Gly Ser Leu Asp Phe Phe Ser Leu Glu Thr His Thr
    1025                1030                1035

Ala Leu Ser Pro Leu Gln Phe Arg Gly Thr Pro Gly Arg Gly Ser
    1040                1045                1050

Ser Pro Ala Ser Pro Val Tyr Ser Ser Ser Asp Thr Val Ala Cys
    1055                1060                1065

His Leu Thr His Thr Val Pro Cys Ala His Gln Lys Pro Ile Thr
    1070                1075                1080

Ala Leu Lys Ala Ala Ala Gly Arg Leu Val Thr Gly Ser Gln Asp
    1085                1090                1095

His Thr Leu Arg Val Phe Arg Leu Glu Asp Ser Cys Cys Leu Phe
    1100                1105                1110

Thr Leu Gln Gly His Ser Gly Ala Ile Thr Thr Val Tyr Ile Asp
    1115                1120                1125

Gln Thr Met Val Leu Ala Ser Gly Gly Gln Asp Gly Ala Ile Cys
    1130                1135                1140

Leu Trp Asp Val Leu Thr Gly Ser Arg Val Ser His Val Phe Ala
    1145                1150                1155

His Arg Gly Asp Val Thr Ser Leu Thr Cys Thr Thr Ser Cys Val
    1160                1165                1170

Ile Ser Ser Gly Leu Asp Asp Leu Ile Ser Ile Trp Asp Arg Ser
    1175                1180                1185

Thr Gly Ile Lys Phe Tyr Ser Ile Gln Gln Asp Leu Gly Cys Gly
    1190                1195                1200

Ala Ser Leu Gly Val Ile Ser Asp Asn Leu Leu Val Thr Gly Gly
    1205                1210                1215

Gln Gly Cys Val Ser Phe Trp Asp Leu Asn Tyr Gly Asp Leu Leu
    1220                1225                1230

Gln Ser Thr Trp Gly Arg Thr Val Arg Pro Ser Leu Pro Ala Arg
    1235                1240                1245

Ser Trp Cys Trp Thr Thr Leu Pro Leu Ser Ala Thr Leu Ala Val
    1250                1255                1260

Ser Ser Ala Trp Cys Met Cys Pro Leu Cys Trp Arg Ser Trp Thr
    1265                1270                1275

Glu Arg Arg Ala Ser Leu Pro Arg Gln Glu Ala Gly Val Leu Cys
    1280                1285                1290

Gly Gly Gln Cys Thr Glu Pro Gly Leu Gly Gly Lys Ser Arg Val
    1295                1300                1305

```
Ser  Ser  Ser  Arg  Cys  Leu  Leu  Thr  Val  Ile  Ile  Leu  Asn  Phe  Phe
     1310                1315                1320

Lys  Lys  Pro  Tyr  His  His  Leu  Ser  Gly  Thr  Leu  Gly
     1325                1330                1335
```

<210> SEQ ID NO 9
<211> LENGTH: 45
<212> TYPE: PRT
<213> ORGANISM: homo sapien

<400> SEQUENCE: 9

```
Thr  Val  Tyr  Leu  Gly  Lys  Asn  Ser  Glu  Ala  Gln  Pro  Ala  Arg  Gln  Ile
1              5                   10                  15

Leu  Val  Leu  Asp  Asn  Ala  Ala  Ile  Val  Cys  Asn  Phe  Gly  Ser  Glu  Leu
               20                  25                  30

Ser  Leu  Val  Tyr  Val  Pro  Ser  Val  Leu  Glu  Lys  Leu  Asp
               35                  40                  45
```

<210> SEQ ID NO 10
<211> LENGTH: 101
<212> TYPE: PRT
<213> ORGANISM: homo sapien

<400> SEQUENCE: 10

```
Ser  Thr  Trp  Gly  Arg  Thr  Val  Arg  Pro  Ser  Leu  Pro  Ala  Arg  Ser  Trp
1              5                   10                  15

Cys  Trp  Thr  Thr  Leu  Pro  Leu  Ser  Ala  Thr  Leu  Ala  Val  Ser  Ser  Ala
               20                  25                  30

Trp  Cys  Met  Cys  Pro  Leu  Cys  Trp  Arg  Ser  Trp  Thr  Glu  Arg  Arg  Ala
               35                  40                  45

Ser  Leu  Pro  Arg  Gln  Glu  Ala  Gly  Val  Leu  Cys  Gly  Gly  Gln  Cys  Thr
     50                  55                  60

Glu  Pro  Gly  Leu  Gly  Gly  Lys  Ser  Arg  Val  Ser  Ser  Ser  Arg  Cys  Leu
65                  70                  75                  80

Leu  Thr  Val  Ile  Ile  Leu  Asn  Phe  Phe  Lys  Lys  Pro  Tyr  His  His  Leu
               85                  90                  95

Ser  Gly  Thr  Leu  Gly
               100
```

<210> SEQ ID NO 11
<211> LENGTH: 307
<212> TYPE: DNA
<213> ORGANISM: homo sapien

<400> SEQUENCE: 11

```
acagtctacc tggggaagaa cagtgaggcc cagcctgccc gccagatcct ggtgctggac    60
aacgctgcca ttgtctgcaa ctttggcagt gagctcagcc tggtgtatgt gccctctgtg   120
ctggagaagc tggactgagc gcagggcctc cttgcccagg caggaggctg gggtgctgtg   180
tgggggccaa tgcactgaac ctggacttgg gggaaagagc cgagtatctt ccagccgctg   240
cctcctgact gtaataatat taaactttt taaaaaacca tatcatcatc tgtcaggcac   300
tttggga                                                             307
```

<210> SEQ ID NO 12
<211> LENGTH: 303
<212> TYPE: DNA
<213> ORGANISM: homo sapien

<400> SEQUENCE: 12

```
tctacctggg gaagaacagt gaggcccagc ctgcccgcca gatcctggtg ctggacaacg      60
ctgccattgt ctgcaacttt ggcagtgagc tcagcctggt gtatgtgccc tctgtgctgg     120
agaagctgga ctgagcgcag ggcctccttg cccaggcagg aggctggggt gctgtgtggg     180
ggccaatgca ctgaacctgg acttggggga agagccgag tatcttccag ccgctgcctc      240
ctgactgtaa taatattaaa cttttttaaa aaaccatatc atcatctgtc aggcactttg     300
gga                                                                    303

<210> SEQ ID NO 13
<211> LENGTH: 306
<212> TYPE: DNA
<213> ORGANISM: homo sapien

<400> SEQUENCE: 13
acagucuacc uggggaagaa cagugaggcc cagccugccc gccagauccu ggugcuggac      60
aacgcugcca uugucugcaa cuuuggcagu gagcucagcc ugguguaugu gcccucugug    120
cuggagaagc uggacugagc gcagggccuc cuugcccagg caggaggcug ggugcugug     180 uggggggccaa ugcacugaac cuggacuugg gggaaagagc cgaguaucuu ccagccgcug    240
ccuccugacu guaauaauau uaaacuuuuu uaaaaaaccu aucaucaucu gucaggcacu    300
uuggga                                                                306

<210> SEQ ID NO 14
<211> LENGTH: 302
<212> TYPE: DNA
<213> ORGANISM: homo sapien

<400> SEQUENCE: 14
ucuaccuggg gaagaacagu gaggcccagc cugcccgcca gauccuggug cuggacaacg      60
cugccauugu cugcaacuuu ggcagugagc ucagccuggu guaugugccc ucugugcugg    120
agaagcugga cugagcgcag ggccuccuug cccaggcagg aggcuggggu gcugugugg     180 ggccaaugca cugaaccugg acuuggggga agagccgag uaucuuccag ccgcugccuc      240
cugacuguaa uaauauuaaa cuuuuuaaa aaaccuauca ucaucugucu ggcacuuugg      300
ga                                                                    302

<210> SEQ ID NO 15
<211> LENGTH: 307
<212> TYPE: DNA
<213> ORGANISM: homo sapien

<400> SEQUENCE: 15
acagtctacc tggggaagaa cagtgaggcc cagcctgccc gccagatcct ggtgctggac      60
aacgctgcca ttgtctgcaa ctttggcagt gagctcagcc tggtgtatgt gccctctgtg    120
ctggagaagc tggactgagc gcagggcctc cttgcccagg caggaggctg ggtgctgtg     180 tgggggccaa tgcactgaac ctggacttgg gggaaagagc cgagtatctt ccagccgctg    240
cctcctgact gtaataatat taaacttttt taaaaaacca tatcatcatc tgtcaggcac    300
tttggga                                                               307

<210> SEQ ID NO 16
<211> LENGTH: 303
<212> TYPE: DNA
<213> ORGANISM: homo sapien
```

```
<400> SEQUENCE: 16
tctacctggg gaagaacagt gaggcccagc ctgcccgcca gatcctggtg ctggacaacg      60
ctgccattgt ctgcaactttt ggcagtgagc tcagcctggt gtatgtgccc tctgtgctgg    120
agaagctgga ctgagcgcag ggcctccttg cccaggcagg aggctggggt gctgtgtggg    180
ggccaatgca ctgaacctgg acttggggga aagagccgag tatcttccag ccgctgcctc    240
ctgactgtaa taatattaaa ctttttttaaa aaaccatatc atcatctgtc aggcactttg    300
gga                                                                   303

<210> SEQ ID NO 17
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 17
gtaacaggtc cccgtagttt agg                                              23

<210> SEQ ID NO 18
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 18
cttttgggac ctaaactacg ggg                                              23

<210> SEQ ID NO 19
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 19
cccgtagttt aggtcccaaa agg                                              23

<210> SEQ ID NO 20
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 20 cctttttggga cctaaactac ggg                                             23

<210> SEQ ID NO 21
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 21
ccaggtagac tgtctgtaac agg                                              23
```

<210> SEQ ID NO 22
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 22
tggcagcgtt gtccagcacc agg                                              23

<210> SEQ ID NO 23
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 23
cgttgtccag caccaggatc tgg                                              23

<210> SEQ ID NO 24
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 24
tgttacagac agtctacctg ggg                                              23

<210> SEQ ID NO 25
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 25
cctgttacag acagtctacc tgg                                              23

<210> SEQ ID NO 26
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 26
tccttttggg acctaaacta cgg                                              23

<210> SEQ ID NO 27
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 27
ctgttacaga cagtctacct ggg                                              23

```
<210> SEQ ID NO 28
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 28
tgcccgccag atcctggtgc tgg                                               23

<210> SEQ ID NO 29
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 29
gcacagaggg cacatacacc agg                                               23

<210> SEQ ID NO 30
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 30
ctgggctgtg gtgcaagctt ggg                                               23

<210> SEQ ID NO 31
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 31
tgtcatctca gacaacctgc tgg                                               23

<210> SEQ ID NO 32
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 32
agcaccagga tctggcgggc agg                                               23

<210> SEQ ID NO 33
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 33
ggtgtatgtg ccctctgtgc tgg                                               23

<210> SEQ ID NO 34
```

-continued

```
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 34
tcagacaacc tgctggtgac tgg                                              23

<210> SEQ ID NO 35
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 35
gctgccattg tctgcaactt tgg                                              23

<210> SEQ ID NO 36
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 36
gtccagcacc aggatctggc ggg                                              23

<210> SEQ ID NO 37
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 37
cctgctggtg actggcggcc agg                                              23

<210> SEQ ID NO 38
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 38
gacaacctgc tggtgactgg cgg                                              23

<210> SEQ ID NO 39
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 39
ctgctggtga ctggcggcca ggg                                              23

<210> SEQ ID NO 40
<211> LENGTH: 23
```

```
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 40
actgccaaag ttgcagacaa tgg                                             23

<210> SEQ ID NO 41
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 41
cctgggctgt ggtgcaagct tgg                                             23

<210> SEQ ID NO 42
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 42
ctttggcagt gagctcagcc tgg                                             23

<210> SEQ ID NO 43
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 43
tgtccagcac caggatctgg cgg                                             23

<210> SEQ ID NO 44
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 44
ccaagcttgc accacagccc agg                                             23

<210> SEQ ID NO 45
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 45
cctggccgcc agtcaccagc agg                                             23

<210> SEQ ID NO 46
<211> LENGTH: 23
<212> TYPE: DNA
```

```
<213> ORGANISM: artificial sequence
<220> FEATURE:
<223> OTHER INFORMATION: Guide RNA Recognition Sequence Near SCAP
      Variation

<400> SEQUENCE: 46
ccagcctgcc cgccagatcc tgg                                              23

<210> SEQ ID NO 47
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 47
atgtccttgc ctccaggacc tgg                                              23

<210> SEQ ID NO 48
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 48
ccagggctgt gtctcctttt ggg                                              23

<210> SEQ ID NO 49
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 49
caggatctgg cgggcaggct ggg                                              23

<210> SEQ ID NO 50
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 50
ctacctgggg aagaacagtg agg                                              23

<210> SEQ ID NO 51
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 51
gccagggctg tgtctccttt tgg                                              23

<210> SEQ ID NO 52
<211> LENGTH: 23
<212> TYPE: DNA
<213> ORGANISM: artificial sequence
```

-continued

```
<220> FEATURE:
<223> OTHER INFORMATION: Guide RNA Recognition Sequence Near SCAP
      Variation

<400> SEQUENCE: 52
gccagggctg tgtctcctt tgg                                              23

<210> SEQ ID NO 53
<211> LENGTH: 23
<212> TYPE: DNA
<213> ORGANISM: artificial sequence
<220> FEATURE:
<223> OTHER INFORMATION: Guide RNA Recognition Sequence Near SCAP
      Variation

<400> SEQUENCE: 53
ttgcaccaca gcccaggtcc tgg                                             23
```

US 11,331,332 B2

TREATMENT OF INCREASED LIPID LEVELS WITH STEROL REGULATORY ELEMENT BINDING PROTEIN CLEAVAGE-ACTIVATING PROTEIN (SCAP) INHIBITORS

REFERENCE TO SEQUENCE LISTING

This application includes a Sequence Listing submitted electronically as a text file named 18923802201SEQ, created on Mar. 7, 2020, with a size of 216 kilobytes. The Sequence Listing is incorporated herein by reference.

FIELD

The present disclosure relates generally to the treatment of subjects having increased lipid levels and/or increased triglyceride levels with Sterol Regulatory Element Binding Protein Cleavage-Activating Protein (SCAP) inhibitors, methods of identifying subjects having an increased risk of developing increased lipid levels and/or increased triglyceride levels, methods of detecting SCAP variant nucleic acid molecules and variant polypeptides, and SCAP variant nucleic acid molecules and SCAP variant polypeptides.

BACKGROUND

Increased lipid levels are a well-known complication of obesity. Increased lipid levels are often characterised by hyperinsulinaemia, elevated apolipoprotein B levels, high low-density lipoproteins (LDL) cholesterol concentration, and low high-density lipoproteins (HDL) cholesterol concentration.

Sterol Regulatory Element Binding Proteins (SREBPs) are membrane-bound transcription factors that control the rates of lipid synthesis in animal cells. The proteolytic processing of SREBPs is negatively regulated by sterols. One aspect of sterol regulation is SREBP Cleavage-Activating Protein (SCAP), a polytopic membrane protein that forms a complex with SREBPs in the endoplasmic reticulum (ER). In cultured fibroblasts, SCAP stabilizes the SREBPs and transports them to the Golgi apparatus. Once sterol levels decrease, SCAP dissociates with Insulin-induced gene (Insig) protein and escorts SREBPs to the Golgi, in which they are sequentially cleaved by site-1 and site-2 proteases (S1P and S2P), thereby releasing the N-terminus which then enters into the nucleus to transcribe lipogenesis genes and low-density lipoprotein receptor (LDLR). Mutant cells that lack SCAP have low levels of SREBP precursors, possibly because these proteins are unstable in the absence of SCAP. As a result of these abnormalities, SCAP-deficient CHO cells cannot synthesize cholesterol, and they require external sources of cholesterol for growth. When sterols increase in cells, SCAP no longer transports SREBPs, and proteolytic processing is abolished.

SUMMARY

The present disclosure provides methods of treating a subject having increased total cholesterol, the methods comprising administering a SCAP inhibitor to the subject.

The present disclosure also provides methods of treating a subject having increased LDL, the methods comprising administering a SCAP inhibitor to the subject.

The present disclosure also provides methods of treating a subject having increased serum lipids, the methods comprising administering a SCAP inhibitor to the subject.

The present disclosure also provides methods of treating a subject having increased triglycerides, the methods comprising administering a SCAP inhibitor to the subject.

The present disclosure also provides methods of treating a subject with a therapeutic agent that treats or inhibits an increased lipid level and/or increased triglyceride levels, wherein the subject is suffering from an increased lipid level and/or increased triglyceride levels, the method comprising the steps of: determining whether the subject has a SCAP variant nucleic acid molecule encoding a human SCAP polypeptide by: obtaining or having obtained a biological sample from the subject; and performing or having performed a genotyping assay on the biological sample to determine if the subject has a genotype comprising the SCAP variant nucleic acid molecule; and when the subject is SCAP reference, then administering or continuing to administer to the subject the therapeutic agent that treats or inhibits the increased lipid level and/or increased triglyceride levels in a standard dosage amount, and administering to the subject a SCAP inhibitor; and when the subject is heterozygous for a SCAP variant nucleic acid molecule, then administering or continuing to administer to the subject the therapeutic agent that treats or inhibits the increased lipid level and/or increased triglyceride levels in an amount that is the same as or lower than a standard dosage amount, and administering to the subject a SCAP inhibitor; wherein the presence of a genotype having the SCAP variant nucleic acid molecule encoding the human SCAP polypeptide indicates the subject has a reduced risk of developing the increased lipid level and/or increased triglyceride levels; wherein the increased lipid level is increased serum lipid level, increased total cholesterol, or increased LDL; and wherein the SCAP variant nucleic acid molecule is: i) a genomic nucleic acid molecule having a nucleotide sequence comprising the nucleotide sequence according to SEQ ID NO:12 at positions corresponding to positions 61,695 to 62,267 according to SEQ ID NO:2, or the complement thereof, ii) an mRNA molecule having a nucleotide sequence comprising the nucleotide sequence according to SEQ ID NO:14 at positions corresponding to positions 4,116 to 4,417 according to SEQ ID NO:4, or the complement thereof, or iii) a cDNA molecule having a nucleotide sequence comprising the nucleotide sequence according to SEQ ID NO:16 at positions corresponding to positions 4,116 to 4,417 according to SEQ ID NO:6, or the complement thereof.

The present disclosure also provides methods of identifying a human subject having an increased risk for developing an increased lipid level and/or increased triglyceride levels, wherein the method comprises determining or having determined the presence or absence of a SCAP variant nucleic acid molecule encoding a human SCAP polypeptide in a biological sample obtained from the subject; wherein: when the human subject is SCAP reference, then the human subject has an increased risk for developing the increased lipid level and/or increased triglyceride levels; and when the human subject is heterozygous for a SCAP variant nucleic acid molecule or homozygous for a SCAP variant nucleic acid molecule, then the human subject has a decreased risk for developing the increased lipid level and/or increased triglyceride levels; wherein the SCAP variant nucleic acid molecule is: i) a genomic nucleic acid molecule having a nucleotide sequence comprising the nucleotide sequence according to SEQ ID NO:12 at positions corresponding to positions 61,695 to 62,267 according to SEQ ID NO:2, or the complement thereof, ii) an mRNA molecule having a nucleotide sequence comprising the nucleotide sequence according to SEQ ID NO:14 at positions corresponding to positions 4,116 to 4,417 according to SEQ ID NO:4, or the complement thereof; or iii) a cDNA molecule having a nucleotide sequence comprising the nucleotide sequence according to SEQ ID NO:16 at positions corresponding to positions 4,116 to 4,417 according to SEQ ID NO:6, or the complement thereof.

The present disclosure also provides methods of detecting a human SCAP variant nucleic acid molecule in a human subject comprising assaying a sample obtained from the human subject to determine whether a nucleic acid molecule in the sample comprises a nucleotide sequence comprising: i) the nucleotide sequence according to SEQ ID NO:12 at positions corresponding to positions 61,695 to 62,267 according to SEQ ID NO:2, or the complement thereof; ii) the nucleotide sequence according to SEQ ID NO:14 at positions corresponding to positions 4,116 to 4,417 according to SEQ ID NO:4, or the complement thereof; or iii) the nucleotide sequence according to SEQ ID NO:16 at positions corresponding to positions 4,116 to 4,417 according to SEQ ID NO:6, or the complement thereof.

The present disclosure also provides isolated alteration-specific probes or alteration-specific primers comprising at least about 15 nucleotides, wherein the alteration-specific probes or alteration-specific primers comprise a nucleotide sequence which is complementary to a portion of a nucleotide sequence encoding a human SCAP polypeptide, wherein the portion comprises a position corresponding to: positions 61,694 to 61,695 according to SEQ ID NO:2, or the complement thereof; positions 4,115 to 4,116 according to SEQ ID NO:4, or the complement thereof; or positions 4,115 to 4,116 according to SEQ ID NO:6, or the complement thereof.

The present disclosure also provides isolated nucleic acid molecules comprising a nucleotide sequence encoding a human SCAP polypeptide, wherein the polypeptide comprises the amino acid sequence according to SEQ ID NO:10 at positions corresponding to positions 1,235 to 1,335 according to SEQ ID NO:8.

The present disclosure also provides isolated nucleic acid molecules comprising a nucleotide sequence encoding a human SCAP polypeptide, wherein the nucleotide sequence comprises the nucleotide sequence according to SEQ ID NO:12 at positions corresponding to positions 61,695 to 62,267 according to SEQ ID NO:2, or the complement thereof.

The present disclosure also provides isolated mRNA molecules comprising a nucleotide sequence encoding a human SCAP polypeptide, wherein the nucleotide sequence comprises the nucleotide sequence according to SEQ ID NO:14 at positions corresponding to positions 4,116 to 4,417 according to SEQ ID NO:4, or the complement thereof.

The present disclosure also provides cDNA molecules comprising a nucleotide sequence encoding a human SCAP polypeptide, wherein the nucleotide sequence comprises the nucleotide sequence according to SEQ ID NO:16 at positions corresponding to positions 4,116 to 4,417 according to SEQ ID NO:6, or the complement thereof.

The present disclosure also provides isolated human SCAP polypeptides having an amino acid sequence at least about 90% identical to SEQ ID NO:8, wherein the polypeptide comprises the amino acid sequence according to SEQ ID NO:10 at positions corresponding to positions 1,235 to 1,335 according to SEQ ID NO:8.

The present disclosure also provides molecular complexes comprising an alteration-specific primer or an alteration-specific probe hybridized to: a genomic nucleic acid molecule comprising a nucleotide sequence encoding a human SCAP polypeptide, wherein the alteration-specific primer or the alteration-specific probe is hybridized to a GT dinucleotide at positions corresponding to positions 61,694 to 61,695 according to SEQ ID NO:2, or the complement thereof; an mRNA molecule comprising a nucleotide sequence encoding a human SCAP polypeptide, wherein the alteration-specific primer or the alteration-specific probe is hybridized to a GU dinucleotide at positions corresponding to positions 4,115 to 4,116 according to SEQ ID NO:4, or the complement thereof; or a cDNA molecule comprising a nucleotide sequence encoding a human SCAP polypeptide, wherein the alteration-specific primer or the alteration-specific probe is hybridized to a GT dinucleotide at positions corresponding to positions 4,115 to 4,116 according to SEQ ID NO:6, or the complement thereof.

BRIEF DESCRIPTION OF THE DRAWINGS

The accompanying figures, which are incorporated in and constitute a part of this specification, illustrate several aspects and together with the description serve to explain the principles of the present disclosure.

FIG. 1 shows an association of a SCAP variant with decreased aspartate aminotransferase (Panel A), an association of a SCAP variant with decreased LDL-C (Panel B), and an association of a SCAP variant with decreased total cholesterol (Panel C).

DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, a "nucleic acid," a "nucleic acid molecule," a "nucleic acid sequence," a "polynucleotide," or an "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "comprising" may be replaced with "consisting" or "consisting essentially of" in particular embodiments as desired.

An "isolated" nucleic acid molecule is a polynucleotide that is in a condition other than its native environment, such as apart from blood and animal tissue. In a preferred form, the isolated nucleic acid molecule is substantially free of other polynucleotides, particularly other polypeptides of animal origin. It is preferred to provide the nucleic acid molecule in a highly purified form, i.e., greater than 95% pure, more preferably greater than 99% pure. When used in this context, the term "isolated" does not exclude the presence of the same nucleic acid molecule in alternative physical forms, such as dimers or alternatively phosphorylated or derivatized forms.

It has been observed in accordance with the present disclosure that particular variations in SCAP may associate with decreased LDL, decreased total cholesterol, increased aspartate aminotransferase, and decreased triglyceride levels. It is believed that no human genetic variants of the SCAP gene or protein have any known association with decreased LDL, decreased total cholesterol, increased aspartate aminotransferase, and decreased triglyceride levels.

A rare variant in the SCAP gene segregating with decreased LDL, decreased total cholesterol, increased aspartate aminotransferase, and decreased triglyceride levels has been identified in accordance with the present disclosure. For example, a genetic alteration that results in a deletion of four nucleotides (ACAG) corresponding to positions 61,695 to 61,698 in the human wild type SCAP gene (SEQ ID NO:1) has been observed to indicate that the human having such an alteration may have decreased LDL, decreased total cholesterol, and decreased triglyceride levels. Altogether, the genetic analyses described herein indicate that the SCAP gene and, in particular, a variant in the SCAP gene, may associate with decreased LDL cholesterol, total cholesterol, and decreased triglyceride levels. Therefore, human subjects that are SCAP reference that have an increased risk of developing an increased lipid level and/or increased triglyceride levels may be treated such that the increased lipid level and/or increased triglyceride levels is inhibited, the symptoms thereof are reduced, and/or development of symptoms is repressed. Accordingly, the disclosure provides methods of leveraging the identification of such variants in subjects to identify or stratify risk in such subjects of developing increased lipid levels and/or increased triglyceride levels, such that subjects at risk or subjects with active disease may be treated accordingly. Additionally, the present disclosure provides isolated SCAP variant genomic nucleic acid molecules, variant mRNA molecule, and variant cDNA molecules. Accordingly, provided herein are SCAP variant nucleic acid molecules discovered to potentially be associated with decreased LDL, decreased total cholesterol, and decreased triglyceride levels.

For purposes of the present disclosure, any particular human can be categorized as having one of three SCAP genotypes: i) SCAP reference; ii) heterozygous for a SCAP variant (such as a predicted loss-of-function variant), and iii) homozygous for a SCAP variant (such as a predicted loss-of-function variant). A human in the SCAP reference category does not have a copy of a SCAP variant nucleic acid molecule (such as a predicted loss-of-function variant nucleic acid molecule). A human who is heterozygous for a SCAP variant nucleic acid molecule (such as a predicted loss-of-function variant nucleic acid molecule) has a single copy of a SCAP variant nucleic acid molecule (such as a predicted loss-of-function variant nucleic acid molecule). A human who is homozygous for a SCAP variant nucleic acid molecule (such as a predicted loss-of-function variant nucleic acid molecule) has two copies of a SCAP variant nucleic acid molecule (such as a predicted loss-of-function variant nucleic acid molecule). A SCAP predicted loss-of-function variant nucleic acid molecule is any SCAP nucleic acid molecule (such as, a genomic nucleic acid molecule, an mRNA molecule, or a cDNA molecule) encoding a SCAP polypeptide having a partial loss-of-function, a complete loss-of-function, a predicted partial loss-of-function, or a predicted complete loss-of-function. A human who has a SCAP polypeptide having a partial loss-of-function (or predicted partial loss-of-function) is hypomorphic for SCAP. The SCAP variant nucleic acid molecule can be any nucleic acid molecule encoding SCAP Thr1235fs. It is believed that the SCAP variant nucleic acid molecules described herein encoding SCAP Thr1235fs are SCAP predicted loss-of-function variant nucleic acid molecules.

For human subjects that are genotyped or determined to be SCAP reference, such human subjects have an increased risk of developing an increased lipid level, such as increased LDL and increased total cholesterol, and/or increased triglyceride levels. For human subjects that are genotyped or determined to be either SCAP reference or heterozygous for a SCAP variant nucleic acid molecule (such as a predicted loss-of-function variant), such human subjects can be treated with a SCAP inhibitor.

The present disclosure provides methods of treating a subject having increased serum lipid level, the methods comprising administering a SCAP inhibitor to the subject.

The present disclosure also provides methods of treating a subject having increased total cholesterol, the methods comprising administering a SCAP inhibitor to the subject.

The present disclosure also provides methods of treating a subject having increased LDL, the methods comprising administering a SCAP inhibitor to the subject.

The present disclosure also provides methods of treating a subject having increased triglyceride levels, the methods comprising administering a SCAP inhibitor to the subject.

In any of the embodiments described herein, the increased lipid level is increased serum lipid level, increased total cholesterol, or increased LDL. In some embodiments, the increased lipid level is increased serum lipid level. In some embodiments, the increased lipid level is increased total cholesterol. In some embodiments, the increased lipid level is increased serum cholesterol. In some embodiments, the increased lipid level is increased LDL. In some embodiments, the increased lipid level is increased serum cholesterol.

In some embodiments, the SCAP inhibitor comprises an antisense molecule. Examples of antisense molecules include, but are not limited to, antisense nucleic acid molecules, small interfering RNAs (siRNAs), and short hairpin RNAs (shRNAs). Such antisense molecules can be designed to target any region of a SCAP mRNA. In some embodiments, the antisense RNA, siRNA, or shRNA hybridizes to a sequence within a SCAP genomic nucleic acid molecule or mRNA molecule and decreases expression of the SCAP polypeptide in a cell in the subject. In some embodiments, the SCAP inhibitor comprises an antisense RNA that hybridizes to a SCAP genomic nucleic acid molecule or mRNA molecule and decreases expression of the SCAP polypeptide in a cell in the subject. In some embodiments, the SCAP inhibitor comprises an siRNA that hybridizes to a SCAP genomic nucleic acid molecule or mRNA molecule and decreases expression of the SCAP polypeptide in a cell in the subject. In some embodiments, the SCAP inhibitor comprises an shRNA that hybridizes to a SCAP genomic nucleic acid molecule or mRNA molecule and decreases expression of the SCAP polypeptide in a cell in the subject.

In some embodiments, the SCAP inhibitor comprises a nuclease agent that induces one or more nicks or double-strand breaks at a recognition sequence(s) or a DNA-binding protein that binds to a recognition sequence within a SCAP genomic nucleic acid molecule. The recognition sequence can be located within a coding region of a SCAP gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of a SCAP gene. For example, the recognition sequence can be located from about 10, 20, 30, 40, 50, 100, 200, 300, 400, 500, or 1,000 nucleotides of the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair (i.e., about 15-18 bp for each ZFN), about 36 bp for a TALE protein or TALEN, and about 20 bp for a CRISPR/Cas guide RNA.

In some embodiments, CRISPR/Cas systems can be used to modify a SCAP genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of SCAP nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a SCAP genomic nucleic acid molecule or it can be a nickase that creates a single-strand break in a SCAP genomic nucleic acid molecule. Additional examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Casl0d, CasF, CasG, CasH, Csy1, Csy2, Csy3, Cse1 (CasA), Cse2 (Cas6), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of SCAP genomic nucleic acid molecules can be generated by contacting a cell with a Cas protein and one or more gRNAs that hybridize to one or more gRNA recognition sequences within a target genomic locus in the SCAP genomic nucleic acid molecule. For example, a gRNA recognition sequence can be located within a region of SEQ ID NO:1. As another example, the gRNA recognition sequence can also include or be proximate to a position corresponding to position 61,695 according to SEQ ID NO:1. For example, the gRNA recognition sequence can be located from about 1000, 500, 400, 300, 200, 100, 50, 45, 40, 35, 30, 25, 20, 15, 10, or 5 nucleotides of a position corresponding to position 61,695 according to SEQ ID NO:1. As yet another example, a gRNA recognition sequence can include or be proximate to the start codon of a SCAP genomic nucleic acid molecule or the stop codon of a SCAP genomic nucleic acid molecule. For example, the gRNA recognition sequence can be located from about 10, 20, 30, 40, 50, 100, 200, 300, 400, 500, or 1,000 nucleotides of the start codon or the stop codon.

The gRNA recognition sequences located within a target genomic locus in a SCAP genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a SCAP genomic nucleic acid molecule. An exemplary gRNA is a gRNA effective to direct a Cas enzyme to bind to or cleave a SCAP genomic nucleic acid molecule, wherein the gRNA comprises a DNA-targeting segment that hybridizes to a gRNA recognition sequence located within the SCAP genomic nucleic acid molecule that includes or is proximate to a position corresponding to position 61,695 according to SEQ ID NO:1. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of a position corresponding to position 61,695 according to SEQ ID NO:1. Other exemplary gRNAs comprise a DNA-targeting segment that hybridizes to a gRNA recognition sequence within a SCAP genomic nucleic acid molecule that is located within a region of SEQ ID NO:1. Other exemplary gRNAs comprise a DNA-targeting segment that hybridizes to a gRNA recognition sequence located within a SCAP genomic nucleic acid molecule that includes or is proximate to the start codon or the stop codon. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of the start codon or located from about 5, 10, 15, 20, 25, 30, 35, 40, 45, 50, 100, 200, 300, 400, 500, or 1,000 nucleotides of the start codon or stop codon. The design and synthesis of gRNAs are described in, for example, Mali et al., Science, 2013, 339, 823-826; Jinek et al., Science, 2012, 337, 816-821; Hwang et al., Nat. Biotechnol., 2013, 31, 227-229; Jiang et al., Nat. Biotechnol., 2013, 31, 233-239; and Cong et al., Science, 2013, 339, 819-823. Suitable gRNAs can comprise from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences within the human wild type SCAP gene are set forth in SEQ ID NOS: 17-53.

Guide RNA Recognition Sequences Near SCAP Variation

| Strand | Sequence | SEQ ID NO: |
|---|---|---|
| - | GTAACAGGTCCCCGTAGTTTAGG | 17 |
| + | CTTTTGGGACCTAAACTACGGGG | 18 |
| - | CCCGTAGTTTAGGTCCCAAAAGG | 19 |
| + | CCTTTTGGGACCTAAACTACGGG | 20 |
| - | CCAGGTAGACTGTCTGTAACAGG | 21 |
| - | TGGCAGCGTTGTCCAGCACCAGG | 22 |
| - | CGTTGTCCAGCACCAGGATCTGG | 23 |
| + | TGTTACAGACAGTCTACCTGGGG | 24 |
| + | CCTGTTACAGACAGTCTACCTGG | 25 |
| + | TCCTTTTGGGACCTAAACTACG | 26 |
| + | CTGTTACAGACAGTCTACCTGGG | 27 |
| + | TGCCCGCCAGATCCTGGTGCTGG | 28 |
| - | GCACAGAGGGCACATACACCAGG | 29 |
| + | CTGGGCTGTGGTGCAAGCTTGGG | 30 |
| + | TGTCATCTCAGACAACCTGCTGG | 31 |
| - | AGCACCAGGATCTGGCGGGCAGG | 32 |
| + | GGTGTATGTGCCCTCTGTGCTGG | 33 |
| + | TCAGACAACCTGCTGGTGACTGG | 34 |
| + | GCTGCCATTGTCTGCAACTTTGG | 35 |
| - | GTCCAGCACCAGGATCTGGCGGG | 36 |
| + | CCTGCTGGTGACTGGCGGCCAGG | 37 |
| + | GACAACCTGCTGGTGACTGGCGG | 38 |
| + | CTGCTGGTGACTGGCGGCCAGGG | 39 |
| - | ACTGCCAAAGTTGCAGACAATGG | 40 |
| + | CCTGGGCTGTGGTGCAAGCTTGG | 41 |
| + | CTTTGGCAGTGAGCTCAGCCTGG | 42 |
| - | TGTCCAGCACCAGGATCTGGCGG | 43 |
| - | CCAAGCTTGCACCACAGCCCAGG | 44 |
| - | CCTGGCCGCCAGTCACCAGCAGG | 45 |
| + | CCAGCCTGCCCGCCAGATCCTGG | 46 |
| + | ATGTCCTTGCCTCCAGGACCTGG | 47 |
| + | CCAGGGCTGTGTCTCCTTTTGGG | 48 |
| - | CAGGATCTGGCGGGCAGGCTGGG | 49 |
| + | CTACCTGGGGAAGAACAGTGAGG | 50 |
| - | CCAGGATCTGGCGGGCAGGCTGG | 51 |
| + | GCCAGGGCTGTGTCTCCTTTTGG | 52 |
| - | TTGCACCACAGCCCAGGTCCTGG | 53 |

The Cas protein and the gRNA form a complex, and the Cas protein cleaves the target SCAP genomic nucleic acid molecule. The Cas protein can cleave the nucleic acid molecule at a site within or outside of the nucleic acid sequence present in the target SCAP genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the SCAP genomic nucleic acid molecule to which a DNA-targeting segment of a gRNA will bind.

Such methods can result, for example, in a SCAP genomic nucleic acid molecule in which a region of SEQ ID NO:1 is disrupted, the start codon is disrupted, the stop codon is disrupted, or the coding sequence is deleted. Optionally, the cell can be further contacted with one or more additional gRNAs that hybridize to additional gRNA recognition sequences within the target genomic locus in the SCAP genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the SCAP inhibitor comprises a small molecule. In some embodiments, the SCAP inhibitor is Fatostatin A or PF-429242.

In some embodiments, the methods further comprise detecting the presence or absence of a SCAP predicted loss-of-function variant nucleic acid molecule encoding a human SCAP polypeptide in a biological sample from the subject. In some embodiments, the methods further comprise detecting the presence or absence of a SCAP predicted loss-of-function variant polypeptide in a biological sample from the subject. As used throughout the present disclosure a "SCAP predicted loss-of-function variant nucleic acid molecule" is any SCAP nucleic acid molecule (such as, for example, genomic nucleic acid molecule, mRNA molecule, or cDNA molecule) encoding a SCAP polypeptide having a partial loss-of-function, a complete loss-of-function, a predicted partial loss-of-function, or a predicted complete loss-of-function. For example, the SCAP predicted loss-of-function variant nucleic acid molecule can be any nucleic acid molecule encoding SCAP Thr1235fs (SEQ ID NO:8).

In some embodiments, the SCAP predicted loss-of-function variant nucleic acid molecule is: i) a genomic nucleic acid molecule having a nucleotide sequence comprising a thymine at a position corresponding to position 61,695 according to SEQ ID NO:2; ii) an mRNA molecule having a nucleotide sequence comprising a uracil at a position corresponding to position 4,116 according to SEQ ID NO:4; or iii) a cDNA molecule produced from an mRNA molecule, wherein the cDNA molecule has a nucleotide sequence comprising a thymine at a position corresponding to position 4,116 according to SEQ ID NO:6.

In some embodiments, when the subject is SCAP reference, the subject is also administered a therapeutic agent that treats or inhibits an increased lipid level and/or increased triglyceride levels in a standard dosage amount. In some embodiments, when the subject is heterozygous for a SCAP predicted loss-of-function variant, the subject is also administered a therapeutic agent that treats or inhibits an increased lipid level and/or increased triglyceride levels in a dosage amount that is the same as or lower than the standard dosage amount.

The present disclosure also provides methods of treating a subject with a therapeutic agent that treats or inhibits an increased lipid level and/or increased triglyceride levels, wherein the subject is suffering from an increased lipid level and/or increased triglyceride levels, the method comprising the steps of: determining whether the subject has a SCAP predicted loss-of-function variant nucleic acid molecule encoding a human SCAP polypeptide by: obtaining or having obtained a biological sample from the subject; and performing or having performed a genotyping assay on the biological sample to determine if the subject has a genotype comprising the SCAP predicted loss-of-function variant nucleic acid molecule; and when the subject is SCAP reference, then administering or continuing to administer to the subject the therapeutic agent that treats or inhibits the increased lipid level and/or increased triglyceride levels in a standard dosage amount, and administering to the subject a SCAP inhibitor; and when the subject is heterozygous for a SCAP predicted loss-of-function variant, then administering or continuing to administer to the subject the therapeutic agent that treats or inhibits the increased lipid level and/or increased triglyceride levels in an amount that is the same as or lower than a standard dosage amount, and administering to the subject a SCAP inhibitor; wherein the presence of a genotype having the SCAP predicted loss-of-function variant nucleic acid molecule encoding the human SCAP polypeptide indicates the subject has a reduced risk of developing the increased lipid level and/or increased triglyceride levels. In some embodiments, the subject is SCAP reference. In some embodiments, the subject is heterozygous for a SCAP predicted loss-of-function variant.

The SCAP predicted loss-of-function variant nucleic acid molecule can be any SCAP nucleic acid molecule (such as, for example, genomic nucleic acid molecule, mRNA molecule, or cDNA molecule) encoding a SCAP polypeptide having a partial loss-of-function, a complete loss-of-function, a predicted partial loss-of-function, or a predicted complete loss-of-function. For example, the SCAP predicted loss-of-function variant nucleic acid molecule can be any nucleic acid molecule encoding SCAP Thr1235fs (SEQ ID NO:8).

In some embodiments, the SCAP predicted loss-of-function variant nucleic acid molecule is: i) a genomic nucleic acid molecule having a nucleotide sequence comprising a thymine at a position corresponding to position 61,695 according to SEQ ID NO:2; ii) an mRNA molecule having a nucleotide sequence comprising a uracil at a position corresponding to position 4,116 according to SEQ ID NO:4; and/or iii) a cDNA molecule produced from an mRNA molecule, wherein the cDNA molecule has a nucleotide sequence comprising a thymine at a position corresponding to position 4,116 according to SEQ ID NO:6. In some embodiments, the subject is SCAP reference. In some embodiments, the subject is heterozygous for a SCAP predicted loss-of-function variant.

Detecting the presence or absence of a SCAP predicted loss-of-function variant nucleic acid molecule (such as, for example, a nucleic acid molecule encoding SCAP Thr1235fs) in a biological sample from a subject and/or determining whether a subject has a SCAP predicted loss-of-function variant nucleic acid molecule (such as, for example, a nucleic acid molecule encoding SCAP Thr1235fs) can be carried out by any of the methods described herein. In some embodiments, these methods can be carried out in vitro. In some embodiments, these methods can be carried out in situ. In some embodiments, these methods can be carried out in vivo.

In some embodiments, the detection step, detecting step, or genotyping assay comprises sequencing at least a portion of the nucleotide sequence of the SCAP genomic nucleic acid molecule, the SCAP mRNA molecule, or the SCAP cDNA molecule in the biological sample, wherein the sequenced portion comprises variation(s) that cause a loss-of-function (partial or complete) or are predicted to cause a loss-of-function (partial or complete). For example, in some embodiments, the detection step, detecting step, or genotyping assay comprises sequencing at least a portion of: i) the nucleotide sequence of the genomic nucleic acid molecule encoding the SCAP polypeptide, wherein the sequenced portion comprises a position corresponding to position 61,695 according to SEQ ID NO:2, or the complement thereof; ii) the nucleotide sequence of the mRNA molecule encoding the SCAP polypeptide, wherein the sequenced portion comprises a position corresponding to position 4,116 according to SEQ ID NO:4, or the complement thereof; or iii) the nucleotide sequence of the cDNA molecule encoding the SCAP polypeptide, wherein the sequenced portion comprises a position corresponding to position 4,116 according to SEQ ID NO:6, or the complement thereof. When the sequenced portion of the SCAP genomic nucleic acid molecule in the biological sample comprises: a thymine at a position corresponding to position 61,695 according to SEQ ID NO:2; a uracil at a position corresponding to position 4,116 according to SEQ ID NO:4; or a thymine at a position corresponding to position 4,116 according to SEQ ID NO:6, then the SCAP cDNA molecule in the biological sample is a SCAP predicted loss-of-function variant cDNA molecule.

In some embodiments, the detection step, detecting step, or genotyping assay comprises: a) contacting the biological sample with a primer hybridizing to: i) a portion of the nucleotide sequence of the SCAP genomic nucleic acid molecule that is proximate to a position corresponding to position 61,695 according to SEQ ID NO:2; ii) a portion of the nucleotide sequence of the SCAP mRNA molecule that is proximate to a position corresponding to position 4,116 according to SEQ ID NO:4; and/or iii) a portion of the nucleotide sequence of the SCAP cDNA molecule that is proximate to a position corresponding to position 4,116 according to SEQ ID NO:6; b) extending the primer at least through: i) the position of the nucleotide sequence of the SCAP genomic nucleic acid molecule corresponding to position 61,695 according to SEQ ID NO:2; ii) the position of the nucleotide sequence of the SCAP mRNA molecule corresponding to position 4,116 according to SEQ ID NO:4; and/or iii) the position of the nucleotide sequence of the SCAP cDNA molecule corresponding to position 4,116 according to SEQ ID NO:6; and c) determining whether the extension product of the primer comprises: i) a thymine at a position corresponding to position 61,695 according to SEQ ID NO:2; ii) a uracil at a position corresponding to position 4,116 according to SEQ ID NO:4; and/or iii) a thymine at a position corresponding to position 4,116 according to SEQ ID NO:6. In some embodiments, the determining step comprises sequencing the entire nucleic acid molecule.

In some embodiments, the detection step, detecting step, or genotyping assay comprises: a) amplifying at least a portion of the nucleic acid molecule that encodes the human SCAP polypeptide, wherein the portion comprises: i) a thymine at a position corresponding to position 61,695 according to SEQ ID NO:2, or the complement thereof; ii) a uracil at a position corresponding to position 4,116 according to SEQ ID NO:4, or the complement thereof; and/or iii) a thymine at a position corresponding to position 4,116 according to SEQ ID NO:6, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleotide sequence of the amplified nucleic acid molecule comprising a thymine at a position corresponding to position 61,695 according to SEQ ID NO:2, or the complement thereof; ii) the nucleotide sequence of the amplified nucleic acid molecule comprising a uracil at a position corresponding to position 4,116 according to SEQ ID NO:4, or the complement thereof; and/or iii) the nucleotide sequence of the amplified nucleic acid molecule comprising a thymine at a position corresponding to position 4,116 according to SEQ ID NO:6, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the detection step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to: i) the nucleotide sequence of the amplified nucleic acid molecule comprising a thymine at a position corresponding to position 61,695 according to SEQ ID NO:2, or the complement thereof; ii) the nucleotide sequence of the amplified nucleic acid molecule comprising a uracil at a position corresponding to position 4,116 according to SEQ ID NO:4, or the complement thereof; or iii) the nucleotide sequence of the amplified nucleic acid molecule comprising a thymine at a position corresponding to position 4,116 according to SEQ ID NO:6, or the complement thereof; and detecting the detectable label.

In some embodiments, the SCAP predicted loss-of-function variant nucleic acid molecule is: i) a genomic nucleic acid molecule having a nucleotide sequence lacking nucleotides at positions corresponding to positions 61,695 to 61,698 according to SEQ ID NO:1; ii) an mRNA molecule having a nucleotide sequence lacking nucleotides at positions corresponding to positions 4,116 to 4,119 according to SEQ ID NO:3; and/or iii) a cDNA molecule produced from an mRNA molecule, wherein the cDNA molecule has a nucleotide sequence lacking nucleotides at positions corresponding to positions 4,116 to 4,119 according to SEQ ID NO:5.

In some embodiments, the determining step or detecting step comprises: a) contacting the sample with a primer or alteration-specific primer hybridizing to: i) a portion of the nucleotide sequence of the SCAP genomic nucleic acid molecule that is proximate to positions corresponding to positions 61,695 to 61,698 according to SEQ ID NO:1 or positions 61,694 to 61,695 according to SEQ ID NO:2; ii) a portion of the nucleotide sequence of SCAP mRNA molecule that is proximate to positions corresponding to positions 4,116 to 4,119 according to SEQ ID NO:3, or positions corresponding to positions 4,115 to 4,116 according to SEQ ID NO:4; or iii) a portion of the nucleotide sequence of SCAP cDNA molecule that is proximate to positions corresponding to positions 4,116 to 4,119 according to SEQ ID NO:5, or positions corresponding to positions 4,115 to 4,116 according to SEQ ID NO:6; b) extending the primer or alteration-specific primer at least through: i) the positions corresponding to positions 61,695 to 61,698 according to SEQ ID NO:1 or positions 61,694 to 61,695 according to SEQ ID NO:2; ii) the positions corresponding to positions 4,116 to 4,119 according to SEQ ID NO:3, or positions corresponding to positions 4,115 to 4,116 according to SEQ ID NO:4; or iii) the positions corresponding to positions 4,116 to 4,119 according to SEQ ID NO:5, or positions corresponding to positions 4,115 to 4,116 according to SEQ ID NO:6; and c) determining whether the extension product of the primer or alteration-specific primer lacks: i) nucleotides at positions corresponding to positions 61,695 to 61,698 according to SEQ ID NO:1; ii) nucleotides at positions corresponding to positions 4,116 to 4,119 according to SEQ ID NO:3; or iii) nucleotides at positions corresponding to positions 4,116 to 4,119 according to SEQ ID NO:5.

In some embodiments, the determining step or detecting step comprises: a) amplifying at least a portion of the nucleic acid molecule that encodes the human SCAP polypeptide, wherein the portion comprises: i) nucleotides at positions 61,695 to 61,698 according to SEQ ID NO:1, or nucleotides at positions 61,694 to 61,695 according to SEQ ID NO:2, or the complement thereof; ii) nucleotides at positions 4,116 to 4,119 according to SEQ ID NO:3, or nucleotides at positions 4,115 to 4,116 according to SEQ ID NO:4 or the complement thereof; and/or iii) nucleotides at positions 4,116 to 4,119 according to SEQ ID NO:5, or nucleotides at positions 4,115 to 4,116 according to SEQ ID NO:6, or the complement thereof; b) labeling the amplified nucleic acid molecule with a detectable label; c) contacting the labeled nucleic acid molecule with a support comprising a probe or an alteration-specific probe, wherein the probe or alteration-specific probe comprises a nucleotide sequence which hybridizes under stringent conditions: i) exclusively to the nucleotide sequence of the amplified nucleic acid molecule comprising nucleotides at positions 61,695 to 61,698 according to SEQ ID NO:1, or exclusively to the nucleotide sequence of the amplified nucleic acid molecule comprising nucleotides at positions 61,694 to 61,695 according to SEQ ID NO:2, or the complement thereof; ii) exclusively to the nucleotide sequence of the amplified nucleic acid molecule comprising nucleotides at positions 4,116 to 4,119 according to SEQ ID NO:3, or exclusively to the nucleotide sequence of the amplified nucleic acid molecule nucleotides at positions 4,115 to 4,116 according to SEQ ID NO:4 or the complement thereof; or iii) exclusively to the nucleotide sequence of the amplified nucleic acid molecule comprising nucleotides at positions 4,116 to 4,119 according to SEQ ID NO:5, or exclusively to the nucleotide sequence of the amplified nucleic acid molecule nucleotides at positions 4,115 to 4,116 according to SEQ ID NO:6 or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step or detecting step comprises: contacting the SCAP nucleic acid molecule with a probe comprising a detectable label, wherein the probe comprises a nucleotide sequence which hybridizes under stringent conditions to: i) the nucleotide sequence of the amplified nucleic acid molecule lacking nucleotides at positions corresponding to positions 61,695 to 61,698 according to SEQ ID NO:1, or the complement thereof; ii) the nucleotide sequence of the amplified nucleic acid molecule lacking nucleotides at positions corresponding to positions 4,116 to 4,119 according to SEQ ID NO:3; or iii) the nucleotide sequence of the amplified nucleic acid molecule lacking nucleotides at positions corresponding to positions 4,116 to 4,119 according to SEQ ID NO:5, or the complement thereof; and detecting the detectable label.

In some embodiments, the assay comprises: sequencing a portion of the nucleotide sequence of a SCAP genomic nucleic acid molecule in the sample, wherein the portion sequenced includes positions corresponding to positions 61,695 to 61,698 according to SEQ ID NO:1 or positions 61,694 to 61,695 according to SEQ ID NO:2; positions corresponding to positions 4,116 to 4,119 according to SEQ ID NO:3, or positions corresponding to positions 4,115 to 4,116 according to SEQ ID NO:4; or positions corresponding to positions 4,116 to 4,119 according to SEQ ID NO:5, or positions corresponding to positions 4,115 to 4,116 according to SEQ ID NO:6.

In some embodiments, the assay comprises: a) contacting the sample with a primer or alteration-specific primer hybridizing to: i) a portion of the SCAP genomic sequence that is within 50 nucleotides of a position of the SCAP genomic sequence corresponding to positions 61,695 to 61,698 according to SEQ ID NO:1 or positions 61,694 to 61,695 according to SEQ ID NO:2; ii) a portion of the SCAP mRNA sequence that is within 50 nucleotides of a position of the SCAP mRNA corresponding to positions 4,116 to 4,119 according to SEQ ID NO:3, or positions corresponding to positions 4,115 to 4,116 according to SEQ ID NO:4; or iii) a portion of the SCAP cDNA sequence that is within 50 nucleotides of a position of the SCAP cDNA corresponding to positions 4,116 to 4,119 according to SEQ ID NO:5, or positions corresponding to positions 4,115 to 4,116 according to SEQ ID NO:6; b) extending the primer or alteration-specific primer at least through: i) the position of the SCAP genomic sequence corresponding to positions 61,695 to 61,698 according to SEQ ID NO:1 or positions 61,694 to 61,695 according to SEQ ID NO:2; ii) the position of the SCAP mRNA corresponding to positions 4,116 to 4,119 according to SEQ ID NO:3, or positions corresponding to positions 4,115 to 4,116 according to SEQ ID NO:4; or iii) the position of the SCAP cDNA corresponding to positions 4,116 to 4,119 according to SEQ ID NO:5, or positions corresponding to positions 4,115 to 4,116 according to SEQ ID NO:6; and c) determining whether the extension product of the primer comprises an ACAG sequence at positions: i) corresponding to positions 61,695 to 61,698 according to SEQ ID NO:1; ii) corresponding to positions 4,116 to 4,119 according to SEQ ID NO:3; iii) corresponding to positions 4,116 to 4,119 according to SEQ ID NO:5, or whether the extension product of the alteration-specific primer comprises: i) a GT sequence at positions corresponding to positions 61,694 to 61,695 according to SEQ ID NO:2; ii) a GU sequence at positions corresponding to positions 4,115 to 4,116 according to SEQ ID NO:4; or iii) a GT sequence at positions corresponding to positions 4,115 to 4,116 according to SEQ ID NO:6.

In any of these embodiments, the nucleic acid molecule can be present within a cell obtained from the human subject.

The present disclosure also provides methods of treating a subject with a therapeutic agent that treats or inhibits an increased lipid level and/or increased triglyceride levels, wherein the subject is suffering from an increased lipid level and/or increased triglyceride levels, the method comprising the steps of: determining whether the subject has a variant SCAP polypeptide lacking an amino acid sequence according to SEQ ID NO:9 at positions corresponding to positions 1,235 to 1,279 according to SEQ ID NO:7; by: obtaining or having obtained a biological sample from the subject; and performing or having performed an assay on the biological sample to determine if the subject has the variant SCAP polypeptide; and when the subject does not have the variant SCAP polypeptide, then administering or continuing to administer to the subject the therapeutic agent that treats or inhibits the increased lipid level and/or increased triglyceride levels in a standard dosage amount, and administering to the subject a SCAP inhibitor; and when the subject has the variant SCAP polypeptide, then administering or continuing to administer to the subject the therapeutic agent that treats or inhibits the increased lipid level and/or increased triglyceride levels in an amount that is the same as or lower than a standard dosage amount, and administering to the subject a SCAP inhibitor; wherein the presence of the variant SCAP polypeptide indicates the subject has a reduced risk of developing the increased lipid level and/or increased triglyceride levels.

In any of the embodiments described herein, the increased lipid level is increased serum lipid level, increased total cholesterol, or increased LDL. In some embodiments, the increased lipid level is increased serum lipid level. In some embodiments, the increased lipid level is increased total cholesterol. In some embodiments, the increased lipid level is increased serum cholesterol. In some embodiments, the increased lipid level is increased LDL. In some embodiments, the increased lipid level is increased serum cholesterol.

In some embodiments, increased lipid levels include hyperlipidemia, such as hypercholesterolemia (elevated cholesterol). Increased lipid levels also include hyperlipoproteinemia, which refers to the presence of elevated lipoproteins (usually LDL). In some embodiments, the human subject may have combined hyperlipidemia, which is an elevation of both cholesterol and triglycerides, or may have mixed hyperlipidemia, which is an elevation of triglycerides and LDL. In some embodiments, the human subject may have hypertriglyceridemia, in which the triglyceride level is elevated with regard to the normal average level of triglycerides in a respective reference subject typically of the same ethnic background, age and gender. Typically, triglyceride tests are blood tests that measure the total amount of triglycerides in the blood.

For human subjects that are genotyped or determined to be either SCAP reference or heterozygous for a SCAP predicted loss-of-function variant, such human subjects can be treated with a SCAP inhibitor, as described herein.

Examples of therapeutic agents that treat or inhibit an increased lipid level and/or increased triglyceride levels include, but are not limited to: a spirocyclic azetidinone derivative, a statin, a PPAR agonist, nicotinic acid, niacin, ezetimibe, a PCSK9 inhibitor, an RXR agonist, a hormone, a sulfonylurea-based drug, a biguanide, an α-glucosidase inhibitor, a GLP-1 agonist, and a PPARα/δ dual agonist, or any combination thereof.

Spirocyclic azetidinone derivatives include, but are not limited to those disclosed in, for example, U.S. RE 37,721; U.S. Pat. Nos. 5,631,356; 5,767,115; 5,846,966; 5,698,548; 5,633,246; 5,656,624; 5,624,920; 5,688,787; and 5,756,470; U.S. Publication No. 2002/0137689; and PCT Publication Nos. WO 02/066464, WO 95/08522, and WO96/19450.

Statins include, but are not limited to, atorvastatin, fluvastatin, lovastatin, pitavastatin, pravastatin, rosuvastatin, cerivastatin, and simvastatin.

PPAR agonists include, but are not limited to, a thiazolidinedione or a fibrate. Thiazolidinediones include, but are not limited to, 5-((4-(2-(methyl-2-pyridinylamino) ethoxy) phenyl)methyl)-2,4-thiazolidinedione, troglitazone, pioglitazone, ciglitazone, WAY-120,744, englitazone, AD 5075, darglitazone, and rosiglitazone. Fibrates include, but are not limited to, gemfibrozil, fenofibrate, clofibrate, and ciprofibrate. PPARα/6 dual agonists include, but are not limited to, Elafibranor.

RXR agonists include, but are not limited to, LG 100268, LGD 1069, 9-cis retinoic acid, 2-(1-(3,5,5,8,8-pentannethyl-5,6,7,8-tetrahydro-2-naphthyl)-cyclopropyl)-pyridine-5-carboxylic acid, and 4-((3,5,5,8,8-pentannethyl-5,6,7,8-tetrahydro-2-naphthyl)2-carbonyl)-benzoic acid.

Hormones include, but are not limited to, thyroid hormone, estrogen and insulin. Suitable insulins include, but are not limited, to injectable insulin, transdermal insulin, and inhaled insulin, or any combination thereof. As an alternative to insulin, an insulin derivative, secretagogue, sensitizer or mimetic may be used. Insulin secretagogues include, but are not limited to, forskolin, dibutryl cAMP, and isobutyl-methylxanthine (IBMX).

Sulfonylurea-based drugs include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide.

Biguanides include, but are not limited to, metformin, phenformin and buformin.

α-glucosidase inhibitors include, but are not limited to, acarbose and miglitol.

GLP-1 agonists include, but are not limited to, VICTOZA® and SAXENDA® (liraglutide), BYETTA® and BYDUREON® (exenatide), LYXUMIA® (lixisenatide), TANZEUM® (albiglutide), TRULICITY® (dulaglutide), and OZEMPIC® (semaglutide).

Additional examples of therapeutic agents that treat or inhibit increased triglyceride levels include, but are not limited to: fibric acid derivatives, such as gemfibrozil (Lopid®) and fenofibrate, niacin, and omega-3 fatty acids.

For human subjects that are genotyped or determined to be either SCAP reference or heterozygous for a SCAP predicted loss-of-function variant, such human subjects can also be treated with any one or more of the SCAP predicted loss-of-function polypeptides described herein.

In some embodiments, the dose of the therapeutic agents that treat or inhibit the increased lipid level and/or increased triglyceride levels can be reduced by about 10%, by about 20%, by about 30%, by about 40%, by about 50%, by about 60%, by about 70%, by about 80%, or by about 90% for subjects that are heterozygous for a SCAP predicted loss-of-function variant (i.e., a lower than the standard dosage amount) compared to subjects that are SCAP reference (who may receive a standard dosage amount). In some embodiments, the dose of the therapeutic agents that treat or inhibit the increased lipid level and/or increased triglyceride levels can be reduced by about 10%, by about 20%, by about 30%, by about 40%, or by about 50%. In addition, the dose of therapeutic agents that treat or inhibit the increased lipid level and/or increased triglyceride levels in subjects that are heterozygous for a SCAP predicted loss-of-function variant can be administered less frequently compared to subjects that are SCAP reference.

Administration of the therapeutic agents that treat or inhibit the increased lipid level and/or increased triglyceride levels and/or SCAP inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit the increased lipid level and/or increased triglyceride levels and/or SCAP inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in an increased lipid level and/or increased triglyceride levels, a decrease/reduction in the severity of an increased lipid level and/or increased triglyceride levels (such as, for example, a reduction or inhibition of development or an increased lipid level and/or increased triglyceride levels), a decrease/reduction in symptoms and increased lipid level- and/or increased triglyceride levels-related effects, delaying the onset of symptoms and increased lipid level- and/or increased triglyceride levels-related effects, reducing the severity of symptoms of the increased lipid level- and/or increased triglyceride levels-related effects, reducing the severity of an acute episode, reducing the number of symptoms and increased lipid level- and/or increased triglyceride levels-related effects, reducing the latency of symptoms and increased lipid level- and/or increased triglyceride levels-related effects, an amelioration of symptoms and increased lipid level- and/or increased triglyceride levels-related effects, reducing secondary symptoms, reducing secondary infections, preventing relapse to an increased lipid level and/or increased triglyceride levels, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of increased lipid level and/or increased triglyceride levels development/progression (such as, for example, a complete or partial avoidance/inhibition or a delay), and an increased survival time of the affected host animal, following administration of a therapeutic protocol. Treatment of an increased lipid level and/or increased triglyceride levels encompasses the treatment of subjects already diagnosed as having any form of the increased lipid level and/or increased triglyceride levels at any clinical stage or manifestation, the delay of the onset or evolution or aggravation or deterioration of the symptoms or signs of the increased lipid level and/or increased triglyceride levels, and/or preventing and/or reducing the severity of the increased lipid level and/or increased triglyceride levels.

In some embodiments, the methods further comprise detecting the presence or absence of a SCAP polypeptide in a biological sample from the subject, wherein the SCAP polypeptide comprises an amino acid sequence comprising amino acids at positions corresponding to positions 1,235 to 1,335 according to SEQ ID NO:8, wherein: when the human subject does not have the SCAP polypeptide, then the human subject has an increased risk for developing an increased lipid level and/or increased triglyceride levels; and when the human subject has the SCAP polypeptide, then the human subject has a decreased risk for developing an increased lipid level and/or increased triglyceride levels.

In some embodiments, the detecting step comprises sequencing at least a portion of the SCAP polypeptide that comprises an amino acid sequence comprising amino acids at positions corresponding to positions 1,235 to 1,335 according to SEQ ID NO:8. In some embodiments, the detecting step comprises sequencing the entire polypeptide. In some embodiments, the detecting step comprises an immunoassay for detecting the presence of a polypeptide that comprises an amino acid sequence comprising amino acids at positions corresponding to positions 1,235 to 1,335 according to SEQ ID NO:8.

The present disclosure also provides methods of identifying a human subject having an increased risk for developing an increased lipid level and/or increased triglyceride levels, wherein the method comprises and of the methods described herein for detecting the presence or absence of any of the SCAP predicted loss-of-function variant nucleic acid molecules (such as a genomic nucleic acid molecule, mRNA molecule, and/or cDNA molecule) described herein. When the human subject lacks a SCAP predicted loss-of-function variant nucleic acid molecule (i.e., the human subject is genotypically categorized as SCAP reference), then the human subject has an increased risk for developing an increased lipid level and/or increased triglyceride levels. When the human subject has a SCAP predicted loss-of-function variant nucleic acid molecule (i.e., the human subject is categorized as heterozygous for a SCAP predicted loss-of-function variant or homozygous for a SCAP predicted loss-of-function variant), then the human subject has a decreased risk for developing an increased lipid level and/or increased triglyceride levels. Having a single copy of a SCAP predicted loss-of-function variant nucleic acid molecule is more protective of a human subject from developing an increased lipid level and/or increased triglyceride levels than having no copies of a SCAP predicted loss-of-function variant nucleic acid molecule.

Without intending to be limited to any particular theory or mechanism of action, it is believed that a single copy of a SCAP predicted loss-of-function variant nucleic acid molecule (i.e., heterozygous for a SCAP predicted loss-of-function variant) is protective of a human subject from developing an increased lipid level and/or increased triglyceride levels, and it is also believed that having two copies of a SCAP predicted loss-of-function variant nucleic acid molecule (i.e., homozygous for a SCAP predicted loss-of-function variant) may be more protective of a human subject from developing an increased lipid level and/or increased triglyceride levels, relative to a human subject with a single copy. Thus, in some embodiments, a single copy of a SCAP predicted loss-of-function variant nucleic acid molecule may not be completely protective, but instead, may be partially or incompletely protective of a human subject from developing an increased lipid level and/or increased triglyceride levels. While not desiring to be bound by any particular theory, there may be additional factors or molecules involved in the development of increased lipid level and/or increased triglyceride levels that are still present in a human subject having a single copy of a SCAP predicted loss-of-function variant nucleic acid molecule, thus resulting in less than complete protection from the development of increased lipid level and/or increased triglyceride levels.

The present disclosure also provides methods of identifying a human subject having an increased risk for developing an increased lipid level and/or increased triglyceride levels, wherein the method comprises: detecting the presence or absence of a SCAP predicted loss-of-function polypeptide in a biological sample from the subject, wherein the SCAP predicted loss-of-function polypeptide comprises an amino acid sequence comprising amino acids at positions corresponding to positions 1,235 to 1,335 according to SEQ ID NO:8; wherein: when the human subject does not have a SCAP predicted loss-of-function polypeptide, then the human subject has an increased risk for developing an increased lipid level and/or increased triglyceride levels; and when the human subject has a SCAP predicted loss-offunction polypeptide, then the human subject has a decreased risk for developing an increased lipid level and/or increased triglyceride levels.

In some embodiments, the determining step comprises sequencing at least a portion of the SCAP polypeptide that comprises an amino acid sequence comprising amino acids at positions corresponding to positions 1,235 to 1,335 according to SEQ ID NO:8. In some embodiments, the determining step comprises sequencing the entire polypeptide. In some embodiments, the determining step comprises an immunoassay.

In some embodiments, the human subject is further treated with a therapeutic agent that treats or inhibits the increased lipid level and/or increased triglyceride levels and/or a SCAP inhibitor, as described herein. For example, when the human subject is SCAP reference, and therefore has an increased risk for developing an increased lipid level and/or increased triglyceride levels, the human subject is administered a SCAP inhibitor. In some embodiments, such a subject is also administered a therapeutic agent that treats or inhibits the increased lipid level and/or increased triglyceride levels. In some embodiments, when the subject is heterozygous for a SCAP predicted loss-of-function variant, the subject is administered the therapeutic agent that treats or inhibits the increased lipid level and/or increased triglyceride levels in a dosage amount that is the same as or lower than the standard dosage amount, and is also administered a SCAP inhibitor. In some embodiments, the subject is SCAP reference. In some embodiments, the subject is heterozygous for a SCAP predicted loss-of-function variant.

The present disclosure also provides methods of detecting the presence of a SCAP predicted loss-of-function variant genomic nucleic acid molecule, a SCAP predicted loss-of-function variant mRNA molecule, and/or a SCAP predicted loss-of-function variant cDNA molecule in a biological sample from a subject human. It is understood that gene sequences within a population and mRNA molecules encoded by such genes can vary due to polymorphisms such as single-nucleotide polymorphisms. The sequences provided herein for the SCAP variant genomic nucleic acid molecule, SCAP variant mRNA molecule, and SCAP variant cDNA molecule are only exemplary sequences. Other sequences for the SCAP variant genomic nucleic acid molecule, variant mRNA molecule, and variant cDNA molecule are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any SCAP variant nucleic acid molecule, preliminary processing designed to isolate or enrich the sample for the genomic DNA can be employed. A variety of known techniques may be used for this purpose. When detecting the level of any SCAP variant mRNA, different techniques can be used enrich the biological sample with mRNA. Various methods to detect the presence or level of a mRNA or the presence of a particular variant genomic DNA locus can be used.

In some embodiments, the methods of detecting a human SCAP predicted loss-of-function variant nucleic acid molecule in a human subject comprises assaying a sample obtained from the subject to determine whether a nucleic acid molecule in the sample comprises a nucleotide sequence comprising: i) a thymine at a position corresponding to position 61,695 according to SEQ ID NO:2, or the complement thereof, ii) a uracil at a position corresponding to position 4,116 according to SEQ ID NO:4, or the complement thereof, or iii) a thymine at a position corresponding to position 4,116 according to SEQ ID NO:6, or the complement thereof. In some embodiments, the method is an in vitro method.

In some embodiments, the methods of detecting the presence or absence of a SCAP predicted loss-of-function variant nucleic acid molecule (such as, for example, genomic nucleic acid molecule, mRNA molecule, and/or cDNA molecule) in a subject, comprises: performing an assay on a biological sample obtained from the subject, which assay determines whether a nucleic acid molecule in the biological sample comprises a nucleotide sequence that encodes a thymine at a position corresponding to position 61,695 according to SEQ ID NO:2, or the complement thereof, ii) a uracil at a position corresponding to position 4,116 according to SEQ ID NO:4, or the complement thereof, or iii) a thymine at a position corresponding to position 4,116 according to SEQ ID NO:6, or the complement thereof. In some embodiments, the biological sample comprises a cell or cell lysate. Such methods can further comprise, for example, obtaining a biological sample from the subject comprising a SCAP genomic nucleic acid molecule or mRNA molecule, and if mRNA, optionally reverse transcribing the mRNA into cDNA, and performing an assay on the biological sample that determines that a position of the SCAP genomic nucleic acid molecule, mRNA, or cDNA encodes a thymine at a position corresponding to position 61,695 according to SEQ ID NO:2, or the complement thereof, ii) a uracil at a position corresponding to position 4,116 according to SEQ ID NO:4, or the complement thereof, or iii) a thymine at a position corresponding to position 4,116 according to SEQ ID NO:6, or the complement thereof. Such assays can comprise, for example determining the identity of these positions of the particular SCAP nucleic acid molecule. In some embodiments, the subject is a human. In some embodiments, the method is an in vitro method.

In some embodiments, the assay comprises sequencing at least a portion of the nucleotide sequence of the SCAP genomic nucleic acid molecule, the SCAP mRNA molecule, or the SCAP cDNA molecule in the biological sample, wherein the sequenced portion comprises one or more variations that cause a loss-of-function (partial or complete). For example, in some embodiments, the assay comprises sequencing at least a portion of: i) the nucleotide sequence of the SCAP genomic nucleic acid molecule in the biological sample, wherein the sequenced portion comprises a position corresponding to position 61,695 according to SEQ ID NO:2, or the complement thereof; ii) the nucleotide sequence of a SCAP mRNA molecule in the biological sample, wherein the sequenced portion comprises a position corresponding to position 4,116 according to SEQ ID NO:4, or the complement thereof; or iii) the nucleotide sequence of a SCAP cDNA molecule in the biological sample, wherein the sequenced portion comprises a position corresponding to position 4,116 according to SEQ ID NO:6, or the complement thereof. When the sequenced portion of the SCAP genomic nucleic acid molecule in the biological sample comprises: a thymine at a position corresponding to position 61,695 according to SEQ ID NO:2; a uracil at a position corresponding to position 4,116 according to SEQ ID NO:4; or a thymine at a position corresponding to position 4,116 according to SEQ ID NO:6, then the SCAP cDNA molecule in the biological sample is a SCAP predicted loss-of-function variant cDNA molecule.

In some embodiments, the assay comprises: a) contacting the sample with a primer hybridizing to: i) a portion of the nucleotide sequence of SCAP genomic nucleic acid molecule that is proximate to a position corresponding to position 61,695 according to SEQ ID NO:2; ii) a portion of the nucleotide sequence of SCAP mRNA molecule that is proximate to a position corresponding to position 4,116 according to SEQ ID NO:4; or iii) a portion of the nucleotide sequence of SCAP cDNA molecule that is proximate to a position corresponding to position 4,116 according to SEQ ID NO:6; b) extending the primer at least through: i) the position of the nucleotide sequence of SCAP genomic nucleic acid molecule corresponding to position 61,695 according to SEQ ID NO:2; ii) the position of the nucleotide sequence of SCAP mRNA molecule corresponding to position 4,116 according to SEQ ID NO:4; or iii) the position of the nucleotide sequence of SCAP cDNA molecule corresponding to position 4,116 according to SEQ ID NO:6; and c) determining whether the extension product of the primer comprises: i) a thymine at a position corresponding to position 61,695 according to SEQ ID NO:2; ii) a uracil at a position corresponding to position 4,116 according to SEQ ID NO:4; or iii) a thymine at a position corresponding to position 4,116 according to SEQ ID NO:6. In some embodiments, the assay comprises sequencing the entire nucleic acid molecule. In some embodiments, only SCAP genomic nucleic acid molecule is analyzed. In some embodiments, only SCAP mRNA is analyzed. In some embodiments, only SCAP cDNA obtained from SCAP mRNA is analyzed.

In some embodiments, the assay comprises: a) amplifying at least a portion of the nucleic acid molecule that encodes the human SCAP polypeptide, wherein the portion comprises: i) a thymine at a position corresponding to position 61,695 according to SEQ ID NO:2, or the complement thereof; ii) a uracil at a position corresponding to position 4,116 according to SEQ ID NO:4, or the complement thereof; or iii) a thymine at a position corresponding to position 4,116 according to SEQ ID NO:6, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a thymine at a position corresponding to position 61,695 according to SEQ ID NO:2, or the complement thereof; ii) the nucleic acid sequence of the amplified nucleic acid molecule comprising a uracil at a position corresponding to position 4,116 according to SEQ ID NO:4, or the complement thereof; or iii) the nucleic acid sequence of the amplified nucleic acid molecule comprising a thymine at a position corresponding to position 4,116 according to SEQ ID NO:6, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the assay comprises: contacting the nucleic acid molecule with an alteration-specific probe comprising a detectable label, wherein the alteration-specific probe comprises a nucleotide sequence which hybridizes under stringent conditions to: i) the nucleotide sequence of the amplified nucleic acid molecule comprising a thymine at a position corresponding to position 61,695 according to SEQ ID NO:2, or the complement thereof; ii) the nucleotide sequence of the amplified nucleic acid molecule comprising a uracil at a position corresponding to position 4,116 according to SEQ ID NO:4, or the complement thereof; or iii) the nucleotide sequence of the amplified nucleic acid molecule comprising a thymine at a position corresponding to position 4,116 according to SEQ ID NO:6, or the complement thereof; and detecting the detectable label. Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the human subject.

The SCAP predicted loss-of-function variant nucleic acid molecule can be any SCAP nucleic acid molecule (such as, for example, genomic nucleic acid molecule, mRNA molecule, or cDNA molecule) encoding a SCAP polypeptide having a partial loss-of-function, a complete loss-of-function, a predicted partial loss-of-function, or a predicted complete loss-of-function. For example, the SCAP predicted loss-of-function variant nucleic acid molecule can be any nucleic acid molecule encoding SCAP Thr1235fs (SEQ ID NO:8).

In some embodiments, the assay comprises contacting the biological sample with a primer or probe, such as an alteration-specific primer or alteration-specific probe, that specifically hybridizes to a SCAP variant genomic sequence, variant mRNA sequence, or variant cDNA sequence and not the corresponding wild type SCAP sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a SCAP variant genomic nucleic acid molecule, variant mRNA molecule, or variant cDNA molecule. The hybridization conditions or reaction conditions can be determined by the operator to achieve this result. This nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Accordingly, probes and primers can share about 80%, about 85%, about 90%, about 91%, about 92%, about 93%, about 94%, about 95%, about 96%, about 97%, about 98%, about 99%, or 100% sequence identity or complementarity to the nucleotide sequence of the target nucleic acid molecule.

In some embodiments, to determine whether the SCAP nucleic acid molecule (genomic nucleic acid molecule, mRNA molecule, or cDNA molecule), or complement thereof, within a biological sample comprises a nucleotide sequence encoding a thymine at a position corresponding to position 61,695 according to SEQ ID NO:2, a uracil at a position corresponding to position 4,116 according to SEQ ID NO:4, or a thymine at a position corresponding to position 4,116 according to SEQ ID NO:6, the biological sample may be subjected to an amplification method using a primer pair that includes a first primer derived from the 5' flanking sequence adjacent to a thymine at a position corresponding to position 61,695 according to SEQ ID NO:2, a uracil at a position corresponding to position 4,116 according to SEQ ID NO:4, or a thymine at a position corresponding to position 4,116 according to SEQ ID NO:6, and a second primer derived from the 3' flanking sequence adjacent to a thymine at a position corresponding to position 61,695 according to SEQ ID NO:2, a uracil at a position corresponding to position 4,116 according to SEQ ID NO:4, or a thymine at a position corresponding to position 4,116 according to SEQ ID NO:6, to produce an amplicon that is indicative of the presence of a thymine at a position corresponding to position 61,695 according to SEQ ID NO:2, a uracil at a position corresponding to position 4,116 according to SEQ ID NO:4, or a thymine at a position corresponding to position 4,116 according to SEQ ID NO:6. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions encoding a thymine at a position corresponding to position 61,695 according to SEQ ID NO:2, a uracil at a position corresponding to position 4,116 according to SEQ ID NO:4, or a thymine at a position corresponding to position 4,116 according to SEQ ID NO:6, and at least 1, 2, 3, 4, 5, 6, 7, 8, 9, 10, or more nucleotides on each side of positions encoding a thymine at a position corresponding to position 61,695 according to SEQ ID NO:2, a uracil at a position corresponding to position 4,116 according to SEQ ID NO:4, or a thymine at a position corresponding to position 4,116 according to SEQ ID NO:6. Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

In some embodiments, the methods of detecting the presence or absence of a SCAP variant nucleic acid molecule (such as, genomic nucleic acid molecule, mRNA molecule, and/or cDNA molecule) in a subject, comprises: performing an assay on a biological sample obtained from the subject, which assay determines whether a nucleic acid molecule in the biological sample comprises a GT sequence at positions corresponding to positions 61,694 to 61,695 according to SEQ ID NO:2; a GU sequence at positions corresponding to positions 4,115 to 4,116 according to SEQ ID NO:4; or a GT sequence at positions corresponding to positions 4,115 to 4,116 according to SEQ ID NO:6. Such methods can further comprise, for example, obtaining a biological sample from the subject comprising a SCAP genomic nucleic acid molecule or mRNA molecule, and if mRNA, optionally reverse transcribing the mRNA into cDNA, and performing an assay on the biological sample that determines that a position of the SCAP genomic nucleic acid molecule encodes a GT sequence at positions corresponding to positions 61,694 to 61,695 according to SEQ ID NO:2; or that a position of the SCAP mRNA encodes a GU sequence at positions corresponding to positions 4,115 to 4,116 according to SEQ ID NO:4; or that a position of the SCAP cDNA encodes a GT sequence at positions corresponding to positions 4,115 to 4,116 according to SEQ ID NO:6. Such assays can comprise, for example determining the identity of these positions of the particular SCAP nucleic acid molecule. In some embodiments, the subject is a human. In some embodiments, the method is an in vitro method. The presence of a nucleic acid molecule in the biological sample that comprises GT or GU at the indicated positions means that a variant SCAP nucleic acid molecule is present in the sample.

In some embodiments, the assay comprises sequencing at least a portion of the nucleic acid molecule, wherein the sequenced portion comprises: a GT sequence at positions corresponding to positions 61,694 to 61,695 according to SEQ ID NO:2, or the complement thereof; a GU sequence at positions corresponding to positions 4,115 to 4,116 according to SEQ ID NO:4, or the complement thereof; or a GT sequence at positions corresponding to positions 4,115 to 4,116 according to SEQ ID NO:6, or the complement thereof. The presence of a nucleic acid molecule in the biological sample that comprises GT or GU at the indicated positions means that a variant SCAP nucleic acid molecule is present in the sample.

In some embodiments, to determine whether the nucleic acid molecule complement of a biological sample comprises a nucleotide sequence a GT sequence at positions corresponding to positions 61,694 to 61,695 according to SEQ ID NO:2, or the complement thereof; a GU sequence at positions corresponding to positions 4,115 to 4,116 according to SEQ ID NO:4, or the complement thereof; or a GT sequence at positions corresponding to positions 4,115 to 4,116 according to SEQ ID NO:6, the biological sample may be subjected to an amplification method using a primer pair that includes a first primer derived from the 5' flanking sequence adjacent to a GT sequence at positions corresponding to positions 61,694 to 61,695 according to SEQ ID NO:2, or the complement thereof; a GU sequence at positions corresponding to positions 4,115 to 4,116 according to SEQ ID NO:4, or the complement thereof; or a GT sequence at positions corresponding to positions 4,115 to 4,116 according to SEQ ID NO:6, and a second primer derived from the 3' flanking sequence adjacent to a GT sequence at positions corresponding to positions 61,694 to 61,695 according to SEQ ID NO:2, or the complement thereof; a GU sequence at positions corresponding to positions 4,115 to 4,116 according to SEQ ID NO:4, or the complement thereof; or a GT sequence at positions corresponding to positions 4,115 to 4,116 according to SEQ ID NO:6 to produce an amplicon that is indicative of the presence of the GT sequence at positions corresponding to positions 61,694 to 61,695 according to SEQ ID NO:2, or the complement thereof; a GU sequence at positions corresponding to positions 4,115 to 4,116 according to SEQ ID NO:4, or the complement thereof; or a GT sequence at positions corresponding to positions 4,115 to 4,116 according to SEQ ID NO:65. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs.

Optionally, the primer pair flanks a region including positions encoding a GT sequence at positions corresponding to positions 61,694 to 61,695 according to SEQ ID NO:2; a GU sequence at positions corresponding to positions 4,115 to 4,116 according to SEQ ID NO:4; or a GT sequence at positions corresponding to positions 4,115 to 4,116 according to SEQ ID NO:6, and at least 1, 2, 3, 4, 5, 6, 7, 8, 9, 10, or more nucleotides on each side of positions encoding a GT sequence at positions corresponding to positions 61,694 to 61,695 according to SEQ ID NO:2; a GU sequence at positions corresponding to positions 4,115 to 4,116 according to SEQ ID NO:4; or a GT sequence at positions corresponding to positions 4,115 to 4,116 according to SEQ ID NO:6. Similar amplicons can be generated from the mRNA and/or cDNA sequences.

In some embodiments, the methods of detecting the presence or absence of a SCAP variant nucleic acid molecule (such as, genomic nucleic acid molecule, mRNA molecule, and/or cDNA molecule) in a subject, comprises: performing an assay on a biological sample obtained from the subject, which assay determines whether a nucleic acid molecule in the biological sample comprises a nucleotide sequence lacking: i) nucleotides at positions corresponding to positions 61,695 to 61,698 according to SEQ ID NO:1, or the complement thereof, ii) nucleotides at positions corresponding to positions 4,116 to 4,119 according to SEQ ID NO:3, or the complement thereof, or iii) nucleotides at positions corresponding to positions 4,116 to 4,119 according to SEQ ID NO:5, or the complement thereof.

In some embodiments, the methods of detecting the presence or absence of a SCAP variant nucleic acid molecule (such as, genomic nucleic acid molecule, mRNA molecule, and/or cDNA molecule) in a subject, comprises: performing an assay on a biological sample obtained from the subject, which assay determines whether a nucleic acid molecule in the biological sample comprises ACAG at positions corresponding to positions 61,695 to 61,698 according to SEQ ID NO:1; at positions corresponding to positions 4,116 to 4,119 according to SEQ ID NO:3 or SEQ ID NO:5. In some embodiments, the biological sample comprises a cell or cell lysate. Such methods can further comprise, for example, obtaining a biological sample from the subject comprising a SCAP genomic nucleic acid molecule or mRNA molecule, and if mRNA, optionally reverse transcribing the mRNA into cDNA, and performing an assay on the biological sample that determines that a position of the SCAP genomic nucleic acid molecule encodes an ACAG sequence at positions corresponding to positions 61,695 to 61,698 according to SEQ ID NO:1; or that mRNA encodes an ACAG sequence at positions corresponding to positions 4,116 to 4,119 according to SEQ ID NO:3; or that a position of the SCAP cDNA encodes an ACAG sequence at positions corresponding to positions 4,116 to 4,119 according to SEQ ID NO:5. The presence of a nucleic acid molecule in the biological sample that comprises ACAG at the indicated positions means that a wild type SCAP nucleic acid molecule is present in the sample.

In some embodiments, the assay comprises sequencing at least a portion of the nucleic acid molecule, wherein the sequenced portion comprises: an ACAG sequence at positions corresponding to positions 61,695 to 61,698 according to SEQ ID NO:1, or the complement thereof; an ACAG sequence at positions corresponding to positions 4,116 to 4,119 according to SEQ ID NO:3, or the complement thereof; or an ACAG sequence at positions corresponding to positions 4,116 to 4,119 according to SEQ ID NO:5. The presence of a nucleic acid molecule in the biological sample that comprises ACAG at the indicated positions means that a wild type SCAP nucleic acid molecule is present in the sample.

In some embodiments, the assay comprises: a) amplifying at least a portion of the nucleic acid molecule; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleotide sequence of the amplified nucleic acid molecule lacking nucleotides at positions corresponding to positions 61,695 to 61,698 according to SEQ ID NO:1, or the complement thereof; ii) the nucleotide sequence of the amplified nucleic acid molecule lacking nucleotides at positions corresponding to positions 4,116 to 4,119 according to SEQ ID NO:3; or iii) the nucleotide sequence of the amplified nucleic acid molecule lacking nucleotides at positions corresponding to positions 4,116 to 4,119 according to SEQ ID NO:5, or the complement thereof; and d) detecting the detectable label.

In some embodiments, the assay comprises: contacting the nucleic acid molecule with an alteration-specific probe comprising a detectable label, wherein the alteration-specific probe comprises a nucleotide sequence which hybridizes under stringent conditions to: i) the nucleotide sequence of the amplified nucleic acid molecule lacking nucleotides at positions corresponding to positions 61,695 to 61,698 according to SEQ ID NO:1, or the complement thereof; ii) the nucleotide sequence of the amplified nucleic acid molecule lacking nucleotides at positions corresponding to positions 4,116 to 4,119 according to SEQ ID NO:3; or iii) the nucleotide sequence of the amplified nucleic acid molecule lacking nucleotides at positions corresponding to positions 4,116 to 4,119 according to SEQ ID NO:5, or the complement thereof; and detecting the detectable label.

In some embodiments, to determine whether the nucleic acid molecule complement of a biological sample comprises a nucleotide sequence encoding an ACAG sequence at positions corresponding to positions 61,695 to 61,698 according to SEQ ID NO:1, or the complement thereof; an ACAG sequence at positions corresponding to positions 4,116 to 4,119 according to SEQ ID NO:3, or the complement thereof; or an ACAG sequence at positions corresponding to positions 4,116 to 4,119 according to SEQ ID NO:5, the biological sample may be subjected to an amplification method using a primer pair that includes a first primer derived from the 5' flanking sequence adjacent to an ACAG sequence at positions corresponding to positions 61,695 to 61,698 according to SEQ ID NO:1, or the complement thereof; an ACAG sequence at positions corresponding to positions 4,116 to 4,119 according to SEQ ID NO:3, or the complement thereof; or an ACAG sequence at positions corresponding to positions 4,116 to 4,119 according to SEQ ID NO:5, and a second primer derived from the 3' flanking sequence adjacent to an ACAG sequence at positions corresponding to positions 61,695 to 61,698 according to SEQ ID NO:1, or the complement thereof; an ACAG sequence at positions corresponding to positions 4,116 to 4,119 according to SEQ ID NO:3, or the complement thereof; or an ACAG sequence at positions corresponding to positions 4,116 to 4,119 according to SEQ ID NO:5 to produce an amplicon that is indicative of the presence of the ACAG sequence at positions corresponding to positions 61,695 to 61,698 according to SEQ ID NO:1, or the complement thereof; an ACAG sequence at positions corresponding to positions 4,116 to 4,119 according to SEQ ID NO:3, or the complement thereof; or an ACAG sequence at positions corresponding to positions 4,116 to 4,119 according to SEQ ID NO:5.

Optionally, the primer pair flanks a region including positions encoding an ACAG sequence at positions corresponding to positions 61,695 to 61,698 according to SEQ ID NO:1, or the complement thereof; an ACAG sequence at positions corresponding to positions 4,116 to 4,119 according to SEQ ID NO:3, or the complement thereof; or an ACAG sequence at positions corresponding to positions 4,116 to 4,119 according to SEQ ID NO:5, and at least 1, 2, 3, 4, 5, 6, 7, 8, 9, 10, or more nucleotides on each side of positions encoding an ACAG sequence at positions corresponding to positions 61,695 to 61,698 according to SEQ ID NO:1, or the complement thereof; an ACAG sequence at positions corresponding to positions 4,116 to 4,119 according to SEQ ID NO:3, or the complement thereof; or an ACAG sequence at positions corresponding to positions 4,116 to 4,119 according to SEQ ID NO:5. Similar amplicons can be generated from the mRNA and/or cDNA sequences.

In some embodiments, the assay comprises: a) contacting the sample with a primer hybridizing to: i) a portion of the nucleotide sequence of SCAP genomic nucleic acid molecule that is proximate to positions corresponding to positions 61,695 to 61,698 according to SEQ ID NO:1 or positions 61,694 to 61,695 according to SEQ ID NO:2; ii) a portion of the nucleotide sequence of SCAP mRNA molecule that is proximate to positions corresponding to positions 4,116 to 4,119 according to SEQ ID NO:3, or positions corresponding to positions 4,115 to 4,116 according to SEQ ID NO:4; iii) a portion of the nucleotide sequence of SCAP cDNA molecule that is proximate to positions corresponding to positions 4,116 to 4,119 according to SEQ ID NO:5, or positions corresponding to positions 4,115 to 4,116 according to SEQ ID NO:6; b) extending the primer at least through: i) the positions corresponding to positions 61,695 to 61,698 according to SEQ ID NO:1 or positions 61,694 to 61,695 according to SEQ ID NO:2; ii) the positions corresponding to positions 4,116 to 4,119 according to SEQ ID NO:3, or positions corresponding to positions 4,115 to 4,116 according to SEQ ID NO:4; or iii) the positions corresponding to positions 4,116 to 4,119 according to SEQ ID NO:5, or positions corresponding to positions 4,115 to 4,116 according to SEQ ID NO:6; and c) determining whether the extension product of the primer lacks: i) nucleotides at positions corresponding to positions 61,695 to 61,698 according to SEQ ID NO:1; ii) nucleotides at positions corresponding to positions 4,116 to 4,119 according to SEQ ID NO:3; or iii) nucleotides at positions corresponding to positions 4,116 to 4,119 according to SEQ ID NO:5.

In some embodiments, the assay comprises: sequencing a portion of the SCAP genomic sequence of a nucleic acid molecule in the sample, wherein the portion sequenced includes positions corresponding to positions 61,695 to 61,698 according to SEQ ID NO:1 or positions 61,694 to 61,695 according to SEQ ID NO:2; positions corresponding to positions 4,116 to 4,119 according to SEQ ID NO:3, or positions corresponding to positions 4,115 to 4,116 according to SEQ ID NO:4; or positions corresponding to positions 4,116 to 4,119 according to SEQ ID NO:5, or positions corresponding to positions 4,115 to 4,116 according to SEQ ID NO:6.

In some embodiments, the assay comprises: a) contacting the sample with a primer hybridizing to In some embodiments, the assay comprises: a) contacting the sample with a primer hybridizing to: i) a portion of the SCAP genomic sequence that is within 50 nucleotides of a position of the SCAP genomic sequence corresponding to positions 61,695 to 61,698 according to SEQ ID NO:1 or positions 61,694 to 61,695 according to SEQ ID NO:2; ii) a portion of the SCAP mRNA sequence that is within 50 nucleotides of a position of the SCAP mRNA corresponding to positions 4,116 to 4,119 according to SEQ ID NO:3, or positions corresponding to positions 4,115 to 4,116 according to SEQ ID NO:4; or iii) a portion of the SCAP cDNA sequence that is within 50 nucleotides of a position of the SCAP cDNA corresponding to positions 4,116 to 4,119 according to SEQ ID NO:5, or positions corresponding to positions 4,115 to 4,116 according to SEQ ID NO:6; b) extending the primer at least through: i) the position of the SCAP genomic sequence corresponding to positions 61,695 to 61,698 according to SEQ ID NO:1 or positions 61,694 to 61,695 according to SEQ ID NO:2; ii) the position of the SCAP mRNA corresponding to positions 4,116 to 4,119 according to SEQ ID NO:3, or positions corresponding to positions 4,115 to 4,116 according to SEQ ID NO:4; or iii) the position of the SCAP cDNA corresponding to positions 4,116 to 4,119 according to SEQ ID NO:5, or positions corresponding to positions 4,115 to 4,116 according to SEQ ID NO:6; and c) determining whether the extension product of the primer comprises ACAG sequence at positions: i) corresponding to positions 61,695 to 61,698 according to SEQ ID NO:1; ii) corresponding to positions 4,116 to 4,119 according to SEQ ID NO:3; or iii) corresponding to positions 4,116 to 4,119 according to SEQ ID NO:5, or whether the extension product of the primer comprises i) a GT sequence at positions corresponding to positions 61,694 to 61,695 according to SEQ ID NO:2; ii) a GU sequence at positions corresponding to positions 4,115 to 4,116 according to SEQ ID NO:4; or iii) a GT sequence at positions corresponding to positions 4,115 to 4,116 according to SEQ ID NO:6.

A variety of techniques including, for example, nucleic acid sequencing, nucleic acid hybridization, and nucleic acid amplification. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneously with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na+ ion, typically about 0.01 to 1.0 M Na+ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a human SCAP predicted loss-of-function variant polypeptide comprising performing an assay on a sample obtained from a human subject to determine whether a SCAP polypeptide in the subject contains one or more variations that causes the polypeptide to have a loss-of-function (partial or complete). In some embodiments, the methods detect the presence of a human SCAP predicted loss-of-function polypeptide, and comprise performing an assay on a sample obtained from a human subject to determine whether a SCAP polypeptide in the sample comprises the amino acid sequence according to SEQ ID NO:10 at positions corresponding to positions 1,235 to 1,335 according to SEQ ID NO:8. In some embodiments, the assay is performed on a sample obtained from a human subject to determine whether a SCAP polypeptide in the sample comprises the amino acid sequence according to SEQ ID NO:8. In some embodiments, the detecting step comprises sequencing at least a portion of the polypeptide that comprises positions corresponding to positions 1,235 to 1,335 according to SEQ ID NO:8. In some embodiments, the detecting step comprises sequencing the entire polypeptide. In some embodiments, the detecting step comprises an immunoassay.

The present disclosure also provides isolated nucleic acid molecules that hybridize to SCAP variant genomic nucleic acid molecules (such as SEQ ID NO:2), SCAP variant mRNA molecules (such as SEQ ID NO:4), and/or SCAP variant cDNA molecules (such as SEQ ID NO:6). In some embodiments, the isolated nucleic acid molecules hybridize to the portion of the SCAP nucleic acid molecule that includes: positions corresponding to positions 61,694 to 61,695 or positions 61,695 to 61,698 according to SEQ ID NO:2; positions corresponding to positions 4,115 to 4,116 or positions 4,116 to 4,119 according to SEQ ID NO:4; or positions corresponding to positions 4,115 to 4,116 or positions 4,116 to 4,119 according to SEQ ID NO:6.

The present disclosure also provides isolated nucleic acid molecules that hybridize to SCAP reference genomic nucleic acid molecules (such as SEQ ID NO:1), SCAP reference mRNA molecules (such as SEQ ID NO:3), and/or SCAP reference cDNA molecules (such as SEQ ID NO:5). In some embodiments, the isolated nucleic acid molecules hybridize to the portion of the SCAP nucleic acid molecule that includes: positions corresponding to positions 61,694 to 61,695 or positions 61,695 to 61,698 according to SEQ ID NO:1; positions corresponding to positions 4,115 to 4,116 or positions 4,116 to 4,119 according to SEQ ID NO:3; or positions corresponding to positions 4,115 to 4,116 or positions 4,116 to 4,119 according to SEQ ID NO:5.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, at least about 18000, at least about 19000, or at least about 20000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In preferred embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules comprise or consist of from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In preferred embodiments, the isolated nucleic acid molecules comprise or consist of from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to SCAP variant genomic nucleic acid molecules (such as SEQ ID NO:2), SCAP variant mRNA molecules (such as SEQ ID NO:4), and/or SCAP variant cDNA molecules (such as SEQ ID NO:6) under stringent conditions. In some embodiments, such isolated nucleic acid molecules hybridize to SCAP reference genomic nucleic acid molecules (such as SEQ ID NO:1), SCAP reference mRNA molecules (such as SEQ ID NO:3), and/or SCAP reference cDNA molecules (such as SEQ ID NO:5) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to SCAP variant genomic nucleic acid molecules (such as SEQ ID NO:2), SCAP variant mRNA molecules (such as SEQ ID NO:4), and/or SCAP variant cDNA molecules (such as SEQ ID NO:6). In some embodiments, the isolated nucleic acid molecules comprise or consist of from about 15 to about 100 nucleotides, or from about 15 to about 35 nucleotides. In some embodiments, the isolated nucleic acid molecules comprise or consist of from about 15 to about 100 nucleotides. In some embodiments, the isolated nucleic acid molecules comprise or consist of from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human SCAP polypeptide, wherein the portion comprises a position corresponding to: positions 61,694 to 61,695 or positions 61,695 to 61,698 according to SEQ ID NO:2, or the complement thereof; positions 4,115 to 4,116 or positions 4,116 to 4,119 according to SEQ ID NO:4, or the complement thereof; or positions 4,115 to 4,116 or positions 4,116 to 4,119 according to SEQ ID NO:6, or the complement thereof.

In some embodiments, the alteration-specific probe or alteration-specific primer comprises a nucleotide sequence which is complementary to a portion of a nucleotide sequence comprising positions corresponding to positions 61,694 to 61,695 or positions 61,695 to 61,698 according to SEQ ID NO:2, or the complement thereof.

In some embodiments, the alteration-specific probe or alteration-specific primer comprises a nucleotide sequence which is complementary to a portion of a nucleotide sequence comprising positions corresponding to positions 4,115 to 4,116 or positions 4,116 to 4,119 according to SEQ ID NO:4, or the complement thereof.

In some embodiments, the alteration-specific probe or alteration-specific primer comprises a nucleotide sequence which is complementary to a portion of a nucleotide sequence comprising positions corresponding to positions 4,115 to 4,116 or positions 4,116 to 4,119 according to SEQ ID NO:6, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can also be used to detect the deletion of nucleotides at positions corresponding to positions 61,695 to 61,698 according to SEQ ID NO:1 within the SCAP variant genomic nucleic acid molecule (such as SEQ ID NO:2), or the deletion of nucleotides at positions corresponding to positions 4,116 to 4,119 according to SEQ ID NO:3 within the SCAP variant mRNA molecule (such as SEQ ID NO:4), or the deletion of nucleotides at positions corresponding to positions 4,116 to 4,119 according to SEQ ID NO:5 within the SCAP variant cDNA molecule (such as SEQ ID NO:6). For example, the primers can be used to amplify SCAP variant genomic nucleic acid molecules, or a fragment thereof, comprising the deletion of nucleotides at positions corresponding to positions 61,695 to 61,698 according to SEQ ID NO:1. The primers can also be used to amplify SCAP variant mRNA or a fragment thereof comprising the 4,116 to 4,119 according to SEQ ID NO:3. The primers can also be used to amplify SCAP variant cDNA or a fragment thereof comprising the 4,116 to 4,119 according to SEQ ID NO:5.

The probes and primers described herein can be used to detect the frameshift variation within the SCAP variant genomic nucleic acid molecule (such as SEQ ID NO:2), the frameshift variation within the SCAP variant mRNA molecule (such as SEQ ID NO:4), or the frameshift variation within the SCAP variant cDNA molecule (such as SEQ ID NO:6). For example, the primers can be used to amplify SCAP variant genomic nucleic acid molecules or a fragment thereof comprising the frameshift variation. The primers can also be used to amplify SCAP variant mRNA or a fragment thereof comprising the frameshift variation. The primers can also be used to amplify SCAP variant cDNA or a fragment thereof comprising the frameshift variation.

The present disclosure also provides pairs of primers comprising any of the primers described above. For example, a pair of primers can be used to distinguish the nucleic acid molecule encoding the SCAP reference genomic nucleic acid molecule from the SCAP variant genomic nucleic acid molecule comprising SEQ ID NO:2. If one of the primers' 3'-ends hybridizes to an adenine at position 61,695 (rather than thymine) in a particular SCAP nucleic acid molecule, then the presence of the amplified fragment would indicate the presence of a SCAP reference genomic nucleic acid molecule. Conversely, if one of the primers' 3'-ends hybridizes to a thymine at position 61,695 (rather than adenine) in a particular SCAP nucleic acid molecule, then the presence of the amplified fragment would indicate the presence of a SCAP variant genomic nucleic acid molecule. In some embodiments, the nucleotide of the primer complementary to the thymine at a position corresponding to position 61,695 in SEQ ID NO:2 can be at the 3' end of the primer.

The pairs of primers can be used to distinguish a nucleic acid molecule encoding a SCAP reference genomic nucleic acid molecule (such as SEQ ID NO:1) from a SCAP variant genomic nucleic acid molecule having a deletion of nucleotides at positions corresponding to positions 61,695 to 61,698 according to SEQ ID NO:1 (resulting in SEQ ID NO:2). If one of the primers' 3'-ends hybridizes to the ACAG sequence at positions corresponding to positions 61,695 to 61,698 according to SEQ ID NO:1 (rather than the GT sequence at positions corresponding to positions 61,694 to 61,695 according to SEQ ID NO:2) in a particular SCAP nucleic acid molecule, then the presence of the amplified fragment would indicate the presence of a SCAP reference genomic nucleic acid molecule. Conversely, if one of the primers' 3'-ends hybridizes to the GT sequence at positions corresponding to positions 61,694 to 61,695 according to SEQ ID NO:2 (rather than the ACAG sequence at positions corresponding to positions 61,695 to 61,698 according to SEQ ID NO:1) in a particular SCAP nucleic acid molecule, then the presence of the amplified fragment would indicate the presence of a SCAP variant genomic nucleic acid molecule. In some embodiments, the nucleotides of the primer complementary to the ACAG sequence at positions corresponding to positions 61,695 to 61,698 according to SEQ ID NO:1 or to the GT sequence at positions corresponding to positions 61,694 to 61,695 according to SEQ ID NO:2 can be at the 3' end of the primer.

The pairs of primers can also be used to distinguish a nucleic acid molecule encoding a SCAP reference mRNA molecule (such as SEQ ID NO:3) from a SCAP variant mRNA molecule (such as SEQ ID NO:4). If one of the primers' 3'-ends hybridizes to an adenine at position 4,116 (rather than uracil) in a particular SCAP nucleic acid molecule, then the presence of the amplified fragment would indicate the presence of a SCAP reference mRNA molecule. Conversely, if one of the primers' 3'-ends hybridizes to a uracil at position 4,116 (rather than adenine) in a particular SCAP mRNA molecule, then the presence of the amplified fragment would indicate the presence of a SCAP variant mRNA molecule. In some embodiments, the nucleotide of the primer complementary to the uracil at a position corresponding to position 4,116 in SEQ ID NO:4 can be at the 3' end of the primer.

The pairs of primers can be used to distinguish a nucleic acid molecule encoding a SCAP reference mRNA (such as SEQ ID NO:3) from a SCAP variant mRNA having a deletion of nucleotides at positions corresponding to positions 4,116 to 4,119 according to SEQ ID NO:3 (resulting in SEQ ID NO:4). If one of the primers' 3'-ends hybridizes to the ACAG sequence at positions corresponding to positions 4,116 to 4,119 according to SEQ ID NO:3 (rather than the GU sequence at positions corresponding to positions 4,115 to 4,116 according to SEQ ID NO:4) in a particular SCAP nucleic acid molecule, then the presence of the amplified fragment would indicate the presence of a SCAP reference mRNA molecule. Conversely, if one of the primers' 3'-ends hybridizes to the GU sequence at positions corresponding to positions 4,115 to 4,116 according to SEQ ID NO:4 (rather than the ACAG sequence at positions corresponding to positions 4,116 to 4,119 according to SEQ ID NO:3) in a particular SCAP nucleic acid molecule, then the presence of the amplified fragment would indicate the presence of a SCAP variant mRNA molecule. In some embodiments, the nucleotides of the primer complementary to the ACAG sequence at positions corresponding to positions 4,116 to 4,119 according to SEQ ID NO:3 or to the GU sequence at positions corresponding to positions 4,115 to 4,116 according to SEQ ID NO:4 can be at the 3' end of the primer.

The pairs of primers can also be used to distinguish a nucleic acid molecule encoding a SCAP reference cDNA molecule (such as SEQ ID NO:5) from a SCAP variant cDNA molecule (such as SEQ ID NO:6.) If one of the primers' 3'-ends hybridizes to an adenine at position 4,116 (rather than thymine) in a particular SCAP nucleic acid molecule, then the presence of the amplified fragment would indicate the presence of a SCAP reference cDNA molecule. Conversely, if one of the primers' 3'-ends hybridizes to a thymine at position 4,116 (rather than adenine) in a particular SCAP cDNA molecule, then the presence of the amplified fragment would indicate the presence of a SCAP variant cDNA molecule. In some embodiments, the nucleotide of the primer complementary to the thymine at a position corresponding to position 4,116 in SEQ ID NO:6 can be at the 3' end of the primer.

The pairs of primers can be used to distinguish a nucleic acid molecule encoding a SCAP reference cDNA (such as SEQ ID NO:5) from the SCAP variant cDNA having a deletion of nucleotides at positions corresponding to positions 4,116 to 4,119 according to SEQ ID NO:5 (resulting in SEQ ID NO:6). If one of the primers' 3'-ends hybridizes to the ACAG sequence at positions corresponding to positions 4,116 to 4,119 according to SEQ ID NO:5 (rather than the GT sequence at positions corresponding to positions 4,115 to 4,116 according to SEQ ID NO:6) in a particular SCAP nucleic acid molecule, then the presence of the amplified fragment would indicate the presence of a SCAP reference cDNA molecule. Conversely, if one of the primers' 3'-ends hybridizes to the GT sequence at positions corresponding to positions 4,115 to 4,116 according to SEQ ID NO:6 (rather than the ACAG sequence at positions corresponding to positions 4,116 to 4,119 according to SEQ ID NO:5) in a particular SCAP nucleic acid molecule, then the presence of the amplified fragment would indicate the presence of a SCAP variant cDNA molecule. In some embodiments, the nucleotides of the primer complementary to the ACAG sequence at positions corresponding to positions 4,116 to 4,119 according to SEQ ID NO:5 or to the GT sequence at positions corresponding to positions 4,115 to 4,116 according to SEQ ID NO:6 can be at the 3' end of the primer.

In some embodiments, the probes or primers comprise a nucleotide sequence which hybridizes to a portion of a SCAP genomic nucleic acid molecule, wherein the portion comprises a deletion of nucleotides at positions corresponding to positions 61,695 to 61,698 according to SEQ ID NO:1, or which hybridizes to the complement of this nucleic acid molecule. In some embodiments, the probes or primers comprise a nucleotide sequence which hybridizes to a SCAP genomic nucleic acid molecule comprising SEQ ID NO:2 at a portion comprising a GT sequence at a position corresponding to position 61,694 to 61,695 according to SEQ ID NO:2, or which hybridizes to the complement of this nucleic acid molecule.

In some embodiments, the probes or primers comprise a nucleotide sequence which hybridizes to a portion of a SCAP mRNA molecule, wherein the portion comprises a deletion of nucleotides at positions corresponding to positions 4,116 to 4,119 according to SEQ ID NO:3, or which hybridizes to the complement of this nucleic acid molecule. In some embodiments, the probes or primers comprise a nucleotide sequence which hybridizes to a SCAP mRNA molecule comprising SEQ ID NO:4 at a portion comprising a GU sequence at a position corresponding to position 4,115 to 4,116 according to SEQ ID NO:4, or which hybridizes to the complement of this nucleic acid molecule.

In some embodiments, the probes or primers comprise a nucleotide sequence which hybridizes to a portion of a SCAP cDNA molecule, wherein the portion comprises a deletion of nucleotides at positions corresponding to positions 4,116 to 4,119 according to SEQ ID NO:5, or which hybridizes to the complement of this nucleic acid molecule. In some embodiments, the probes or primers comprise a nucleotide sequence which hybridizes to a SCAP cDNA molecule comprising SEQ ID NO:6 at a portion comprising a GT sequence at a position corresponding to position 4,115 to 4,116 according to SEQ ID NO:6, or which hybridizes to the complement of this nucleic acid molecule.

In the context of the disclosure "specifically hybridizes" means that the probe or primer (such as, for example, the alteration-specific probe or alteration-specific primer) does not hybridize to a nucleic acid sequence encoding a SCAP reference genomic nucleic acid molecule, a SCAP reference mRNA molecule, and/or a SCAP reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The present disclosure also provides molecular complexes comprising or consisting of any of the SCAP nucleic acid molecules (genomic nucleic acid molecules, mRNA molecules, or cDNA molecules), or complement thereof, described herein and any of the alteration-specific primers or alteration-specific probes described herein. In some embodiments, the SCAP nucleic acid molecules (genomic nucleic acid molecules, mRNA molecules, or cDNA molecules), or complement thereof, in the molecular complexes are single-stranded. In some embodiments, the SCAP nucleic acid molecule is any of the genomic nucleic acid molecules described herein. In some embodiments, the SCAP nucleic acid molecule is any of the mRNA molecules described herein. In some embodiments, the SCAP nucleic acid molecule is any of the cDNA molecules described herein. In some embodiments, the molecular complex comprises or consists of any of the SCAP nucleic acid molecules (genomic nucleic acid molecules, mRNA molecules, or cDNA molecules), or complement thereof, described herein and any of the alteration-specific primers described herein. In some embodiments, the molecular complex comprises or consists of any of the SCAP nucleic acid molecules (genomic nucleic acid molecules, mRNA molecules, or cDNA molecules), or complement thereof, described herein and any of the alteration-specific probes described herein.

In some embodiments, the molecular complex comprises or consists of an alteration-specific primer or an alteration-specific probe hybridized to a genomic nucleic acid molecule comprising a nucleotide sequence encoding a human SCAP polypeptide, wherein the alteration-specific primer or the alteration-specific probe is hybridized to: a GT dinucleotide at positions corresponding to positions 61,694 to 61,695 according to SEQ ID NO:2, or the complement thereof. In some embodiments, the molecular complex comprises or consists of a genomic nucleic acid molecule that comprises SEQ ID NO:2.

In some embodiments, the molecular complex comprises or consists of an alteration-specific primer or an alteration-specific probe hybridized to an mRNA molecule comprising a nucleotide sequence encoding a human SCAP polypeptide, wherein the alteration-specific primer or the alteration-specific probe is hybridized to: a GU dinucleotide at positions corresponding to positions 4,115 to 4,116 according to SEQ ID NO:4, or the complement thereof. In some embodiments, the molecular complex comprises or consists of an mRNA molecule that comprises SEQ ID NO:4.

In some embodiments, the molecular complex comprises or consists of an alteration-specific primer or an alteration-specific probe hybridized to a cDNA molecule comprising a nucleotide sequence encoding a human SCAP polypeptide, wherein the alteration-specific primer or the alteration-specific probe is hybridized to: a GT dinucleotide at positions corresponding to positions 4,115 to 4,116 according to SEQ ID NO:6, or the complement thereof. In some embodiments, the molecular complex comprises or consists of a cDNA molecule that comprises SEQ ID NO:6.

In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The present disclosure provides isolated nucleic acid molecules comprising a nucleotide sequence encoding a human SCAP polypeptide, wherein the polypeptide comprises the amino acid sequence according to SEQ ID NO:10 at positions corresponding to positions 1,235 to 1,335 according to SEQ ID NO:8. The present disclosure also provides isolated nucleic acid molecules comprising a nucleotide sequence encoding a human SCAP polypeptide, wherein the polypeptide does not comprise the amino acid sequence according to SEQ ID NO:9 at positions corresponding to positions 1,235 to 1,279 according to SEQ ID NO:7.

In some embodiments, the isolated nucleic acid molecule encodes a SCAP polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprises the amino acid sequence according to SEQ ID NO:10 at positions corresponding to positions 1,235 to 1,335 according to SEQ ID NO:8.

In some embodiments, the isolated nucleic acid molecule encodes a SCAP polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:8, and does not comprise the amino acid sequence according to SEQ ID NO:9 at positions corresponding to positions 1,235 to 1,279 according to SEQ ID NO:7.

In some embodiments, the nucleic acid molecule encodes a SCAP polypeptide comprising SEQ ID NO:8. In some embodiments, the nucleic acid molecule encodes a SCAP polypeptide consisting of SEQ ID NO:8.

The nucleotide sequence of a SCAP reference genomic nucleic acid molecule is set forth in SEQ ID NO:1. Referring to SEQ ID NO:1, positions 61,695 to 61,698 of the SCAP reference genomic nucleic acid molecule are ACAG. Referring to SEQ ID NO:1, positions 61,694 to 61,695 of the SCAP reference genomic nucleic acid molecule are GA. Referring to SEQ ID NO:1, positions 61,695 to 62,271 of the SCAP reference genomic nucleic acid molecule comprise the nucleotide sequence of SEQ ID NO:11.

A variant genomic nucleic acid molecule of SCAP exists, wherein the nucleotides ACAG at positions 61,695 to 61,698 of the SCAP reference genomic nucleic acid molecule (see, SEQ ID NO:1) are omitted. The nucleotide sequence of this SCAP predicted loss-of-function variant genomic nucleic acid molecule is set forth in SEQ ID NO:2. Referring to SEQ ID NO:2, positions 61,695 to 61,698 of the variant SCAP genomic nucleic acid molecule are TCTA. Referring to SEQ ID NO:2, positions 61,694 to 61,695 of the variant SCAP genomic nucleic acid molecule are GT. Referring to SEQ ID NO:2, positions 61,695 to 62,267 of the variant SCAP genomic nucleic acid molecule comprise the nucleotide sequence of SEQ ID NO:12.

The present disclosure provides isolated genomic nucleic acid molecules comprising or consisting of a nucleotide sequence encoding a human SCAP polypeptide, wherein the nucleotide sequence comprises the nucleotide sequence according to SEQ ID NO:12 at positions corresponding to positions 61,695 to 62,267 according to SEQ ID NO:2, or the complement thereof. These genomic nucleic acid molecules lack the nucleotides ACAG at positions corresponding to positions 61,695 to 61,698 according to SEQ ID NO:1.

In some embodiments, the isolated genomic nucleic acid molecules comprise or consist of a nucleotide sequence encoding a human SCAP polypeptide, wherein the nucleotide sequence comprises the nucleotides TCTA at positions corresponding to positions 61,695 to 61,698 according to SEQ ID NO:2. These genomic nucleic acid molecules lack the nucleotides at positions corresponding to positions 61,695 to 61,698 according to SEQ ID NO:1.

In some embodiments, the isolated genomic nucleic acid molecules comprise or consist of a nucleotide sequence encoding a human SCAP polypeptide, wherein the nucleotide sequence comprises the nucleotides GT at positions corresponding to positions 61,694 to 61,695 according to SEQ ID NO:2. These genomic nucleic acid molecules lack the nucleotides at positions corresponding to positions 61,695 to 61,698 according to SEQ ID NO:1.

The present disclosure provides isolated genomic nucleic acid molecules comprising or consisting of a nucleotide sequence encoding a human SCAP polypeptide, wherein the nucleotide sequence lacks the nucleotides at positions corresponding to positions 61,695 to 61,698 according to SEQ ID NO:1, or the complement thereof.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises the nucleotide sequence according to SEQ ID NO:12 at positions corresponding to positions 61,695 to 62,267 according to SEQ ID NO:2, or the complement thereof. Herein, if reference is made to percent sequence identity, the higher percentages of sequence identity are preferred over the lower ones.

In some embodiments, the isolated SCAP genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and lacks the nucleotides at positions corresponding to positions 61,695 to 61,698 according to SEQ ID NO:1, or the complement thereof. Herein, if reference is made to percent sequence identity, the higher percentages of sequence identity are preferred over the lower ones.

In some embodiments, the isolated SCAP genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises the nucleotides TCTA at positions corresponding to positions 61,695 to 61,698 according to SEQ ID NO:2, or the complement thereof. These genomic nucleic acid molecules lack the nucleotides at positions corresponding to positions 61,695 to 61,698 according to SEQ ID NO:1. Herein, if reference is made to percent sequence identity, the higher percentages of sequence identity are preferred over the lower ones.

In some embodiments, the isolated SCAP genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises the nucleotides GT at positions corresponding to positions 61,694 to 61,695 according to SEQ ID NO:2, or the complement thereof. These genomic nucleic acid molecules lack the nucleotides at positions corresponding to positions 61,695 to 61,698 according to SEQ ID NO:1. Herein, if reference is made to percent sequence identity, the higher percentages of sequence identity are preferred over the lower ones.

In some embodiments, the isolated SCAP genomic nucleic acid molecules comprise SEQ ID NO:2. In some embodiments, the isolated SCAP genomic nucleic acid molecules consist of SEQ ID NO:2.

In some embodiments, the isolated SCAP genomic nucleic acid molecules comprise less than the entire genomic DNA sequence. In some embodiments, the isolated genomic nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, at least about 18000, at least about 20000, at least about 22000, at least about 24000, at least about 26000, at least about 28000, at least about 30000, at least about 32000, at least about 34000, at least about 36000, at least about 38000, at least about 40000, at least about 42000, at least about 44000, at least about 46000, at least about 48000, at least about 50000, at least about 52000, at least about 54000, at least about 56000, at least about 58000, at least about 60000, or at least about 62000 contiguous nucleotides of SEQ ID NO:2. In some embodiments, the isolated genomic nucleic acid molecules comprise or consist of at least about 1000 to at least about 2000 contiguous nucleotides of SEQ ID NO:2. In some embodiments, these isolated genomic nucleic acid molecules comprise the nucleotide sequence according to SEQ ID NO:12 at positions corresponding to positions 61,695 to 62,267 according to SEQ ID NO:2, or comprise the nucleotides TCTA at positions corresponding to positions 61,695 to 61,698 according to SEQ ID NO:2, or comprise the nucleotides GT at positions corresponding to positions 61,694 to 61,695 according to SEQ ID NO:2.

The nucleotide sequence of a SCAP reference mRNA molecule is set forth in SEQ ID NO:3. Referring to SEQ ID NO:3, positions 4,116 to 4,119 of the SCAP reference mRNA molecule are ACAG. Referring to SEQ ID NO:3, positions 4,115 to 4,116 of the SCAP reference mRNA molecule are GA. Referring to SEQ ID NO:3, positions 4,116 to 4,421 of the SCAP reference mRNA molecule comprise the nucleotide sequence of SEQ ID NO:13.

A variant mRNA molecule of SCAP exists, wherein the nucleotides ACAG at positions 4,116 to 4,119 of the SCAP reference mRNA molecule (see, SEQ ID NO:3) are omitted. The nucleotide sequence of this SCAP predicted loss-of-function variant mRNA molecule is set forth in SEQ ID NO:4. Referring to SEQ ID NO:4, positions 4,116 to 4,119 of the variant SCAP mRNA molecule are UCUA. Referring to SEQ ID NO:4, positions 4,115 to 4,116 of the variant SCAP mRNA molecule are GU. Referring to SEQ ID NO:4, positions 4,116 to 4,417 of the variant SCAP mRNA molecule comprise the nucleotide sequence of SEQ ID NO:14.

The present disclosure provides isolated SCAP mRNA molecules comprising or consisting of a nucleotide sequence encoding a human SCAP polypeptide, wherein the nucleotide sequence comprises the nucleotide sequence according to SEQ ID NO:14 at positions corresponding to positions 4,116 to 4,417 according to SEQ ID NO:4, or the complement thereof. These mRNA molecules lack the nucleotides at positions corresponding to positions 4,116 to 4,119 according to SEQ ID NO:3.

In some embodiments, the isolated SCAP mRNA molecules comprise or consist of a nucleotide sequence encoding a human SCAP polypeptide, wherein the nucleotide sequence comprises the nucleotides UCUA at positions corresponding to positions 4,116 to 4,119 according to SEQ ID NO:4. These mRNA molecules lack the nucleotides at positions corresponding to positions 4,116 to 4,119 according to SEQ ID NO:3.

In some embodiments, the isolated SCAP mRNA molecules comprise or consist of a nucleotide sequence encoding a human SCAP polypeptide, wherein the nucleotide sequence comprises the nucleotides GU at positions corresponding to positions 4,115 to 4,116 according to SEQ ID NO:4. These mRNA molecules lack the nucleotides at positions corresponding to positions 4,116 to 4,119 according to SEQ ID NO:3.

The present disclosure provides isolated SCAP mRNA molecules comprising or consisting of a nucleotide sequence encoding a human SCAP polypeptide, wherein the nucleotide sequence lacks the nucleotides at positions corresponding to positions 4,116 to 4,119 according to SEQ ID NO:3, or the complement thereof.

In some embodiments, the isolated SCAP mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4, and comprises the nucleotide sequence according to SEQ ID NO:14 at positions corresponding to positions 4,116 to 4,417 according to SEQ ID NO:4, or the complement thereof. Herein, if reference is made to percent sequence identity, the higher percentages of sequence identity are preferred over the lower ones.

In some embodiments, the isolated SCAP mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4, and comprises the nucleotides UCUA at positions corresponding to positions 4,116 to 4,119 according to SEQ ID NO:4, or the complement thereof. Herein, if reference is made to percent sequence identity, the higher percentages of sequence identity are preferred over the lower ones.

In some embodiments, the isolated SCAP mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4, and comprises the nucleotides GU at positions corresponding to positions 4,115 to 4,116 according to SEQ ID NO:4, or the complement thereof. Herein, if reference is made to percent sequence identity, the higher percentages of sequence identity are preferred over the lower ones.

In some embodiments, the isolated SCAP mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4, and lacks the nucleotides at positions corresponding to positions 4,116 to 4,119 according to SEQ ID NO:3, or the complement thereof. Herein, if reference is made to percent sequence identity, the higher percentages of sequence identity are preferred over the lower ones.

In some embodiments, the isolated SCAP mRNA molecules comprise SEQ ID NO:4. In some embodiments, the isolated SCAP mRNA molecules consist of SEQ ID NO:4.

The nucleotide sequence of a SCAP reference cDNA molecule is set forth in SEQ ID NO:5. Referring to SEQ ID NO:5, positions 4,116 to 4,119 of the SCAP reference cDNA molecule are ACAG. Referring to SEQ ID NO:5, positions 4,115 to 4,116 of the SCAP reference cDNA molecule are GA. Referring to SEQ ID NO:5, positions 4,116 to 4,421 of the SCAP reference cDNA molecule comprise the nucleotide sequence of SEQ ID NO:15.

A variant cDNA molecule of SCAP exists, wherein the nucleotides ACAG at positions 4,116 to 4,119 of the SCAP reference cDNA molecule (see, SEQ ID NO:5) are omitted. The nucleotide sequence of this SCAP predicted loss-of-function variant cDNA molecule is set forth in SEQ ID NO:6. Referring to SEQ ID NO:6, positions 4,116 to 4,119 of the variant SCAP cDNA molecule are TCTA. Referring to SEQ ID NO:6, positions 4,115 to 4,116 of the variant SCAP cDNA molecule are GT. Referring to SEQ ID NO:6, positions 4,116 to 4,417 of the variant SCAP cDNA molecule comprise the nucleotide sequence of SEQ ID NO:16.

The present disclosure provides isolated SCAP cDNA molecules comprising or consisting of a nucleotide sequence encoding a human SCAP polypeptide, wherein the nucleotide sequence comprises the nucleotide sequence according to SEQ ID NO:16 at positions corresponding to positions 4,116 to 4,417 according to SEQ ID NO:6, or the complement thereof. These cDNA molecules lack the nucleotides at positions corresponding to positions 4,116 to 4,119 according to SEQ ID NO:5.

In some embodiments, the isolated SCAP cDNA molecules comprise or consist of a nucleotide sequence encoding a human SCAP polypeptide, wherein the nucleotide sequence comprises the nucleotides TCTA at positions corresponding to positions 4,116 to 4,119 according to SEQ ID NO:6. These cDNA molecules lack the nucleotides at positions corresponding to positions 4,116 to 4,119 according to SEQ ID NO:5.

In some embodiments, the isolated SCAP cDNA molecules comprise or consist of a nucleotide sequence encoding a human SCAP polypeptide, wherein the nucleotide sequence comprises the nucleotides GT at positions corresponding to positions 4,115 to 4,116 according to SEQ ID NO:6. These cDNA molecules lack the nucleotides at positions corresponding to positions 4,116 to 4,119 according to SEQ ID NO:5.

The present disclosure provides isolated SCAP cDNA molecules comprising or consisting of a nucleotide sequence encoding a human SCAP polypeptide, wherein the nucleotide sequence lacks the nucleotides at positions corresponding to positions 4,116 to 4,119 according to SEQ ID NO:5, or the complement thereof.

In some embodiments, the isolated SCAP cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and comprises the nucleotide sequence according to SEQ ID NO:16 at positions corresponding to positions 4,116 to 4,417 according to SEQ ID NO:6, or the complement thereof. Herein, if reference is made to percent sequence identity, the higher percentages of sequence identity are preferred over the lower ones.

In some embodiments, the isolated SCAP cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and comprises the nucleotides TCTA at positions corresponding to positions 4,116 to 4,119 according to SEQ ID NO:6, or the complement thereof. Herein, if reference is made to percent sequence identity, the higher percentages of sequence identity are preferred over the lower ones.

In some embodiments, the isolated SCAP cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and comprises the nucleotides GT at positions corresponding to positions 4,115 to 4,116 according to SEQ ID NO:6, or the complement thereof. Herein, if reference is made to percent sequence identity, the higher percentages of sequence identity are preferred over the lower ones.

In some embodiments, the isolated SCAP cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and lacks the nucleotides at positions corresponding to positions 4,116 to 4,119 according to SEQ ID NO:5, or the complement thereof. Herein, if reference is made to percent sequence identity, the higher percentages of sequence identity are preferred over the lower ones.

In some embodiments, the isolated SCAP cDNA molecules comprise SEQ ID NO:6. In some embodiments, the isolated SCAP cDNA molecules consist of SEQ ID NO:6.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that genomic nucleic acid molecules, mRNA molecules, and cDNA sequences within a population can vary due to polymorphisms such as single-nucleotide polymorphisms. The examples provided herein are only exemplary sequences. Other sequences are also possible.

In some embodiments, the isolated SCAP mRNA molecules or cDNA molecules comprise less than the entire mRNA or cDNA sequence. In some embodiments, the isolated cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, at least about 2700, at least about 2800, at least about 2900, at least about 3000, at least about 3100, at least about 3200, at least about 3300, at least about 3400, at least about 3500, at least about 3600, at least about 3700, at least about 3800, at least about 3900, at least about 4000, at least about 4100, at least about 4200, at least about 4300, or at least about 4400 contiguous nucleotides of SEQ ID NO:6. In some embodiments, the isolated cDNA molecules comprise or consist of at least about 400 to at least about 500 contiguous nucleotides of SEQ ID NO:4 (for mRNA) or SEQ ID NO:6 (for cDNA). In some embodiments, the isolated cDNA molecules comprise or consist of at least about 1000 to at least about 2000 contiguous nucleotides of SEQ ID NO:4 (for mRNA) or SEQ ID NO:6 (for cDNA). In some embodiments, these isolated mRNA molecules comprise the nucleotide sequence according to SEQ ID NO:14 at positions corresponding to positions 4,116 to 4,417 according to SEQ ID NO:4, or comprise the nucleotides UCUA at positions corresponding to positions 4,116 to 4,119 according to SEQ ID NO:4, or comprise the nucleotides GU at positions corresponding to positions 4,115 to 4,116 according to SEQ ID NO:4. In some embodiments, these isolated cDNA molecules comprise the nucleotide sequence according to SEQ ID NO:16 at positions corresponding to positions 4,116 to 4,417 according to SEQ ID NO:6, or comprise the nucleotides TCTA at positions corresponding to positions 4,116 to 4,119 according to SEQ ID NO:6, or comprise the nucleotides GT at positions corresponding to positions 4,115 to 4,116 according to SEQ ID NO:6.

Also provided herein are functional polynucleotides that can interact with the disclosed nucleic acid molecules. Functional polynucleotides are nucleic acid molecules that have a specific function, such as binding a target molecule or catalyzing a specific reaction. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous label. Such labels include, for example, chemiluminescents, metals, tags, enzymes, radiolabels, pigments, dyes, chromogens, spin labels, and fluorescent labels. Labels also include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, modified sugar, or modified phosphate group, or that incorporates a non-natural moiety in its structure.

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient.

The amino acid sequence of a SCAP reference polypeptide is set forth in SEQ ID NO:7. Referring to SEQ ID NO:7, positions 1,235 to 1,279 of the SCAP reference polypeptide comprise the amino acid sequence according to SEQ ID NO:9.

A variant polypeptide of SCAP exists, wherein the deletion of nucleotides ACAG at positions 61,695 to 61,698 of the SCAP reference genomic nucleic acid molecule (see, SEQ ID NO:1) are omitted, thus resulting in a frameshift causing a variant C-terminus for the variant SCAP polypeptide. The amino acid sequence of this SCAP predicted loss-of-function variant polypeptide is set forth in SEQ ID NO:8. Referring to SEQ ID NO:8, positions 1,235 to 1,335 of the SCAP variant polypeptide comprise the amino acid sequence according to SEQ ID NO:10.

The present disclosure also provides isolated human SCAP polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:8, wherein the polypeptide comprises the amino acid sequence according to SEQ ID NO:10 at positions corresponding to positions 1,235 to 1,335 according to SEQ ID NO:8. Herein, if reference is made to percent sequence identity, the higher percentages of sequence identity are preferred over the lower ones.

The present disclosure also provides isolated human SCAP polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:8, wherein the polypeptide lacks the amino acids at positions corresponding to positions 1,235 to 1,279 according to SEQ ID NO:7. Herein, if reference is made to percent sequence identity, the higher percentages of sequence identity are preferred over the lower ones.

In some embodiments, the amino acid sequence of the isolated human SCAP polypeptide comprises or consists of SEQ ID NO:8.

In some embodiments, the isolated SCAP polypeptides comprise or consist of an amino acid sequence at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 550, at least about 600 at least about 650, at least about 700, at least about 750, at least about 800, at least about 850, at least about 900, at least about 950, at least about 1000, at least about 1050, or at least about 1100 contiguous amino acids of SEQ ID NO:8. In some embodiments, the isolated polypeptides also comprise the amino acid sequence according to SEQ ID NO:10 at positions corresponding to positions 1,235 to 1,335 according to SEQ ID NO:8. In some embodiments, the isolated polypeptides also lack the amino acids at positions corresponding to positions 1,235 to 1,279 according to SEQ ID NO:7. In this regard, the longer fragments are preferred over the shorter ones.

The isolated SCAP polypeptides disclosed herein can comprise an amino acid sequence of a naturally occurring SCAP polypeptide, or can comprise a non-naturally occurring sequence. In some embodiments, the naturally occurring sequence can differ from the non-naturally occurring sequence due to conservative amino acid substitutions.

In some embodiments, the isolated polypeptides comprise non-natural or modified amino acids or peptide analogs. For example, there are numerous D-amino acids or amino acids which have a different functional substituent than the naturally occurring amino acids.

The SCAP reference polypeptides can be used, for example, to screen for compounds that act as antagonists, which can be used to treat subjects who are either SCAP reference or heterozygous for a SCAP predicted loss-offunction nucleic acid molecule. The variant SCAP polypeptides (such as the SCAP predicted loss-of-function polypeptides described herein) can be used, for example, to screen for compounds that act as agonists, which can be used to treat subjects who are either SCAP reference or heterozygous for a SCAP predicted loss-of-function nucleic acid molecule.

The present disclosure also provides nucleic acid molecules encoding any of the polypeptides disclosed herein. This includes all degenerate sequences related to a specific polypeptide sequence. Thus, while each particular nucleic acid sequence may not be written out herein, each and every sequence is in fact disclosed and described herein through the disclosed polypeptide sequences.

The present disclosure also provides compositions comprising any one or more of the nucleic acid molecules and/or any one or more of the polypeptides disclosed herein. In some embodiments, the compositions comprise a carrier.

The present disclosure also provides methods of producing any of the SCAP polypeptides or fragments thereof disclosed herein. Such SCAP polypeptides or fragments thereof can be produced by any suitable method.

The present disclosure also provides cells comprising any one or more of the nucleic acid molecules and/or any one or more of the polypeptides disclosed herein. The cells can be in vitro, ex vivo, or in vivo. Nucleic acid molecules can be linked to a promoter and other regulatory sequences so they are expressed to produce an encoded protein.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to the reference sequence. In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide or nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a human SCAP polypeptide, wherein the nucleotide sequence comprises a thymine at a position corresponding to position 61,695 according to SEQ ID NO:2 means that if the nucleotide sequence of the SCAP genomic nucleic acid molecule is aligned to the sequence of SEQ ID NO:2, the SCAP sequence has a thymine residue at the position that corresponds to position 61,695 of SEQ ID NO:2. The same applies for mRNA molecules comprising a nucleotide sequence encoding a human SCAP polypeptide, wherein the nucleotide sequence comprises a uracil at a position corresponding to position 4,116 according to SEQ ID NO:4. The same applies for cDNA molecules comprising a nucleotide sequence encoding a human SCAP polypeptide, wherein the nucleotide sequence comprises a thymine at a position corresponding to position 4,116 according to SEQ ID NO:6. In other words, these phrases refer to a nucleic acid molecule encoding a SCAP polypeptide, wherein the genomic nucleic acid molecule has a nucleotide sequence that comprises a thymine residue that is homologous to the thymine residue at position 61,695 of SEQ ID NO:2 (or wherein the mRNA molecule has a nucleotide sequence that comprises a uracil residue that is homologous to the uracil residue at position 4,116 of SEQ ID NO:4; or wherein the cDNA molecule has a nucleotide sequence that comprises a thymine residue that is homologous to the thymine residue at position 4,116 of SEQ ID NO:6).

As described herein, a position within a SCAP genomic nucleic acid molecule that corresponds to position 61,695 according to SEQ ID NO:2 can be identified by performing a sequence alignment between the nucleotide sequence of a particular SCAP nucleic acid molecule and the nucleotide sequence of SEQ ID NO:2. A variety of computational algorithms exist that can be used for performing a sequence alignment to identify a nucleotide position that corresponds to, for example, position 17,922 in SEQ ID NO:2. For example, by using the NCBI BLAST algorithm (Altschul et al., Nucleic Acids Res., 1997, 25, 3389-3402) or CLUST-ALW software (Sievers and Higgins, Methods Mol. Biol., 2014, 1079, 105-116) sequence alignments may be performed. However, sequences can also be aligned manually.

The present disclosure also provides therapeutic agents that treat or inhibit an increased lipid level and/or increased triglyceride levels for use in the treatment of an increased lipid level and/or increased triglyceride levels (for use in the preparation of a medicament for treating an increased lipid level and/or increased triglyceride levels) in a human subject, wherein the human subject has: a genomic nucleic acid molecule having a nucleotide sequence encoding a human SCAP polypeptide, wherein the nucleotide sequence comprises a thymine at a position corresponding to position 61,695 according to SEQ ID NO:2, or the complement thereof; an mRNA molecule having a nucleotide sequence encoding a human SCAP polypeptide, wherein the nucleotide sequence comprises a uracil at a position corresponding to position 4,116 according to SEQ ID NO:4, or the complement thereof; a cDNA molecule having a nucleotide sequence encoding a human SCAP polypeptide, wherein the nucleotide sequence comprises a thymine at a position corresponding to position 4,116 according to SEQ ID NO:6, or the complement thereof; and/or a SCAP polypeptide comprising an amino acid sequence according to SEQ ID NO:10 at positions corresponding to positions 1,235 to 1,335 according to SEQ ID NO:8. The anti-increased lipid level agents can be any of the anti-increased lipid level agents described herein.

The present disclosure also provides SCAP inhibitors for use in the treatment of an increased lipid level and/or increased triglyceride levels (for use in the preparation of a medicament for treating an increased lipid level and/or increased triglyceride levels) in a human subject, wherein the human subject has: a genomic nucleic acid molecule having a nucleotide sequence encoding a human SCAP polypeptide, wherein the nucleotide sequence comprises a thymine at a position corresponding to position 61,695 according to SEQ ID NO:2, or the complement thereof; an mRNA molecule having a nucleotide sequence encoding a human SCAP polypeptide, wherein the nucleotide sequence comprises a uracil at a position corresponding to position 4,116 according to SEQ ID NO:4, or the complement thereof; a cDNA molecule having a nucleotide sequence encoding a human SCAP polypeptide, wherein the nucleotide sequence comprises a thymine at a position corresponding to position 4,116 according to SEQ ID NO:6, or the complement thereof; and/or a SCAP polypeptide comprising an amino acid sequence according to SEQ ID NO:10 at positions corresponding to positions 1,235 to 1,335 according to SEQ ID NO:8. The SCAP inhibitors can be any of the SCAP inhibitors described herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: A Frameshift Variant in SCAP May be Associated with Decreased LDL Levels in the Old Order Amish pLOF polymorphisms and missense variants obtained from the Old Order Amish cohort were analyzed. The results (see, Table 1 and FIG. 1, Panels A-C) show significant association of the rs746678809 located in the SCAP gene with increased aspartate aminotransferase levels, decreased LDL-C, and decreased triglyceride levels.

TABLE 1

Association of SCAP rs746678809 Variant with Decreased Aspartate Aminotransferase Levels, Decreased LDL-C and Decreased Triglycerides

| | Trait | P-Value | Effect* | Ref - Het - Alt |
|---|---|---|---|---|
| SCAP | Aspartate Aminotransferase | 7.57e−4 | 11.67 u/L | 5605 - 3 - 0 |
| 3:47413987:ACTGT:A | LDL-C | 0.160 | −29.41 mg/dL | 5929 - 3 - 0 |
| p.Thr979fs | LDL-C (adj.for APOB p.R3527Q) | 0.160 | −29.41 mg/dL | 5929 - 3 - 0 |
| p.Thr1235fs | Total Cholesterol | 0.041 | −57.96 mg/dL | 5935 - 3 - 0 |
| | Total Cholesterol (adj. for APOB p.R3527Q) | 0.324 | −23.87 mg/dL | 5935 - 3 - 0 |
| | Triglycerides (adj. for APOC3 p.R19*) | 0.127 | −39.29 mg/dL | 5802 - 3 - 0 |

*All traits were adjusted for age, age$^2$, sex, and study.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject having increased total cholesterol, increased low density lipoprotein (LDL), increased serum lipid level, or increased triglycerides, the method comprising administering a SCAP inhibitor to the subject, wherein the SCAP inhibitor comprises an antisense nucleic acid molecule, a Cas protein and guide RNA (gRNA) that hybridizes to a gRNA recognition sequence within a SCAP genomic nucleic acid molecule, or a small molecule SCAP inhibitor.

2. The method according to claim 1, further comprising detecting the presence or absence of a SCAP variant nucleic acid molecule encoding a human SCAP polypeptide in a biological sample from the subject, wherein the SCAP variant nucleic acid molecule is: i) a genomic nucleic acid molecule having a nucleotide sequence comprising the nucleotide sequence according to SEQ ID NO:12 at positions corresponding to positions 61,695 to 62,267 according to SEQ ID NO:2, or the complement thereof, ii) an mRNA molecule having a nucleotide sequence comprising the nucleotide sequence according to SEQ ID NO:14 at positions corresponding to positions 4,116 to 4,417 according to SEQ ID NO:4, or the complement thereof, or iii) a cDNA molecule having a nucleotide sequence comprising the nucleotide sequence according to SEQ ID NO:16 at positions corresponding to positions 4,116 to 4,417 according to SEQ ID NO:6, or the complement thereof; and when the subject is SCAP reference, the subject is also administered a therapeutic agent that treats or inhibits an increased lipid level and/or an increased triglyceride level in a standard dosage amount, and when the subject is heterozygous for a SCAP variant nucleic acid molecule, the subject is also administered a therapeutic agent that treats or inhibits an increased lipid level and/or an increased triglyceride level in a dosage amount that is the same as or lower than the standard dosage amount.

3. A method of treating a subject with a therapeutic agent that treats or inhibits an increased lipid level and/or an increased triglyceride level, wherein the subject is suffering from an increased lipid level and/or an increased triglyceride level, the method comprising the steps of:
  determining whether the subject has a SCAP variant nucleic acid molecule encoding a human SCAP polypeptide by:
    obtaining or having obtained a biological sample from the subject; and
    performing or having performed a genotyping assay on the biological sample to determine if the subject has a genotype comprising the SCAP variant nucleic acid molecule; and
  when the subject is SCAP reference, then administering or continuing to administer to the subject the therapeutic agent that treats or inhibits the increased lipid level and/or an increased triglyceride level in a standard dosage amount, and administering to the subject a SCAP inhibitor; and
  when the subject is heterozygous for the SCAP variant nucleic acid molecule, then administering or continuing to administer to the subject the therapeutic agent that treats or inhibits the increased lipid level and/or an increased triglyceride level in an amount that is the same as or lower than a standard dosage amount, and administering to the subject a SCAP inhibitor;
  wherein the presence of a genotype having the SCAP variant nucleic acid molecule encoding the human SCAP polypeptide indicates the subject has a reduced risk of developing the increased lipid level and/or an increased triglyceride level;
  wherein the SCAP variant nucleic acid molecule is: i) a genomic nucleic acid molecule having a nucleotide sequence comprising the nucleotide sequence according to SEQ ID NO:12 at positions corresponding to positions 61,695 to 62,267 according to SEQ ID NO:2, or the complement thereof, ii) an mRNA molecule having a nucleotide sequence comprising the nucleotide sequence according to SEQ ID NO:14 at positions corresponding to positions 4,116 to 4,417 according to SEQ ID NO:4, or the complement thereof, or iii) a cDNA molecule having a nucleotide sequence comprising the nucleotide sequence according to SEQ ID NO:16 at positions corresponding to positions 4,116 to 4,417 according to SEQ ID NO:6, or the complement thereof; and
  wherein the SCAP inhibitor comprises an antisense nucleic acid molecule, a small interfering RNA (siRNA), a short hairpin RNA (shRNA) that hybridizes to a SCAP mRNA, a Cas protein and guide RNA (gRNA) that hybridizes to a gRNA recognition sequence within a SCAP genomic nucleic acid molecule, or a small molecule SCAP inhibitor.

4. A method of identifying a human subject having an increased risk for developing an increased lipid level and/or increased triglyceride level, wherein the method comprises determining or having determined the presence or absence of a SCAP variant nucleic acid molecule encoding a human SCAP polypeptide in a biological sample obtained from the subject; wherein: when the human subject is SCAP reference, then the human subject has an increased risk for developing the increased lipid level and/or increased triglyceride level; and when the human subject is heterozygous for the SCAP variant nucleic acid molecule or homozygous for the SCAP variant nucleic acid molecule, then the human subject has a decreased risk for developing the increased lipid level and/or increased triglyceride level; wherein the SCAP variant nucleic acid molecule is: i) a genomic nucleic acid molecule having a nucleotide sequence comprising the nucleotide sequence according to SEQ ID NO:12 at positions corresponding to positions 61,695 to 62,267 according to SEQ ID NO:2, or the complement thereof, ii) an mRNA molecule having a nucleotide sequence comprising the nucleotide sequence according to SEQ ID NO:14 at positions corresponding to positions 4,116 to 4,417 according to SEQ ID NO:4, or the complement thereof, or iii) a cDNA molecule having a nucleotide sequence comprising the nucleotide sequence according to SEQ ID NO:16 at positions corresponding to positions 4,116 to 4,417 according to SEQ ID NO:6, or the complement thereof.

5. A method of detecting a human Sterol Regulatory Element Binding Protein Cleavage-Activating Protein (SCAP) variant nucleic acid molecule in a human subject comprising assaying a sample obtained from the human subject to determine whether a nucleic acid molecule in the sample comprises a nucleotide sequence comprising: i) the nucleotide sequence according to SEQ ID NO:12 at positions corresponding to positions 61,695 to 62,267 according to SEQ ID NO:2, or the complement thereof; ii) the nucleotide sequence according to SEQ ID NO:14 at positions corresponding to positions 4,116 to 4,417 according to SEQ ID NO:4, or the complement thereof or iii) the nucleotide sequence according to SEQ ID NO:16 at positions corresponding to positions 4,116 to 4,417 according to SEQ ID NO:6, or the complement thereof.

6. The method according to claim 5, wherein the assay comprises sequencing at least a portion of the nucleic acid molecule, wherein the sequenced portion comprises: i) positions corresponding to positions 61,694 to 61,695 according to SEQ ID NO:2, or the complement thereof; ii) positions corresponding to positions 4,115 to 4,116 according to SEQ ID NO:4, or the complement thereof; or iii) positions corresponding to positions 4,115 to 4,116 according to SEQ ID NO:6, or the complement thereof.

7. The method according to claim 6, wherein the assay comprises:
a) contacting the sample with a primer hybridizing to: i) a portion of the nucleotide sequence of SCAP genomic nucleic acid molecule that is proximate to positions corresponding to positions 61,694 to 61,695 according to SEQ ID NO:2; ii) a portion of the nucleotide sequence of SCAP mRNA molecule that is proximate to positions 4,115 to 4,116 according to SEQ ID NO:4; or iii) a portion of the nucleotide sequence of SCAP cDNA molecule that is proximate to positions corresponding to positions 4,115 to 4,116 according to SEQ ID NO:6;
b) extending the primer at least through: i) the position of the nucleotide sequence of SCAP genomic nucleic acid molecule corresponding to positions 61,694 to 61,695 according to SEQ ID NO:2; ii) the position of the nucleotide sequence of SCAP mRNA molecule corresponding to positions 4,115 to 4,116 according to SEQ ID NO:4; or iii) the position of the nucleotide sequence of SCAP cDNA molecule corresponding to positions 4,115 to 4,116 according to SEQ ID NO:6; and
c) determining whether the extension product of the primer comprises: i) positions corresponding to positions 61,694 to 61,695 according to SEQ ID NO:2; ii) positions corresponding to positions 4,115 to 4,116 according to SEQ ID NO:4; or iii) positions corresponding to positions 4,115 to 4,116 according to SEQ ID NO:6.

8. An isolated alteration-specific probe or alteration-specific primer comprising at least about 15 nucleotides, wherein the alteration-specific probe or alteration-specific primer comprises a nucleotide sequence which is complementary to a portion of a nucleotide sequence encoding a human Sterol Regulatory Element Binding Protein Cleavage-Activating Protein (SCAP) polypeptide, wherein the portion comprises a position corresponding to: i) positions 61,694 to 61,695 according to SEQ ID NO:2, or the complement thereof; ii) positions 4,115 to 4,116 according to SEQ ID NO:4, or the complement thereof; or iii) positions 4,115 to 4,116 according to SEQ ID NO:6, or the complement thereof, and wherein the alteration-specific probe or alteration-specific primer further comprises a detectable label, modified base, modified sugar, or modified phosphate group.

9. A cDNA molecule comprising a nucleotide sequence encoding a human Sterol Regulatory Element Binding Protein Cleavage-Activating Protein (SCAP) polypeptide, wherein the nucleotide sequence comprises the nucleotide sequence according to SEQ ID NO:16 at positions corresponding to positions 4,116 to 4,417 according to SEQ ID NO:6, or the complement thereof.

10. The cDNA molecule, or the complement thereof, according to claim 9, wherein the nucleic acid molecule comprises SEQ ID NO:6.

11. A molecular complex comprising an alteration-specific primer or an alteration-specific probe hybridized to:
a genomic nucleic acid molecule comprising a nucleotide sequence encoding a human SCAP polypeptide, wherein the alteration-specific primer or the alteration-specific probe is hybridized to a GT dinucleotide at positions corresponding to positions 61,694 to 61,695.

12. The molecular complex according to claim 11, further comprising a non-human polymerase.

13. A method of treating a subject having increased total cholesterol, increased low density lipoprotein (LDL), increased serum lipid level, or increased triglycerides, the method comprising administering a SCAP inhibitor to the subject, wherein the subject has a SCAP variant nucleic acid molecule encoding a human SCAP variant polypeptide.

14. The method according to claim 13 wherein, the SCAP inhibitor comprises an antisense nucleic acid molecule, a small interfering RNA (siRNA), a short hairpin RNA (shRNA) that hybridizes to a SCAP mRNA, a Cas protein and guide RNA (gRNA) that hybridizes to a gRNA recognition sequence within a SCAP genomic nucleic acid molecule, or a small molecule SCAP inhibitor.

15. The method according to claim 13, wherein the SCAP variant nucleic acid molecule is: i) a genomic nucleic acid molecule having a nucleotide sequence comprising the nucleotide sequence according to SEQ ID NO:12 at positions corresponding to positions 61,695 to 62,267 according to SEQ ID NO:2, or the complement thereof, ii) an mRNA molecule having a nucleotide sequence comprising the nucleotide sequence according to SEQ ID NO:14 at positions corresponding to positions 4,116 to 4,417 according to SEQ ID NO:4, or the complement thereof, or iii) a cDNA molecule having a nucleotide sequence comprising the nucleotide sequence according to SEQ ID NO:16 at positions corresponding to positions 4,116 to 4,417 according to SEQ ID NO:6, or the complement thereof.

16. The method according to claim 3, wherein the SCAP inhibitor comprises an siRNA.

* * * * *